US005885829A

United States Patent [19]
Mooney et al.

[11] Patent Number: 5,885,829
[45] Date of Patent: Mar. 23, 1999

[54] ENGINEERING ORAL TISSUES

[75] Inventors: David J. Mooney; Robert B. Rutherford, both of Ann Arbor, Mich.

[73] Assignee: The Regents of the University of Michigan, Ann Arbor, Mich.

[21] Appl. No.: 864,494

[22] Filed: May 28, 1997

Related U.S. Application Data

[60] Provisional application No. 60/018,450, May 28, 1996.
[51] Int. Cl.$^6$ .............................. C12N 5/00; C12N 5/02; C12N 5/08; C12N 15/09
[52] U.S. Cl. ............................ 435/325; 424/49; 424/422; 424/435; 435/69.5; 435/374; 435/378
[58] Field of Search .................................... 435/69.1, 325, 435/69.4, 69.5, 69.6, 365, 393, 366, 374, 378; 422/422, 423, 424, 435, 49, 85.1, 93.7; 514/12, 21

[56] References Cited

U.S. PATENT DOCUMENTS

| | | | |
|---|---|---|---|
| 4,963,489 | 10/1990 | Naughton et al. | 435/1.1 |
| 5,032,508 | 7/1991 | Naughton et al. | 435/32 |
| 5,266,480 | 11/1993 | Naughton et al. | 435/371 |
| 5,443,950 | 8/1995 | Naughton et al. | 435/1.1 |
| 5,518,915 | 5/1996 | Naughton et al. | 424/422 |
| 5,567,612 | 10/1996 | Vacanti et al. | 435/366 |
| 5,624,840 | 4/1997 | Naughton et al. | 435/395 |
| 5,759,830 | 6/1998 | Vacanti et al. | 435/180 |
| 5,770,193 | 6/1998 | Vacanti et al. | 424/93.7 |
| 5,770,417 | 6/1998 | Vacanti et al. | 435/180 |

FOREIGN PATENT DOCUMENTS

| | | |
|---|---|---|
| 40 40 872 | 7/1992 | Germany . |
| WO 88/03785 | 6/1988 | WIPO . |
| WO 92/07573 | 5/1992 | WIPO . |
| WO 92/16181 | 10/1992 | WIPO . |
| WO 98/22041 | 5/1998 | WIPO . |

OTHER PUBLICATIONS

Bohl, K. et al., "Synthetic Extracellular Matrices for Engineering Dental Pulp," Abstract distributed a *Fifth World Biomaterials Congress*, Toronto, Canada, May 29, 1996.

Gombotz and Pettit, "Biodegradable polymers for protein and peptide drug delivery," *Bioconjugate Chem.*, 6:332–351, 1995.

Goshima et al., "The origin of bone formed in composite grafts of porous calcium phosphate ceramic loaded with marrow cells," *Clin. Orthopod. Rel. Res.*, 269:274–283, 1991.

Green et al., "Growth of cultured human epidermal cells into multiple epithelia suitable for grafting," *Proc. Natl. Acad. Sci. USA*, 76:5665–5668, 1979.

Gu, et al., "Expression of genes for bone morphogenetic proteins and receptors in human dental pulp", *Archives of Oral Biology*, 41(10):919–23, 1996.

Hansbrough et al., "Evaluation of a biodegradable matrix containing cultured human fibroblasts as a dermal replacement beneath meshed skin grafts on athymic mice," *Surgery*, 4:438–446, 1992.

Hubbell, "Biomaterials in tissue engineering," *Bio/Technology*, 13:565–576, 1995.

Langer and Vacanti, "Tissue engineering," *Science*, 260:920–926, 1993.

Laurencin et al., "Use of polyphosphazenes for skeletal tissue regeneration," *J. Biomed. Mater. Res.*, 27:963–973, 1993.

Lesot et al., "Experimental Induction of odontoblast Differentiation and Stimulation During Reparative Processes," *Cells and Materials*, 3:201–217, 1993.

Mikos et al., "Preparation of poly (glycolic acid) bonded fiber structures for cell attachment and transplantion," *J. Biomed. Mat. Res.*, 27:183, 1993.

Mikos et al., "Prevascularization of porous biodegradable polymers," *Biotech. bioeng.*, 42:716–723, 1993.

Mooney and Vacanti, "Tissue engineering using cells and synthetic polymers," *Trans. Rev.*, 7:153–162, 1993.

Mooney et al., "Design and fabrication of biodegradable polymer devices to engineer tubular tissues," *Cell Transplantation*, 3:203, 1994.

Mooney et al., "Transplantation of hepatocytes using porous, biodegradable sponges," *Transplan. Proc.*, 26(6):4025–4026, 1994.

Mooney et al., "Biodegradable Sponges for Hepatocyte Transplantation," *J. Biomed. Mat. Res.*,29:959–965, 1995.

Mooney et al., "Fabricating Tubular Devices From Polymers of Lactic and Glycolic Acid for Tissue Engineering," *Tiss. Eng.*, 1:107–118, 1995.

Mooney et al., "Stabilized Polyglycolic Acid Fibre–Based Tubes for Tissue Engineering," *Biomaterials*, 17:115–124, 1996.

Mooney et al., "Engineering dental pulp–like tissue in vitro," *Biotechnol. Prog.* 12(6):865–868, 1996.

Mooney, et al., "Localized delivery of epidermal growth factor improves the survival of transplanted hepatocytes," *Biotechnology and Bioengineering*, 50(4):422–429, 1996.

Mooney et al., "Novel approach to fabricate porous sponges of poly(D,Llactic–co–glycolic acid) without the use of organic solvents," *Biomaterials*, 17(14):1417–1422, 1996.

Mooney, et. al., "Tissue engineering: Tubular tissues," In: *Yearbook of Cell and Tissue Transplantion*, Lanza and Chick (Ed.), pp. 275–282, 1996.

Nakashima, "Induction of Dentin Formation on Canine Amputated Pulp by Recombinant Human Bone Morphogenetic Protieins (BMP)–2 and –4," *J. Dent Res.*, 73:1515–1522, 1994.

(List continued on next page.)

*Primary Examiner*—Nancy Degen
*Attorney, Agent, or Firm*—Arnold, White & Durkee

[57] ABSTRACT

Disclosed are methods for regenerating dental and oral tissues from viable cells using ex vivo culture on a structural matrix. The regenerated oral tissues and tissue-matrix preparations thus provided have both clinical applications in dentistry and oral medicine and are also useful in in vitro toxicity and biocompatibility testing.

109 Claims, 11 Drawing Sheets

OTHER PUBLICATIONS

Putnam, and Mooney, "Tisue engineering using synthetic extracellular matrices," *Nature Medicine* 2(7):824–826, 1996.

Rutherford et al, "Induction of Reparative Dentine Formation in Monkeys by Recombinant Human Osteogenic Protein–1," *Archs Oral Biol.*, 38:571–576, 1993.

Rutherford et al., "Platelet derived and insulin–like growth factors stimulate regeneration of periodontal attachment in monkeys," *J. Perio Res.*, 27:285–290, 1992.

Rutherford et al., "The Time–Course of the Induction of Reparative Dentine Formation in Monkeys by Recombinant Human Osteogenic Protein–1," *Arch Oral Biol.*, 39:833–838, 1994.

Rutherford et al., "Transdentinal Stimulation of Reparative Dentine formation by Osteogenic Protein–1," *Archs. Oral Biol.*, 40:681–683, 1995.

Rutherford et al., "Platelet–derived growth factor and dexamethasone combined with a collagen matrix induced regeneration of the periodontium in monkeys," *J. Clin. Perio*, 20:537–544, 1993.

Yannas et al., "Wound tissue can utilize a polymeric template to synthesize and functional extension of skin," *Science*, 215:174–176, 1981.

Yannas et al., "Synthesis and characterization of a model of extracellular matrix that induces partial regeneration of adult mammalian skin," *Proc. Natl. Acad. Sci. USA*, 86:933–937, 1989.

Bouvier, Joffre and Magloire, "In Vitro Mineralization of a Three–Dimensional Collagen Matrix by Human Dental pulp Cells in the Presence of Chondroitin Sulphate," *Archs Oral Biol.*, 35(4):301–309, 1990

Rutherford et al., "Synergistic Effects of Dexamethasone on Platelet–Derived Growth Factor Mitogenesis In Vitro," *Archs Oral Biol.*, 37(2):139–145, 1992.

Sasaki et al., "Inhibition of Wound Contraction bt Papaverine: In Vitro Analysis with a Submucosal Tissue Model," *Annals of Plastic Surgery*, 27(6),Dec. 1991.

Suwa et al., "Inductive Effect of Bovine Bone Morphogenetic Protein on Human Dental Pulp Tissue In Vitro," *13–Mammalian Biochem.*, 122:707, 1995, Abstract No. 77691w.

Ueda, Ebata, and Kaneda, "In Vitro Fabrication of Bioartificial Mucosa for Reconstruction of Oral Mucosa: Basic Research and Clinical Application," *Annals of Plastic Surgery*, 27(6), Dec. 1991.

International Search Report dated Sep. 29, 1997 (UMIC:019P).

ENGINEERING ORAL TISSUES

The present application claims the priority of U.S. Provisional Patent Application Serial No. 60/018,450 filed May 28, 1996, abandoned, the entire text of which is specifically incorporated by reference herein without disclaimer.

BACKGROUND OF THE INVENTION

1. Field of the Invention

The present invention relates generally to the fields of dentistry and oral biology. More particularly, it concerns the generation of oral tissues from viable cells using ex vivo culture on a structural matrix. The regenerated oral tissues provided herein may be used in a variety of clinical applications and also in in vitro biocompatibility testing.

2. Description of Related Art

A major goal of dental research is the development of effective clinical approaches to promote the regeneration of oral tissues following various insults or diseases. While synthetic materials have been successfully utilized as restorative materials for dental tissues for a number of years (Craig, 1989), these materials do not replace the normal structure and function of the lost tissue and are incapable of remodeling/repairing in the face of ongoing insult or stimulation.

One such example is that of root canal therapy. Approximately 15 million patients in the U.S. require a root canal each year. Here, necrotic pulp tissue resulting from trauma or bacterial infection is removed and replaced with a non-viable synthetic material. The synthetic material is clearly unable to provide the biological functions of pulp tissue, and failure leads to tooth loss.

Engineering new tissues from cultured cells represents a new approach to treat patients suffering from the loss or malfunction of certain tissues (Langer and Vacanti, 1994). However, with the limited exception of oral mucosa, the techniques of cell and tissue culture have not been successfully applied in the engineering of oral tissues. Current cell culture techniques, such as those used in the regeneration of skin, and even oral mucosa, are not transferable to the regeneration of other oral tissues as the existing techniques produce epithelia which require an appropriate connective tissue bed in vivo for successful grafting. The art therefore lacks appropriate techniques for the production of tissues ex vivo that will repair and regenerate specific oral connective tissues in vivo.

Dental pulp is a loose connective tissue that provides dentinogenic, nutritive, sensory and defensive functions to the tooth (Chiego, 1994). Dentin is produced by specialized cells, odontoblasts, which reside in dental pulp. Tertiary dentinogenesis is often initiated following injury to or loss of dentin by the original odontoblasts, or if lost, by unidentified cells which differentiate into odontoblasts (Lesot et. al., 1993).

Dental pulp and other oral tissues may be capable of regenerating following injury, but the specific mechanisms underlying pulp regeneration and reparative dentinogenesis have not been identified. As there is little known about such processes, the ability to culture or regenerate dental pulp and other oral tissues has been severely hampered. The development of methodology by which to culture oral tissues would thus represent a significant breakthrough in this field.

SUMMARY OF THE INVENTION

The present invention seeks to overcome these and other drawbacks inherent in the prior art by providing methods and compositions for use in culturing, engineering and reconstructing oral tissues. The invention generally concerns the ex vivo culture of viable oral tissue cells in combination with a structural matrix, or scaffold, that results in the proliferation of the cells, the production of extracellular matrix, and their organization into a new tissue structure. The regenerated oral tissue or matrix-tissue structure may then be implanted back in the body to form a new functional oral tissue. Methods of using such tissues or matrix-tissue preparations for in vivo drug delivery and for in vitro toxicity and biocompatibility testing are also provided.

In certain embodiments, the present invention provides methods for culturing oral tissue cells, which methods generally comprise growing viable oral tissue cells, or "starter cells", on a matrix in vitro under conditions effective and for a period of time sufficient to allow proliferation of viable oral tissue cells.

The method may comprise growing viable oral tissue cells on a three dimensional matrix in vitro under conditions effective and for a period of time sufficient to allow proliferation of viable oral tissue cells to form a three dimensional structure comprising viable oral tissue cells. Alternatively, the method may comprise growing viable oral tissue cells on a three dimensional matrix in vitro under conditions effective and for a period of time sufficient to allow proliferation of viable oral tissue cells to form a three dimensional biological structure of viable oral tissue cells.

Further, the method may comprise growing viable oral tissue cells on a three dimensional matrix or framework in vitro under conditions effective and for a period of time sufficient to allow proliferation of viable oral tissue cells to form a three dimensional structure comprising viable oral tissue cells on or around said matrix or framework. Or the method may comprise growing viable oral tissue cells on a matrix, preferably a three dimensional matrix or scaffold, in vitro under conditions effective and for a period of time sufficient to allow proliferation of viable cells that express at least one marker indicative of oral tissue cells.

The method may comprise growing viable oral tissue cells on a matrix, preferably a three dimensional matrix, in vitro under conditions effective and for a period of time sufficient to allow proliferation of viable cells that express one or more markers indicative of oral tissue cells. Alternatively, the method may comprise growing viable oral tissue cells on a matrix, preferably a three dimensional matrix, in vitro under conditions effective and for a period of time sufficient to allow proliferation of viable cells that express a plurality of markers indicative of oral tissue cells.

The invention also provides a method for culturing oral tissue cells, comprising growing viable cells obtained from an oral tissue on a three dimensional matrix in vitro under conditions effective and for a period of time sufficient to allow proliferation of viable oral tissue cells. The method may alternatively comprise growing viable oral tissue cells on a preferably three dimensional matrix in vitro under conditions effective and for a period of time sufficient to allow proliferation of viable oral tissue cells in functional association with said matrix or said three dimensional matrix.

The invention further provides a method for culturing oral tissue cells, comprising growing viable cells obtained from an oral tissue in functional association with a three dimensional matrix in vitro under conditions effective and for a period of time sufficient to allow proliferation of viable oral tissue cells to form a three dimensional biological structure comprising cells that express at least one marker indicative of oral tissue cells. The invention also provides a method for culturing oral tissue cells, comprising growing viable cells obtained from an oral tissue in functional association with a three dimensional matrix in vitro under conditions effective and for a period of time sufficient to allow proliferation of viable oral tissue cells to form a three dimensional biological tissue structure, the cells of which tissue express at least one marker indicative of oral tissue cells.

Alternatively, the method may comprise comprising growing viable cells obtained from an oral tissue in functional association with a three dimensional matrix in vitro under conditions effective and for a period of time sufficient to allow proliferation of viable oral tissue cells to form a three dimensional biological oral tissue structure, comprising cells expressing at least one marker indicative of oral tissue cells. Or the method may comprise growing viable cells obtained from an oral tissue in functional association with a three dimensional matrix in vitro under conditions effective and for a period of time sufficient to allow proliferation of viable oral tissue cells to form a three dimensional biological oral tissue structure, the cells of which oral tissue structure express a plurality of biological markers indicative of oral tissue cells.

After inoculation of the cells, the three-dimensional framework may be incubated in an appropriate nutrient medium. Many commercially available media such as RPMI 1640, Fisher's, Iscove's, McCoy's, and the like may be suitable for use. The three-dimensional oral tissue may be suspended in the medium during the incubation period in order to maximize proliferative activity. In addition, the culture may be "fed" periodically to remove the spent media, depopulate released cells, and add fresh media.

The matrices of the present invention are "structural" matrices that provide a scaffold for the cells to guide the process of tissue formation. Thus, the "structural matrices" can be considered to be "three-dimensional matrices", rather than simple two dimensional supports. It will be understood that the scaffolding matrices of the present invention are distinct from the inert plastic or glass ware that is used in routine cell culture. Not that plastic or glass is entirely incompatible with the present invention, if modified or combined with other matrix elements to form the required scaffold-like matrix.

Thus, in preferred aspects, the present invention provides a three-dimensional, multi-layer cell and tissue culture system. In particular, a culture system for the long term culture of cells and tissues in vitro in an environment that more closely approximates that found in vivo is provided. The culture system described herein provides for proliferation and appropriate cell maturation to form structures analogous to oral tissue counterparts in vivo. The resulting oral tissues survive for prolonged periods, express oral tissue specific markers, perform oral tissue-specific functions, and maintain oral tissue architecture following in vivo implantation. The oral tissue cultures have a variety of applications ranging from transplantation or implantation in vivo, to screening cytotoxic compounds and pharmaceutical compounds in vitro, to the production of biologically active molecules in "bioreactors". When grown in this three-dimensional system, the proliferating oral tissue cells mature and segregate properly to form components of oral tissues analogous to counterparts found in vivo.

The invention is based, in part, on the discovery that growth of oral tissue cells in three dimensions sustains active proliferation of oral tissue cells in culture for longer periods of time than conventional systems. This may be due, in part, to the increased surface area of the three-dimensional support framework which results in a prolonged period of active proliferation of oral tissue cells. These proliferating cells elaborate proteins, secreted extracellular matrix components, growth factors and regulatory factors necessary to support the long term proliferation of oral tissue cells inoculated onto the matrix. The production of the fibrous or stromal extracellular matrix tissue that is deposited on the matrix is conducive for the long term growth of the oral tissues in vitro. In addition, the three-dimensionality of the framework allows for a spatial distribution which more closely approximates conditions in vivo for the particular oral tissues, allowing for the formation of microenvironments conducive to cellular maturation and migration. The growth of cells in the presence of this support may be further enhanced by adding growth or regulatory factors, various components of extracellular matrix and other materials to the support itself or by coating the support with these materials.

Proliferation of cells occurs in vitro and appears to be contingent upon the geometry of the culture framework; and, when established on biodegradable framework, these cell/matrix co-cultures are capable of regenerating oral tissue architecture at ectopic sites and retain their ability to synthesize tissue-specific proteins. This cell and tissue culture system may have applications as a substrate for toxicity testing and, when grown on a biocompatible or biodegradable polymer framework, to be implanted into subjects. Furthermore, genetically engineered cells maintain the expression of their exogenous gene long term when grown in the culture system of the present invention.

The openings of the three dimensional framework or scaffold should be of an appropriate size to allow the cells to stretch across the openings. Maintaining actively growing cells which stretch across the framework enhances the production of growth factors which are elaborated by the cells, and hence will support long term cultures. In fact, any shape or structure of matrix that allows the cells to stretch and continue to replicate and grow for lengthy time periods will work in accordance with the invention. It may be preferable to avoid the presence of a confluent monolayer in the vicinity of the three-dimensional culture, as this may "shut down" the growth of cells.

The invention also provides various methods for generating, or reconstructing, oral tissues. A first method generally comprises culturing or propagating viable oral tissue cells, or "starter cells", on a matrix in vitro under conditions effective and for a period of time sufficient to allow formation of an oral tissue sample. This tissue approaches physiologic conditions found in vivo to a greater degree than other tissue culture systems. The three-dimensional cell culture system is applicable to the proliferation of cells and formation of tissues.

The "starter cells" may be enriched for a particular cell type prior to culture on the matrix. Particular cell types may be selected through the use of antibodies to cell surface markers specific for a particular type of cell. Alternatively unwanted cell types may be "negatively selected" by using antibodies specific for a marker on the surface of the unwanted cell type. Both selection protocols can be accomplished using monoclonal antibodies of an appropriate isotype or subclass.

One may obtain the composition comprising viable cells from an oral tissue and immediately culture the viable cells of the composition on a matrix in vitro under conditions effective and for a period of time sufficient to allow the formation of an oral tissue sample. One may also obtain a composition isolated at an earlier time, or by another person, and even stored for a moderate time period, and then culture the viable cells on a matrix in vitro at a later date. Where the cultures are to be maintained for long periods of time or cryopreserved, non-degradable materials such as nylon, dacron, polystyrene, polyacrylates, polyvinyls, teflons, cotton, etc. may be preferred.

Compositions comprising viable cells in accordance with the present invention may be "obtained" by one party and "cultured", or otherwise manipulated as disclosed herein, by another party. Likewise, the regenerated tissue may be utilized by yet another party, either in clinical or veterinary practice or in screening embodiments. It will therefore be understood that each aspect of the present invention does not have to be executed by the same person or people, or as a series of consecutive steps without interruption.

The terms "culture" and "culturing", as used herein, are preferably used to indicate culture media and techniques that are known by those of skill in the art to result in successful culture of cells, preferably, mammalian cells, and most preferably, oral tissue cells. It will be understood that various media compositions, pH, temperature, and the like will be suitable.

It will also be understood that the use of antibiotics is particularly preferred, especially as cells cultured from oral tissues are typically associated with microbes, such as yeast and bacteria, and the antibiotics will be effective to combat such microbes. One or more antibiotics, or a cocktail thereof, will generally be used in the present invention in an amount effective to allow the culture and growth of oral tissue cells, without the significant growth or proliferation of microbial cells, such as yeast and bacterial cells. The use of "amounts effective" to achieve the desired results will be known to those of skill in the art.

In certain preferred embodiments, antibiotics will generally be used in larger amounts than those connected with culture of other mammalian tissue cells. For example, up to about 2 or 3 times the normal concentrations of antibiotics and antimycotics may be used. It will also be understood that the amounts of the antibiotics or cocktails will be optimized to suit a particular circumstance. By way of example only, where a tissue sample from a diseased or infected tissue is used, one of skill in the art will understand that increasing the amounts of antibiotics employed will generally be advisable.

The use of antibiotics and antimycotics in the tissue culture of the present invention may be continued as long as desired. In this manner, the term "culturing viable cells on a matrix ex vivo under conditions effective and for a period of time sufficient to allow the formation of an oral tissue sample" means that the continued use, types and amounts of antibiotics is at the discretion of the skilled artisan carrying out the method as disclosed herein.

The oral tissues and viable cell compositions for use in the present invention will preferably be "autologous" cells and tissues, which are intended for return to the animal or human from which they were obtained. This approach might be especially advantageous where immunological rejection of the transplant and/or graft versus host disease is likely. It is a particular advantage of the invention that this can now be achieved. However, the use of other types of cells is certainly not excluded. Therefore, "allogeneic" cells and tissues, from another animal of the same species, and even "xenogeneic" cells and tissues, from another species of animal are contemplated for use herewith.

The reconstructive methods of the present invention may also be defined as methods which generally comprise obtaining a composition comprising viable cells from an oral tissue of an animal, culturing the viable cells of the composition on a matrix ex vivo under conditions effective and for a period of time sufficient to allow the formation of an oral tissue sample that resembles the corresponding native tissue sample and reconstructing the oral tissue of the animal in vivo by application of the oral tissue sample.

The reconstructive methods described above may be effected in vivo by the application of a regenerated oral tissue sample that has been separated from the matrix to form a regenerated oral tissue sample substantially free from matrix components prior to application of the tissue to the animal. Alternatively, tissue reconstruction may be achieved by the application of a regenerated oral tissue sample that remains in combination with the matrix.

Such methods are also applicable for replacing lost or damaged oral tissue, as may be caused by, e.g., an infection that leads to necrotic oral tissue. An example of such a method is one which generally comprises obtaining an oral tissue composition that comprises at least some viable cells, culturing the viable cells of the composition on a biocompatible matrix ex vivo under conditions effective and for a period of time sufficient to allow the regeneration of an oral tissue sample within the matrix and replacing the lost or damaged oral tissue of the animal by implanting the matrix containing the regenerated oral tissue sample into the lost or damaged tissue site.

An oral tissue composition that comprises sufficient viable cells to subsequent allow the regeneration of an oral tissue may be obtained from part of a damaged tissue site that is itself to be treated, or from the near surroundings of a lost tissue. Although damaged or infected tissue may contain certain non-viable cells, this does not negate the usefulness of the invention in culturing and regenerating oral tissues from the viable cells present in such a sample. Increased amounts of antibiotics, or cocktails thereof, should generally be used in these contexts.

In other embodiments, an oral tissue composition that comprises viable cells may be obtained from an oral tissue site that is compatible with, but distinct from, the tissue site to be treated. Such compatible tissues are those including the same general structure and/or containing cells of equivalent regenerative capacity to the tissue site to be treated. By way of example only, in performing a restorative procedure on a given tooth, a compatible tissue sample may be obtained from a distinct, healthy tooth, including an extracted tooth.

Viable cells can also be obtained from an oral tissue site that is compatible with the site to be treated by virtue of comprising cells that are capable of forming or regenerating cells of the tissue site that is to be treated. A currently preferred example is that of using a single, easily biopsied tissue, such as gingiva, as the source of cells for the in vitro or ex vivo development of oral neotissue constructs.

In preferred aspects of the invention, the viable starting cells are gingival cells obtained from a gingival tissue sample. In certain embodiments of the invention, the gingival cells are cultured to form a tissue sample that comprises viable gingival submucosal, dental pulp tissue, dentin tissue, cementum tissue, periodontal tissue, oral submucosa tissue or tongue tissue cells. In alternate embodiments of the invention, the gingival cells are cultured to form a gingival submucosal, dental pulp, dentin, cementum, periodontal, oral submucosa or tongue tissue sample. In further aspects of the invention a mixture of viable starting cells is used.

In particular aspects of the invention the tissue sample formed comprises viable dental pulp, dentin, gingival submucosa, cementum, periodontal, oral submucosa or tongue tissue cells. The tissue sample thus formed is a dental pulp, dentin, gingival submucosa, cementum, periodontal, oral submucosa or tongue tissue sample.

The tissue sample may be formed by culturing viable starting cells obtained from an oral tissue sample enriched in dental pulp-derived fibroblasts. In certain aspects of the invention the viable starting cells enriched in dental pulp-derived fibroblasts are obtained from an extracted tooth. In particular embodiments of the present invention, the viable starting cells enriched in dental pulp-derived fibroblasts are obtained from a tissue sample extracted from a tooth that remains in an animal. Additionally, the tissue sample may be formed by culturing viable starting cells obtained from an oral tissue sample enriched in gingival submucosal fibroblasts.

In other aspects of the invention the tissue sample formed may comprise viable dentin, gingival submucosa, cementum, periodontal, oral submucosa or tongue tissue cells. Thus, the tissue samples formed may be dentin, gingival submucosa, cementum, periodontal, oral submucosa or tongue tissue sample. In these aspects, the tissue samples may be formed by culturing viable starting cells obtained from an oral tissue sample enriched in dental pulp, gingival submucosal fibroblast, periodontal ligament or oral submucosal fibroblast cells.

In further embodiments of the invention the tissue sample formed may comprise viable oral tissue cells of at least two different cell types. In other embodiments of the invention the tissue sample formed may comprise a plurality of distinct viable oral tissue cells.

Gingival samples are contemplated for use in the present invention for the regeneration of dental pulp, dentin, periodontal tissue, and bone, as well as oral submucosa and gingival submucosa (subgingival connective tissue). Using a gingival tissue sample means that a tooth does not need to be extracted in order to obtain pulp or periodontal ligament fibroblasts as a source of cells. Gingival biopsies are obtainable by routine dental procedures with little or no attendant donor site morbidity.

The use of gingival cells is currently preferred for the induction of mineralized oral connective tissues, such as dentin, cementum and bone. However, the generation of muscle cells as part of the tongue regeneration is not excluded as the gingival fibroblasts may be engineered to differentiate into muscle cells.

In certain preferred embodiments, the invention concerns the generation of a matrix-cell preparation and the "culture" or maintenance of such a preparation for a period of time before implantation or further use, during which time further cell proliferation and tissue regeneration occurs. Accordingly, the present invention also provides methods for generating an oral tissue which generally comprise obtaining a composition that comprises sufficient numbers of viable cells from an oral tissue, culturing the cells of the composition, preferably using antibiotics or cocktails thereof, implanting the cells on a matrix in vitro to form a matrix-cell preparation and maintaining the matrix-cell preparation under conditions effective and for a period of time sufficient to allow the formation of an oral tissue sample.

These methods may also be further defined as methods for generating oral tissue which generally comprise isolating an oral tissue composition that comprises at least some viable cells from an oral tissue, expanding the viable cells in culture without allowing the significant growth of microbes, implanting the expanded, cultured cells onto an adherent matrix in vitro to form a matrix-cell preparation and maintaining the preparation under conditions effective and for a period of time sufficient to allow cell proliferation and organization into an oral tissue sample that resembles, e.g., structurally and functionally, the corresponding native tissue sample.

In terms of regenerating oral tissue for use in tissue reconstruction, the present invention also provides methods which generally comprise obtaining a composition that comprises at least some viable cells from an oral tissue of an animal, culturing the viable cells, preferably in the presence of an amount of an antimicrobial or antibiotic effective to inhibit the growth of microbes, seeding the cultured cells on a matrix to form an ex vivo matrix-cell preparation, culturing the matrix-cell preparation under conditions effective and for a period of time sufficient to allow proliferation and organization of the cells to form an oral tissue sample associated with the matrix and implanting the cultured oral tissue sample into an oral tissue site of the animal to effect reconstruction of the oral tissue.

It will be understood that the oral tissue sample may again be separated from the matrix prior to application to the animal. Equally, the oral tissue sample may be applied to the animal in combination with the matrix, wherein the matrix would preferably be a biocompatible matrix. Implantation of a cultured matrix-cell preparation into a specific oral tissue site of an animal to effect reconstruction of oral tissue may involve a biodegradable matrix or a non-biodegradable matrix, depending on the intended function of the preparation.

The present invention may also be used in connection with other standard techniques of dentistry and oral medicine. The local or systemic administration of antimicrobials in connection with the tissue administration described herein is also contemplated.

Although by no means required, in certain embodiments the oral cell and tissue culture methods of the present invention may utilize certain factors that regulate the growth and/or the function of oral tissue cells. Such exogenous factors may be used in the context of cell or tissue culture ex vivo and/or in the modulation of cell or tissue function in vivo, following delivery to the animal as part of the reimplantation process.

Growth factors and regulatory factors need not be added to the media since these types of factors are elaborated by the three-dimensional cells. However, the addition of such factors, or the inoculation of other specialized cells may be used to enhance, alter or modulate proliferation and cell maturation in the cultures. The growth and activity of cells in culture can be affected by a variety of growth factors such as insulin, growth hormones, somatomedins, colony stimulating factors, erythropoietin, cytokines and other growth factors. Other factors which regulate proliferation and/or differentiation include prostaglandins and interleukins.

Accordingly, the present invention further provides cell culture methods where viable oral tissue cells are cultured in the presence of one or more exogenous factors that stimulate the growth or proliferation of the cells. Further, the cells may be cultured on a matrix in the presence of at least one exogenous factor that stimulates the growth or proliferation of the cells on the matrix. The cells, tissues and matrix-tissues may also be cultured and/or maintained in the presence of one or more exogenous factors that inhibit adverse processes, such as those factors that inhibit cell death and apoptosis. Any such factor or factors may be semi-purified, purified, natural or recombinant.

In another embodiment of the invention the viable oral tissue cells are provided with an exogenous gene that expresses an exogenous factor in the cells. The exogenous gene may be provided on a recombinant vector comprising the exogenous gene encoding the exogenous factor, wherein the recombinant vector expresses the exogenous gene in the cells. The exogenous gene may be provided to the cells prior to seeding the cells on the matrix, towards the beginning of the in vitro matrix culture process or towards the end of the in vitro matrix culture process.

In certain embodiments of the invention the exogenous gene expresses an exogenous factor that stimulates the growth or proliferation of the cells. In other aspects, the exogenous gene expresses an exogenous therapeutic factor that is released by the cells. A wide variety of exogenous therapeutic factors are contemplated for use in the present invention, as exemplified by antibiotics, growth factors, cytokines, blood clotting factors and insulin. The use of a particular therapeutic agent will be dependent on the condition in the animal that is to be treated, and are generally well known to those of skill in the art.

In further embodiments, the exogenous factor or factors used to further stimulate the growth or proliferation of the cells in culture (or to inhibit cell death), either before or during the matrix culture phase, may be an exogenous growth or proliferation factor produced by a cell or population of cells that is co-cultured with the cells and/or tissues to be regenerated. The present invention thus contemplates the use of natural cells that elaborate growth factors, hormones, cytokines, and other autocrine, paracrine, hormonal and neurotransmitter-like stimulants in the culture and matrix-culture phases of oral tissue regeneration.

In still further embodiments, the growth factor, hormone, cytokine, hormone, neurotransmitter, cell death inhibitor, or like molecule may be released into the cell, tissue or matrix-tissue culture by a recombinant cell engineered to produce the growth factor, hormone, cytokine, hormone, neurotransmitter or desired molecule. The exogenous factor may be produced by a recombinant cell by providing the cell with the exogenous factor on a recombinant vector that expresses the factor in the recombinant cell. Recombinant engineering for protein production and secretion is now routine in the art.

Thus, the three-dimensional culture system of the invention may afford a vehicle for introducing genes and gene products in vivo for use in gene therapies. For example, using recombinant DNA techniques, a gene for which a patient is deficient could be placed under the control of a viral or tissue-specific promoter. The recombinant DNA construct containing the gene could be used to transform or transfect a host cell which is cloned and then clonally expanded in the three-dimensional culture system. The three-dimensional culture which expresses the active gene product, could be implanted into an individual who is deficient for that product. The engineered oral tissues would thus act as an "implantable pump", for the in vivo production and secretion of a desired gene product. Additionally, should the need arise to halt production of the exogenous gene, the tissue could simply be removed from the animal.

The use of the three-dimensional culture in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the three-dimensional cultures of the invention allow for expansion of the number of transfected cells and amplification (via cell division) of transfected cells. Preferably, the expression control elements used should allow for the regulated expression of the gene so that the product is synthesized only when needed in vivo. The promoter chosen would depend, in part upon the type of tissue and cells cultured. Cells and tissues which are capable of secreting proteins are preferable.

In the context of tissue application in vivo, regenerated oral tissue may be applied to an oral tissue site of an animal in the presence of one or more exogenous factors that stimulate the growth or proliferation of the tissue in the animal, and/or cells that naturally produce such factors and/or cells that have been engineered to produce such factors. Further, a biocompatible matrix containing a regenerated oral tissue sample may be implanted into a lost or damaged tissue site of an animal in the presence of one or more exogenous factors or cells that stimulate the growth or proliferation of the tissue in the animal, or promotes vascularization of the tissue or effects other beneficial results.

It can thus be seen that the present invention provides methods for delivering factors, such as growth factors, to oral tissues within an animal, which methods generally comprise culturing a composition that comprises at least some viable oral tissue cells on a matrix in vitro under conditions effective and for a period of time sufficient to allow formation of an oral tissue sample and delivering the sample to the oral tissue site in the presence of an exogenous factor. Such methods may also be generally defined as including the steps of obtaining at least some viable cells from an oral tissue, culturing the cells on a biocompatible matrix in vitro under conditions effective and for a period of time sufficient to allow formation of a cultured matrix-cell preparation, admixing the matrix-cell preparation with at least one selected factor and applying the matrix-cell selected factor admixture to an oral tissue site of an animal.

The invention further provides methods for delivering stimulatory and growth factors to oral tissues within an animal, which methods generally comprise culturing a composition that comprises at least some viable oral tissue cells on a matrix in vitro under conditions effective and for a period of time sufficient to allow formation of an oral tissue sample and delivering the sample to the oral tissue site in the presence of a natural cell, a recombinant cell or a population of cells that produce such factors. Biocompatible matrices may also be used to prepare a matrix-cell preparation which is admixed with a native or recombinant cell that produces at least one selected factor and applied to an oral tissue site of an animal.

A wide variety of structural matrices may be used in the context of the present invention. In certain embodiments, the matrices will preferably be biocompatible matrices. Naturally, any embodiment that concerns the application of a matrix, or substantial portions thereof, to an oral tissue site will require the matrix to be such a biocompatible matrix. Where in vivo application of a matrix-tissue sample is contemplated, the biocompatible matrix may be a biodegradable matrix, a slowly biodegradable matrix or a non-biodegradable matrix, depending on the particular tissue and clinical application. The use of non-biodegradable matrices is routine in dentistry and will be suitable for certain cases. The use of biodegradable compounds in clinical situations is equally established, and is contemplated for use in other embodiments of the invention.

In contrast, other embodiments of the present invention do not require the use of a biocompatible matrix. For example, where the method involves the complete or substantial degeneration of the matrix prior to application of the cultured tissue sample to an animal, the biocompatibility of the initial starting matrix is not particularly important. Similarly, where the method involves the removal or "harvest" of regenerated tissue from the matrix, the biocompatibility of the matrix is largely irrelevant. In the former situation, the matrix may be both generally unstable, labile or chemically degradable, and also non-biocompatible. In the latter case, a non-biocompatible matrix may be either degradable or non-degradable, so long as the tissue can be isolated substantially free from the non-biocompatible elements of the matrix prior to administration to the body.

Preferred matrices for use in the present invention will generally be those that define a space for the subsequent tissue development. Such matrices include hydrogels, or porous matrices such as fiber-based or sponge-like matrices.

In certain embodiments, synthetic matrices, as exemplified by synthetic polymer matrices, may be used. The matrices may be homopolymers or heteropolymers. Certain examples of such synthetic matrices are polylactic acid (PLA) polymer matrices, polyglycolic acid (PGA) polymer matrices and polylactic acid-polyglycolic acid (PLGA) copolymer matrices. Both the stereoisomeric forms are contemplated to be useful. Chemically, these may also be termed poly-(L-lactic acid), PLA or PLLA, and poly-(D,L-lactic acid), PDLLA. PLGA may also be written poly-(D, L-lactic-co-glycolic acid).

Such PLA, PGA and PLGA matrices may take various forms, including fiber matrices, tubular matrices and sponge matrices. The sponge matrices may include PLA and polyvinyl alcohol (PVA).

Further examples of appropriate synthetic matrices are polyanhydrides, polyesters, polyorthoesters, and poly(amino acids), polypeptides, polyethylene oxide, polyphosphazenes, various block copolymers, such as those consisting of ethylene oxide and propylene oxide (e.g., Pluronic surfactant; BASF Corp.), and blends of polymers from this group and with other polymers. Further polymers are detailed herein in Example IV. Ceramics, such as calcium phosphate matrices, may also be employed in the present invention.

The three-dimensional support framework may be of any material and/or shape that allows cells to attach to it (or can be modified to allow cells to attach to it), and allows cells to grow in more than one layer. A number of different materials may be used to form the framework, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE; teflon), thermanox (TPX), nitrocellulose, cotton, polyglycolic acid (PGA), cat gut sutures, cellulose, gelatin, dextran, etc. Any of these materials may be woven into a mesh, for example, to form the three-dimensional framework.

The matrix may be composed of individual matrix components, and the individual matrix components may be coated with a coating agent. In further aspects of the invention the matrix is a synthetic fiber matrix, the individual fiber components of which matrix are coated with a collagen coating agent, a polylysine coating agent or an FBS coating agent.

Certain materials, such as nylon, polystyrene, etc., may be poor substrates for cellular attachment. When these materials are used as the three-dimensional support framework, it may be advisable to pre-treat the matrix prior to inoculation of cells in order to enhance the attachment of cells to the framework. For example, prior to inoculation with cells, nylon screens could be treated with 0.1M acetic acid, and incubated in polylysine, FBS, and/or collagen to coat the nylon. Polystyrene could be similarly treated using sulfuric acid. Where the three-dimensional culture is itself to be implanted in vivo, it may be preferable to use biodegradable materials such as PGA, catgut suture material, collagen, polylactic acid, or hyaluronic acid. For example, these materials may be woven into a three-dimensional framework such as a collagen sponge.

In other embodiments, matrices for use in the invention may be naturally-derived matrices or "biomatrices". Preferred examples of biomatrices are those extracted from or resembling the extracellular matrix (ECM). These matrices may be termed ECM polymer matrices. One currently preferred example of a naturally-derived, or "ECM matrix", is a collagen matrix, such as type I collagen.

Further suitable examples of naturally-derived matrices include laminin-rich gels, alginate, agarose and other polysaccharides, gelatin, fibrin glues, and hyaluronic acid derivatives. Any such matrix, and blends of these materials with other polymers or other materials, is contemplated for use in the present invention.

In certain embodiments, "second generation matrices" or second generation ECM matrices may be used. These are exemplified by synthetic polymer matrices that have appended, i.e., are operatively attached to, one or more biologically active molecules. Such biologically active molecules include saccharides, polysaccharides, amino acids, peptides, polypeptides, proteoglycans, glycoproteins, and the like. Thus, these matrices have functions of both natural and synthetic matrices. They may include the products of synthetic chemistry and recombinant protein production.

The present invention is generally applicable to the culture and regeneration of a variety of oral tissues and structures. By way of example only, one may mention dental pulp tissue, dentin, periodontium, bone, cementum, gingival submucosa, oral submucosa, salivary gland tongue and taste bud tissues.

A currently preferred application of the present invention is in the culture and regeneration of dental pulp tissue. In such embodiments, dental pulp tissue is generally regenerated by culturing gingival tissues or dental pulp-derived cells, such as fibroblasts. However, the culture of other cells within an extracted dental pulp tissue, such as odontoblasts, may also contribute to the regeneration of dental pulp tissue according to the present invention.

In certain embodiments, the tissue for use in the regeneration process will be obtained from the gingiva. Gingival samples are readily obtainable by routine biopsy.

In other embodiments, an original sample of dental pulp tissue for use in the regeneration process will be obtained from a healthy tooth, such as an extracted molar or wisdom tooth.

In further embodiments, the sample of dental pulp tissue containing the starter cells for regeneration will be obtained, or salvaged, from the tooth to be operated on. In the latter process, the biological material isolated from a given tooth will be used to regenerate healthy tissue from the viable cells that exist in the extracted sample, notwithstanding the fact that certain non-viable cells will likely be present in such a sample. The existence of certain non-viable cells, and/or cells not of oral tissue origin, in a sample extracted from a diseased or damaged tooth does not generally negate the operativity of the tissue regeneration methods of the present invention. The determination of whether a given sample is appropriate for use in tissue regeneration will be straightforward to those of skill in the art in light of the present disclosure. Using tissue samples obtained from a single tooth has the advantage that a distinct healthy tooth does not have to be invaded in order to obtain the viable cells.

It will be understood by those of ordinary skill in the art that the regeneration of a particular oral tissue from a starting tissue sample will require a sample to be obtained that comprises viable cells capable of regenerating the particular oral tissue desired.

The use of gingival samples is contemplated to be advantageous as this can give rise to regenerated tissues of dental pulp, dentin, periodontium, cementum, bone, oral submucosa, gingival submucosa, and even has the potential to regenerate striated muscle cells.

In regard to other exemplary tissues:

to culture and regenerate dentin tissue, one would obtain a sample containing dental pulp cells or gingival submucosal fibroblasts;

to regenerate periodontal tissue, one would generally obtain a tissue sample containing periodontal ligament cells or gingival submucosal fibroblasts;

to culture and regenerate gingival submucosal tissue (subgingival connective tissue), one would generally use a sample containing gingival submucosal fibroblasts;

to regenerate an oral submucosal tissue, a tissue sample comprising oral submucosal fibroblasts would be used; and to generate a tongue tissue sample, one would generally use a tissue sample containing gingival submucosal fibroblasts.

Dental pulp, oral and gingival submucosal tissues are advantageous as they are constitutively capable of tissue regeneration. However, the use of viable cells isolated from the oral or gingival submucosa in the regeneration of other tissues, such as dental pulp, dentin, cementum, periodontal ligament and bone, will be understood to involve, in certain embodiments, the induction of particular developmental pathways by, e.g., the addition of specific protein factors or exposure to particular conditions. Genetic engineering to induce, promote or assist in the development of a particular tissue is also contemplated.

The invention further provides a method for culturing oral tissue cells, comprising growing viable starting cells obtained from an oral tissue sample in functional association with a three dimensional matrix in vitro under conditions effective and for a period of time sufficient to allow proliferation and organization of viable oral tissue cells to form a three dimensional biological structure comprising cells that express at least one marker indicative of oral tissue cells. In particular embodiments of the invention the viable oral cells are analyzed to confirm the presence of at least one biological marker indicative of oral tissue cells.

The invention also provides a method for generating an oral tissue sample, comprising growing viable starting cells obtained from an oral tissue sample in functional association with a three dimensional matrix in vitro under conditions effective and for a period of time sufficient to allow proliferation and organization of viable oral tissue cells to form a three dimensional oral tissue structure comprising a population of cells that comprise at least one sub-population of cells that express one or more biological markers indicative of oral tissue cells.

In a particular embodiment of the invention, the viable starting cells are obtained from a gingival tissue sample. The viable oral cells of the present invention may form a three dimensional biological structure. In certain aspects, the viable oral cells form a three dimensional oral tissue structure. In a further embodiment of the invention, the three dimensional biological or oral tissue structure resembles the corresponding native oral tissue.

Additionally, the present invention provides a method for reconstructing an oral tissue or for replacing lost or damaged oral tissue in an animal, comprising obtaining a composition comprising viable starting cells from an oral tissue sample of an animal, culturing the viable starting cells of said composition on a matrix ex vivo under conditions effective and for a period of time sufficient to allow the formation of a tissue sample that comprises oral tissue cells that resemble the corresponding native oral tissue cells and applying said tissue sample to an oral tissue site in vivo to reconstruct the oral tissue or to replace the lost or damaged oral tissue of the animal.

The viable starting cells may be obtained from a gingival tissue sample. Alternatively, the viable starting cells may be obtained from an oral tissue sample that is obtained from an oral tissue site compatible with, but distinct from, the oral tissue to be reconstructed or replaced. The viable starting cells may also be obtained from an oral tissue sample that is obtained from the damaged oral tissue site to be reconstructed or replaced.

In a particular aspect of the invention, the viable starting cells are cultured on the matrix in vitro in the presence of an amount of an antimicrobial agent effective to inhibit the growth of microbial cells in the culture. In another embodiment of the invention, the viable starting cells are pre-cultured in vitro for a period of time effective to prepare an expanded population of viable cells for culture on said matrix in vitro.

The tissue samples of the invention may be separated from the matrix prior to application to the animal, or may be applied to the animal in combination with the matrix.

In a particular aspect of the invention, the tissue sample has a structure that resembles the corresponding native oral tissue structure. In an additional aspect of the invention the tissue sample is applied to the oral tissue site to be reconstructed or replaced in the presence of an exogenous factor that stimulates the growth or proliferation of the tissue in the animal. In a further aspect of the invention, the exogenous factor is produced by a cell that is also applied to the oral tissue site of said animal. In still further aspects of the present invention, the exogenous factor-producing cell is a recombinant cell engineered to produce said factor. Alternatively, the exogenous factor-producing cell may be a cultured oral tissue cell of the applied tissue sample, the cell being provided with an exogenous gene that expresses said exogenous factor. In certain aspects, the cell is provided with a recombinant vector that comprises the exogenous gene.

In a particular embodiment of the invention, the oral tissue cells of the tissue sample are provided with an exogenous gene that expresses an exogenous factor in the cells prior to application of said tissue sample to said animal. In various aspects of the invention, the exogenous gene is provided to the cells prior to the culture of the cells on the matrix, towards the beginning of the in vitro matrix culture process, or towards the end of the in vitro matrix culture process.

In one aspect of the invention, the exogenous gene expresses an exogenous factor that stimulates the growth or proliferation of the oral tissue cells of the tissue sample when applied to the animal. In another aspect of the invention, the exogenous gene expresses an angiogenic factor that stimulates the growth or proliferation of blood vessels in or around the oral tissue cells of the tissue sample following application to the animal. In a further aspect of the invention, the exogenous gene expresses a factor that inhibits apoptosis in the oral tissue cells of the tissue sample following application to the animal.

In yet further aspects, the exogenous gene expresses an exogenous therapeutic factor, such as an antibiotic, a growth factor, a hormone, a cytokine, a blood clotting factor or insulin, that is released by the cells of the tissue following application to the animal.

In certain exemplary embodiments, the present invention provides methods and compositions for filling root canals. One such method generally comprises obtaining dental pulp tissue comprising at least some viable dental pulp cells from an animal, either from the tooth to be treated, from a distinct, healthy tooth, or from gingival submucosal fibroblasts; culturing the cells of the tissue on a matrix ex vivo, generally using antimicrobials, and under conditions effective and for a period of time sufficient to allow the regeneration of dental pulp tissue in connection with the matrix; and implanting the regenerated dental pulp tissue into the tissue space of the root canal.

In a particular embodiment of the invention, the starting oral tissue sample is enriched in dental pulp-derived fibroblasts. In certain aspects of the invention, the starting oral tissue sample is obtained from the dental pulp tissue of an extracted tooth. In alternative aspects, the starting oral tissue sample is obtained from a dental pulp tissue sample obtained from a tooth that remains in an animal. In other aspects, the dental pulp tissue sample is obtained from a healthy molar or wisdom tooth of said animal distinct from the target tooth. In yet other embodiments, the dental pulp tissue sample is obtained from the target tooth to be treated. In particular aspects, the starting oral tissue sample is enriched in gingival submucosal fibroblasts.

The regenerated dental pulp tissue may be separated distinct from the matrix prior to application into the tissue space of the root canal or it may be applied to the tissue space of the root canal in combination with the matrix, wherein the matrix is a substantially biocompatible matrix.

Such methods may also be defined as those which generally comprise the steps of a) removing dental pulp tissue, such as infected dental pulp tissue, from the root of a diseased or damaged tooth of an animal to create a root chamber;

b) obtaining a tissue sample comprising at least some viable cells capable of regenerating into dental pulp cells, e.g., a dental pulp sample from a tooth of the animal, or a sample containing gingival submucosal fibroblasts, and culturing the tissue sample on a biocompatible matrix ex vivo, optionally in the presence of an exogenous factor that stimulates the growth or proliferation of the tissue in the matrix, and under conditions effective and for a period of time sufficient to allow the formation of a matrix-tissue preparation containing regenerated dental pulp tissue; and c) implanting isolated regenerated dental pulp tissue, or a combined matrix-regenerated dental pulp tissue preparation, into the root chamber created in step (a).

The tissue sample comprising at least some viable cells capable of regenerating into dental pulp cells obtained in step (b), above, may be dental pulp tissue obtained from the tooth in step (a), which tissue comprises at least some viable dental pulp cells. In a first alternative, the tissue sample comprising at least some viable cells capable of regenerating into dental pulp cells may be obtained from a distinct, healthy tooth, such as a molar or wisdom tooth of the animal, which may tooth may be extracted for the purposes of obtaining the necessary sample. In a further alternative, the tissue sample obtained in step (b) may be obtained from a gingival sample comprising gingival submucosal fibroblasts.

In certain exemplary embodiments, the methods for filling a root canal may be defined as those which comprise the steps of a) removing dental pulp tissue, such as infected dental pulp tissue, from the root of a diseased or damaged tooth of an animal to create a cleansed root chamber;

b) placing a temporary implant in said root chamber;

c) obtaining viable tissue comprising at least some cells capable of regenerating into dental pulp tissue, i.e., "viable dental pulp-regenerative tissue", such as a dental pulp tissue sample from a tooth of the animal, e.g., a healthy molar or wisdom tooth of the animal, or a gingival sample comprising gingival submucosal fibroblasts;

d) culturing viable fibroblast cells from the tissue of step (c) in vitro, generally using an effective amount of at least one antimicrobial;

e) implanting the cultured cells from step (d) on a biocompatible matrix to form a matrix-cell preparation;

f) maintaining the matrix-cell preparation of step (e) under conditions effective and for a period of time sufficient to allow the formation of matrix-tissue preparation containing regenerated dental pulp tissue;

g) admixing the matrix-tissue preparation of step (f) with an exogenous factor that stimulates the growth of proliferation of oral tissue to create a matrix-tissue factor admixture;

h) removing the temporary implant of step (b) from the root chamber of step (a); and i) implanting the matrix-tissue factor admixture of step (g) into the root chamber re-created in step (h).

The invention further provides a method for delivering a selected factor to an animal, comprising culturing viable oral tissue cells on a matrix in vitro under conditions effective and for a period of time sufficient to allow formation of a tissue sample that comprises viable oral tissue cells and delivering said tissue sample to an oral tissue site of an animal in the presence of a selected factor. The method may be characterized as comprising the steps of culturing viable oral tissue cells on a matrix in vitro under conditions effective and for a period of time sufficient to allow formation of a tissue sample that comprises viable oral tissue cells, admixing the oral tissue cells with the selected factor, and applying the admixture of oral tissue cells and the selected factor to the oral tissue site of the animal.

In another aspect of the invention, the selected factor is produced by a cell and the cell is delivered to the oral tissue site in the presence of the tissue sample. The method may be characterized as comprising the steps of culturing viable oral tissue cells on a matrix in vitro under conditions effective and for a period of time sufficient to allow formation of a tissue sample that comprises viable oral tissue cells, admixing the oral tissue cells with a second population of cells that produces the selected factor, and applying the admixture of oral tissue cells and the second population of cells that produce the selected factor to the oral tissue site of the animal.

In a further embodiment of the invention, the selected factor is produced by a recombinant cell engineered to produce the factor and the recombinant cell is delivered to the oral tissue site in the presence of said tissue sample. The method may be characterized as comprising the steps of culturing viable oral tissue cells on a matrix in vitro under conditions effective and for a period of time sufficient to allow formation of a tissue sample that comprises viable oral tissue cells, obtaining a recombinant cell engineered to produce the factor, admixing the oral tissue cells and the recombinant cell engineered to produce the factor, and delivering the admixture of oral tissue cells and the recombinant cell engineered to produce the factor to the oral tissue site of the animal.

In yet other embodiments, the selected factor is produced by an oral tissue cell of the delivered tissue sample, the oral tissue cell being provided with an exogenous gene that expresses said selected factor. The method may be characterized as comprising the steps of culturing viable oral tissue cells on a matrix in vitro under conditions effective and for a period of time sufficient to allow formation of a tissue sample that comprises viable oral tissue cells, providing an exogenous gene encoding the selected factor to the oral tissue cells, and administering the oral tissue cells provided with the exogenous gene encoding the selected factor to the oral tissue site of the animal. In a particular aspect of the invention, the exogenous gene is provided to the oral tissue cells prior to culturing on the matrix.

In a particular aspect of the invention the selected factor stimulates the growth or proliferation of the oral tissue cells of the tissue sample delivered to said animal. In another aspect of the invention, the selected factor stimulates the growth or proliferation of blood vessels in or around the oral tissue cells of the tissue sample delivered to the animal. In a further aspect of the invention, the selected factor provides an oral therapeutic benefit upon delivery to an oral tissue site of an animal. In still other aspects of the invention, the selected factor provides a systemic therapeutic benefit upon delivery to an oral tissue site of an animal and subsequent uptake into the systemic circulation of the animal. In a particular aspect of the invention, the selected factor is subsequently removed from the animal by removing the delivered tissue sample from the oral tissue site of the animal.

The invention also provides various compositions which may be used in the context of tissue regeneration in vivo and also in a number of in vitro screening embodiments. A first composition in accordance with the present invention is a population of cultured oral tissue cells, substantially free from microbial cells, which oral tissue cells are prepared by a process generally comprising growing a composition comprising at least some viable oral tissue cells on a matrix in vitro under conditions effective and for a period of time sufficient to allow proliferation of viable oral tissue cells.

Further populations of cells in accordance with this invention are those substantially microbe-free populations of cells prepared by processes comprising growing compositions comprising at least some viable oral tissue cells on a matrix in vitro in the presence of at least one exogenous factor that stimulates the growth or proliferation of the cells and under conditions effective and for a period of time sufficient to allow proliferation of viable oral tissue cells.

In further embodiments, the invention provides various regenerated, substantially microbe-free, oral tissue samples including dental pulp, dentin, periodontium, gingival submucosa, oral submucosa and tongue tissue samples. The oral tissue samples of the invention are generally characterized as being regenerated and having a structure, generally a three-dimensional structure, that corresponds to the natural tissue. The oral tissue samples may be further characterized as those prepared by a process comprising culturing a composition comprising at least some viable oral tissue cells on a matrix in vitro under conditions effective and for a period of time sufficient to allow formation of an oral tissue sample.

The regenerated dental pulp, dentin, periodontium, gingival submucosa, oral submucosa or tongue tissues of the invention may be further defined as those regenerated oral tissue samples prepared by a process that comprises culturing a composition comprising viable oral tissue cells on a matrix in vitro to form a cultured matrix-cell preparation and maintaining the matrix-cell preparation in the presence of at least one exogenous factor, which may be a purified factor, or a factor produced by a natural cell, or a recombinant cell, wherein the factor stimulates the growth or proliferation of the cells and under conditions effective and for a period of time sufficient to allow the formation of a regenerated oral tissue sample.

In still further embodiments, this invention provides matrices that are associated with or that contain, i.e., "house", a cultured or regenerated oral tissue sample. In certain embodiments, the matrix will be a biocompatible matrix, allowing administration of the tissue-containing matrix to an oral tissue site of an animal. It may also be a slowly biodegradable matrix.

The methods and matrix-tissue preparations of the present invention are advantageous in that they allow the generation of a three dimensional oral tissue sample, rather than a two dimensional layer of cultured cells. Accordingly, the invention provides three dimensional matrices, including biocompatible matrices, that are associated with or that house cultured or regenerated oral tissue samples prepared by a process which generally comprises obtaining a composition including at least some viable oral tissue cells and culturing the cells on a biocompatible matrix in vitro under conditions effective and for a period of time sufficient to allow proliferation and organization of the cells to form an oral tissue sample associated with or housed within the matrix.

In certain embodiments, the matrix-tissue preparations of the invention are those that are associated with or house a regenerated oral tissue sample prepared by a process comprising obtaining a viable oral tissue cell composition and culturing the cells on a matrix in vitro to form a cultured matrix-cell preparation and maintaining the matrix-cell preparation in the presence of an exogenous factor that stimulates the growth or proliferation of the cells and under conditions effective and for a period of time sufficient to allow proliferation and organization of the cells to form an oral tissue sample within the matrix.

In currently preferred embodiments, the present invention provides polylactic acid (PLA) polymer, polyglycolic acid (PGA) polymer or polylactic-polyglycolic acid (PLGA) co-polymer matrices in combination with a regenerated dental pulp tissue sample. Further, currently preferred compositions are those comprising PLA, PGA or PLGA fiber or sponge matrices associated with, or housing, a regenerated dental pulp tissue sample, prepared by a process comprising culturing viable fibroblasts from a dental pulp or gingival submucosal sample on a PLA, PGA or PLGA matrix in vitro under conditions effective and for a period of time sufficient to allow proliferation and organization of the fibroblasts to form a dental pulp tissue sample associated with the matrix.

The invention further provides a method for testing the suitability of a candidate substance for use in the oral cavity, comprising applying said candidate substance to a regenerated, three-dimensional oral tissue sample and analyzing the effect of said substance on the viability of said tissue sample. The three-dimensional liver cultures may be used in vitro to screen a wide variety of compounds, such as cytotoxic compounds, growth/regulatory factors, pharmaceutical agents, etc. To this end, the cultures are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the three-dimensional system may be assessed.

The three-dimensional oral tissue culture system of the invention can be used in a variety of applications. These include but are not limited to transplantation or implantation of the cultured cells in vivo; screening cytotoxic compounds, carcinogens, mutagens growth/regulatory factors, pharmaceutical compounds, etc., in vitro; elucidating the mechanism of certain diseases; studying the mechanism by which drugs and/or growth factors operate; diagnosing and monitoring cancer in a patient; gene therapy; and the production of biologically active products, to name but a few. For transplantation or implantation in vivo, either the oral tissues from the culture or the entire three-dimensional culture could be implanted, depending upon the need. Three-dimensional-tissue culture implants may, according to the invention, be used to replace or augment existing tissue, to introduce new or altered tissue, or to join together biological tissues or structures.

In yet another application, the three-dimensional culture system may be used as a "bioreactor" to produce cellular products in large quantities, including products of exogenous genes transferred into the cultured cells. For example, a cell which naturally produces large quantities of a particular biological product (e.g., a growth factor, regulatory factor, peptide hormone, antibody, etc.), or a host cell genetically engineered to produce a foreign gene product, could be clonally expanded using the three-dimensional culture system in vitro. If the transformed cell excretes the gene product into the nutrient medium, the product may be readily isolated from the spent or conditioned medium using standard separation techniques well known to those of skill in the art. A "bioreactor" could be devised which would take advantage of the continuous flow method for feeding the three-dimensional cultures in vitro. Essentially, as fresh media is passed through the three-dimensional culture, the gene product will be washed out of the culture along with the cells released from the culture. The gene product could be isolated (e.g., by HPLC column chromatography, electrophoresis, etc.) from the outflow of spent or conditioned media.

Other uses are not excluded, such as aiding in the diagnosis and treatment of malignancies and diseases. For example, a biopsy of oral tissue may be taken from a patient suspected of having a malignancy. If the biopsy cells are cultured in the three-dimensional system of the invention, malignant cells will be clonally expanded during proliferation of the culture. This will increase the chances of detecting a malignancy and, therefore, increase the accuracy of the diagnosis. Moreover, the patient's culture could be used in vitro to screen cytotoxic and/or pharmaceutical compounds in order to identify those that are most efficacious; i.e., those that kill the malignant or diseased cells, yet spare the normal cells. These agents could then be used to therapeutically treat the patient.

In still further embodiments, the present invention provides oral or dental kits comprising regenerated tissues, or matrix-tissue preparations, in accordance with the present invention. The kits may generally be defined as those comprising, in suitable container means, a regenerated oral tissue sample, or a three dimensional matrix associated with or housing a regenerated oral tissue sample. The kits of the invention include both therapeutic kits and test or assay kits. The therapeutic kits provide tissues and biocompatible matrix-tissue preparations for administration to an animal or human subject. The test kits are generally intended for use in conducting in vitro assays to determine whether a candidate substance is suitable for use in the oral cavity.

In yet still further embodiments, the invention thus provides methods for testing the suitability of a candidate substance for use in the oral cavity, comprising applying a candidate substance to an isolated regenerated oral tissue or to a three dimensional matrix associated with a regenerated oral tissue sample and analyzing the effect of the substance on the viability of the tissue sample. It will be readily understood that a candidate substance that adversely affects the tissue sample will not be suitable for use in the mouth. These methods of the invention may thus be defined as methods for testing the oral toxicity or biocompatibility of a compound.

In an exemplary embodiment, the invention further provides a dental test kit comprising, in suitable container means, a PLA, PGA or PLGA matrix in combination with a regenerated three dimensional dental pulp tissue sample. Such a kit would be useful in methods for testing the suitability of a candidate substance or compound for use in dental practices such as tooth filling or root canal procedures.

Thus, the cultured oral tissue cells or regenerated tissue sample of the invention may be used in the preparation of a medicament for use in reconstructing an oral tissue or for replacing lost or damaged oral tissue of an animal. In one aspect of the invention, the medicament is intended for use in reconstructing an oral tissue or for replacing lost or damaged oral tissue of an animal at a site compatible with, but distinct from, the oral tissue site from which the original starting cells were obtained. In a further aspect of the invention, the medicament is intended for use in reconstructing an oral tissue or for replacing lost or damaged oral tissue of an animal at the same site from which the starting cells were obtained.

In a particular embodiment of the invention, the cultured oral tissue cells or regenerated tissue sample of the medicament are separated from the matrix prior to application to an animal. In a further embodiment of the invention, the cultured oral tissue cells or regenerated tissue sample of the medicament are applied to the animal in combination with the matrix.

In another embodiment of the invention, the cultured oral tissue cells or regenerated tissue sample of the medicament are applied to the oral tissue site to be reconstructed or replaced in the presence of an exogenous factor that stimulates the growth or proliferation of the cells or tissue in the animal. In a particular aspect of the invention, the exogenous factor is produced by a cell that is also applied to the oral tissue site of the animal. The exogenous factor-producing cell may be a recombinant cell engineered to produce said factor, or a cultured oral tissue cell of the cultured cells or regenerated tissue of the medicament, the cell being provided with an exogenous gene that expresses said exogenous factor.

In another embodiment of the invention, the oral tissue cells of the cultured cells or regenerated tissue of the medicament are provided with an exogenous gene that expresses an exogenous factor in said cells prior to application of the medicament to said animal. In one aspect, the oral tissue cells of the cultured cells or regenerated tissue of the medicament are provided with said exogenous gene by providing said exogenous gene to the viable starting cells before culturing the cells on the matrix, towards the beginning of the in vitro matrix culture process, or towards the end of the in vitro matrix culture process.

In certain aspects of the invention, the exogenous gene expresses an exogenous factor that stimulates the growth or proliferation of the oral tissue cells of the tissue sample when the medicament is applied to the animal. In other aspects, the exogenous gene expresses an angiogenic factor that stimulates the growth or proliferation of blood vessels in or around the oral tissue cells of the tissue sample when the medicament is applied to the animal. In yet other embodiments of the invention, the exogenous gene expresses an exogenous therapeutic factor that is released by the cells of the tissue following application of the medicament to the animal.

In a further embodiment of the invention, the medicament is intended for use in filling a root canal. In an additional embodiment, the medicament is intended for use in filling the root canal of an existing tooth using cultured oral tissue cells or a regenerated tissue sample derived from an extracted tooth. In a further embodiment of the invention, the medicament is intended for use in filling the root canal of an existing tooth using cultured oral tissue cells or a regenerated tissue sample derived from a distinct, healthy molar or wisdom tooth. In yet another embodiment of the invention, the medicament is intended for use in filling the root canal of an existing tooth using cultured oral tissue cells or a regenerated tissue sample derived from the same tooth.

The cultured oral tissue cells or regenerated tissue sample of the present invention may be used in combination with a selected factor in the preparation of a medicament for use in delivering a selected factor to an animal by administering the medicament to an oral tissue site of an animal. In one aspect of the invention, the selected factor is produced by a cell and said cell is included within said medicament. In another aspect of the invention, the selected factor is produced by a recombinant cell engineered to produce said factor and said recombinant cell is included within said medicament.

Alternatively, the selected factor may be produced by an oral tissue cell of the cultured cells or regenerated tissue of the medicament, said oral tissue cell being provided with an exogenous gene that expresses said selected factor. In certain aspects, the selected factor is an orally therapeutic factor that provides therapeutic benefit upon administration of the medicament to an oral tissue site of an animal. In a particular aspect of the invention, the selected factor is a systemically active therapeutic factor that provides systemic therapeutic benefit upon administration of the medicament to an oral tissue site of an animal and subsequent uptake into the systemic circulation of the animal. In a further aspect of the invention, the selected factor is subsequently removed from said animal by removing the medicament from the oral tissue site of the animal.

In an additional aspect of the invention, the cultured oral tissue cells or regenerated tissue sample is used in the preparation of a test kit for testing the suitability of a candidate substance for use in the oral cavity.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 10A. Biological activity of EGF released from microspheres and control EGF. Quantitation of the number of cells with labeled nuclei following $^3$H-thymidine autoradiography, and thus in S phase of the cell cycle. Cells were cultured in medium containing various concentrations of EGF which had not been incorporated into microspheres (Soluble EGF), or in medium containing 10 ng/ml of EGF released from microspheres (Microspheres). FIG. 10B. The change in the number of cells present in culture dishes from day 1 to day 4 in medium containing various concentrations of EGF which was not incorporated into microspheres (Soluble EGF), or in medium containing 10 ng/ml of EGF released from microspheres (Microspheres). Values represent the mean and standard error of the mean calculated from the results of 3 studies which were all done in quadruplicate. The change in cell number was calculated relative to the cell number at day 1.

FIG. 11A. Growth of fibroblasts over time on PGA constructs. FIG. 11B. Growth of fibroblasts over time within a collagen gel. Values represent the mean and standard deviation calculated from 3–4 samples at each time point.

DESCRIPTION OF ILLUSTRATIVE EMBODIMENTS

Figure 1:
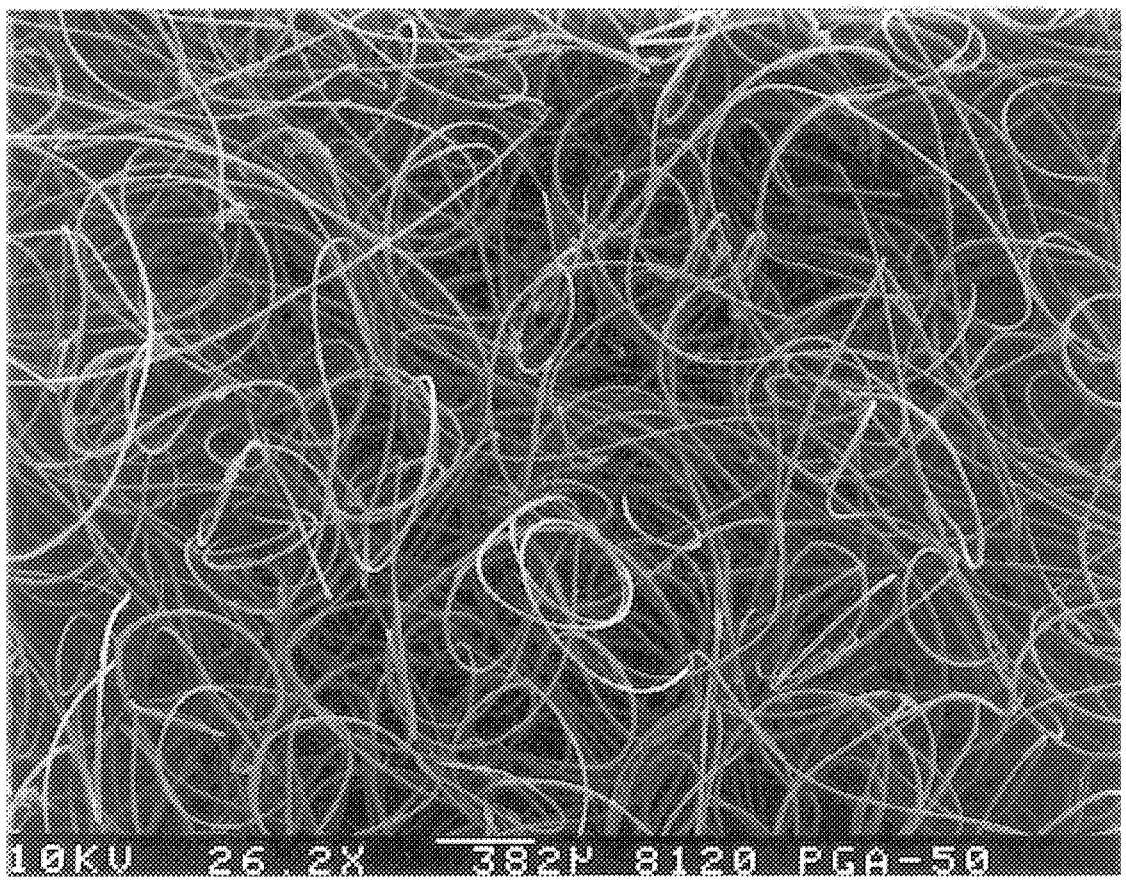
FIG. 1. Photomicrograph of polyglycolic acid fiber-based mesh utilized as synthetic extracellular matrix. A size bar is shown on the photomicrograph.

In many situations, damage to oral tissues cannot be effectively repaired. This leads to alternations in the form and function of these tissues. Such alterations may give rise to deformities of the face, jaws and teeth which may be disfiguring as well as disabling. Loss of teeth leads to collapse of the dental arch and malpositioning of remaining teeth. Malpositioning may increase susceptibility to diseases such as caries, gingivitis, and periodontitis which in turn can lead to additional tooth loss. Tooth loss leads to diminished mastication, and eventually to a diminution in the size of the jaw bones rendering prosthetic reconstruction more difficult. It will be understood that oral tissue damage is painful to the individual and costly to society.

Injury or infection of adult dental pulp often necessitates root canal therapy. This terminates dentin formation and subsequent tooth maturation. Unfortunately, the synthetic materials currently utilized to replace lost tooth structure are not capable of completely replacing the function of the lost tissue, and often fail over time. The engineering of dental pulp and other oral tissues from cultured cells would thus represent a marked step forward in dentistry and oral medicine.

If effective oral tissue engineering techniques could be developed they would provide an effective alternative to many of the present inadequate treatment strategies. These include many dental procedures, areas related to periodontal disease and, also, more substantial procedures, such as the repair of resectioned tissue, for example upon removal of cancerous growths and tumors.

This invention provides the necessary methods for use in creating new oral tissues, such as dental pulp, using a tissue engineering approach. In the tissue-engineering of the invention, the cells of interest are isolated from a tissue, multiplied in culture, and subsequently induced to form a new three-dimensional tissue. The invention particularly concerns the use of synthetic extracellular matrices in the culture and engineering of new oral tissues.

Current cell culture techniques, such as those used in the regeneration of skin and/or oral mucosa, are not suitable for use in connection with the oral tissues embodied in this invention since the existing techniques produce epithelia which require an appropriate connective tissue bed in vivo for successful grafting. The techniques described herein produce tissues ex vivo which will repair and regenerate specific oral connective tissues in vivo.

While not desiring to be tied to any particular mechanism by which the invention works, a number of factors inherent in the three-dimensional culture system may contribute to its success. Firstly, the three-dimensional framework provides a greater surface area for protein deposition, and consequently, for the adherence of cells. Secondly, because of the three-dimensionality of the framework, cells continue to actively grow, in contrast to cells in monolayer cultures, which grow to confluence, exhibit contact inhibition, and cease to grow and divide. The elaboration of growth and regulatory factors by replicating cells may be partially responsible for stimulating proliferation and regulating differentiation of cells in culture. Thirdly, the three-dimensional framework allows for a spatial distribution of cellular elements which is more analogous to that found in the counterpart tissue in vivo. Fourthly, the increase in potential volume for cell growth in the three-dimensional system may allow the establishment of localized microenvironments conducive to cellular maturation. Fifthly, the three-dimensional framework maximizes cell-cell interactions by allowing greater potential for movement of migratory cells, and for the establishment of communications between the various types of cells in the adherent layer. Lastly, it has been recognized that maintenance of a differentiated cellular phenotype requires not only growth/differentiation factors but also the appropriate cellular interactions. The present invention effectively recreates the tissue microenvironment.

Various issues are addressed in the oral tissue engineering of the present invention. First, the appropriate cell types are described; cells can be isolated from a variety of different tissue sources, and expanded in culture. Second, suitable matrices are described, for use in growing tissue ex vivo for later separation and use, and/or for use in transplanting the matrix and tissue into the body to stimulate further cells to grow into the matrix from the surrounding tissue. Third, methods for using the tissues and matrix materials in an integrated manner are described in order to create a tissue replacement with the appropriate structure and function. Screening assays are also described.

A. Cells and Tissues

In the present invention, viable cells are obtained from a specific oral tissue and are cultured in vitro. In general, in tissue engineering with other tissues, a first question is often whether to transplant cells to a desired site, or to provide an environment inductive or conductive to the formation of the desired tissue from cells already present in the host tissue. The present invention provides methods that are suitable for achieving both goals—as it provides tissue transplantation itself and, if desired, a matrix structure to induce further tissue formation.

1. Sources of Cells

In certain embodiments of the present invention, the cells for use in tissue regeneration and transplantation will be obtained from an oral tissue site of the animal or patient to be treated. These are "autologous cells" that give rise to "autologous tissues". However, the use of cells from another animal of the same species (or person) is certainly not excluded. These would be "allogeneic cells and tissues". Further, cells from tissues of other animals, "xenogeneic cells and tissues" could also be used.

The use of autologous cells eliminates concern over cell rejection, avoids the issue of immunosuppressants, and is attractive in a variety of scenarios. Although two procedures on the animal or patient are required, this does not cause a particular disadvantage in dentistry and oral medicine as the tissue sites are easily accessible. The time required to expand the cells into a tissue sample, which creates a time-lapse before treatment can be completed, is also not of any particular concern in dentistry and oral medicine as any acute disease or injury requiring immediate therapy can likely be treated with a temporary measure in the intervening time period.

As allogeneic tissue is widely used in humans in whole organ transplantation, it is also a viable source for cells for use in the present invention. The tissue could be immediately available for use in large quantities in a variety of procedures. Immunosuppressive drugs are available if required to prevent tissue rejection. The use of xenogeneic cells is not excluded from the scope of this invention, although the present invention is advantageous in that it is particularly suitable for use with autologous cells.

2. Oral Tissues

Each tooth consists of a crown and either single or multiple roots. By definition, the anatomical crown is covered by the highly calcified layer of enamel. The remainder of the crown is composed of another calcified tissue, the dentin, which contains a central chamber filled with the living tissue of the tooth, the pulp. The dentin and pulp also constitute the tissues of the root. However, the outer surface of the root is covered by yet another calcified tissue termed cementum. The enamel and cementum meet around the neck, or cervical margin, of the tooth and form the cemento-enamel junction. This junction is not normally seen on the portion of the tooth exposed to the oral cavity because the epithelial tissue covering the alveolar process, the gingiva, extends for a short distance onto the crown.

The dental pulp consists of loose connective tissue derived from ectomesenchymal cells and is confined within the pulp chamber and root canals of the tooth. The pulp contains cells that provide odontogenic, nutritive, sensory, and defensive functions to the mature pulp and allows for preservation of vitality during normal homeostatic maintenance and during wound repair after injury.

The mature dental pulp can be divided into two compartments: The odontogenic zone and the pulp proper. The odontogenic zone includes the odontoblasts, which are the cells responsible for the production of predentin and dentin, the cell-free zone, the cell-rich zone, and the parietal plexus of nerves. The pulp proper includes the majority of the remaining area of the pulp and consists primarily of fibroblasts and extracellular matrix, blood vessels, and nerves. As the pulp ages, the volume decreases with a corresponding increase in dentin thickness. Numerous studies have demonstrated that the dental pulp has an inherent capacity to respond to wounding in the absence of other inflammatory insults.

The most predominant cell type in the dental pulp is the fibroblast, but the pulp also contains odontoblasts, blood cells, Schwann cells, endothelial cells, and undifferentiated mesenchymal cells. Cells involved in the immune response, such as macrophages, mast cells, antigen processing cells (dendritic cells), and plasma cells can also be found in the pulp during periods of inflammation.

Odontoblasts are terminally differentiated, polarized pulpal cells derived from the cranial neural crest, which are found in a peripheral layer closely associated with the predentin. The major function of odontoblasts is the synthesis and secretion of the fibers and extracellular matrix (ECM) of the predentin and biomineralization of the dentin.

The cell bodies form an irregularly columnar, epithelial-like layer on the inner aspect of the dentin. The proximal surface of the cell body is adjacent to pulp cells, and the distal extremity is tapered and embedded in predentin, an unmineralized layer of dentin-like material.

The major protein produced by the odontoblast is type I collagen and is secreted into the extracellular space at the predentin interface. Non-collagenous components of the extracellular matrix of predentin and dentin, including proteoglycans, glycosaminoglycans, phosphoproteins, and γ-carboxyglutamate-containing proteins, are also synthesized and secreted by odontoblasts.

The functioning odontoblasts continue to produce predentin throughout the life of the tooth. Odontoblasts retain the ability to upregulate protein synthetic activity in response to trauma after aging.

The remainder of the pulp consists of a "stromal" tissue containing nerves, blood vessels, and lymphatics. The stromal tissue is composed of cells and extracellular material. There appears to be only one type of cell, resembling mesenchyme but capable of producing extracellular material, including collagen. Thus, the cell can equally be termed a fibroblast, or simply a pulpal cell.

Fibroblasts are the most numerous cells found in the dental pulp. They are stellate-shaped cells with long cytoplasmic extensions that contact adjacent fibroblasts or odontoblasts through gap-junctional processes. Fibroblasts synthesize and secrete type I and type III collagen, and other ECM components of the pulp, including proteoglycans and glycosaminoglycans.

Collagen is the most abundant connective tissue protein and occurs in several specific isotopes, types I through XII. Each is recognized as a specific genetic product differing in amino acid and polypeptide composition. In the pulp, type I and type III are the most abundant, with other types, such as IV and V, as minor constituents.

Fibroblasts or undifferentiated mesenchymal cells also have an important role in wound healing mechanisms in the pulp. The fibroblasts of the cell-rich zone are thought to differentiate into odontoblasts after the right stimulus—for example, growth factor, a bone morphogenic protein (BMP), cytokine, or inflammatory mediator, released during wounding from the exposed predentin or dentin, or inflammatory cells that have migrated to the wound site.

There are many other cells found in a vital dental pulp. Perivascular cells are found in the dental pulp closely associated with the vasculature. These cells have been reported to be important in wound-healing mechanisms associated with pulpal repair mechanisms. Perivascular cells have also been shown to proliferate in response to an iatrogenic exposure of the dental pulp, and are thought to possibly provide replacement cells for the odontoblast layer in wounds where the cell-rich layer has been destroyed.

Endothelial cells line the lumen of the pulpal blood vessels and contribute to the basal lamina by producing type IV collagen, an afibrillar collagen. They have been shown to proliferate after a pulp exposure in an attempt to neovascularize the wounded area during the process of wound healing.

Class II antigen processing cells have been demonstrated by immunohistochemical methods in both the normal and inflamed pulp. Other vascular-derived cells found in the pulp during an inflammatory condition include mast cells, B- and T-lymphocytes, polymorphonuclear neutrophils, and macrophages. These blood cells are of paramount importance in fighting infection in the pulp because of the substances they contain: histamine, serotonin, cytokines, growth factors, and other cellular mediators. Schwann cells can also be found, which cells envelope nerve processes with a myelin sheath.

Dentin forms the bulk of the tooth. It is lined on its outer aspect by enamel on the crown and by cementum on the root.

The youngest layer of dentin formed at any particular time is adjacent to the junction between the odontoblast cell body and its major process. This layer of young dentin is essentially unmineralized, and ends abruptly in contact with the mature dentin. The predentin is an irregular meshwork of collagenous fibrils that tend to be thin closer to the cell body and somewhat larger in diameter near the mature dentin.

Mature dentin is associated with glycoproteins, an increased diameter of the collagenous fibrils, and a sudden and dramatic mineralization related to these fibrils. The layer of mature dentin is very thick in functional teeth.

The outer surface of the root is covered by a relatively thin layer of a bone-like mineralized tissue called cementum. Cementum consists of a matrix of calcified collagenous fibrile, glycoproteins, and mucopolysaccharides. The outermost layer of cementum is an uncalcified precementum produced by the discontinuous layer of irregularly shaped cementoblasts.

The firm epithelium from the mucogingival junction (line) to the teeth is the gingiva. It extends around each tooth, and meets the regular oral mucosa at a less well-defined inner mucogingival junction.

Gingiva is a stratified squamous epithelium with deep papillary projections from the underlying lamina propria. The latter contains a rich capillary network that is consequently brought relatively close to the surface. The epithelium is firmly attached to the lamina propria by hemidesmosomes related to the basal lamina and collagenous anchoring fibrils that originate from the hemidesmosomes and form loops in the lamina propria. Collagenous fibrils from the lamina propria itself pass through these loops, thus contributing to the firm attachment between the two tissues. The basal layer of the epithelium is cuboidal and shows numerous mitotic figures, which provide for the renewal of this epithelium. Toward the surface of the epithelium, the cells flatten to form a compact layer in which the cells are partially filled with keratin but the nucleus and some organelles survive. Thus, the dozen or so cell layers at the surface are keratinized but not dead.

This epithelium differs from that of the skin, where the resulting layer of dead, cornified cells forms the dry surface of the skin. The gingival generative process, which is called parakeratosis, is thus different to the orthokeratosis of the skin. Gingiva is a strong resilient epithelium that turns over rapidly enough to withstand and heal the trauma and abrasion caused by chewing.

The lamina propria of the gingiva is firmly attached to the periosteum of the alveolar bone except as it approaches to within 1 or 2 mm of the crown surface. This narrow band of gingiva surrounding each tooth is called the "free gingiva" as opposed to the rest of the gingiva, which is "attached" to the alveolar bone.

Hemidesmosomes are responsible for the attachment of the gingiva as a continuous cuff around the tooth. This attached cuff fulfills the essential function of sealing off the access route from the mouth to the periodontal tissues. Breakdown of this seal results in gingival infections (gingivitis) and invasion by microorganisms, leading to periodontal disease.

By understanding oral tissue anatomy, as outlined above, and in light of the present disclosure, one of ordinary skill in the art will readily be able to select an appropriate tissue source for use in the tissue regeneration methods disclosed herein.

3. Viable Cells

The methods of the present invention generally require the isolation of compositions comprising viable cells from oral tissues. In this context, the term "viable cells" means that the cells are capable of proliferating and, preferably, regenerating to form an oral tissue when subjected to the methods described herein. The choice of appropriate viable cells will be readily determinable to one of skill in the art. For example, when the intention is to culture and regenerate dental pulp tissue, one will obtain a composition comprising viable cells that are capable of producing such dental pulp tissue or gingival submucosal fibroblasts. This is exemplified in the present invention by obtaining a tissue sample that comprises dental pulp-derived fibroblasts. However, this is just one exemplary embodiment of the present invention.

It will be understood by those of skill in the art that the tissue regeneration methods of this invention are widely applicable to the culture of several oral tissues. One may mention, by way of example only, dentin, periodontium, gingival submucosa, oral submucosa and tongue tissues. Naturally, one would choose a starting composition from an appropriate location in order to ensure that the composition contains cells capable of regenerating into the desired tissue structure.

The source of dental pulp for use in tissue regeneration may be from a damaged tooth that still contains certain viable cells or from another, healthy tooth, distinct from the tooth that requires the restorative procedure. The odontoblasts of the dental pulp are also suitable for use in generating dentin.

The source of cells for the regeneration of the periodontium is that portion of the tissues which remains attached to a freshly extracted tooth. These tissue fragments containing viable cells are scraped from the tooth root surface using a sharp instrument such as a curette or scalpel blade.

For the gingiva and oral mucosa, superficial split-thickness biopsies of these tissues are obtained by routine clinical procedures. The tissues are suspended in DMEM, 10% fetal bovine serum, supplemented with agents such as, e.g., penicillin, streptomycin and neomycin, and minced to pieces approximately 1–2 $mm^2$, and placed into tissue culture vessels. This is best done within 24 hours of biopsy. When sufficient numbers of cells have migrated from the cultured tissue pieces (explants) and proliferated, the cultures are harvested diluted into more vessels and/or cryopreserved. Cells may also be obtained by mincing the tissues, and then digesting the pieces with enzymes such as collagenase.

In order to regenerate an oral tissue in accordance with the present invention, one may obtain a composition consisting only of, or predominantly of, healthy, viable cells. Using the regeneration of dental pulp as an example, such a composition could be obtained by isolating dental pulp from a healthy tooth of an animal, such as a healthy molar or wisdom tooth. The viable autologous cells would then be regenerated into a tissue sample that could be reapplied to a diseased or damaged tooth of the same animal.

However, it is important to note that the above technique is not the only embodiment of the present invention. In fact, the invention may be used to regenerate healthy oral tissues, such as dental pulp, by obtaining a less than completely healthy oral tissue and regenerating the viable cells from said tissue by culture on a matrix, as described herein. These aspects of the invention are based, in part, on the fact that cells are routinely cultured from oral tissues which are coated with large numbers of microbes such as yeast and bacteria. Since these microbes proliferate in the cell culture media, antibiotics are routinely added at up to 3 times the normal concentrations of antibiotics and antimycotics.

Another embodiment of the present invention utilizes viable cells isolated from oral or gingival submucosa to regenerate other tissues such as dental pulp, dentin, cementum, periodontal ligament and bone. Such cells propagated in vitro, seeded onto scaffold and developed in vitro, would be constitutively capable, genetically engineered or induced by the addition of specific protein factors to produce the specific tissue of interest when implanted in vivo.

In general terms, following isolation of an oral tissue sample that contains the desired viable cells, the composition would first be cultured in vitro in order to expand the population of viable cells. Although not required as part of the regenerative methods of the invention, this pre-culture step is generally recommended in order to provide a larger population of starting cells.

A wide variety of standard cell culture techniques are available that may be used in this aspect of the invention. Virtually any culture medium and technique may be used, so long as the chosen method results in maintenance, or preferably proliferation, of the viable cells that one wishes to regenerate. Such techniques will be known to the ordinary skilled artisans. Further, the texts of Freshney (1994) and Janda et al., (1991) are fully incorporated herein by reference to even further describe animal cell culture techniques.

Although a full discussion of standard cell culture techniques and media is not believed to be necessary as part of the present disclosure, one may mention, by way of example, the use of higher than usual antibiotics in the cell culture procedures. The use of up to about 2 or 3 times higher than the normal concentrations of antibiotics and antimycotics is believed to be particularly effective. In using a tissue sample from an infected tooth, e.g., during a root canal procedure, increasing the amounts of antimicrobials will generally be preferred.

The use of antimicrobial agents that are readily available and commonly used, such as penicillin, streptomycin, neomycin and erythromycin, is generally preferred, although any one or a combination of antimicrobials may be employed, as desired. The penicillins are known to be effective against certain species of Gram-positive cocci, Gram-negative cocci, Gram-positive bacilli and Gram-negative bacilli.

B. Matrices

After obtaining the cells, culture and tissue regeneration generally involves the use of a structural matrix. The matrix acts as a scaffold for the cells to guide the process of tissue formation. Although the majority of mammalian cell types are anchorage dependent, and will die if not provided an adhesion substrate, the matrices of the present invention are not simply an adhesive substrate. Petri dishes and other non-matrix structures are generally used in cell culture, whereby cell monolayers result, however, this does not lead to tissue regeneration. It will be understood that simple dishes, vials and other receptacles are not "matrices" in the context of the present invention, although it is possible that the materials from which they are formed may be adapted for this purpose by design and/or combination with other matrix elements.

The materials utilized to fabricate a matrix for use in the present invention can generally be categorized into three types: naturally derived materials, including extracellular matrix (ECM) molecules, such as collagens and hyaluronic acid, and polysaccharides, such as alginate; synthetic materials, including any one of a variety of polymers; and relatively new materials that incorporate specific cell recognition signals found in ECM molecules.

1. Naturally-Derived Matrices

Any one of a variety of naturally-derived matrix-like materials may be used to provide a framework for tissue growth in accordance with the present invention. Where the matrix, or substantial portions thereof, will later be reapplied to an oral tissue site in the body, one will generally prefer to use a matrix that is derived from a biological tissue that is compatible with the tissue to which it will be readministered. Such biocompatibility requires that the matrix does not cause any significant adverse or untoward reactions when administered to the animal. By using a biocompatible matrix significant immune responses and inflammatory reactions will be avoided.

A large number of naturally-derived matrix-like materials are available that may be used in tissue regeneration in accordance with this invention, including those matrices fabricated from human, animal or plant tissue. Potential advantages of these types of materials are their biocompatibility and their biological activity. As many of these molecules are found within tissues, they may not induce any foreign body reactions and are presumably receptive to the cell-mediated remodeling that occurs during tissue repair and regeneration (Murphy et al., 1990; Yannas et al., 1989).

The primary, secondary and tertiary structure of a variety of ECM molecules have been defined, as have specific cellular molecules involved in ECM recognition. Cells contain transmembrane receptors that specifically bind defined amino acid sequences present in ECM molecules (Hynes, 1987). The binding of cellular receptors to ECM molecules starts a sequence of events that can alter both cell growth and tissue-specific gene expression (Schwartz and Ingber, 1994). A variety of growth factors are also known to associate with the ECM in tissues. ECM molecules may serve as a repository of these factors for cells adherent to the ECM (Folkman and Klagsbrun, 1987; Reid, 1990; Stoker et al., 1990). One may precisely regulate where transplanted or induced cells adhere to the matrix, and their exposure to specific growth factors by utilizing specific ECM molecules to fabricate a matrix. This may allow the gene expression of cells present in the matrix to be tightly regulated.

Type I collagen, the most prevalent ECM molecule in the body, is readily isolated from animal tissues and has been extensively utilized to fabricate cell delivery devices (Green et al., 1979; Yannas et al., 1981; Bell et al., 1981; Stern et al., 1990; Cavallaro et al., 1994). This material can be processed into a wide variety of structures for use in the present invention, e.g., films, sponges and fibers (Green et al., 1979; Yannas et al., 1981; Bell et al., 1981; Stern et al., 1990; Cavallaro et al., 1994). The structure and resultant mechanical properties of collagen-based scaffolds can be regulated by the process utilized to extract the collagen from tissues (Cavallaro et al., 1994), and by various crosslinking processes. Collagen molecules may be crosslinked physically by dehydrothermal (Koide et al., 1993) or UV radiation treatments, or chemically by using various chemical agents (Cavallaro et al., 1994; Koide et al., 1993; DeLustro et al., 1990). However, the inflammatory response to these materials and their erosion rate are dependent on the specific cross-linking agent that is utilized (Cavallaro et al., 1994; Anselme, 1992; Koide et al., 1993).

Suitable collagen matrices are described, for example, in U.S. Pat. Nos. 4,347,234; 4,390,519; 4,394,370; 4,409,332; 4,538,603; 4,585,797; 4,703,108; 4,837,285; 4,975,527; 5,081,106; 5,128,136; 5,162,430; 5,197,977 and 5,206,028; each incorporated herein by reference. Although not previously proposed for use regenerating oral tissues ex vivo, the biocompatibility of collagen matrices is thus well known in the art. If desired, therefore, a collagen-tissue preparation could also be applied to a tissue site of an animal. Mineralized collagen, as disclosed in U.S. Pat. No. 5,231,169, incorporated herein by reference, may also be used in the present invention.

Type I collagen may also be combined with glycosaminoglycans to form gels which mimic native dermal tissue (Yannas et al., 1981; Stern et al., 1990; Heimbach et al., 1988). A variety of other ECM molecules, including laminin (Dixit, 1994; Guenard et al., 1992), have been utilized as cell delivery matrices, and any such matrix may be used in the context of the present invention.

Polysaccharides may also be used as matrices in accordance with this invention. Alginate, a polysaccharide isolated from seaweed, is used as a cell delivery vehicle. Water soluble sodium alginate readily binds calcium, forming an insoluble calcium alginate hydrocolloid (Sutherland, 1991). These gentle gelling conditions have made alginate a popular material to encapsulate cells for transplantation (Lim and Sun, 1980; O'Shea et al., 1984; Ricordi et al., 1988; Sullivan et al., 1991; Lacy et al., 1991; Levesque et al., 1992; Soon-Shiong et al., 1994; Dixit, 1994; Kasai et al., 1994), and as an injectable cell delivery vehicle (Atala et al., 1994).

The potential advantages of these natural materials have made them popular for fabricating tissue engineering matrices, and they may certainly be used in the context of the present invention. However, these materials also have a number of disadvantages. Many of these materials are isolated from human or animal tissue, and are not available in large quantities. They suffer from large batch-to-batch variations, and are typically expensive. Additionally, these materials exhibit a limited range of physical properties (e.g., mechanical strength, erosion times). These drawbacks led the present inventors to contemplate using synthetic materials to fabricate matrices for use in many aspects of this invention.

2. Synthetic Matrices

In certain aspects, synthetic polymers are attractive scaffold materials as they can be readily produced with a wide range of reproducible properties and structures. Polymer matrices also provide mechanical support against compressive and tensile forces, thus maintaining the shape and integrity of the scaffold in the aggressive environments of the body.

The morphology of the matrix can guide the structure of an engineered tissue (Vacanti et al., 1988), including the size, shape and vascularization of the tissue (Mooney et al., 1994a, 1994b, 1995b, 1996a). The ideal matrix should also elicit specific cellular functions and direct cell-cell interactions. Tissue engineering matrices function as synthetic extracellular matrices, and the proper design of these matrices allows them to exhibit the required range of mechanical and biological functions.

Synthetic polymeric materials can usually be precisely controlled in material properties and quality. Moreover, synthetic polymers can be processed with various techniques and supplied consistently in large quantities. The mechanical and physical properties of synthetic polymers can be readily adjusted through variation of molecular structures so as to fulfill their functions without the use of either fillers or additives. Table 1 outlines different structural factors of polymers that can be used to adjust a variety of critical properties.

TABLE 1

Structural Variables used to Control Biodegradable Polymer Properties

| Variables | Effects | Examples |
| --- | --- | --- |
| Incorporation of both natural and/or non-natural monomers | May reduce/eliminate immunologic response often found in naturally-derived polymers | Non-immunologic PGA and PLA (vs. collagens) |
| Incorporation of labile groups in polymer chain | Control kinetics of biodegradation | Hydrolyzable ester bond in PGA |
| Incorporation of functional groups in side chains | Control chemical and physical properties of polymers | Hydrophilic, hydrophobic and amphiphilic polyphosphazenes |
| Incorporation of chiral centers in polymer chains | Control physical and mechanical properties of polymer | Semi-crystalline L-PLA and amorphous D,L-PLA |
| Possibility of utilizing multiple monomers | Control properties of polymers | Glycolic and lactic acids PLGA |
| Use of natural compounds as monomers | Biocompatible breakdown products | Lactic acid in PLA |
| Use of different polymer architectures | Control physical and mechanical properties of polymers | Branched polymers exhibit lower viscosity than linear ones |

Adapted from Wong and Mooney, 1997.

A variety of synthetic biodegradable polymers can be utilized to fabricate oral tissue engineering matrices. In general, these materials are utilized as structural elements in the scaffold, to deliver the tissue, or to achieve both purposes. Poly(glycolic acid) (PGA), poly(lactic acid) (PLA) and poly(lactic acid)-poly(glycolic acid) (PLGA) polymers are commonly used synthetic polymers in tissue engineering. These polymers are also extensively utilized in other biomedical applications such as drug delivery and are FDA approved for a variety of applications (Huang, 1989).

A number of PGA, PLA and PLGA and other synthetic polymer matrices are known in the art, and are further described herein, any one or more of which may be used in the context of the present invention. By way of example only, one may mention the PGA, PLA and PLGA formulations disclosed in any one of U.S. Pat. Nos. 5,366,734; 5,366,733; 5,366,508; 5,360,610; 5,350,580; 5,324,520; 5,324,519; 5,324,307; 5,320,624; 5,308,623; 5,288,496; 5,281,419; 5,278,202; 5,278,201; 5,271,961; 5,268,178; 5,250,584; 5,227,157; 5,192,741; 5,185,152; 5,171,217; 5,143,730; 5,133,755; 5,108,755; 5,084,051; 5,080,665; 5,077,049; 5,051,272; 5,011,692; 5,007,939; 5,004,602; 4,961,707; 4,938,763; 4,916,193; 4,898,734; 4,898,186; 4,889,119; 4,844,854; 4,839,130; 4,818,542; 4,744,365; 4,741,337; 4,623,588; 4,578,384; 4,568,559; 4,563,489; 4,539,981; 4,530,449; 4,384,975; 4,300,565; 4,279,249; 4,243,775; 4,181,983; 4,166,800; 4,137,921 each incorporated herein by reference.

Where a matrix is to be administered to an oral tissue site, another reason for preferring a synthetic material is that the surface properties of synthetic materials can be easily and reproducibly altered, as necessary. Plasma modification and grafting of relatively inert substances, such as polyethylene oxide or polyvinyl alcohol, can mask the chemistry of the bulk matrix (Peppas and Langer, 1994). The specific structure of adsorbed polymer coatings can be controlled by varying the chemical structure and molecular weight polydispersity of the coating polymer (Dan and Tirrell, 1993). Molecular self-assembly strategies can also be used to define the protein and cellular interactions with material surfaces (Prime and Whitesides, 1991; Singhvi et al., 1994).

3. Biodegradable Matrices

Matrices fabricated from biodegradable materials will erode over time in the body to yield a completely natural tissue. These matrices will not induce any chronic inflammatory responses, and cannot serve as a long-term site for infection. Biodegradable polymers have been utilized to engineer tissues that will be structurally integrated with the host tissue (Langer and Vacanti, 1993; Heimbach et al., 1988; Hansbrough et al., 1992; Mooney et al., 1994a; 1994b; 1995a; 1995b; 1996a; Johnson et al., 1994; Dixit, 1994; Kasai et al., 1994; Mooney and Vacanti, 1993). In addition, the use of synthetic, biodegradable matrices will often be advantageous as the degradation time of such synthetic matrices can be designed to coincide with the formation of a new tissue from the cultured cells.

While there are a variety of biodegradable polymers (Gilding, 1981; Peppas and Langer, 1994), polymers composed of monomers naturally present in the body (e.g., lactic acid, α-amino acids) are preferred for use in certain aspects of the invention. Polymers of lactic acid, glycolic acid, and copolymers of the two have been utilized to fabricate tissue engineering matrices (Heimbach et al., 1988; Hansbrough et al., 1992; Mooney et al., 1994a; 1994b; 1995a; 1995b; 1996a; Johnson et al., 1994; Mooney and Vacanti, 1993). These polymers are readily processed into a variety of configurations, including fibers (Frazza and Schmitt, 1971), porous sponges (Mooney et al., 1995a; Mooney and Vacanti, 1993) and tubular structures (Mooney et al., 1995b).

The regular structure of homopolymers of lactic and glycolic acid results in a crystalline structure (Gilding, 1981). Copolymers containing significant quantities of both monomers are amorphous (Gilding, 1981). This polymer family's widely varying mechanical and erosion properties (Table 2) results both from the varying crystallinity, and the differing hydrophobicity of lactic and glycolic acid (Gilding, 1981). Regenerated oral tissues of this invention can thus be delivered using matrices with a wide range of pre-defined degradation times and mechanical properties, where the matrices are fabricated from this family of polymers (Mooney et al., 1995b).

TABLE 2

Typical Yield Stress Values and Erosion Times for Polymers of Lactic and Glycolic Acid

| POLYMER | YIELD STRESS (Kpsi)* | TIME FOR 50% EROSION† |
|---|---|---|
| polyglycolic acid | 11.2 | 4 weeks |
| 50/50 poly (D,L-lactic-co-glycolic acid) | 7.7 | 6 |
| 85/15 poly (D,L-lactic-co-glycolic acid) | 6.3 | 20 |
| poly (D,L-lactic acid) | 6.6 | 35 |
| poly (L-lactic acid) | 8.5 | >56 |

Adapted from Wong and Mooney, 1997.
*Values represent the mean of 5 measurements obtained using Instron testing with ASTM methods. Data is adapted from Medisorb (Cincinnati, OH) product data.
†The time at which ½ of the polymer has eroded polymer mass = ½ initial mass) following immersion in a buffered saline solution maintained at 37° C.

Those of skill in the art will understand that the PLA, PGA and PLGA polymers are just one example of biodegradable polymer matrices that may be used in this invention. Further biodegradable matrices include polyanhydrides, polyorthoesters, and poly(amino acids) (Peppas and Langer, 1994). Any such matrix may be utilized to fabricate a biodegradable polymer matrix with controlled properties for use in this invention. Further biodegradable polymers that produce non-toxic degradation products are listed in Table 3.

TABLE 3

Main Polymers Recognized as Biodegradable

Synthetic

Polypeptides
Polydepsipeptides
Nylon-2/nylon-6 copolyamides
Aliphatic polyesters Poly(glycolic acid) (PGA) and copolymers
Poly(lactic acid) (PLA) and copolymer
Poly(alkylene succinates)
Poly(hydroxy butyrate) (PHB)
Poly(butylene diglycolate)
Poly(ε-caprolactone) and copolymers
Polydihydropyrans
Polyphosphazenes
Poly(ortho ester)
Poly(cyano acrylates)
Natural Modified polysaccharides
cellulose, starch, chitin
Modified proteins
collagen, fibrin Adapted from Wong and Mooney, 1997.

Although the preferred use of the biodegradable matrices in the present invention is for administration to an oral tissue site in conjunction with an oral tissue sample, the biodegradable matrices may also be used to regenerate an oral tissue sample that is subsequently to be isolated free from the matrix. The tissue sample may then be readministered to an oral tissue site of an animal.

It will of course be understood that biodegradable matrices for use in the invention are not confined to being synthetic matrices. A number of naturally-derived matrix-like materials may be used that will eventually biodegrade in an in vivo environment. Thus, in the context of the present invention, the term biodegradable is not necessarily synonymous with synthetic matrices.

4. Non-Biodegradable Matrices

Although biodegradable matrices will have advantages in certain embodiments, they are by no means required for use in practicing the present invention. Those of skill in the art will understand that there are at least two scenarios in which non-degradable matrices are envisioned for use. First, a non-degradable matrix may be used to regenerate an oral tissue sample that is subsequently to be isolated free from the matrix. The tissue sample may then be readministered to an oral tissue site of an animal. The function of the matrix in this context thus ceases once the tissue has been regenerated and removed from the structural matrix.

In a second embodiment, the regenerated oral tissue sample may remain in contact with the matrix and the matrix-tissue preparation may be administered to the required oral tissue site of an animal. In clinical situations that currently employ the use of a permanent synthetic material implant, the administration of an implant-tissue combination would not, of course, be associated with any disadvantages. However, it will also be appreciated that such non-degradable matrices will need to be biocompatible if they are to be administered to an animal. This is in contrast to the first situation described above, where the isolation of the regenerated tissue from the matrix means that the biocompatibility of the original matrix is generally irrelevant.

Calcium phosphate ceramics are non-biodegradable matrices that are extensively used in engineering bone tissue (Ducheyne, 1988) and may be used in the present invention. A suitable ceramic that may be used is described in U.S. Pat. No. 4,596,574, incorporated herein by reference.

Both hydroxyapatite and tricalcium phosphate, and mixtures of the two, may be utilized. These materials can be coated over metal implants (Lemons, 1988), used with the tissue implant as an additional bone inductive or conductive material (Ducheyne, 1988; Jarcho, 1981), or used as a cell delivery vehicle (Goshima et al., 1991). These materials only release calcium and phosphate as breakdown products. They display no local or systemic toxicity, and become directly bonded to adjacent bone tissue with no intervening fibrous capsule (Ducheyne, 1988). The erosion and mechanical properties of these materials are controlled by the specific chemical composition and processing conditions (Lemons, 1988).

Applications of hydroxyapatite, tricalcium phosphate, and mixtures thereof are currently limited by their brittle nature and generally poor mechanical properties (Jarcho, 1981). However, this is not a drawback in the context of the present invention. First, where the tissue is to isolated from the matrix prior to use, this would not be a significant limitation. Further, where both the matrix and the regenerated oral tissue are to be administered, the presence of the natural tissue will negate any drawbacks that the matrix may have, as the matrix will be a supplement to the tissue, not the only material to be relied upon.

Further non-biodegradable polymers include semipermeable polymers such as poly(acrylonitrile-co-vinyl chloride) (Emerich et al., 1992; Sagan et al., 1993; Guenard et al., 1992), polylysine (Lim and Sun, 1980; O'Shea et al., 1984; Ricordi et al., 1988; Sullivan et al., 1991; Lacy et al., 1991; Levesque et al., 1992; Soon-Shiong et al., 1994), cellulose acetate (Yang et al., 1994) and polysulfone (Yang et al., 1994). Although generally intended for use in immobilized cells, the use of such polymers in the context of the present invention is certainly not excluded. These polymers may also be used with a variety of gels, including alginate and polyphosphazenes.

Polyphosphazenes are synthetic polymers, and aqueous solutions of polyphosphazenes will gel in the presence of specific ions (Cohen et al., 1990). These polymers can be used in the same manner as alginate. The exceedingly stable backbone of these synthetic polymers allows significant alterations in side-group functionality without losing the gentle, physiologic gelling conditions (Allcock et al., 1988).

5. Synthetic Matrices that Mimic Natural Materials

There are advantages and disadvantages of both natural materials, e.g., collagens, and synthetic materials, e.g., polyglycolic acids. Synthetic materials that incorporate design concepts or specific biological activities of natural biomaterials may combine the advantages of both types of materials. The reproducible, large-scale synthesis and flexible properties of synthetic polymers can be combined with the biocompatibility and biological activity of natural materials. Such materials may be used in this invention.

Amino acid sequences in ECM molecules that are responsible for specific biological activities, e.g., cell binding, have been identified in recent years (Hynes, 1987; Hynes, 1990). This means researchers are able to design synthetic materials that are capable of precise cellular interactions. Genetic engineering approaches are being utilized to prepare artificial proteins with a desired backbone structure and amino acid side chains that promote cell adhesion (McGrath et al., 1992). These artificial proteins can be expressed in bacterial cells, isolated and purified, and utilized to form matrices or coat other surfaces (Anderson et al., 1994). This approach offers tremendous control over both the properties (bulk and surface) of the material, and its ability to interact with cells.

Traditional synthetic routes are also being used to develop biodegradable polymers that contain cell recognition peptides as side chains (Barrera et al., 1993). The advantages of synthetic polymers, such as polylactide, can be combined with the specific biological activity of ECM molecules with this approach. A similar approach is the synthesis of short amino acid chains containing a desired functional group that can be covalently bonded or adsorbed onto matrices fabricated from other synthetic materials (Hubbell, 1995). Such biomimetic synthetic polymers and cell-adhesion peptides are proposed for use as implants for tissue regeneration and transplantation (Hubbell, 1995). These and any of the foregoing or other "second generation" matrices may be used in the context of the present invention.

Bone achieves its high mechanical moduli by combining organic and inorganic materials, and this principle is being utilized to synthesize new ceramic materials. Apatite crystals are being synthesized by nucleation and growth around poly(amino acids) (Stupp and Ciegler, 1992). This results in an intimate dispersion of the organic molecules within the ceramic, and improves the mechanical properties of the ceramic (Stupp et al., 1993). This process may mimic the process of natural bone formation, and these materials show promise in engineering bone tissue (Stupp et al., 1993). Such materials may also be used in aspects of this invention.

C. Regeneration Methodology

The regeneration methodology first involves cell seeding onto the three dimensional matrix. Cells can be seeded under static or stirred conditions. Cells can be seeded in a one time administration, continuously added, or added in batches. Any desired method and apparatus may be used to seed the cells onto the matrix. Exemplary methods are described herein in the detailed examples. In stirred conditions, a cell suspension is mixed with scaffolds and agitated to enhance the number and frequency of cell contacts with the matrix to maximize cell adhesion to the matrix.

As will be appreciated by those of skill in the art, 37° C. is generally the preferred temperature for seeding and culture, especially with human cells. However, a wide range of temperatures are contemplated to be useful, ranging from about 4° C. to approximately 50° C. The temperatures may be further optimized for different animals in veterinary procedures.

The conditions of seeding and matrix-cell maintenance will preferably be optimized to enhance cell-matrix contact, to maximize cell-matrix adhesion and to favor native tissue regeneration. Although certain variations in cell numbers, seeding techniques, culture media and buffers, temperatures, incubation times, and the like, may be advisable in certain circumstances, all such variations will be routine to those of skill in the art. It is well understood that certain parameters can be varied in order to improve the yield or activity of components in biological processes. Any such variations practiced in connection with regenerating oral tissues ex vivo using three dimensional matrices will thus be understood to be encompassed within the present invention.

As described above, different oral tissues will likely be engineered using different starting cells that are appropriate for the tissue of interest, e.g., pulp-derived cells for pulp, gingival derived cells for gingival submucosa. However, it is also contemplated that cells not taken from the tissue of interest will be useful, which cells are induced to express the appropriate phenotype, e.g., by exposure to specific conditions in culture, via the introduction of foreign genes or an increased number of copies of natural structural or regulatory genes, or combinations of such methods.

A variety of criteria are available to assess the characteristics of the regenerated tissue. Using one or more of a range of structural and functional characteristics, the properties of the regenerated tissues may be correlated with those of the natural oral tissues. By way of example only, one may mention: the gross histology and microstructure (using TEM and SEM); the matrix composition and organization; the cellular expression of specific genes, at the level of gene transcription, mRNA levels, or the presence of specific proteins, e.g., membrane receptors or matrix molecules; the total cellularity and types of cells present; and the mechanical strength and/or stability of tissue. Techniques for carrying out such assays are routine and well known to those of skill in the art.

An exemplary, but by no means limiting, list of markers which are contemplated for use in the present invention includes: human gene markers for fibrous connective tissue (produced by either pulp or gingival fibroblasts) for cellular fibronectin or collagen type I, and III, measurable as protein or RNA; human gene markers for fibrous connective tissue (produced by either pulp or gingival fibroblasts) for BMP receptors BMPR-A1, -AII, -II or Act (activin) RI, BMP-2, -4 or -7, or MSX-2, a homeobox containing transcription factor which has been implicated as a mediator of BMP signals during tissue (including tooth) development, measurable as RNA and perhaps necessary to be responsible to BMP induction of bone or dentin formation; and alkaline phosphatase enzyme activity, which is associated with cells such as osteoblasts and odontoblasts involved in mineralized tissue formation.

Additional markers include dentinsialposphophoryn (DSPP), a putative specific marker for dentin, and bone sialoprotein, osteonectin and osteocalcin, which are highly enriched in bone. Markers for use for the buccal mucosa include cytokeratins 4 and 13. Further, markers for use in identification of taste buds include cytokeratins 8, 18 and 19, which are present in taste buds but absent in the surrounding mucosa.

D. Exogenous Factors

If desired, protein growth factors that affect the proliferation of cells and tissues may be used in conjunction with the engineering processes of the present invention. Likewise, cells that naturally elaborate such factors and/or recombinant cells engineered to produce and secrete such factors may also be used to further stimulate the proliferation of cells and tissues, or to direct the development of a given tissue over another tissue when using starter cells that have the natural capacity to regenerate a number of different oral tissues.

It is preferable that the tissue-specific function of the cells in the engineered oral tissue be maintained. The function of cultured cells is strongly dependent on the presence of specific growth factors and ECM molecules (Stoker et al., 1990). For example, cells can be switched from a phase of tissue-specific gene expression to one of proliferation simply by altering the ECM presentation to the cell (Mooney et al., 1992).

The microenvironment of an engineered tissue following transplantation may also be regulated during the process of tissue development, and perhaps beyond this time. Specific ECM molecules, growth factors, mechanical signals and/or mass transport conditions may be required to ensure optimal development of oral tissues with appropriate structure and function following application of the regenerated tissue to the oral tissue site.

As the regenerated oral tissues of the present invention will be placed into an appropriate oral tissue microenvironment, the ability of the cells of the tissues to maintain a desired program of gene expression is not considered to pose a problem. However, if desired, any one of a variety of delivery matrices that incorporate specific ECM molecules may be used to supplement the correct signaling to transplanted and/or the host's own cells (Green et al., 1979; Yannas et al., 1981; Bell et al., 1981; Stern et al., 1990; Compton et al., 1989; Dixit, 1994; Kasai et al., 1994; Cavallaro et al., 1994; Anselme, 1992; Koide et al., 1993; Guenard et al., 1992).

Synthetic materials that incorporate specific peptides to enhance cell adhesion (McGrath et al., 1992; Barrera et al., 1993; Hubbell, 1993) may be used, including those that incorporate a variety of different peptides in order to mimic the multi-functional nature of ECM molecules (Hynes, 1990). Growth factors promoting tissue development may be lacking or deficient in the host tissue site that the engineered tissue is applied to. To address this concern, traditional controlled drug delivery technology may be integrated with tissue engineering to provide transplanted cells with specific growth factors in their local environment.

Mechanical signals are known to regulate the development of a variety of tissues, including muscle (Vandenburgh et al., 1991), and bone (Carter et al., 1989). For example, engineered tendons that are not subjected to mechanical loading do not develop mechanical moduli as high as normal tendons, even though they appear to be histologically identical (Cao et al., 1994). Mechanical stimuli (e.g., strain, shear) also clearly regulate the gene expression of cultured cells (Frangos, 1993). To engineer an optimally functional oral tissue it may be necessary to provide the correct mechanical stimuli during the process of tissue development.

The mass transport between the engineered oral tissue and the host should be also considered. It will be understood that the metabolic requirements, e.g., oxygen, of the developing tissue must be met, or the cells within the tissue will die.

1. Growth Factors

The use of growth factors in the context of cell proliferation and culture is generally well known in the art, although growth factors, other than those naturally present in the serum at low levels, have not been used in conjunction with oral tissue regeneration on a structural matrix ex vivo. However, in that growth factors are routinely used in other contexts, one of skill in the art will readily understand how to apply growth factors in the context of the present invention following a reading of the instant disclosure.

In general terms, it will be understood that a growth factor that has already been established to have a beneficial physiological effect on a particular cell type should be chosen for use in regenerating tissue containing such cells. Certain growth factors may be used to stimulate the proliferation of a wide number of cell types, whereas other growth factors may have a more limited or defined cell-specificity. Growth factors may also be used to reduce serum requirements, particularly where the use of xenogenic serum represents a problem.

The choice of a particular growth factor and cell combination will be a routine matter for one of skill in the art. By way of example only, one may mention platelet-derived growth factor, PDGF (such as PDGF-BB), which may be used either alone or in combination with dexamethasone; insulin-like growth factor I, basic fibroblast growth factor (bFGF); and epidermal growth factor (EGF).

PDGF-BB and dexamethasone are effective for the growth of pulp, periodontal ligament and gingival fibroblasts (Rutherford et al., 1992a, 1992b; 1993a), and are particularly proposed for use in connection with these aspects of the invention. U.S. Pat. No. 5,149,691, incorporated herein by reference, describes the use of combinations of PDGF and dexamethasone for the repair and regeneration of tissues in vivo. U.S. Pat. Nos. 5,376,636 and 5,149,691, each incorporated herein by reference, also describe the use of PDGF and glucocorticoids in tissue regeneration. Any such teachings may be used in connection with the present invention. It is also known that this combination and PDGF/IGF-1 induce regeneration of the periodontium in an animal model of periodontitis (Rutherford et al., 1992b; 1993a).

In addition to bFGF, another angiogenic factor that may be used is VEGF. Differentiation inducing factors are likely to be useful, e.g., EGF and the like. Other hormones, such as insulin, steroids, and particularly, anti-inflammatory agents are also contemplated for use herewith.

BMP proteins may be employed in certain aspects of the present invention, such as those described in U.S. Pat. Nos. 4,795,804; 4,877,864; 4,968,590; 5,011,691; 5,013,649; 5,106,748; 5,108,753; 5,116,738; 5,141,905; 5,166,058 and 5,187,076, each incorporated herein by reference. For example, the inventors have demonstrated that a single application of BMP-7 to a freshly and partially amputated dental pulp induced reparative dentinogenesis in ferrets, monkeys and humans (Rutherford et al., 1993b, 1994, 1995). Additionally, the inventors have demonstrated that BMP-7 induced bone when implanted in gingiva, indicating that gingiva possess cells that are capable of forming mineralized tissue such as bone.

The growth factors or stimulatory agents that are useful in the context of the present invention may be purified from natural sources or may be recombinantly prepared proteins. They may be obtained from commercial sources, if desired. Those of skill in the art will know how to obtain and use such growth factors in the context of tissue regeneration in light of the present disclosure.

2. Cells that Produce Growth Factors

It will be understood that the exogenous factors for use herewith may be produced by a population of cells that is co-cultured with the matrix-tissue and/or that is administered to the oral tissue of an animal with the tissue sample or matrix-tissue sample The use of natural cells that elaborate any of the aforementioned or other growth factors, hormones or cytokines is thus contemplated. Such cells may be autologous cells that have also been proliferating in culture ex vivo. Certain cells, such as T cells or B cells, may be enriched in the cell population, if desired.

Equally, recombinant cells engineered to produce the growth factors, hormones, cytokines, hormone, neurotransmitters and the like may also be employed. Recombinant engineering for protein production and secretion, generally using recombinant vectors, is now routine in the art, and is described in further detail herein below. The culture of many mammalian cells is, in itself, a routine procedure (*Tissue Culture,* 1973, incorporated herein by reference). Examples of useful host cell lines that may so engineered include, for example, VERO cells, HeLa cells, Chinese hamster ovary (CHO) cell lines, and W138, BHK, COS-7, 293 and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences. For use in mammalian cells, the control functions on the expression vectors are often obtained from viral material. For example, commonly used promoters are derived from polyoma, Adenovirus 2, and frequently, from Simian Virus 40 (SV40). The early and late promoters of SV40 virus are particularly useful because both are obtained easily from the virus as a fragment which also contains the SV40 viral origin of replication. It is also possible to utilize promoter or control sequences normally associated with the desired gene sequence, provided such control sequences are compatible with the host cell systems.

In mammalian cell vector systems, the origin of replication may be obtained from either construction of the vector to include an exogenous origin, such as may be derived from SV40 or other viral (e.g., Polyoma, Adeno, VSV, BPV) source, or may be obtained from the host cell chromosomal replication mechanism. If the vector is integrated into the host cell chromosome, the latter is often sufficient.

The use of exogenous growth factors to positively influence the engraftment, proliferation and vascularization of implanted cells and tissues is exemplified herein by the use of EGF, matrices and hepatocytes in liver regeneration studies.

3. Factors that Prevent or Inhibit Apoptosis

A number of factors are contemplated for use in the present invention, based on their ability to block, prevent, or reduce apoptosis. The factors contemplated for use with the present invention include, but are not limited to, the following compounds. The calcium ionophore A23187 has been shown to block apoptosis in certain systems, such as when interleukin-3 (IL-3) is withdrawn from IL-3 dependent cells. The thiol compounds pyrrolidine and dithiocarbamate have also been shown to inhibit apoptosis. N-Acetyl-L-cysteine has been shown to prevent apoptotic death of neuronal cells (Ferrari et al., 1995) and TNF-α induced apoptosis in U937 cells (Cossarizza et al., 1995). Nakajima et al. (1994) showed that actinomycin D, while a potent inducer of apoptosis in many cell lines, has been shown to suppress programmed cell death of PC12 cells induced by etoposide, an inhibitor of topoisomerase II These studies also showed that cycloheximide, nerve growth factor and epidermal growth factor also rescued PC12 cells from etoposide-induced death. Insulin-like growth factor-I (IGF-1) and the IGF-1 receptor were also shown to inhibit etoposide-induced apoptosis in BALB/c 3T3 cells (Sell et al., 1995).

3-Aminobenzamide has been shown to be an inhibitor of UV-induced apoptosis (Malorni et al., 1995). Aphidocolin potentiates apoptosis induced by arabinosyl nucleosides in leukemia cell lines, and inhibits vincristine-induced apoptosis in the p53-negative human prostate cancer cell line PC-3 (Borner et al., 1995). L-Ascorbic acid (vitamin C), catalase, follicle stimulating hormone, N-acetyl-L-cysteine, vasoactive intestinal peptide, cyclic GMP, hCG, interleukin-1β (IL-1β) and superoxide dismutase have all been shown to inhibit or suppress apoptosis in cultured rat ovarian follicles (Flaws et al., 1995; Tilly and Tilly 1995; Chun et al., 1995). Aurintricarboxylic acid has been shown to inhibit apoptotic cell death in various cell types induced by a variety of factors (Benchokroun et al., 1995).

BAPTA/AM [1,2,-bis(o-Aminophenoxy)ethane-N,N,N', N'-tetraacetic acid tetra (acetoxymethyl) ester] inhibits thapsigargin-induced apoptosis in rat thymocytes (Jiang et al., 1994). Caffeine has been shown to prevent apoptosis and cell cycle effects induced by camptothecin and topotecan in HL-60 cells (Traganos et al., 1993). Calpain inhibitor I inhibits apoptosis in thymocytes and metamyelocytes (Squier et al., 1994), while leupeptin, calpain inhibitor II and the E64 class of serine protease inhibitors have also been shown to inhibit activation-induced programmed cell death (Sarin et al., 1994). Cyclosporin A has been shown to prevent anti-IgM and ionomycin-induced apoptosis in BLB cell lines.

The general serine protease inhibitor 3,4-dichloroisocoumarin and the specific thiol reagent N-ethyl maleimide were shown to block apoptotic internucleosomal DNA cleavage in thymocytes without the involvement of endonucleases (Cain et al., 1994). The cysteine protease inhibitors E64 and leupeptin, the calpain selective inhibitor acetyl-leucyl-leucyl-normethional, and the serine protease inhibitors diisopropylfluorophosphate and phenylmethylsulfonyl fluoride were all shown to selectively block T-cell receptor-triggered programmed cell death in murine T-cell hybridoma and in activated peripheral T-cells (Sarin et al., 1993). Tetrodotoxin, nimodipine, verapamil, flunarizine and R56865 all protect bovine chromaffin cells from veratridine-induced cell death (Maroto et al., 1994). Caspase inhibitors are also contemplated for use as apoptosis inhibitors.

Forskolin and insulin growth factor-1 (IGF-1) both have been shown to inhibit apoptosis in cerebellar granule cells, although by distinct mechanisms (Galli et al., 1995). The protein tyrosine kinase inhibitors genistein and herbimycin A have both been shown to prevent anti-CD3 monoclonal antibody-induced thymic apoptosis (Migita et al., 1994). Interleukin-6 (IL-6) inhibits constitutive, protein synthesis-independent apoptosis of murine B-cell hybridoma 7TD1 (Liu et al., 1994). The protein phosphatase inhibitors calyculin A and okadaic acid inhibit glucocorticoid-induced apoptosis in T-cell hybridomas (Gjertsen et al., 1994), and calyculin A is known to prevent γ-radiation induced apoptosis in Burkitt's lymphoma cell line BM13674.

The protein kinase C activator phorbol-12-myristate-13-acetate inhibits apoptosis induced by the Fas antigen (Tepper et al., 1995). 1-Pyrrolidinecarbodithioic acid prevents apoptosis in human promyeolocytic leukemia HL-60 cells and in thymocytes (Bessho et al., 1994). The calcium-channel blockers nifedipine and nisoldipine, as well as the endonuclease inhibitor aurintricarboxylic acid have been shown to block apoptosis in cultured human endothelial cells (Escargueil-Blanc et al., 1997). Spermine has been shown to inhibit morphological apoptosis, and the antioxidant thioredoxin inhibits apoptosis in Jurkat T-cells and human PBL blasts (Sata et al., 1995). Additionally, the protease inhibitors $N^\alpha$-Tosyl-L-Phe chloromethyl ketone, $N^\alpha$-Tosyl-L-Lys chloromethyl ketone, and to a lesser extent $N^\alpha$-Tosyl-L-Arg methyl ester inhibit apoptosis in thymocytes (Bruno et al., 1992).

4. Factors that Promote Angiogenesis

The successful engineering of new oral tissue requires the establishment of a vascular network in the new tissue. Case reports of successful tooth transplantation suggest that pulp tissue may be capable of reestablishing vascular connections (Myers and Fountain, 1974). However the inventors contemplate the use of factors that promote angiogenesis to support the neovascularization of the engineered oral tissues.

The induction of angiogenesis is mediated by a variety of factors, any of which may be used in conjunction with the present invention (Folkman and Klagsbrun, 1987, and references cited therein, each incorporated herein in their entirety by reference). Examples of angiogenic factors includes, but is not limited to: vascular endothelial growth factor (VEGF) or vascular permeability factor (VPF); members of the fibroblast growth factor family, including acidic fibroblast growth factor (aFGF) and basic fibroblast growth factor (bFGF); interleukin-8 (IL-8); epidermal growth factor (EGF); platelet-derived growth factor (PDGF) or platelet-derived endothelial cell growth factor (PD-ECGF); transforming growth factors alpha and beta (TGF-α, TGF-β); tumor necrosis factor alpha (TNF-α); hepatocyte growth factor (HGF); granulocyte-macrophage colony stimulating factor (GM-CSF); insulin growth factor-1 (IGF-1); angiogenin,; angiotropin; fibrin and nicotinamide (Folkman, 1986, 1995; Auerbach and Auerbach, 1994; Fidler and Ellis, 1994; Folkman and Klagsbrun, 1987; Nagy et al., 1995)

5. Cytokines

As discussed above, in certain embodiments the use of particular cytokines in conjunction with the growth of oral tissues is preferred. Table 4 below is an exemplary, but not limiting, list of additional cytokines and related factors contemplated for use in the present invention.

TABLE 4

| Cytokine | Reference |
| --- | --- |
| human IL-1α | March et. al., Nature, 315:641, 1985 |
| murine IL-1α | Lomedico et al., Nature, 312:458, 1984 |
| human IL-1β | March et al., Nature, 315:641, 1985; Auron et al., Proc. Natl. Acad. Sci. USA, 81:7907, 1984 |
| murine IL-1β | Gray, J. Immunol., 137:3644, 1986; Telford, NAR, 14:9955, 1986 |
| human IL-1ra | Eisenberg et al., Nature, 343:341, 1990 |
| human IL-2 | Taniguchi et al., Nature, 302:305, 1983; Maeda et al., Biochem. Biophys. Res. Commun., 115:1040, 1983 |
| human IL-2 | Taniguchi et al., Nature, 302:305, 1983 |
| human IL-3 | Yang et al., Cell, 47:3, 1986 |
| murine IL-3 | Yokota et al., Proc. Natl. Acad. Sci. USA, 81:1070, 1984; Fung et al., Nature, 307:233, 1984; Miyatake et al., Proc. Natl. Acad. Sci. USA, 82:316, 1985 |
| human IL-4 | Yokota et al., Proc. Natl. Acad. Sci. USA, 83:5894, 1986 |
| murine IL-4 | Norma et al., Nature, 319:640, 1986; Lee et al., Proc. Natl. Acad. Sci. USA, 83:2061, 1986 |
| human IL-5 | Azuma et al., Nuc. Acids Res., 14:9149, 1986 |
| murine IL-5 | Kinashi et al., Nature, 324:70, 1986; Mizuta et al., Growth Factors, 1:51, 1988 |
| human IL-6 | Hirano et al., Nature, 324:73, 1986 |
| murine IL-6 | Van Snick et al., Eur. J. Immunol., 18:193, 1988 |
| human IL-7 | Goodwin et al., Proc. Natl. Acad. Sci. USA, 86:302, 1989 |
| murine IL-7 | Namen et al., Nature, 333:571, 1988 |
| human IL-8 | Schmid et al., J. Immunol., 139:250, 1987; Matsushima et al., J. Exp. Med., 167:1883, 1988; Lindley et al., Proc. Natl. Acad. Sci. USA, 85:9199, 1988 |
| human IL-9 | Renauld et al., J. Immunol., 144:4235, 1990 |
| murine IL-9 | Renauld et al., J. Immunol., 144:4235, 1990 |
| human Angiogenin | Kurachi et al., Biochemistry, 24:5494, 1985 |
| human GROα | Richmond et al., EMBO J., 7: |

TABLE 4-continued

| Cytokine | Reference |
|---|---|
| | 2025, 1988 |
| murine MIP-1α | Davatelis et al., J. Exp. Med., 167: 1939, 1988 |
| murine MIP-1β | Sherry et al., J. Exp. Med., 168: 2251, 1988 |
| human MIF | Weiser et al., Proc. Natl. Acad. Sci. USA, 86:7522, 1989 |
| human G-CSF | Nagata et al., Nature, 319:415, 1986; Souza et al., Science, 232: 61, 1986 |
| human GM-CSF | Cantrell et al., Proc. Natl. Acad. Sci. USA, 82:6250, 1985; Lee et al., Proc. Natl. Acad. Sci. USA, 82:4360, 1985; Wong et al., Science, 228:810, 1985 |
| murine GM-CSF | Gough et al., EMBO J., 4:645, 1985 |
| human M-CSF | Wong, Science, 235:1504, 1987; Kawasaki, Science, 230; 291, 1985; Ladner, EMBO J., 6:2693, 1987 |
| human EGF | Smith et al., Nuc. Acids Res., 10: 4467, 1982; Bell et al., NAR, 14: 8427, 1986 |
| human TGF-α | Derynck et al., Cell, 38:287, 1984 |
| human FGF acidic | Jaye et al., Science, 233:541, 1986; Gimenez-Gallego et al., Biochem. Biophys. Res. Commun., 138:611, 1986; Harper et al., Biochem., 25:4097, 1986 |
| human β-ECGF | Jaye et al., Science, 233:541, 1986 |
| human FGF basic | Abraham et al., EMBO J., 5:2523, 1986; Sommer et al., Biochem. Biophys. Res. Comm., 144:543, 1987 |
| murine IFN-β | Higashi et al., J. Biol. Chem., 258:9522, 1983; Kuga, NAR, 17:3291, 1989 |
| human IFN-γ | Gray et al., Nature, 295:503, 1982; Devos et al., NAR, 10:2487, 1982; Rinderknecht, J. Biol. Chem., 259:6790, 1984 |
| human IGF-I | Jansen et al., Nature, 306:609, 1983; Rotwein et al., J. Biol. Chem., 261:4828, 1986 |
| human IGF-II | Bell et al., Nature, 310:775, 1984 |
| human β-NFG chain | Ullrich et al., Nature, 303:821, 1983 |
| human PDGF A chain | Betsholtz et al., Nature, 320:695, 1986 |
| human PDGF B chain | Johnsson et al., EMBO J., 3:921, 1984; Collins et al., Nature, 316: 748, 1985 |
| human TGF-β1 | Derynck et al., Nature, 316:701, 1985 |
| human TNF-α | Pennica et al., Nature, 312:724, 1984; Fransen et al., Nuc. Acids Res., 13:4417, 1985 |
| human TNF-β | Gray et al., Nature, 312:721, 1984 |
| murine TNF-β | Gray et al., Nucl. Acids Res., 15: 3937, 1987 |
| human E-Selectin | Bevilacqua et al., Science, 243: 1160, 1989; Hensley et al., J. Biol. Chem., 269:23949, 1994 |
| human ICAM-1 | Simmons et al., Nature, 331:624, 1988 |
| human PECAM | Simmons et al., J. Exp. Med., 171: 2147, 1990 |
| human VCAM-1 | Hession et al., J. Biol. Chem., 266: 6682; Osborn et al., Cell, 59:1203, 1989 |
| human L-Selectin (membrane bound) | Ord et al., J. Biol. Chem., 265: 7760, 1990; Tedder et al., J. Exp. Med., 170:123, 1989 |
| human L-Selectin (soluble form) | Ord et al., J. Biol. Chem., 265: 7760, 1990; Tedder et al., J. Exp. Med., 170:123, 1989 |

TABLE 4-continued

| Cytokine | Reference |
|---|---|
| human Calcitonin | Le Moullec et al., FEBS Lett., 167: 93, 1984 |
| human Hirudin (*E. coli* optimized) | Dodt et al., FEBS Lett., 165:180, 1984 |

E. Clinical Applications

Oral tissues engineered in accordance with the present invention have evident clinical utility in the regeneration of oral tissues and structures in vivo. Inducing or speeding up the overall regeneration process by administering regenerated tissue to the site of injury is beneficial as it lessens the chance that the body will attempt to repair the injury, leading to the formation of scar tissue and the loss of normal tissue structure and function.

Tissues engineered using autologous cells will likely be those first used in a clinical setting. In a specific embodiment of the invention, dental pulp tissues have already been regenerated. Such dental pulp tissues will be useful in effecting the repair of dental pulp and reparative dentin formation following disease or surgical manipulation.

The regenerated dental pulp tissues were made by isolating fibroblasts from human dental pulp and multiplying them in culture. These cells were seeded onto synthetic extracellular matrices fabricated from fibers (approximately 15 $\mu$m in diameter) of polyglycolic acid (PGA). The pulp-derived cells adhered to the fibers and proliferated over time.

New tissues were formed over 60 days in culture that histologically resembled native dental pulp tissue. These new tissues also had a cellularity in the same range as adult human pulp. Immunohistochemical and histochemical analysis of the extracellular matrix revealed that it contained type I collagen and cellular fibronectin; normal constituents of mature dental pulp tissue.

Although the present tissue regeneration and transplantation methods are considered to be effective in and of themselves, the application of the regenerated tissue may be combined with growth factors (e.g., Folkman and Klagsbrun, 1987) in certain applications, e.g., to stimulate blood vessel formation (angiogenesis) or to promote cell growth. Angiogenesis can also be promoted by controlling the microstructure of the matrix (Mooney et al., 1994b; Mikos et al., 1993b).

Direct local application of recombinant growth factors (e.g., BMP-2) has been shown to induce reparative dentinogenesis in dogs and primates when placed on partially amputated dental pulps (Rutherford et. al., 1993b; Nakashima, 1994; Rutherford et. al., 1994), or on a freshly cut dental surface ("transdentinal" application; Rutherford et. al., 1995). However, in many clinical situations no pulp remains to stimulate. The present invention provides new, preferably autologous, pulp tissue to replace lost pulp tissue and form reparative dentin.

As an example, autologous pulp-derived fibroblasts are obtained from healthy molars or wisdom teeth and are expanded in culture to engineer the new pulp tissues for use in diseased teeth. Alternatively, tissue extracted from the original diseased tooth may itself be used to regenerate dental pulp by expanding and culturing the viable cells that remained in the extracted material.

Ultimately, the successful engineering of new oral tissue requires the establishment of a vascular network in the new tissue and the development of an appropriate synthetic scaffold for cell transplantation. Case reports of successful tooth transplantation suggest that pulp tissue may be capable of reestablishing vascular connections (Myers and Fountain, 1974) and reinnervating (Holland and Robinson, 1987).

The demonstration that neovascularization and reinnervation can occur in transplanted teeth with intact pulps argues that these components of tissue repair may readily occur in the pulp tissue developed ex vivo. Such tissues will be less dense and therefore more easily penetrated than fully mature dental pulp. Additionally whereas revascularization is essential for survival of the implanted tissue the same case has not been and is likely not true for reinnervation. Therefore, the regenerated pulp tissue of the present invention represent an ideal starting material for the successful engineering of new oral tissue.

The importance and application of other regenerated oral tissues of the present invention will be apparent to those of skill in the art in light of the present disclosure. For example, the present invention's use in engineering periodontal tissue is important as periodontal disease is one of the most significant oral health problems in the USA. Approximately 35% of the U.S. population is estimated to have periodontitis and 80% of these also suffer from gingivitis.

The generation of new periodontal tissue occurs by using staring cells from the periodontal ligament or gingival submucosa, as described above. After tissue growth ex vivo, the regenerated tissue would be applied to the exposed root surface and immediately adjacent tissues using the Modified Widman approach. It is contemplated that a combination of tissue and growth factor delivery will provide a particularly advantageous means of regenerating a healthy periodontium.

It will also be understood that for most oral applications the use of antimicrobials/antibiotics may be important in order to minimize infection of the tissue during development and to resolve certain oral diseases. The local or systemic administration of antimicrobials in connection with the present invention is thus contemplated.

Antibiotics of choice for common pathogens include, e.g., penicillins, ampicillin, amoxicillin, erythromycin, cephalosporins, tetracyclines and the like. Antibiotics such as these may be used clinically at a range of doses, as is known to those of skill in the art. Depending on the circumstances, antimicrobial agents will preferably be used orally, although parenteral treatment regimens are not excluded. Appropriate doses are well known to those of skill in the art, and are further described in various publications, such as Reese and Betts (1993), incorporated herein by reference. Table 5 and Table 6 of Reese and Betts (1993) are particularly incorporated herein by reference to provide ready reference to the currently recommended doses of a variety of antimicrobial agents.

F. Screening Assays

The regenerated oral tissues obtained from the present invention may also be used as novel systems for testing the toxicity and/or biocompatibility of materials and chemicals intended for use in dentistry and oral medicine.

In such novel systems, the three-dimensional human tissues obtained from the invention represent a more physiologically relevant system than standard two-dimensional cell culture models currently utilized for in vitro testing of biocompatibility (Schmaltz, 1994).

In general, one may use a three-dimensional oral tissue of the invention to test for the cytotoxicity, mutagenicity and/or neoplastic transformation of cells exposed to a variety of agents or combinations thereof. The following texts describe suitable methods that exemplify those that may be used in connection with this invention: von Recum (1986); Ecobichon (1992); Barile (1994); Black (1992); Kumar et al., (1992); and Darnell et al., (1990): each incorporated herein by reference.

The ADA specifications are guidelines that govern the materials and devices used in dentistry (restorative dental materials are defined by the FDA as "devices"). The philosophy requires that a tiered system be used, starting with initial tests (in vitro and in vivo), followed by secondary tests (more involved in vivo tests), and then usage tests—which place the material into actual use, usually in higher animals (monkeys or dogs).

Many of the tests in the ADA specification are out of date, however, they are still being used. The ADA specification currently relies heavily on animal testing. The present invention provides valuable alternatives to the out-dated methods of the initial tests and should also reduce the amount of animal testing to a minimum, as the initial tests are more relevant when performed a three dimensional native-like oral tissue.

Using the invention's system for in vitro biocompatibility testing, one of skill in the art would be able to define an unacceptable level of toxicity in order to identify an agent as unsafe for human and/or veterinary use. Acceptable levels of no or minimal toxicity would identify an agent as safe for human and/or veterinary use. If necessary, results from the present in vitro biocompatibility test could be initially correlated with the ADA specifications and industry standards to yield results more instantly interpretable by those of skill in the art.

G. Engineering of Cells

As described herein above, recombinant cells engineered to produce a variety of exogenous factors, hormones, cytokines, hormone, neurotransmitters and the like are contemplated for use in the present invention. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences. Once the desired vector construct is obtained, it may be delivered into the desired cells by a number of different techniques.

1. Promoters and Enhancers

Recombinant vectors form important further aspects of the present invention. The term "expression vector or construct" means any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid, for example, to generate antisense constructs.

Particularly useful vectors are contemplated to be those vectors in which the coding portion of the DNA segment, whether encoding a full length protein or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid to control RNA polymerase initiation and expression of the gene.

The promoter may be in the form of the promoter that is naturally associated with a particular gene, as may be obtained by isolating the 5' non-coding sequences located upstream of the coding segment or exon, for example, using recombinant cloning and/or PCR technology, in connection with the compositions disclosed herein (PCR technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a particular gene in its natural environment. Such promoters may include promoters normally associated with other genes, and/or promoters isolated from any other bacterial, viral, eukaryotic, or mammalian cell.

Naturally, it will be important to employ a promoter that effectively directs the expression of the DNA segment in the selected cell type chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Tables 5 and 6 below list several elements/promoters which may be employed, in the context of the present invention, to regulate gene expression. This list is not intended to be exhaustive of all the possible elements involved in the promotion of transgene expression but, merely, to be exemplary thereof. Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

TABLE 5

Inducible Elements

| Element | Inducer | References |
| --- | --- | --- |
| MT II | Phorbol Ester (TFA) Heavy metals | Palmiter et al., 1982; Haslinger and Karin, 1985; Searle et al., 1985; Stuart et al., 1985; Imagawa et al., 1987; Karin ®, 1987; Angel et al., 1987b; McNeall et al., 1989 |
| MMTV (mouse mammary tumor virus) | Glucocorticoids | Huang et al., 1981; Lee et al., 1981; Majors and Varmus, 1983; Chandler et al., 1983; Lee et al., 1984; Fonta et al., 1985; Sakai et al., 1986 |
| β-Interferon | poly(rI)X poly(rc) | Tavernier et al., 1983 |
| Adenovirus 5 E2 | Ela | Imperiale and Nevins, 1984 |
| Collagenase | Phorbol Ester (TPA) | Angle et al., 1987a |
| Stromelysin | Phorbol Ester (TPA) | Angle et al., 1987b |
| SV40 | Phorbol Ester (TFA) | Angel et al., 1987b |
| Murine MX Gene | Interferon, Newcastle Disease Virus | |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | Ela, SV40 Large T Antigen | Taylor et al., 1989; Taylor and Kingston, 1990a,b |
| Proliferin | Phorbol Ester-TPA | Mordacq and Linzer, 1989 |
| Tumor Necrosis Factor | FMA | Hensel et al., 1989 |
| Thyroid Stimulating Hormone α Gene | Thyroid Hormone | Chatterjee et al., 1989 |

TABLE 6

Other Promoter/Enhancer Elements

| Promoter/Enhancer | References |
|---|---|
| Immunoglobulin Heavy Chain | Hanerji et al., 1983; Gilles et al., 1983; Grosschedl and Baltimore, 1985; Atchinson and Perry, 1986, 1987; Imler et al., 1987; Weinberger et al., 1988; Kiledjian et al., 1988; Porton et al., 1990 |
| Immunoglobulin Light Chain | Queen and Baltimore, 1983; Picard and Schaffner, 1984 |
| T-Cell Receptor | Luria et al., 1987, Winoto and Baltimore, 1989; Redondo et al., 1990 |
| HLA DQ α and DQ β | Sullivan and Peterlin, 1987 |
| β-Interferon | Goodbourn et al., 1986; Fujita et al., 1987; Goodbourn and Maniatis, 1985 |
| Interleukin-2 | Greene et al., 1989 |
| Interleukin-2 Receptor | Green et al., 1989; Lin et al., 1990 |
| MHC Class II 5 | Koch et al., 1989 |
| MHC Class II HLA-DRα | Sherman et al., 1989 |
| β-Actin | Kawamoto et al., 1988; Ng et al., 1989 |
| Muscle Creatine Kinase | Jaynes et al., 1988; Horlick and Benfield, 1989; Johnson et al., 1989a |
| Prealbumin (Transthyretin) | Costa et al., 1988 |
| Elastase I | Omitz et al., 1987 |
| Metallothionein | Karin et al., 1987; Culotta and Hamer, 1989 |
| Collagenase | Pinkert et al., 1987; Angel et al., 1987 |
| Albumin Gene | Pinkert et al., 1987, Tronche et al., 1989, 1990 |
| α-Fetoprotein | Godbout et al., 1988; Campere and Tilghman, 1989 |
| t-Globin | Bodine and Ley, 1987; Perez-Stable and Constantini, 1990 |
| β-Globin | Trudel and Constantini, 1987 |
| e-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $a_{1\text{-Antitrypain}}$ | Latimer et al., 1990 |
| H2B (TH2B) Histone | Hwang et al., 1990 |
| Mouse or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor | Pech et al., 1989 |
| Duchenne Muscular Dystrophy | Klamut et al., 1990 |
| SV40 | Banerji et al., 1981; Moreau et al., 1981; Sleigh and Lockett, 1985; Firak and Subramanian, 1986; Herr and Clarke, 1986; Imbra and Karin, 1986; Kadesch and Berg, 1986; Wang and Calame, 1986; Ondek et al., 1987; Kuhl et al., 1987 Schaffner et al., 1988 |
| Polyoma | Swartzendruber and Lehman, 1975; Vasseur et al., 1980; Katinka et al., 1980, 1981; Tyndell et al., 1981; Dandolo et al., 1983; deVilliers et al., 1984; Hen et al., 1986; Satake et al., 1988; Campbell and Villarreal, 1988 |
| Retroviruses | Kriegler and Botchan, 1982, 1983; Levinson et al., 1982; Kriegler et al., 1983, 1984a,b, 1988; Bosze et al., 1986; Miksicek et al., 1986; Celander and Haseltine, 1987; Thiesen et al., 1988; Celander et al., 1988; Chol et al., 1988; Reisman and Rotter, 1989 |
| Papilloma Virus | Campo et al., 1983; Lusky et al., 1983; Spandidos and Wilkie, 1983; Spalholz et al., 1985; Lusky and Botchan, 1986; Cripe et al., 1987; Gloss et al., 1987; Hirochika et al., 1987, Stephens and Hentschel, 1987; Glue et al., 1988 |
| Hepatitis B Virus | Bulla and Siddiqui, 1986; Jameel and Siddiqui, 1986; Shaul and Ben-Levy, 1987; Spandau and Lee, 1988; Vannice and Levinson, 1988 |
| Human Immunodeficiency Virus | Muesing et al., 1987; Hauber and Cullan, 1988; Jakobovits et al., 1988; Feng and Holland, 1988; Takebe et al., 1988; Rowen et al., 1988; Berkhout et al., 1989; Laspia et al., 1989; Sharp and Marciniak, 1989; Braddock et al., 1989 |
| Cytomegalovirus | Weber et al., 1984; Boshart et al., 1985; Foecking and Hofstetter, 1986 |
| Gibbon Ape Leukemia Virus | Holbrook et al., 1987; Quinn et al., 1989 |

2. Marker Genes

The present invention also provides recombinant candidate screening and selection methods which are based upon whole cell assays and which, preferably, employ a reporter gene that confers on its recombinant hosts a readily detectable phenotype that emerges only under conditions where a general DNA promoter positioned upstream of the reporter gene is functional. Generally, reporter genes encode a polypeptide (marker protein) not otherwise produced by the host cell which is detectable by analysis of the cell culture, e.g., by fluorometric, radioisotopic or spectrophotometric analysis of the cell culture.

In other aspects of the present invention, a genetic marker is provided which is detectable by standard genetic analysis techniques, such as DNA amplification by PCR™ or hybridization using fluorometric, radioisotopic or spectrophotometric probes.

a. Screening

Exemplary enzymes include esterases, phosphatases, proteases (tissue plasminogen activator or urokinase) and other enzymes capable of being detected by their activity, as will be known to those skilled in the art. Contemplated for use in the present invention is green fluorescent protein (GFP) as a marker for transgene expression (Chalfie et al., 1994). The use of GFP does not need exogenously added substrates, only irradiation by near UV or blue light, and thus has significant potential for use in monitoring gene expression in living cells.

Other particular examples are the enzyme chloramphenicol acetyltransferase (CAT) which may be employed with a radiolabelled substrate, firefly and bacterial luciferase, and the bacterial enzymes β-galactosidase and β-glucuronidase. Other marker genes within this class are well known to those of skill in the art, and are suitable for use in the present invention.

b. Selection

Another class of reporter genes which confer detectable characteristics on a host cell are those which encode polypeptides, generally enzymes, which render their transformants resistant against toxins. Examples of this class of reporter genes are the neo gene (Colberre-Garapin et al., 1981) which protects host cells against toxic levels of the antibiotic G418, the gene conferring streptomycin resistance (U.S. Pat. No. 4,430,434), the gene conferring hygromycin B resistance (Santerre et al., 1984; U.S. Pat. Nos. 4,727,028, 4,960,704 and 4,559,302), a gene encoding dihydrofolate reductase, which confers resistance to methotrexate (Alt et al., 1978), the enzyme HPRT, along with many others well known in the art (Kaufman, 1990).

3. Antisense

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within the cells of the present invention.

Antisense constructs may be designed to bind to the promoter and other control regions, exons, introns or even exon-intron boundaries of a gene. It is contemplated that effective antisense constructs will often include regions complementary to intron/exon splice junctions. Thus, antisense constructs with complementarity to regions within 50–200 bases of an intron-exon splice junction are contemplated for use herewith. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether the expression of genes having complementary sequences is affected.

"Antisense" or "complementary" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression.

4. Ribozymes

Another method for inhibiting gene expression contemplated in the present invention is via ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Several different ribozyme motifs have been described with RNA cleavage activity (Symons, 1992). Examples that are expected to function equivalently for the down regulation of gene expression include sequences from the Group I self splicing introns including Tobacco Ringspot Virus (Prody et al., 1986), Avocado Sunblotch Viroid (Palukaitis et al., 1979; Symons, 1981), and Lucerne Transient Streak Virus (Forster and Symons, 1987). Sequences from these and related viruses are referred to as hammerhead ribozyme based on a predicted folded secondary structure.

Other suitable ribozymes include sequences from RNase P with RNA cleavage activity (Yuan et al., 1992, Yuan and Altman, 1994, U.S. Pat. Nos. 5,168,053 and 5,624,824), hairpin ribozyme structures (Berzal-Herranz et al., 1992; Chowrira et al., 1993) and Hepatitis Delta virus based ribozymes (U.S. Pat. No. 5,625,047). The general design and optimization of ribozyme directed RNA cleavage activity has been discussed in detail (Haseloff and Gerlach, 1988, Symons, 1992, Chowrira et al., 1994; Thompson et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozyme, the cleavage site is a dinucleotide sequence on the target RNA is a uracil (U) followed by either an adenine, cytosine or uracil (A,C or U) (Perriman et al., 1992; Thompson et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al., (1994) and Lieber and Strauss (1995), each incorporated by reference. The identification of operative and preferred sequences for use in targeted ribozymes is simply a matter of preparing and testing a given sequence, and is a routinely practiced "screening" method known to those of skill in the art.

5. DNA Delivery

In order to effect expression of a gene construct, the expression construct must be delivered into a cell. Several methods for the transfer of genetic constructs into cells are contemplated by the present invention. The particular method employed may depend upon when the DNA construct is to be transferred into the cells. It is generally preferred to introduce the DNA segment to the cells before seeding the cells onto the matrix. In one embodiment of the present invention, the expression construct may consist only of naked recombinant DNA or plasmids. Transfer of the construct may be performed by any of the methods mentioned which physically or chemically permeabilize the cell membrane.

a. Electroporation

In certain preferred embodiments of the present invention, the genetic construct is introduced into cells via electroporation. Electroporation involves the exposure of a suspension of cells and DNA to a high-voltage electric discharge. Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

It is contemplated that electroporation conditions for cells from different sources may be optimized. One may particularly with to optimize such parameters as the voltage, the capacitance, the time and the electroporation media composition. The execution of other routine adjustments will be known to those of skill in the art.

b. Particle Bombardment

Another method for transferring a naked DNA construct into cells involves particle bombardment. This method depends on the ability to accelerate DNA-coated microprojectiles to a high velocity allowing them to pierce cell membranes and enter cells without killing them (Klein et al., 1987). The microprojectiles used have consisted of biologically inert substances such as tungsten, platinum or gold beads. It is contemplated that in some instances DNA precipitation onto metal particles would not be necessary for DNA delivery to a recipient cell using particle bombardment. It is contemplated that particles may contain DNA rather than be coated with DNA. Hence it is proposed that DNA-coated particles may increase the level of DNA delivery via particle bombardment but are not, in and of themselves, necessary.

Several devices for accelerating small particles have been developed. One such device relies on a high voltage discharge to generate an electrical current, which in turn provides the motive force (Yang et al., 1990). Another method involves the use of a Biolistic Particle Delivery System, which can be used to propel particles coated with DNA through a screen, such as stainless steel or Nytex screen, onto a filter surface covered with cells in suspension. The screen disperses the particles so that they are not delivered to the recipient cells in large aggregates. It is believed that a screen intervening between the projectile apparatus and the cells to be bombarded reduces the size of projectile aggregates and may contribute to a higher frequency of transformation by reducing the damage inflicted on the recipient cells by projectiles that are too large.

For the bombardment, cells in suspension are preferably concentrated on filters, or alternatively on solid culture medium. The cells to be bombarded are positioned at an appropriate distance below the macroprojectile stopping plate. If desired, one or more screens are also positioned between the acceleration device and the cells to be bombarded.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity or either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of primordial germ cells.

Accordingly, it is contemplated that one may wish to adjust various of the bombardment parameters in small scale studies to fully optimize the conditions. One may particularly wish to adjust physical parameters such as gap distance, flight distance, tissue distance and helium pressure. One may also optimize the trauma reduction factors by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art.

c. Viral Transformation i. Adenoviral Infection

One method for delivery of the transgenic constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a transgenic construct that has been cloned therein.

The vector comprises a genetically engineered form of adenovirus. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

ii. AAV Infection

Adeno-associated virus (AAV) is an attractive vector system for use in the present invention as it has a high frequency of integration and it can infect nondividing cells, thus making it useful for delivery of genes into mammalian cells in tissue culture (Muzyczka, 1992). AAV has a broad host range for infectivity (Tratschin, et al., 1984; Laughlin, et al., 1986; Lebkowski, et al., 1988; McLaughlin, et al., 1988), which means it is applicable for use with the present invention. Details concerning the generation and use of rAAV vectors are described in U.S. Pat. No. 5,139,941 and U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt, et al., 1994; Lebkowski, et al., 1988; Samulski, et al., 1989; Shelling and Smith, 1994; Yoder, et al., 1994; Zhou, et al., 1994; Hermonat and Muzyczka, 1984; Tratschin, et al., 1985; McLaughlin, et al., 1988) and genes involved in human diseases (Flotte, et al., 1992; Luo, et al., 1994; Ohi, et al., 1990; Walsh, et al., 1994; Wei, et al., 1994). Recently, an AAV vector has been approved for phase I human trials for the treatment of cystic fibrosis.

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski, et al., 1989; McLaughlin, et al., 1988; Kotin, et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994a; Clark et al., 1995). Cell lines carrying the rAAV DNA as an integrated provirus can also be used (Flotte et al., 1995).

iii. Retroviral Infection

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a transgene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

iv. Other Viral Vectors

Other viral vectors may be employed as constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

d. Calcium Phosphate Co-Precipitation or DEAE-Dextran

In other preferred embodiments of the present invention, the transgenic construct is introduced to the cells using calcium phosphate co-precipitation. Mouse primordial germ cells have been transfected with the SV40 large T antigen, with excellent results (Watanabe et al., 1997). Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

e. Direct Microinjection or Sonication Loading

Further embodiments of the present invention include the introduction of the transgenic construct by direct microinjection or sonication loading. Direct microinjection has been used to introduce nucleic acid constructs into Xenopus oocytes (Harland and Weintraub, 1985), and LTK fibroblasts have been transfected with the thymidine kinase gene by sonication loading (Fechheimer et al., 1987).

f. Liposome Mediated Transformation

In a further embodiment of the invention, the transgenic construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a transgenic construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1.

g. Adenoviral Assisted Transfection

In certain embodiments of the present invention, the transgenic construct is introduced into the cell using adenovirus assisted transfection. Increased transfection efficiencies have been reported in cell systems using adenovirus coupled systems (Kelleher and Vos, 1994; Cotten et al., 1992; Curiel, 1994), and the inventors contemplate using the same technique to increase transfection efficiencies.

h. Receptor Mediated Transfection

Still further constructs that may be employed to deliver the transgenic construct to the target cells are receptor-mediated delivery vehicles. These take advantage of the selective uptake of macromolecules by receptor-mediated endocytosis that will be occurring in the target cells. In view of the cell type-specific distribution of various receptors, this delivery method adds a degree of specificity to the present invention. Specific delivery in the context of another mammalian cell type is described by Wu and Wu (1993; incorporated herein by reference).

Certain transgenic delivery constructs comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Ferkol et al., 1993; Perales et al., 1994; Myers, EPO 0273085), which establishes the operability of the technique.

In other embodiments, the DNA delivery vehicle component may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the delivery vehicles may be a liposome itself, which will preferably comprise one or more lipids or glycoproteins that direct cell-specific binding. For example, Nicolau et al. (1987) employed lactosyl-ceramide, a galactose-terminal asialoganglioside, incorporated into liposomes and observed an increase in the uptake of the insulin gene by hepatocytes. It is contemplated that the transgenic constructs of the present invention can be specifically delivered into the target cells in a similar manner.

6. Homologous Recombination

Although genetic transformation tends to be quite efficient, it is also accompanied by problems associated with random insertion. Random integration can lead to the inactivation of essential genes, or to the aberrant expression of the introduced gene. Additional problems associated with genetic transformation include mosaicism due to multiple integrations, and technical difficulties associated with generation of replication defective recombinant viral vectors.

Some of these drawbacks can be overcome by the utilization of a technique known as homologous recombination (Koller and Smithies, 1992). This technique allows the precise modification of existing genes, overcomes the problems of positional effects and insertional inactivation, and allows the inactivation of specific genes, as well as the replacement of one gene for another. Methods for homologous recombination are described in U.S. Pat. No. 5,614,396, incorporated herein in its entirety by reference.

Thus a preferred method for the delivery of transgenic constructs involves the use of homologous recombination. Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, a site for integration is selected within the host cell. Sequences homologous to the integration site are then included in a genetic construct, flanking the selected gene to be integrated into the genome. Flanking, in this context, simply means that target homologous sequences are located both upstream (5') and downstream (3') of the selected gene. These sequences should correspond to some sequences upstream and downstream of the target gene. The construct is then introduced into the cell, thus permitting recombination between the cellular sequences and the construct.

As a practical matter, the genetic construct will normally act as far more than a vehicle to insert the gene into the genome. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, this technique may be used to "knock-out" (delete) or interrupt a particular gene. This is accomplished by including a mutated or vastly deleted form of the heterologous gene between the flanking regions within the construct. The arrangement of a construct to effect homologous recombination might be as follows:

... vector•5'-flanking sequence•selected gene•selectable marker gene•flanking sequence-3'•-vector ...

Thus, using this kind of construct, it is possible, in a single recombinatorial event, to (i) "knock out" an endogenous gene, (ii) provide a selectable marker for identifying such an event and (iii) introduce a transgene for expression.

Another refinement of the homologous recombination approach involves the use of a "negative" selectable marker. One example of the use of the cytosine deaminase gene in a negative selection method is described in U.S. Pat. No. 5,624,830. The negative selection marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

H. Kits

All the essential materials and reagents required for the various aspects of the present invention may be assembled together in a kit. The kits of the present invention also will typically include a means for containing the vials comprising the desired components in close confinement for commercial sale such as, e.g., injection or blow-molded plastic containers into which the desired vials are retained. Irrespective of the number or type of containers, the kits of the invention are typically packaged with instructions for use of the kit components.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Isolation and Expansion of Pulp-derived Fibroblasts

Cells were explanted and propagated from adult human dental pulps, as described by Rutherford et. al. (1992a). Teeth are sectioned into coronal and root fragments and the pulps extirpated with a spoon excavator. This is best done within 24 hours of extraction. If the pulp tissues cannot be harvested immediately, it is best to store the teeth at 4° C. submerged in DMEM supplemented with penicillin, streptomycin and neomycin at three times normal concentration (3×).

The tissues are suspended in DMEM, 10% fetal bovine serum, supplemented with penicillin, streptomycin, and neomycin (3×) and minced to pieces approximately 1–2 mm$^2$, and placed into 25 ml tissue culture flasks. When sufficient numbers of cells have migrated from the cultured tissue pieces (explants) and proliferated so as to nearly cover the surface of the flask, the cultures are harvested, diluted, and placed into more vessels or concentrated and cryopreserved.

Cells were then cultured in DMEM (GIBCO; Grand Island, N.Y.) supplemented with penicillin/streptomycin (GIBCO), and 10% fetal calf serum (Hyclone; Logan, Utah). Standard cell culture methods were employed. Cells between passages 5 to 8 were used in all studies.

EXAMPLE II

Cell Seeding and Culture on Synthetic Matrices

Cells were seeded onto a non-woven matrix (thickness=3 mm; bulk density=50 mg/cc) formed from polyglycolic acid (PGA) fibers (12 μm in diameter) (Albany Intl.; Taunton Mass.).

The PGA fibers were prepared by extrusion of molten polymer, which was subsequently drawn out and annealed to maximize the crystallinity. The fibers were then cut, typically into 2 inch lengths, and the cut fibers were crimped. The crimped fibers were then assembled into a mat with the fibers randomly arranged. Fiber mats were then "needled", using a board of needles so that the fibers became entangled. The needled mats were then pressed with a heated platen to produce a product with the desired thickness and bulk density.

Matrices with desired dimensions are then cut and sterilized prior to use. A variety of sterilization techniques are possible, including γ-radiation and the use of ethylene oxide.

Cells, confluent in tissue cultured flasks, were rinsed with phosphate buffered saline, and incubated with 0.05% trypsin/0.5 mM EDTA to remove adherent cells. Cells from multiple flasks were pooled, and the cells concentrated to $5\times10^6$ cells/ml in the tissue culture medium. Each PGA scaffold (1×1 cm square) was placed in a well of a 6-well dish (Fisher Sci.), and seeded with 0.25 ml of the cell suspension.

Seeded scaffolds were placed in an incubator (5% $CO_2$, 37° C.) for 30 minutes to allow cell adhesion, and 2 ml of tissue cultured medium was then added to each scaffold. Alternatively, $1\times10^6$ cells/ml in 5 ml of tissue culture medium was incubated with the scaffold for 24 hours by stirring in a spinner flask at 20–30 rpm. Scaffolds were cultured for time periods ranging from 1 to 60 days.

EXAMPLE III

Tissue Regeneration

A. Analytical Methods

Gross measurements were made of the cell-polymer constructs at each time point. Samples were prepared for visualization with a scanning electron microscope by fixing with a 1% solution of glutaraldehyde, dehydrating in methanol, and sputter coated (Desk II; Denton Vacuum, Cherry Hill, N.J.) with gold. Photomicrographs were taken on Polaroid™ 55 film. Samples were prepared for sectioning and staining by fixing with a solution of 3.7% formalin in phosphate buffered saline. Thin sections (5 $\mu$m) were cut and stained with hematoxylin and eosin using standard techniques.

The density of cells in histological sections of cell-polymer constructs and native pulp tissue (adult third molars) was determined by counting the number of cellular nuclei per area. Photomicrographs were taken with Kodak Gold™ film.

The DNA content of cell-polymer constructs was determined using a variation of a dye binding assay (Kim et al., 1988). In brief, cell-polymer constructs were flash frozen in liquid nitrogen, lyophilized, and stored at –70° C. The samples were subsequently digested in a solution of 0.5 mg/ml Proteinase K (Sigma; St. Louis Mo.), 1% SDS, 50 mM Tris-HCl, 0.1M EDTA, 0.2M NaCl at a pH of 9.0. The digestion was carried out at 55° C. for 6 hr with occasional gentle agitation. The DNA content in digested samples was determined by assaying the binding of a dye, Hoechst 33258, that specifically binds DNA (Kim et. al., 1988) with a fluorimeter (DynaQuant 2000; Hoefer Sci. Inst.; San Francisco Calif.). Calibration of the fluorimeter was performed with known concentrations of calf thymus DNA (Hoefer Sci. Inst.), and a calibration curve was constructed for this assay using known numbers of cultured cells.

Cell densities were determined by dividing the number of cells in each construct (determined with DNA assay) by the volume of the tissue (determined with gross measurement).

B. Results

The polymer scaffolds utilized as synthetic extracellular matrices were comprised of a non-woven array of polyglycolic acid fibers (FIG. 1).

Figure 2:
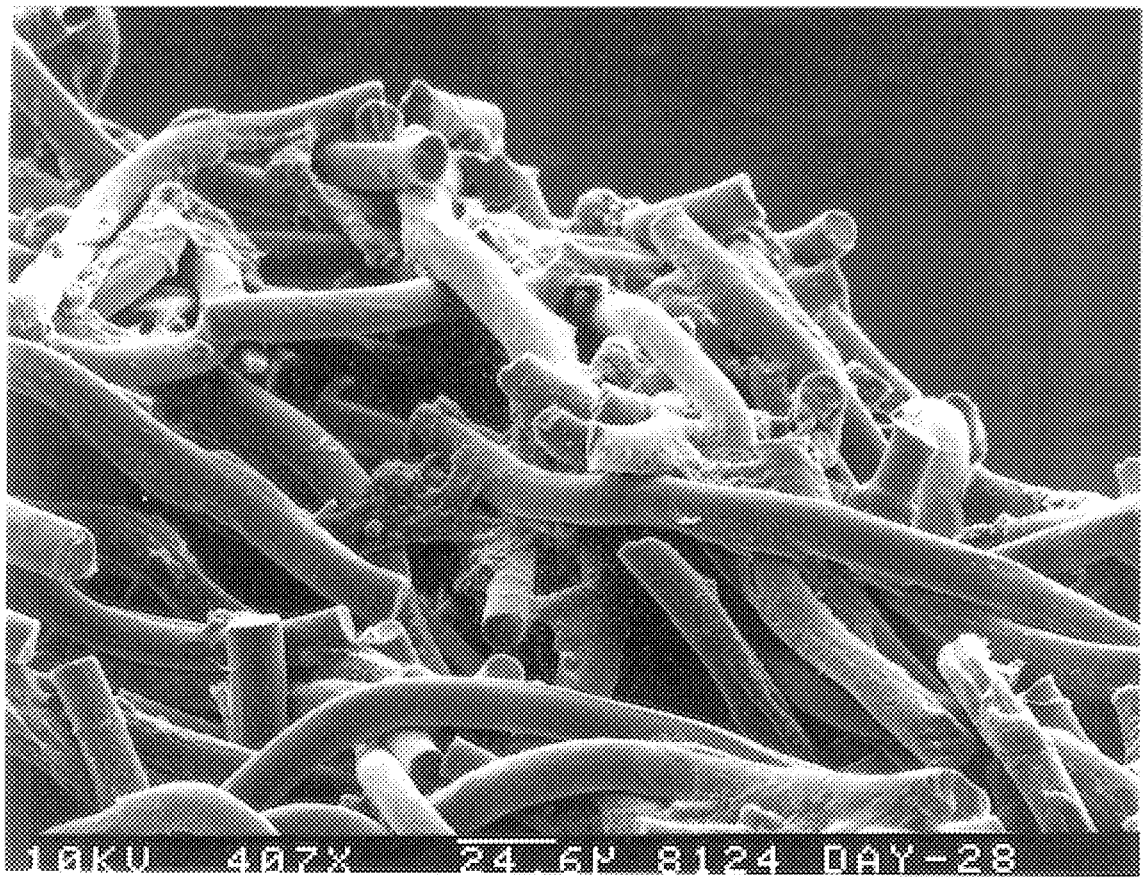
FIG. 2. Photomicrograph of pulp-derived fibroblasts seeded on polymer matrix. Cell-polymer constructs were visualized using a scanning electron microscope, and size bars are shown on the photomicrographs.

Pulp-derived fibroblasts adhered to the polyglycolic acid fibers of the polymer mesh following cell seeding, spread extensively over the fibers and spanned the polymer fibers (FIG. 2). Quantitation of the number of adherent cells after one day in culture revealed that $2.6\pm0.8\times10^5$ cells were present in each scaffold. This corresponds to an initial cell density of approximately $9\times10$ cells/ml.

Figure 3:
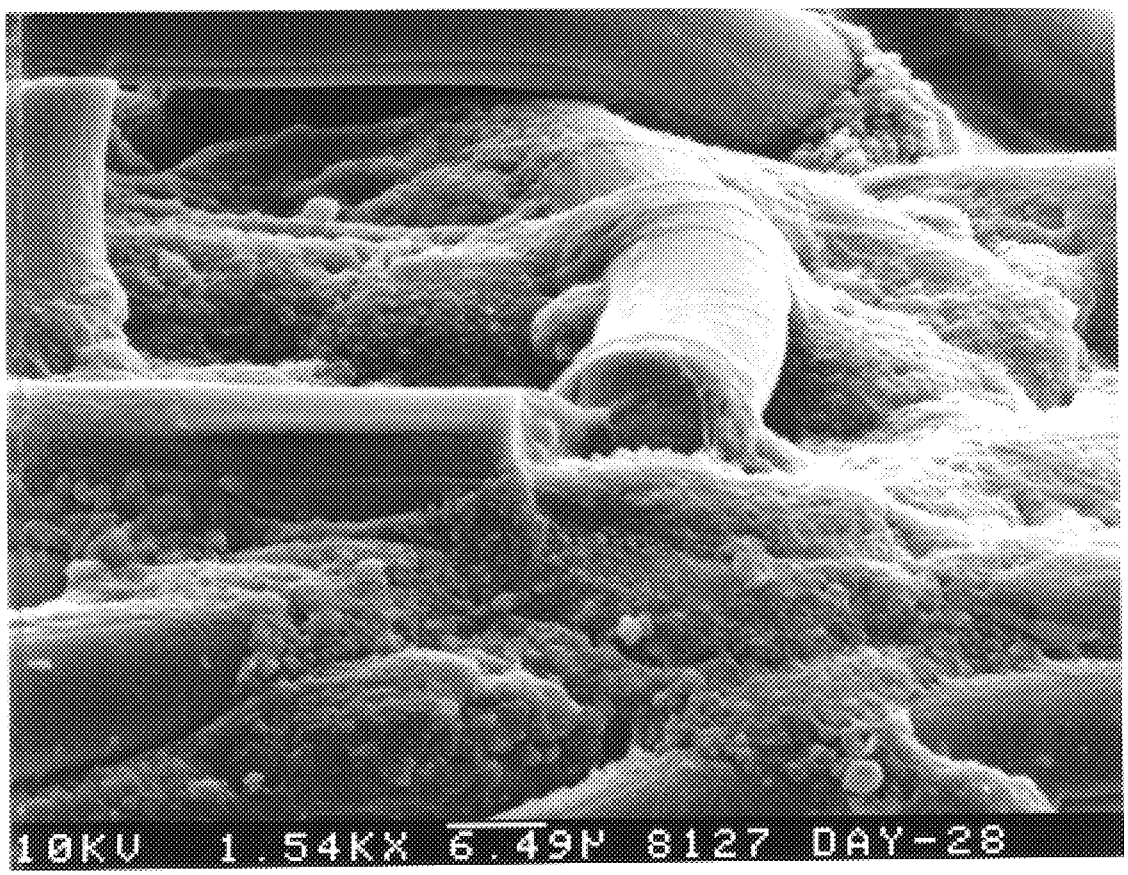
FIG. 3. Photomicrograph of pulp-derived fibroblast filling the interstices between polymer fibers. Cell-polymer constructs were visualized using a scanning electron microscope, and size bars are shown on the photomicrographs.
Figure 4A:
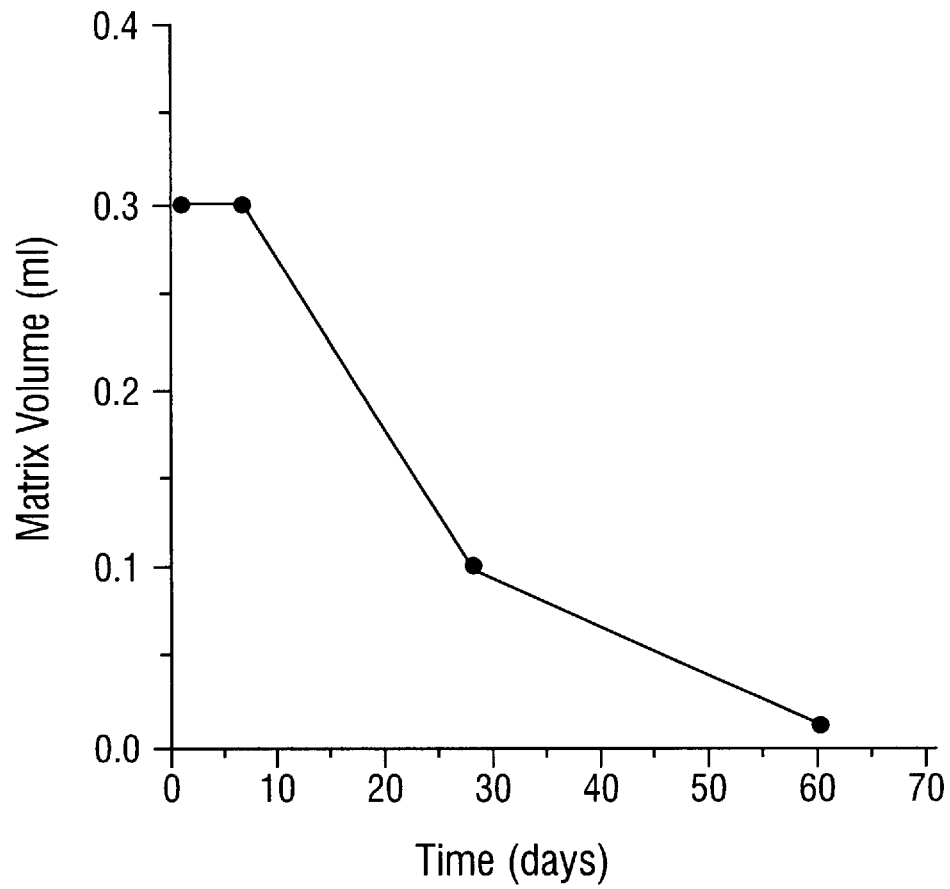
FIG. 4. Change in the cell density of cell-polymer constructs over time in culture. Values represent the mean calculated from 2–4 samples at each time point.
Figure 4B:
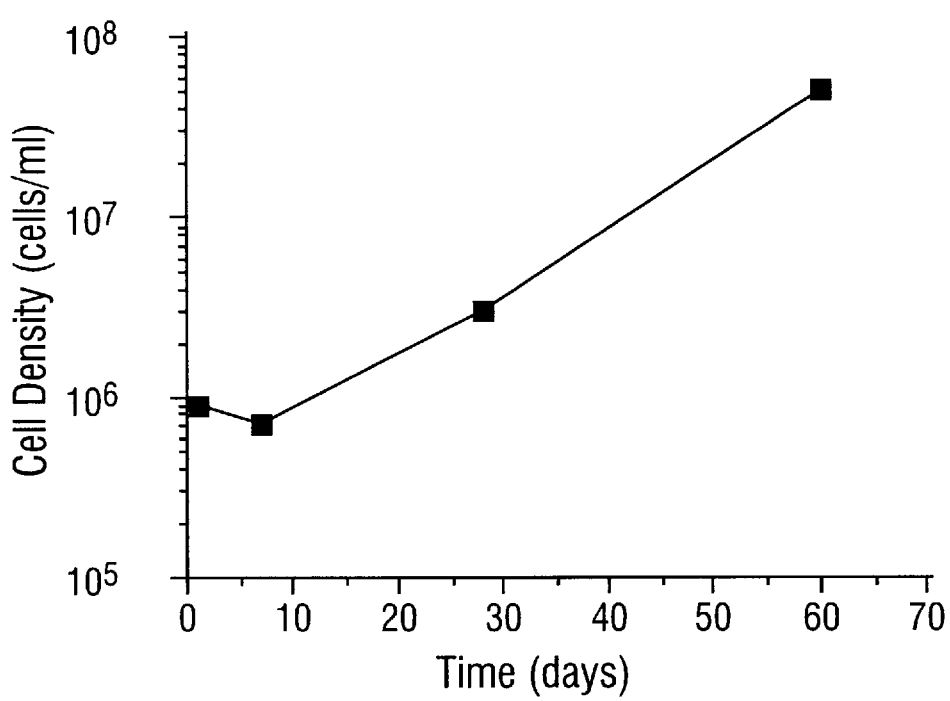

The cells proliferated on the scaffolds over time, and ultimately occupied the spaces between polymer fibers (FIG. 3). Calculation of the cellular density in these tissues over time revealed an increase of almost two orders of magnitude to a final density of $4.6\times10^7$ cells/ml at 60 days (FIG. 4).

The mean cellularity calculated from histological cross-sections of 3 freshly extracted pulp tissues was $1500\pm400$ cells/mm$^2$, while the engineered pulp tissues had a mean cellularity of $330\pm50$ and $2700\pm1100$ cells/mm$^2$ after 28 and 60 days, respectively, in culture. Thus, the cellularity of the engineered tissues was in the same range as the equivalent adult tissue.

Photomicrographs of histological sections of engineered pulp tissue stained with hematoxylin and eosin showed a gross similarity to normal adult pulp tissue.

EXAMPLE IV

Biodegradable Polymer Matrices

Synthetic, biodegradable polymers are used as they are attractive scaffold materials that can be readily produced with a wide range of reproducible properties and structures.

A. Structural Materials

1. PGA and PLA

Aliphatic polyesters of the poly($\alpha$-hydroxy acids) have the general formula —[—O—CH(R)—CO—]— which derive from corresponding HO—CH(R)—COOH where R=H in the case of glycolic acid (GA) and R=CH3 in the case of lactic acid (LA), the latter being chiral, i.e., D- or L-isomer is possible. These polymers have been used in bone osteosynthesis and reconstruction (Vert et al., 1984) and in drug delivery (Gombotz and Pettit, 1995).

a. Synthesis

PGA and PLA can be prepared by two different routes, namely, polycondensation and ring opening polymerization (ROP). Generally, the simple polycondensation is less expensive, but the resulting polymers have low and uncontrolled molecular weight and it is difficult to prepare copolymers (Gilding and Reed, 1979, Kricheldorf and Kreiser-Saunders, 1996). It is believed that the antimony trioxide catalyst typically used to effect polycondensation acts as both polymerizing and depolymerizing agent. Moreover, glycolic and lactic acids have a great tendency to cyclodimerize under these conditions and this renders simple polycondensation an unsuitable method.

The preferred method for producing high molecular weight polymers is ROP of the cyclic dimer, glycolide (and/or lactide). Depending on the catalyst involved, three different mechanisms have been reported: cationic, anionic and insertion. Among these, the insertion mechanism using metal alkoxides or carboxylates is the most desirable pathway and is the choice in commercial production (Frazza and Schmitt, 1971). Typical examples of catalysts of this class are aluminum, zinc, titanium, zirconium, antimony, tin(IV) and tin(II) alkoxides or carboxylates.

The insertion mechanism allows the preparation of high molecular weight polylactides without racemization up to temperatures above 150° C. (Kricheldorf and Kreiser-Saunders, 1996). The mechanism of ROP of lactones has been reviewed by Penczek and Slomkowski (1989). The tin catalyst, tin(II) octoate, was used extensively because of its acceptance by the FDA as a food stabilizer.

The polymerization of glycolide can be carried out in bulk at 220° C. for 4 h, at which time a 96% conversion and molecular weights from $10^4$ to $10^6$ have been reported. Copolymerization of glycolide with lactide has also been investigated. The reactivity ratios at 200° C. have been found to be 2.8 for glycolide and 0.2 for lactide. This indicates that copolymers of glycolic and lactic acids will have broad compositional ranges, with glycolide always being preferentially polymerized at low conversions and lactide being incorporated to ever-increasing extents as the glycolide is depleted (Gilding and Reed, 1979).

During the advanced stages of most ROPs, additional reactions such as ester-ester interchange and chain unzipping may take place. The extents of these reactions are affected by the reactivity of the ester moieties. These events can have a significant effect on the composition of the final product. Due to the ester exchange, cyclic dimer, trimer and, to a less extent, cyclic oligomers could be found along with the reformed monomer. In the case of copolymerization, additional randomization of the polymer chain would occur as a consequence of the ester-ester exchange of different ester moieties (Shalaby and Johnson, 1994). The microstructures of PLGA copolymers can be determined by both proton and carbon NMR spectroscopy (Ksaperczyk, 1996). It has been reported that the block lengths increase and, at the same time, the extent of transesterification decreases with decreasing polymerization temperature.

b. Properties of PGA and PLA Tissue Engineering
(1) Mechanical Strength and Morphology PGA was first developed as the synthetic absorbable suture, Dexon (Frazza and Schmitt, 1971). PGA has high crystallinility, a high melting point and low solubility in organic solvents (Table 7). The polymer (fiber grade, inherent viscosity=1.2–1.6 dL/g in hexafluoro-isopropanol) can be spun into multifilament or monofilament yarns for the production of braided and monofilament sutures, respectively (Frazza and Schmitt, 1971; Chujo et al., 1967). A typical suture braid has a tensile strength of 80–100 Kpsi (Table 8). Owing to the hydrophilic nature of PGA, Dexon sutures tend to lose their mechanical strength rapidly (50%) over a period of 2 weeks and are absorbed in about 4 weeks after implantation (Frazza and Schmitt, 1971; Reed and Gilding, 1981; Katz and Turner, 1970).

TABLE 7

Crystallinity and Thermal Properties of PGA, PLA and Copolymers

|  | % Crystallinity | Tm | Tg |
|---|---|---|---|
| PGA | 46–52 | 225 | 36 |
| 90:10 PGLA | 40 | 210 | 37 |
| 50:50 PGLA | 0 | None | 55 |
| PLA | 37 | 185 | 57 |
| dl-PLA | 0 | None | N/A |

Adapted from Wong and Mooney, 1997.

TABLE 8

Mechanical Properties of PGA and 90:10 PGLA

|  | PGA (Dexon) | 90:10 PGLA (Vicryl) |
|---|---|---|
| Tensile strength (Kpsi) | 106 | 95 |
| Knot strength (Kpsi) | 65 | 63 |
| Elongation (%) | 24 | 25 |

Adapted from Wong and Mooney, 1997.

The presence of an extra methyl group poly(L-lactic acid) (PLA) or poly(D-lactic acid) (d-PLA) makes them more hydrophobic than PGA. For instance, films of PLA only take up approximately 2% water (Gilding and Reed, 1979). In addition, the ester bond in PLA is less labile to hydrolysis due to steric hindrance of the methyl group. Therefore, PLA degrades much slower than PGA (Reed and Gilding, 1981) and has higher solubility in organic solvents.

PLA is employed much more often than d-PLA, since the hydrolysis of PLA yields L-lactic acid which is the naturally occurring stereoisomer of lactic acid. Whereas PLA possesses about 37% crystallinity, the optically inactive poly (DL-lactic acid) (dl-PLA) is amorphous. The difference in the crystallinity of dl-PLA and PLA has important practical outgrowths. For instance, the amorphous dl-PLA is usually considered in drug delivery application where a homogeneous dispersion of the active species within a monophasic matrix is desired (Engelberg and Kohn, 1991). However, the semicrystalline PLA is preferred in case where high mechanical strength and toughness are required, for example, in orthopedic devices (Leenslag et al., 1987, Vainionpaa et al., 1987; Hay et al., 1988). It is pertinent to note that γ-irradiation of PLA causes chain scission, crosslinking and a decrease in crystallinity (Gupta and Deshmuth, 1983). Therefore, caution should be taken when sterilizing the polymer matrices by γ-irradiation.

To widen the range of materials properties exhibited by PGA, copolymers of GA and LA (PLGA) have been studied. Whereas PGA is highly crystalline, PLGA usually exhibit lower crystallinity and Tm (Gilding and Reed, 1979). For example, while PGA and PLA are partially crystalline, 50:50 PLGA is entirely amorphous. These morphological changes result in an increase in the rates of hydration and hydrolysis. Thus, copolymers tend to degrade more rapidly than PGA and PLA (Mooney et al., 1995b).

(2) Biodegradation

The degradation mechanism of PGA and copolymers in vitro is usually regarded as bulk erosion (Gombotz and Pettit, 1995). This is evident from the fact that a significant molecular weight decrease usually precedes monomer release from the polymer samples. This mechanism of degradation may be undesirable in certain applications. The relatively rapid release of large quantities of acid (glycolic and/or lactic acids) may lead to a local acidosis if a large mass of these polymers is present in a concentrated form (e.g., a solid pin). However, highly porous scaffolds are typically utilized in tissue engineering applications, and contain a relatively low mass of polymer per unit volume The highly porous structure of the scaffolds assists cell penetration as well as polymer degradation (Mooney et al., 1994b; 1995a; 1995b). The rate of degradation will be affected by the morphology of the scaffold and the large surface areas speed up the diffusion of water molecules into the bulk of the polymers when they are placed in an aqueous environment (e.g., in vivo).

The polymers undergo random chain scission by simple hydrolysis of the ester bond linkage and the monomer diffuses out of the polymer bulk into water (Reed and Gilding, 1981). It is important to note that loss of mechanical strength of PGA is faster when the polymer is incubated at a temperature higher than its Tg. This indicates that the glassy state protects PGA from hydrolysis since all short term chain motions are frozen. Water diffusion, and therefore hydrolysis, is more facile at temperatures above Tg. It is also relevant to mention that the Tg's of PGA and some copolymers are very close to the physiological temperature. Polymeric materials may undergo significant structural change after implantation due to water penetration and loss of mechanical strength. It is also speculated that enzymatic action may partially contribute to biodegradation of PGA in vivo.

The chemical compositions and the ratio of monomers used in the polymerization reaction strongly influence the degradation characteristics of the copolymer. The degradation rates for copolymers of GA and LA have been shown to be influenced by factors which affect polymer chain packing, i.e., crystallinity, and hydrophobicity. Since degradation is induced by hydrolysis, a crystalline structure or hydrophobic polymer composition disfavors dissolution and degradation.

Gombotz and Pettit (1995) summarized the specific factors affecting copolymer crystallinity and hydrophobicity: (i) the ratio of lactide to glycolide monomer in the copolymer, (ii) the stereoregularity of the monomer units in the polymer affects polymer chain packing, (iii) randomness of lactide and glycolide decrease the ability of chains to crystallize, and (iv) low molecular weight polymers degrade faster than high molecular weight polymers, especially when the end groups are free acid rather than capped with ester or other groups. Mass loss from polymer samples comprised of PLA is insignificant in the experimental time period (~50 weeks). However, those comprised of copolymers of GA and LA or dl-PLA degrade much faster (the higher the glycolic acid content, the higher the degradation rate) (Mooney et al., 1995b).

The presence of monomers and low molecular weight cyclic oligomers in absorbable polymers should be avoided, for they degrade much more rapidly than the polymers and can lead to undesirable chemical and biological effects. (Shalaby and Johnson, 1994) It has been shown that polylactide with increased monomer content exhibits a higher rate of bioabsorption and a more drastic decrease of molecular weight. (Nakamura et al., 1989)

2. Other Chemistries for Tissue Engineering
  a. Chemical Modifications of PGA/PLA Little modification of these polymers is possible because there are no other functional groups on the side chain, except the methyl of the lactic acid residue. One possibility to modify the properties of these polymers is to form copolymers with residues having more diverse side chain structures, e.g., lysine.

A new monomer, 3-(Ne-benzoxycarbonyl-L-lysyl)-6-L-methyl-2,5-morpholinedione, was bulk copolymerized with L,L-lactide in the presence of stannous octoate as catalyst using the same ROP techniques utilized for lactide and glycolide (Barrera et al., 1993). The lysine content was determined by NMR technique to be approximately 1.3 mole %.

A poly(lactide-co-lysine) functionalized with peptide containing the arginine-glycine-aspartate (RGD) sequence was prepared by removal of the benzyoxycarbonyl protecting group on the lysyl residue and peptide coupling. The peptide concentration was found to be approximately 3.1 mmol/g which could be translated into a peptide surface density of 310 fmol/cm$^2$. A surface density of as low as 1 fmol/cm$^2$ of an RGD peptide has been previously determined to promote cell adhesion to an otherwise nonadherent surface (Massia and Hubbell, 1991). Therefore, by carefully processing the copolymer, biodegradable films with cell adhering properties can be prepared from the copolymer of lactide and lysine.

Other strategies have also been employed to widen the properties of polylactides. For example, PLA has also been synthesized as an acrylic macromonomer and subsequently copolymerized with polar acrylic monomers (e.g., 2-hydroxyethylmethacrylate) (Barakat et al., 1996). These polymers were studied as amphiphilic graft copolymers for drug delivery purposes. The surface properties of these polymers may be controlled by the ratio of the PLA graft length and copolymer content, and can be potentially used to control the drug release profile and biodistribution. Other examples of this approach include grafting PLA blocks to geraniol and pregnenolone (Kricheldorf and Kreiser-Saunders, 1996).

b. Other Polyesters

Properties of polyesters can also be varied by changing the structures of the polymer backbones. Polycaprolactone (PCL), having two more carbon atoms than PGA on the polymer backbone, has been studied as a substrate for biodegradation and as a matrix for drug release systems (Huang, 1989). Its degradation in vivo is much slower than PGA, therefore, it is suitable for controlled release devices with long in vivo life times (1–2 years). PCL can be prepared by anionic ring opening polymerization of ε-caprolactone using metal hydroxide initiators (Jerome and Teyssie, 1989).

Poly-β-hydroxy acid can be prepared by both cationic and anionic ring opening polymerizations (Penczek and Slomkowski, 1989; Jerome and Teyssie, 1989). For example, 100% syndiotactic poly(β-DL-hydroxybutyrate) has been prepared by treating the corresponding lactone with cyclic dibutyltin initiators to yield high molecular weight polymers (Kricheldorf and Lee, 1995). Bacteria also produce the chiral, isotactic poly(β-D-hydroxybutyrate) as a highly crystalline biopolymer (Holmes, 1988).

Numerous analogs of poly(β-hydroxy acid) have been synthesized either chemically by the ring opening polymerization or biologically by feeding unusual carbon sources to bacteria (Timmins and Lenz, 1994). The microbial synthesis of polyesters has been reviewed by Gross (1994). Due to their biocompatibility and biodegradability, different blends of polycaprolactone, poly(β-hydroxybutyrate) and other polymers have been fabricated for medical devices (Yasin and Tighe 1992), drug delivery applications (Wang, 1989) and cell microencapsulation (Giunchedi et al., 1994; Embleton and Tighe, 1993).

Surface-eroding polymer matrices are attractive for a variety of tissue engineering applications. The monomer release would be steady over the lifetime of the matrices in contrast to PLA and PGA. In addition, the gradual loss of polymer from the surface of the scaffold may allow the surrounding tissue to serially fill the space vacated by the polymer.

Polyorthoesters are an example of surface-eroding polymers. The hydrophobic character of the polymer limits water penetration and hydrolysis to only the exterior surface of the polymer matrix (Heller, 1985). Thus the surface erosion is much faster than that of the bulk. The chemical and physical properties of polyorthoesters have been reviewed (Heller and Daniels, 1994) and depend on the chemical structures of the constituent monomers. For example, reaction of bis (ketene acetal) with rigid trans-cyclohexane dimethanol produce a rigid polymer with a Tg of 110° C., whereas that of the flexible diol 1,6-hexanediol produces a soft material having a Tg of 20° C. Mixture of the two diol results in polymers having intermediate Tg.

Degradation of the polymers is acid-induced, and degradation rates can be increased by adding acidic excipients or by increasing the hydrophilicity of the polymer matrix. Conversely, degradation can be retarded by using basic excipients such as Mg(OH)$_2$ (Gombotz and Pettit, 1995). Current applications of these polymers include sustained drug delivery as well as hard and soft tissue fixation (Heller and Daniels, 1994).

Polyorthoformate, polycarbonate, poly(oxyethylene glycolate), poly(1,4-butylene diglycolate) and polyurethane are other biodegradable polymers that may have applications in tissue engineering. Many of these polymers have been previously been utilized as drug delivery matrices (Huang, 1989).

There are therefore a large number of polyesters and analogs that are biodegradable. Their mechanical properties can be controlled largely by the chemical structures of the constituent building blocks and can be varied from tough to elastic. The biocompatibility of these polymers is presumed to result from non-toxic degradation products. Bioactive elements can be attached to this class of materials in order to mimic natural extracellular matrix molecules.

c. Polypeptides

Proteins, one of the most important biomolecules in nature, belong to this class of biopolymers. However, polypeptides of a single amino acid or copolymers of were generally regarded as impractical industrial materials (Nathan and Kohn, 1994). Amino acid N-carboxyanhydrides were prepared as the monomeric starting materials, and this added considerably to the cost of all polypeptides. These polymers were thus expensive even if they were derived from cheap amino acids. In addition, it was almost impossible to control the sequence of the protein polymers using random copolymerization techniques. Most polypeptides are insoluble in common organic solvents. The need for exotic solvent systems to process these materials combined with their thermal instability made them poor engineering materials.

A number of recent approaches may, however, bypass these difficulties. Advances in genetic engineering have enabled investigators to obtain protein polymers by inserting DNA templates of predetermined sequences into the genome of bacteria. Collagen-like, silk-like, and silk-elastin-like proteins have been synthesized by this technique (Goldberg et al., 1989; Cappello et al., 1990; McGrath et al., 1992).

The general concept (O'Brien, 1993) involves the incorporation of amino acid sequences with desired properties, e.g., cell adhesion or elasticity, into the protein polymers to produce materials of predetermined structure and controlled properties. For example, a cell adhering sequence of RGD has been incorporated into silk-like protein polymers in a manner such that the tripeptide sequence is exposed for cell attachment (Tirrell et al., 1994).

Investigators have also developed chemical synthetic techniques that are complementary to the genetic approach to prepare such materials. For instance, different rigid non-peptide, organic segments have been combined with leucine-glutamine-proline, a sequence of the calcium binding domain of bovine amelogenins, using a completely synthetic approach (Sogah et al., 1994). The advantage of this class of protein-based hybrid polymers is the virtually unlimited choice of building blocks for the polymers. In contrast, genetically engineered proteins can only make use of the 20 natural and a limited number of unnatural amino acids for the construction of polymers.

Rigid organic segments have been used to reduce the conformational flexibility of the peptide chain through the formation of peptide secondary structures (e.g., β-sheet or β-turns). Controlled folding of the polymer backbone has been reported using such ordered building blocks (Wong, 1996). The potential application of these materials to tissue engineering is significant. These synthetic techniques allow precise control of material properties, while maintaining the freedom and flexibility to design protein-like materials with desirable biological and chemical properties. These properties may make this class of materials desirable matrices for tissue engineering applications.

Urry and coworkers have also studied elastin protein-based polymers as biocompatible materials. These polymers, also known as bioelastic materials, are elastomeric polypeptides comprised of the general repeating sequences glycine-any amino acid-glycine-valine-proline (GXGVP). The polymers were synthesized by the self condensation of the activated p-nitrophenol ester of the pentapeptide building blocks (Prasad et al., 1985). The molecular weight of these polymers are considered to be higher than 50 000. The polymers can be cross-linked by γ-irradiation to form an insoluble matrix without detectable residue destruction. Cell adhesion sequences (e.g., RGD) and enzymatic sites have been incorporated into the polymers for cell attachment and catalytic activity studies, respectively. Synthesis utilizing genetic engineering approach has also been reported. These class of polymers have been reported to exhibit excellent biocompatibility (Urry et al., 1995; Urry, 1993).

One specific polypeptide $(GVGVP)_n$ has been shown to undergo an inverse temperature transition in water (Urry, 1988a; Urry, 1988b). The mechanism of such elasticity has been demonstrated to be entropic in nature and is apparently due to the internal chain dynamics of the ordered polypeptide structure. This is contrary to the common belief that the elasticity of elastin, similar to synthetic polymers, is due to random chain network and random end-to-end distances (Alberts et al., 1983). The transition temperature can be controlled by the amino acid composition, pH and phosphorylation, electrochemical, photochemical and chemical reactions of prosthetic groups. Therefore, a device that converts chemical energy into mechanical work can be constructed.

d. Blends, Interpenetrating Networks (IPN) and Composites

Although there are large number of polymer blends described in the literature, only those blends that contain biodegradable polymers and/or natural components will be applicable in the context of oral tissue engineering where the matrix itself is administered along with the tissue. The use of polymer blends or composites (polymeric composite materials) as biomaterials is a concept that nature exploits in assembling ECM in tissue. The ECM of tissues typically contains a composite of different macromolecules and non-macromolecular materials. For example, glycoaminoglycans, which are usually covalently linked to proteins to form proteoglycans, constitutes a gel-like, highly hydrated structure substance in the which the collagen fibers are embedded (Wight et al., 1991; Giusti et al., 1993).

Blends of fibrin and polyurethane have previously been formed by a combined phase-inversion and spray process to produce highly porous small-diameter vascular prostheses. (Giusti et al., 1985, Soldani et al., 1992) These materials exhibit high thermal stability, and their tensile behavior ranged from that of an elastic polyurethane tube to that of a natural blood vessel. Hydrogels of fibrin and poly(vinyl alcohol), blends or IPNs of collagen and poly(vinyl alcohol), blends of hyaluronic acid with poly(vinyl alcohol) or poly (acrylic acid), and blends based on esters of hyaluronic acid have been reported (Giusti et al., 1993). These materials may be suitable for a variety of applications including soft tissue replacement, drug delivery, nerve-guide growth and cardiovascular devices. This class of materials has great potential owing to the large number of readily available synthetic polymers that can be mixed with biopolymers.

B. Immobilization Materials

Immobilization materials are utilized to physically confine active biologic components (e.g., enzymes, proteins, cell organelles and cells) while they are carrying out their biological functions. The choice of matrices for cell immobilization have been reviewed by Scouten (1995).

1. Polysaccharides

Polysaccharides are carbohydrates characterized by the presence of a repeating structure in which the interunit linkages are of the O-glycoside type. The hydrophilicity of polysaccharides, along with the ease in which they can be formed into hydrogels, makes these materials ideal for many tissue engineering applications in which one desires to immobilize cells within a matrix. The variety of saccharides monomers (~200) and the variety of possible O-glycoside linkages result in a diversity of polysaccharide structures and conformations. Polysaccharides may be derived from different sources including plants (starch, cellulose), animal (glycogen), algae and seaweeds (alginate and agarose) and microorganisms. These materials are usually considered as naturally-derived products. However, since polysaccharides are widely utilized as immobilization materials, they are used here as standards to which other synthetic materials are compared.

a. Algal Polysaccharides: Alginate and Agarose

Algal polysaccharides have been the most commonly utilized immobilization materials. This is due to their gentle gelling conditions, widespread availability, and relative biocompatibility. The main starting sources of alginate are species of brown algae (Phaeophyceae). The algae are typically subjected to a number of processing steps to produce pure alginate which is the major polysaccharide present and may comprise up to 40% of the dry weight. It is part of the intracellular matrix and exists, in the native state, as a mixed salt of the various cations found in sea water (e.g., $Mg^{2+}$, $Ca^{2+}$, $Sr^{2+}$, $Ba^{2+}$ and $Na^+$). Due to selectivity of cation binding, the native alginate is mainly found in the insoluble gel form, which results from cross-linking of alginate chains by $Ca^{2+}$.

All alginates are copolymers of D-mannuronate (M) and L-guluronate (G). However, alginates from different algal sources have different compositions, and thus, different physical and mechanical properties. The block length of monomer units, and overall composition of the alginate and molecular weight, determine the properties of alginates. For example, calcium alginates rich in G are stiff materials (Sutherland, 1991).

Alginate selectively binds divalent metal ions such as $Ba^{2+}$, $Sr^{2+}$ and $Ca^{2+}$. The binding selectivity increases with G content, and polymannuronate is essentially non-selective. The calcium ions are, therefore, selectively bound between sequences of polyguluronate residue, and are held between diaxially linked L-guluronate residues which are in the $^1C_4$ chair conformation. The calcium ions are thus packed into the interstices between polyguluronate chains associated pairwise and this structure is named the "egg-box" sequence. The ability to form a junction zone depends on the length of the G-blocks in different alginates. Since the mechanical strength of alginate gels depend on the block lengths and M/G content, there have been efforts to modify the M/G ratio by alginase to increase the G content (Skjak-Braek et al., 1986). It is expected that chemically modified alginate would also produce materials of desirable properties. For example, bacterial alginates that contains acetyl groups generally exhibit different physical and mechanical properties from those of algal sources (Ott and Day, 1995).

Alginate can be gelled under mild conditions, allowing cell immobilization with little damage. Binding of $Mg^{2+}$ and monovalent ions to alginate does not induce gelation of alginate in aqueous solution (Sutherland, 1991). However, exposure of alginate to soluble calcium leads to a preferential binding of calcium and subsequent gelling. These gentle gelling conditions are in contrast to the large temperature or solvent changes typically required to induce similar phase changes in most materials.

Alginates have been utilized as immobilization matrices for cell (Smidsrod and Skjak-Braek, 1990), as an injectable matrix for engineering cartilaginous tissue to treat vesicoureteral reflux in various animal models (Atala et al., 1993 and Atala et al., 1994), and as injectable microcapsules containing islet cells to treat animal models of diabetes (Sun et al., 1984).

The open lattice structure and wide distribution of pore sizes in calcium alginate preclude the controlled release of large molecules (e.g., proteins) from these materials and limits the use of pure alginate for entrapment of whole cells or cell organelles (Smidsrod and Skjak-Braek, 1990). However, alginate membrane can be modified by incorporating other polymeric elements (e.g., lysine, poly(ethylene glycol), poly(vinyl alcohol) or chitosan) (Polk et al., 1994, Kung et al., 1995). These modified systems have been used to control the release of proteins from alginate beads. Haemostatic swabs made of calcium alginate have also been clinically utilized to reduce blood loss during surgical procedures. The calcium ions in alginate may assist the blood clotting process by activating platelets and clotting factor VII (Blair et al., 1990).

Agarose is another type of marine algal polysaccharide. In contrast to alginate, agarose forms thermally reversible gels. Agarose will set at concentrations in excess of 0.1%, depending on the sulfate content, and at temperatures considerably below (~40° C.) the gel-melting temperature (~90° C.). The latter parameter is correlated to the methoxy content. The proposed gel structure is bundles of associated double helices and the junction zones consist of multiple chain aggregations (Yalpani, 1988). Agarose has been used largely in gels for electrophoresis of proteins and nucleic acids. However, agarose gels have also been used as supporting materials for electrophoresis of bacteriophages (Serwer, 1987) and migration studies of leukocytes (Kallen et al., 1977). Although applications in tissue engineering have not been reported, its adjustable gelling behavior may render low temperature melting agarose a suitable injectable and immobilization matrix material.

b. Other Polysaccharides

Microbial polysaccharides are ubiquitous in nature and very abundant biopolymers. They are of interest because of their unusual and useful functional properties. Some of these properties are summarized by Kaplan et al. (1994) as: (i) film-forming and gel-forming capabilities, (ii) stability over broad temperature ranges, (iii) biocompatibility (natural products avoid the release/leaching of toxic metals, residual chemicals, catalyst, or additives), (iv) unusual rheological properties, (v) biodegradability, (vi) water solubility in the native state or reduced solubility if chemically modified, and (vii) thermal processability for some of these polymers. Some examples of microbial polysaccharide are listed in Table 9. It is worthy to note that gellan, one of the microbial polysaccharides, has been investigated as immobilization materials for enzymes and cells (Doner and Douds, 1995).

TABLE 9

Some Polysaccharides Synthesized by Microorganisms

| Polymers[a] | Structure |
| --- | --- |
| Fungal | |
| Pullulan (N) | 1,4-1,6-α-D-Glucan |
| Scleroglucan (N) | 1,3-1,6-α-D-Glucan |
| Chitin (N) | 1,4-β-D-Acetyl glucosamine |
| Chitosan (C) | 1,4-β-D-N-Glucosamine |
| Elsinan (N) | 1,4-1,3-α-D-Glucan |
| Bacterial | |
| Xanthan gum (A) | 1,4-β-D-Glucan with D-mannose; D-glucuronic acid as side groups |
| Curdlan (N) | 1,3-β-D-Glucan (with branching) |
| Dextran (N) | 1,6-α-D-Glucan with some 1,2-1,3-1,4-α-linkages |
| Gellan (A) | 1,4-β-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N = neutral, A = anionic and C = cationic.
Adapted from Wong and Mooney, 1997.

2. Non-Natural Hydrogels
   a. Polyphosphazenes

Polyphosphazenes contain inorganic backbones comprised of alternating single and double bonds between nitrogen and phosphorus atoms, in contrast to the carbon-carbon backbone in most other polymers. The uniqueness of polyphosphazenes stems from the combination of this inorganic backbone with versatile side chain functionalities that can be tailored for different applications. The degradation of polyphosphazenes results in the release of phosphate and ammonium ions along with the side groups (Allcock, 1989; Scopelianos, 1994).

Linear, uncross-linked polymers can be prepared by thermal ring opening polymerization of $(NPCl_2)_3$ and the chloro group replaced by amines, alkoxides or organometallic reagents to form hydrolytically stable, high molecular weight poly(organophosphazenes). Depending on the properties of the side groups, the polyphosphazenes can be hydrophobic, hydrophilic or amphiphilic. The polymers can be fabricated into films, membranes and hydrogels for biomedical applications by cross-linking or grafting (Lora et al., 1991; Allcock et al., 1988; Allcock, 1989). Bioerodible polymers for drug delivery devices have been prepared by incorporating hydrolytic side chains of imidazole (Laurencin et al., 1987) for skeletal tissue regeneration (Laurencin et al., 1993). Non-degradable phosphazenes have been used as denture liner (Razavi et al., 1993). Their use in the present invention is thus particularly contemplated.

b. Poly(vinyl alcohol) (PVA)

PVA is not synthesized directly but is the deacetylated product of poly(vinyl acetate). Polyvinyl acetate is usually prepared by radical polymerization of vinyl acetate (bulk, solution or emulsion polymerizations) (Finch, 1973). PVA is formed by either alcoholysis, hydrolysis or aminolysis processes of poly(vinyl acetate). The hydrophilicity and water solubility of PVA can be readily controlled by the extent of hydrolysis and molecular weight. PVA has been widely used as thickening and wetting agent.

PVA gels can be prepared by cross-linking with formaldehyde in the presence of sulfuric acid (Schwartz et al., 1960). These formaldehyde-cross-linked PVA materials have been used as prosthesis for a variety of plastic surgery applications including breast augmentation (Clarkson, 1960 and Peters and Smith, 1981), diaphragm replacement (Haupt and Myers, 1960) and bone replacement (Camerson and Lawson, 1960). However, a variety of complications were found after long term implantation, including calcification of the PVA (Peters and Smith, 1981).

More recently, PVA was made into an insoluble gel using a physical cross-linking process. These gels were prepared with a repeated freezing-thawing process. This causes structural densification of the hydrogel due to the formation of semicrystalline structures. The use of this gel in drug delivery applications has been reported (Peppas and Scott, 1992; Ficek and Peppas, 1993). However, PVA is not truly biodegradable due to the lack of labile bonds within the polymer bond. Only low molecular weight materials are advisable to be used as implant materials.

c. Poly(ethylene oxide) (PEO)

PEO or polyethylene glycol can be produced by the anionic or cationic polymerization of ethylene oxide using a variety of initiators (Boileau, 1989; Penczek and Kubisa, 1989). PEO is highly hydrophilic and biocompatible, and has been utilized in a variety of biomedical applications including preparation of biologically relevant conjugates (Zalipsky, 1995), induction of cell membrane fusion (Lentz, 1994) and surface modification of biomaterials (Amiji and Park, 1993). Different polymer architectures have been synthesized and some of their applications in medicine have been recently reviewed (Merrill, 1993). For example, PEO can be made into hydrogels by γ-ray or electron beam irradiation and chemical crosslinking (Cima et al., 1995; Belcheva et al., 1996). These hydrogels have been used as matrices for drug delivery and cell adhesion studies.

d. Pluronics

Pluronic polyols or polyoxamers are block copolymers of PEO and poly(propylene oxide and are usually synthesized by anionic polymerization in the form of a ABA triblock using a difunctional initiator (Schmolka, 1972). Pluronics F 127, which contains 70% ethylene oxide and 30% propylene oxide by weight with an average molecular weight of 11,500, is the most commonly used gel-forming polymer matrix to deliver proteins (Gombotz and Pettit, 1995).

This polymer exhibits a reversible thermal gelation in aqueous solutions at a concentration of 20% or more (Schmolka, 1972). Thus, the polymer solution is a liquid at room temperature but gels rapidly in the body. Although the polymer is not degraded by the body, the gels dissolve slowly and the polymer is eventually cleared. This polymer has been utilized in protein delivery (Morikawa et al., 1987; Jushasz et al., 1989) and skin burn treatments (Pautian et al., 1993).

e. PGA-PEO Hydrogels

Although PGA is not water soluble, bioerodible hydrogels based on photopolymerized PGA-PEO copolymers have been synthesized and their biological activities investigated. (Sawhney et al., 1993; Sawhney et al., 1994; Hill-West et al., 1994). Macromonomers having a poly(ethylene glycol) central block, extended with oligomers of α-hydroxy acids (e.g., oligo(dl-lactic acid) or oligo(glycolic acid)) and terminated with acrylate groups were synthesized. These hydrogels were designed to form direct contacts with tissues or proteins following photopolymerization, and act as a barrier.

These gels degrade upon hydrolysis of the oligo(α-hydroxy acid) regions into poly(ethylene glycol), the α-hydroxy acid, and oligo(acrylic acid). The degradation rate of these gels could be tailored from less than 1 day to 4 months by appropriate choice of the oligo(α-hydroxy acid). The macromonomer could be polymerized using non-toxic photoinitiators with visible light without excess heating or local toxicity. The hydrogels polymerized in contact with tissue adhere tightly to the underlying tissue. In contrast, the gels were nonadhesive if they were polymerized prior to contact with tissue. These hydrogels have been utilized in animal models to prevent post-surgical adhesion and thrombosis of blood vessels and initimal thickening following balloon catheterization.

It can thus be seen that there are a large number of synthetic biodegradable polymers that may be used in the oral tissue engineering invention described herein. Established polymer chemistries enable one to tailor properties of the synthetic polymers by using different i) functional groups (either on the backbone or side chain), ii) polymer architectures (linear, branched, comb or star), and iii) combinations of polymer species physically mixed (polymer blends or interpenetrating networks) or chemically bonded (copolymers) (Gombotz and Pettit, 1995). The current preference for PGA and related polyesters is partially due to their established safety in human applications, and the projected approval of the Food and Drug Administration. PLGA can also be used with specific peptide sequences incorporated into the polymer. Polymers constituted of building blocks similar to components of ECM, e.g., carbohydrates and peptides, may also be used.

EXAMPLE V

Fabricating Tubular Matrices

As described above, polymers of lactic and glycolic acid are attractive candidates to fabricate devices to transplant cells and engineer new tissues. These polymers are biocompatible, and exhibit a wide range of erosion times and mechanical properties. This example describes the fabrication and characterization, in vitro and in vivo, of hollow, tubular devices from porous films of various polymers of this family.

Porous films of these polymers were formed using a particulate leaching technique, and sealed around teflon cylinders to form hollow tubular devices. The erosion rate of devices was controlled by the specific polymer utilized for fabrication, and ranged from months to years.

Devices fabricated from a 50/50 copolymer of D,L-lactic acid and glycolic acid were completely eroded by 2 months, while devices fabricated from a homopolymer of L-lactic acid showed little mass loss after 1 year. Erosion times for devices fabricated from the other polymers [poly-(D,L-lactic acid) and a 85/15 copolymer] were between these two extremes.

Devices were capable of resisting significant compressional forces (150 mN) in vitro, and the compression resistance was controlled by the polymer utilized to fabricate the devices. The ability of the devices to maintain their structure after implantation into animals was also dependent of the specific polymer utilized to fabricate the device. These results indicate that it is possible to fabricate tubular devices for tissue engineering applications that exhibit a wide range of erosion rates and mechanical properties.

To engineer a new tissue from a group of originally disorganized cells, the inventors reasoned that the cells must be provided with structural cues to organize appropriately. They therefore focused on fabricating polymer scaffolds to serve these purposes from biodegradable polymers.

Homopolymers of lactic acid [poly (L-lactic acid) (PLA) and poly (D,L-lactic acid) (PDLLA)], glycolic acid [polyglycolic acid (PGA)], and copolymers of lactic and glycolic acid (PLGA) are attractive candidates for fabricating tissue engineering scaffolds. These polymers have been used in medical devices for over 20 years (Frazza and Schmitt, 1971), and are generally considered to be biocompatible. The crystallinity, mechanical properties, and erosion times of these polymers is regulated by the ratio of lactic:glycolic acid (Gilding, 1981). This example describes the fabrication and characterization of tubular cell delivery devices from a range of polymers of the lactic and glycolic acid. Devices with a wide range of compression resistance and erosion times can be fabricated by utilizing PLA, PDLLA, and PLGA.

A. Materials

PLA, PDLLA, and the 85/15 and 50/50 PLGA were purchased from Medisorb (Cincinnati, Ohio), chloroform from Mallinckrodt (Paris, Ky.), polystyrene standards from Polysciences (Warrington, Pa.), aluminum backed tape from Cole-Parmer (Chicago, Ill.), phosphate buffered saline and DMEM medium from Gibco (Grand Island, N.Y.), Tmax film from Kodak, Lewis rats, 250 to 300 g, from Charles River (Wilmington, Mass.), and methoxyflurane from Pitman-Moore Inc. (Mundelein, Ill.).

Molecular weights of the various polymers were determined by gel permeation chromatography (Perkin-Elmer, Series 10, Newton Centre, Mass.), using polystyrene standards to generate a calibration curve. PLA had a molecular weight ($M_w$) of 74,000 ($M_w/M_n$=1.6); poly-(D,L lactic) acid had $M_w$=77,000 ($M_w/M_n$=1.8); 85/15 copolymer had $M_w$=69,000 ($M_w/M_n$=1.9); 50/50 copolymer $M_w$=43,400 ($M_w/M_n$=1.43). Differential scanning calorimetry was utilized to confirm the amorphous nature of all of the polymers except PLLA, which exhibited the expected crystallinity.

B. Device Fabrication

Hollow tubes were formed by a two-step process; porous films of the polymers were first fabricated, and these films were then formed into hollow tubes. To fabricate porous films, the polymer was dissolved in chloroform to form a 1.56% solution (w/v). Eight ml of this solution was cast into a 5 cm glass petri dish covered with a sheet of aluminum backed tape. Sieved sodium chloride crystals (150<d<250 μm) were dispersed evenly over the solution (0.375 g NaCl/dish), and the chloroform was allowed to evaporate at room temperature. A polymer film with entrapped NaCl particles resulted.

The salt particles were leached out of the film by immersion in 800 ml of deionized water for 48 hr at 37° C. with constant shaking. The water was changed every 8 hr during the leaching period. This procedure yielded a highly porous, thin membrane. Sections were cut from the resulting films (1.3×1.5 cm), with a razor blade, and rolled around Teflon cylinders with an outer diameter of 0.32 cm. The surfaces of the films that were adjacent to the aluminum backed tape were always placed adjacent to the Teflon cylinder.

The overlapping ends of the film were sealed together by briefly exposing one edge to chloroform, and manually pressing the overlapping ends together. The chloroform temporarily dissolved the polymer on the surface of each of the overlapping ends, and after the chloroform evaporated the overlapping ends were sealed together. The tubes were then slipped off of the teflon template. The ends were closed by placing a circular piece of the same porous films over the ends, and sealing as above with chloroform. Tubes 1.5 cm long, with an inner diameter of 0.32 cm resulted. Tubes were lyophilized to remove residual solvent, and sterilized by exposure to ethylene oxide for 24 hr at room temperature.

C. Device Characterization

For scanning electron microscopic examination, samples were gold coated using a Sputter Coater (Desk II, Denton Vacuum, Cherry Hill, N.J.). An environmental scanning electron microscope (ElectroScan; Wilmington, Mass.) was operated at 30 kV with a water vapor environment of 5 Torr to image samples. Photomicrographs were taken with Polaroid 55 film.

The porosity and pore size distribution of devices was analyzed by mercury porosimetry (Poresizer 9320, Micromeritics, Norcross, Ga.) using a solid penetrometer with a 5 ml bulb volume (920-61707-00, Micromeritics). The void volume and pore size distribution of polymer devices were determined as previously described (Mikos et al., 1994).

Thermal mechanical analysis was performed with a TMA 7 (Perkin Elmer Corp; Norwalk, Conn.) using a compression probe with a circular tip (d=3.0 mm). All testing was done at a constant temperature of 37° C. Tubes were placed on their sides for testing (axis of tube lumen perpendicular to axis of force application), and the change in device diameter (parallel to direction of force application) was followed during and after force application. The compressional forces applied to the tubes in vivo will also be exerted predominantly in a radial direction. The resulting deformations were normalized to the initial device diameter.

The degradation and erosion characteristics of bonded devices was assayed by placing individual tubes in 5 ml of phosphate buffered saline, pH 7.4, and incubating under static conditions at 37° C. Samples were removed from this solution at set times, air dried, lyophilized, and weighed. The degradation of devices was determined by dissolving samples in chloroform and determining the molecular weight using gel permeation chromatography. The mass loss was analyzed by weighing lyophilized devices before and after the incubation period.

The release of lactic acid was assayed enzymatically with lactic dehydrogenase using a kit from Sigma Chemical. The release of glycolic acid was quantitated with a colorimetric assay (Tan, 1978) which involves decarboxylating glycolic acid in the presence of concentrated sulfuric acid to form formaldehyde, followed by reaction of formaldehyde with chromotropic acid to yield a colored product which can be quantitated spectrophotometrically.

D. Implantation of Devices

Polymer constructs were implanted into the mesentery and omentum of Lewis rats as previously described (Mooney et al., 1994b). The mesenteric tissue or omentum was rolled around the devices to promote tissue invasion and neovascularization of the implants from all sides. Implants were secured in place with sutures of 7-0 Ethilar (Davis and Geck). The implants were subsequently removed after 7–28 days, and fixed in 10% buffered formalin. Inhalation anesthesia with methoxyflurane was always utilized. Thin sections were cut from paraffin-embedded tissue, and histological sections were stained with hematoxylin and eosin. Photomicrographs were taken with Kodak Tmax film using a Nikon inverted microscope.

E. Results

The pore structure of films formed with the particulate leaching technique could be controlled by varying the ratio of polymer to salt in the film fabrication process. Films fabricated with a polymer/salt ratio of 1/3 exhibited large pores on the air surface, approximately the size of the salt particles utilized to form the pores. These films had much smaller pores on the surface of the film exposed to the teflon tape-coated glass surface. These pores corresponded closely in structure to the salt particles utilized to create the device porosity.

Decreasing the ratio of polymer to salt from 1/3 to 1/24 resulted in the formation of larger pores on the air surface of the films, and these pores were not as uniform as the pores formed at lower salt loadings. Larger pores also formed on the film surface exposed to the glass dish as the polymer to salt ratio was decreased. At a very low ratio (1/12) both sides of the films exhibited a similar pore structure.

Films fabricated from all polymers (PLLA, PDLLA, 50/50 PLGA, and 85/15 PLGA) could be readily formed into hollow tubes. There was no significant differences in the pliability of films formed from the different polymers. However, films formed using a polymer/salt ratio lower than 1/12 were quite brittle, and the manipulation needed to form tubes from these films often resulted in their fracture.

Films fabricated using a polymer/salt ratio of 1/3 were utilized to fabricate the tubular devices used in all subsequent studies. These films had a thickness of 320±50 $\mu$m (mean±sd, n=36), a porosity of 87±4% (n=12), and a volume average pore diameter of 150±50 $\mu$m (n=12).

Figure 5A:
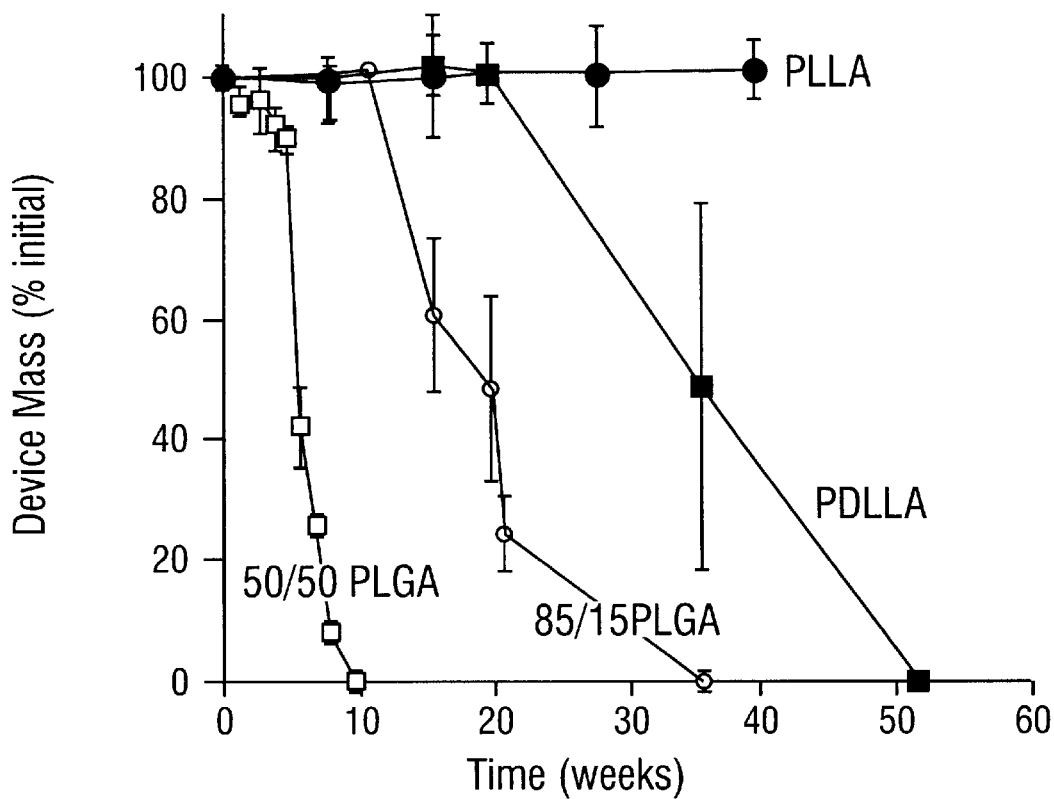
FIG. 5A. The erosion kinetics (mass loss) of devices was regulated by the polymer from which they were fabricated. All masses were normalized to the initial device mass. Values represent the mean and standard deviation calculated from 4 samples at each time point.
Figure 5B:
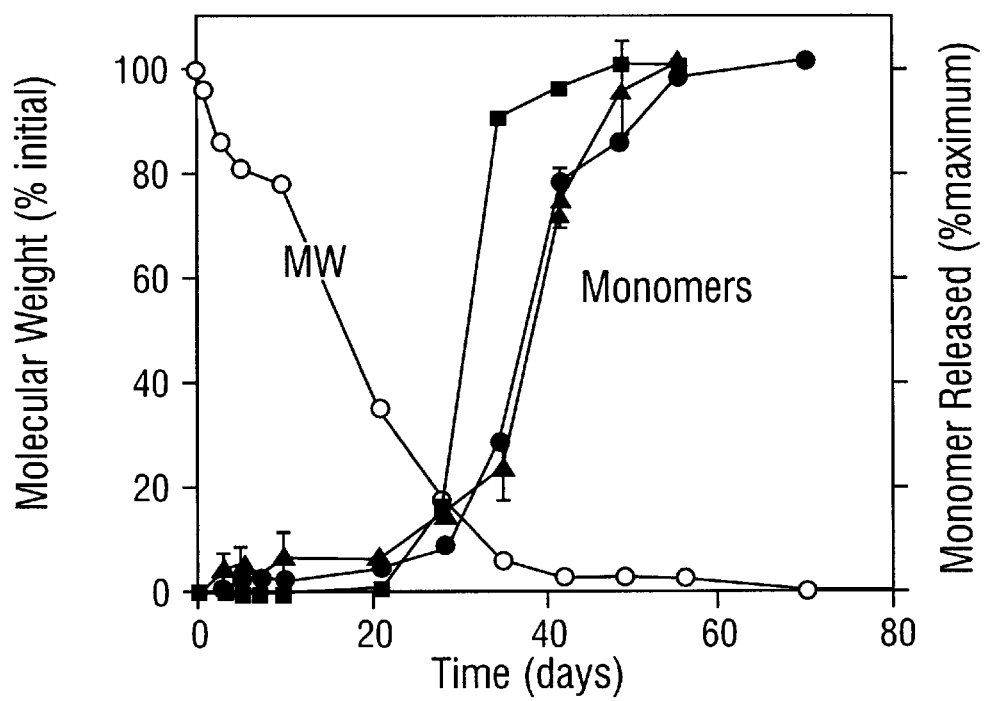
FIG. 5B. The molecular weight (MW: o) of devices fabricated from 50/50 PLGA rapidly decreased in vitro. Glycolic acid (■), D-lactic acid (●), and L-lactic acid (▲) were released from the devices once the molecular weight reached a low value. Values for the monomer release were normalized to the monomer mass initially present in the device. The maximum monomer that could be released per device was calculated using the measured initial device mass. Values for the polymer molecular weight were normalized to the initial molecular weight.

To determine the erosion characteristics of devices fabricated from various polymers, devices were placed in a phosphate buffered saline solution and maintained at 37° C. under static conditions for varying times. Devices fabricated from 50/50 PLGA began to lose significant mass after approximately 7 weeks, and were completely eroded (100% mass loss) by 10 weeks (FIG. 5A). Devices fabricated from 85/15 PLGA did not exhibit any weight loss until after 10 weeks, but were completely eroded by 35 weeks. PDLLA devices exhibited no mass loss until 20 weeks, and PLLA devices had no weight loss over 40 weeks. No significant monomer release was found until the polymer had degraded to a low molecular weight (approximately 9000) (FIG. 5B). D-lactic acid and L-lactic acid were released with identical kinetics from 50/50 devices, and glycolic acid was released more rapidly (FIG. 5B).

The compression resistance of devices was next tested. Devices fabricated from all four polymers resisted compression by moderate forces (50 mN), but the ability of devices to withstand a larger compressional force (150 mN) was dependent on the polymer used in fabrication. PLLA tubes exhibiting the least compression under this force, and 50/50 PLGA devices exhibiting the greatest. The compression was viscoelastic in all cases, as the devices only partially decompressed after the force was removed. While devices fabricated from PLLA and PDLLA consistently resisted this load, PLGA devices did not exhibit a consistent response. The 50/50 PLGA tubes showed the greatest variability, as testing of multiple tubes gave widely varying results. Devices which compressed greater than 50% after force application typically showed little elastic recoil after the force was removed. Thus, devices which compressed more than this were considered to fail at this loading, and the failure rates of devices fabricated from the various polymers is given in Table 10.

TABLE 10

In vitro and In vivo Compression Test Failure of Devices

| Polymer | In vitro | | In vivo | |
| --- | --- | --- | --- | --- |
| | Number of Samples | Failure Rate[a] | Number of Samples | Failure Rate[b] |
| PLLA | 6 | 0% | 2 | 0% |
| PDLLA | 5 | 20% | 6 | 0% |
| 85/15 PLGA | 5 | 40% | 9 | 44% |
| 50/50 PLGA | 16 | 58% | 6 | 50% |

[a]Compression testing was performed with a force of 150 mN. A device was considered to fail if it compressed to less than 50% of the original diameter.
[b]Devices were implanted into the mesentery or omentum of Lewis rats for 7–28 days.
Histological sections were examined, and devices were considered to fail if they compressed and did not maintain their original, tubular shape.

The devices fabricated using this technique are useful in transplanting cells and serve as a templated guiding the formation of a native tissue structure from the transplanted cells and the host tissue. Devices were implanted in the mesentery and omentum of Lewis rats to determine if they would guide the formation of a native, tubular tissue in vivo. These sites are easily accessed surgically, are well vascularized, and are attractive locations to engineer soft tissues (Johnson et al., 1994).

Devices were implanted by placing them on the omentum or on a leaf of the mesentery which had been isolated on surgical gauze, and then rolling the mesentery/omentum over the device. Devices were immobilized using several sutures, and the mesentery/omentum and construct were replaced within the abdominal cavity.

In the first days following implantation, there was an acute inflammatory response to the devices. Fibrin deposition and macrophage infiltration was noted within the pores of the devices by three days. Fibrovascular tissue formed in the pores of the devices and on the luminal surface over 7–14 days. Capillary ingrowth through the pores accompanied the fibrous tissue ingrowth. Fibrovascular tissue occupied a greater percentage of the devices' lumens over time, until the lumen was completely filled in with this tissue by 28 days. The closure of the devices' lumens would presumably be prevented by a lining of epithelial cells (e.g., transplanted enterocytes).

The ability of devices to maintain their structure and induce the formation of a tubular tissue was dependent on the polymer utilized to fabricate the devices. All PLLA and PDLLA devices maintained their structure in vivo, while devices fabricated from the other polymers were not as stable (Table 10).

This example shows that tubular devices have been fabricated from biodegradable polymers of lactic and glycolic acid using a reproducible technique. The pore structure of the devices can be controlled by the processing conditions. The erosion kinetics and mechanical properties of the devices can be controlled by varying the polymer utilized to fabricate the devices.

This example also shows the tubular devices can be used to engineer tubular tissue structures in animals. The tubular devices and tissues are only exemplary of how a polymer matrix can be used to provide a 3-D structure required to match a native tissue structure. Particular devices optimized for oral tissues can thus be generated.

The porosity of an implanted device affects the diffusion of factors into the device, the mechanical properties, and the ability of fibrovascular tissue to invade the device. Fibrovascular tissue ingrowth is necessary if one desires to engineer a tissue that is structurally integrated with the host tissue. This process leads to the formation of a vascular network which supplies the metabolic needs of the developing tissue. This will readily occur in oral tissue transplants. The rate of the tissue ingrowth is a function of the device porosity and pore size (Wesloski et al., 1961; White et al., 1981; Mooney et al., 1994b; Mikos et al., 1993b).

The pore structure of devices fabricated in this study were not symmetrical unless a very low ratio of polymer/salt was utilized in the fabrication procedure. The small pores on the luminal surface of the devices may be advantageous for some applications as they allow cells seeded onto the luminal surface to readily organize into a confluent sheet (Mooney et al., 1994a). However, this asymmetry likely slows diffusion of factors between the luminal side and exterior of the device, and may also retard fibrovascular tissue ingrowth.

Different erosion times may be required of devices utilized to engineer various tissues. The erosion kinetics of devices fabricated in this example was governed by the polymer utilized to fabricate the devices. The time for complete erosion could be varied between 10 weeks and over a year by varying which polymer was utilized to fabricate the device.

The thin membranes of these devices experience bulk degradation, and little mass loss or monomer release is noted until the polymer molecular weight has fallen quite low (FIG. 5A and FIG. 5B). This leads to a relatively rapid monomer release, however, the low mass of monomer in highly porous devices such as these is unlikely to lead to any significant systemic problems. Also, the diffusional and connective transport of fluids through the tissue will likely clear the monomers rapidly with little local build-up.

The compression resistance of devices utilized in tissue engineering applications can be an important feature. For embodiments where the devices are to serve as templates, guiding the development of the desired tissue structure, they must maintain their own structure. The compression resistance of the tubular devices fabricated in this study were dependent on the polymer utilized to fabricate the devices. Devices fabricated from both PLLA and PDLLA resisted compressional forces and maintained their structure both in vitro and in vivo. Devices fabricated from PLGA did not resist compressional forces as well either in vitro or in vivo. The compression resistance of tubes fabricated from 50/50 PLGA was inconsistent at high compression forces (150 mN).

While the magnitude of the compressive forces that are exerted on implanted devices by the surrounding tissue are unclear, they are significant and will likely vary depending on the implant site. Devices which were stable to large compressional forces in vitro (150 mN) were also stable after implantation into the mesentery of laboratory rats. The results of the current study suggest that devices fabricated from PLGA may need to be mechanically stabilized if they are to maintain their structure in vivo.

The compression resistance of devices was studied in vitro by applying a constant force on the tubes. Contact between the compression tip and the tubes was not analyzed, and will likely change as the tubes compress. For this reason, results were reported for compressional forces, not stresses. Calculation of stresses using the entire contact area of the compression probe would give the most conservative estimate of mechanical moduli.

The tubular devices described in this example are useful for transplanting a variety of cell types to engineer different oral tissues. Cells can be readily seeded into the devices, where they adhere and organize and form an oral tissue ex vivo. A tubular, vascularized tissue is created by implanting such tissue-containing devices in animals. In the present study, fibrovascular tissue ingrowth continued until the lumen of the devices was filled, but an epithelial cell lining (e.g., transplanted enterocytes) would likely prevent this closure. The erosion time and mechanical properties of these devices can be predicted, and matched to the requirements for a specific tissue.

EXAMPLE VI

Stabilized Tubular Matrices

Another method to stabilize PGA meshes, described in this example, is to atomize solutions of poly (L-lactic acid) (PLLA) and a 50/50 copolymer of poly (D,L-lactic-co-glycolic acid) (PLGA) dissolved in chloroform and to spray over meshes formed into hollow tubes. The PLLA and PLGA coated the PGA fibers and physically bonded adjacent fibers. The pattern and extent of bonding was controlled by the concentration of polymer in the atomized solution, and the total mass of polymer sprayed on the device. The compression resistance of devices increased with the extent of bonding, and PLLA bonded tubes resisted larger compressive forces than PLGA bonded tubes. Tubes bonded with PLLA degraded more slowly than devices bonded with PLGA.

Implantation of PLLA bonded tubes into rats revealed that the devices maintained their structure during fibrovascular tissue ingrowth, resulting in the formation of a tubular structure with a central lumen. The potential of these devices to engineer specific tissues was exhibited by the finding that smooth muscle cells and endothelial cells seeded onto devices in vitro formed a tubular tissue with appropriate cell distribution.

In this study, the inventors formed PGA fiber meshes by physically bonding adjacent fibers using a spray casting method. Poly L-lactic acid (PLLA) or a 50/50 copolymer of lactic and glycolic acid (PLGA) was dissolved in chloroform, atomized, and sprayed over a PGA mesh formed into a tubular structure. Following solvent evaporation, a physically bonded structure resulted, and the pattern and extent of PGA fiber bonding was controlled by the processing conditions.

These tubular devices were capable of withstanding large compressive forces in vitro (50–200 mN), and maintained their structure in vivo. The specific mechanical stability was dictated by the extent of physical bonding and the polymer utilized to bond the PGA fibers.

A. Tube Fabrication and Characterization

Materials are as described in the previous example. Rectangles (1.3×3.0 cm) of the non-woven mesh of PGA fibers were wrapped around a teflon cylinder (o.d.=3.0 mm) to form a tube, and the two overlapping ends were manually interlocked to form a seam. The teflon cylinders were then rotated at 20 rpm using a stirrer (Caframo; Wiarton, Ontario, Canada). Solutions of PLLA and PLGA dissolved in chloroform (1–15% w:v) were placed in a dental atomizer (Devilbus Corp.), and sprayed over the rotating PGA mesh from a distance of 6 inches using a nitrogen stream (18 psi) to atomize the polymer solution.

The PLGA and PLLA had molecular weights (Mw) of 43,400 (Mw/Mn=1.43) and 74,100 (Mw/Mn=1.64), respectively. Molecular weights were determined by gel permeation chromatography, as described above.

While PLLA and copolymers of lactic and glycolic acid are soluble in chloroform, PGA is very weakly soluble in this solvent. Thus, the PGA fibers are largely unchanged by this process. After spraying was completed, the tubes were lyophilized to remove residual solvent, removed from the teflon cylinder, and cut into specific lengths. The tubes were sterilized by exposure to ethylene oxide for 24 hr, followed by degassing for 24 hr.

The mass of PLLA and PLGA that bonded to the PGA scaffolds was determined by weighing PGA devices before and after spraying. Electron microscopy, mechanical analysis and erosion characteristics were as described above.

B. Implantation of Tubes and Cell Seeding

Polymer constructs were implanted into the omentum of syngeneic Lewis rats as previously described shown above.

To introduce bovine aortic smooth muscle cells (passage 6-9) into the polymeric delivery devices, 1 ml of a cell suspension containing from 5–20×10$^5$ cells/ml was injected into the interior of each tube using a 1 ml syringe and a 22 gauge needle. The cell suspension was retained in the tubes by placing a small plug of the PGA fibers at both ends of the tubes during the cell adhesion period. Devices were incubated at 37° C. in an atmosphere of 10% $CO_2$ to allow for cell adhesion and proliferation. The tubes were manually rotated periodically using a sterile forceps during the period of cell adhesion to promote even cell seeding.

Cell-polymer devices were kept in DMEM medium, containing 5% calf serum, 100 U/ml penicillin and 100 mg/ml streptomycin during this time. The seeding protocol was repeated 7 days later to ensure even seeding of cells within the devices. Ten days later, a cell suspension of bovine aortic endothelial cells (passage 6-9) was similarly seeded onto the tubes. After 4 more days the devices were fixed in formalin, embedded in paraffin, sectioned and stained (hematoxylin and eosin) using standard techniques.

Sections were stained for the presence of desmin (a smooth muscle specific protein) and Factor 8 (specific for endothelial cells) using standard immunohistochemical protocols. Antibodies for this analysis were purchased from Shandon (Pittsburgh, Pa.). The endothelial cells and smooth muscle cells were isolated from bovine aortas using a collagenase digestion, and were obtained from Dr. Judah Folkman.

C. Results

1. Bonding Tubes with PLLA

To determine whether PGA scaffolds could be stabilized by physically bonding adjacent fibers, chloroform containing dissolved PLLA (1–15% w:v) was sprayed over the exterior surface after the PGA mesh was wrapped around a teflon cylinder to form a tube. The PLLA formed a coating over the exterior PGA fibers after the solvent evaporated, and physically bonded adjacent fibers. The tubes formed in this manner could be easily removed from the teflon cylinder for characterization and use.

The pattern of bonding was controlled by the concentration of the PLLA in the atomized solution, even though the time of spraying was adjusted to maintain an approximately constant mass of PLLA on the devices under the various conditions. Spraying with a solution containing 1 or 5% PLLA resulted in extensive bonding of PGA fibers without significantly blocking the pores of the PGA mesh. Spraying with a 10% solution of PLLA also bonded fibers, but resulted in the formation of a PLLA film on the exterior surface of the PGA mesh that contained only small pores. Spraying with a solution containing 15% PLLA had a similar effect, although the polymer film that formed was less organized. In all cases, the PLLA coated and bonded fibers only on the exterior surface of the PGA mesh, as no coating or bonding of fibers was observed on the interior surface of the PGA mesh.

Figure 6:
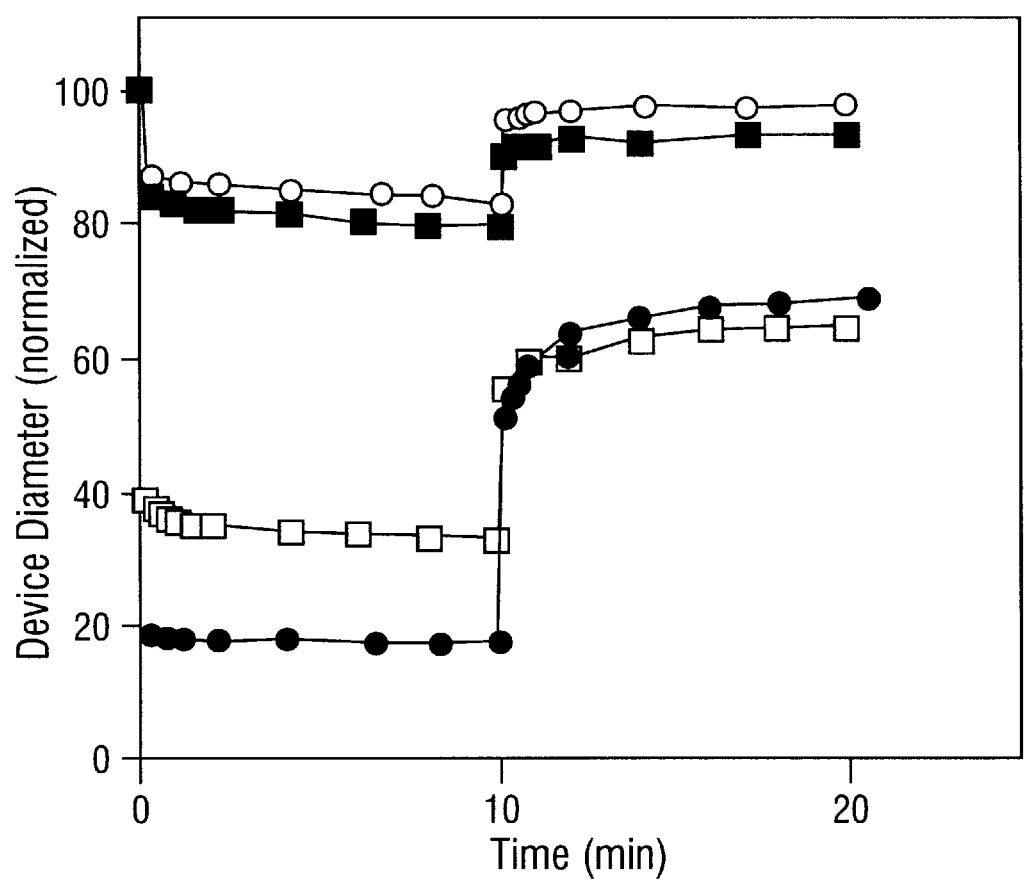
FIG. 6. Representative strain diagrams of tubes formed from the PGA mesh after spraying with a solution containing 1% (□), 5% (■), 10% (o), and 15% (●) PLLA. Devices were subjected to a compressive force of 200 mN applied in a direction perpendicular to the axis of the device lumen starting at 0 minutes. The force was removed at 10 minutes, and the change in the diameter of the tube (parallel to the direction of force application) was monitored both during and after the time of force application, and normalized to the initial diameter.

The compression resistance of bonded tubes was assessed in vitro to determine which patterns of bonding resulted in the most stable devices. Unbonded tubes were completely crushed by a force of 5 mN, but bonded tubes were capable of resisting forces in excess of 200 mN. However, the ability of bonded tubes to resist a given compressional force was dependent on the pattern of bonding (FIG. 6). For example, tubes bonded with 1 or 15% PLLA were significantly compressed by a force of 200 mN, while tubes bonded with a solution of 5 or 10% PLLA were only slightly compressed by this force. The compression was viscoelastic in all cases, as the devices only partially decompressed after the force was removed. Uniform properties were observed with respect to the position along and around a tube.

To determine if the extent, as well as the pattern, of bonding could vary the compression resistance of tubes, an atomized dispersion of 5% PLLA was then sprayed over the devices for different times. Lengthening the spraying time from 10 to 60 seconds increased the mass of PLLA on the devices. Infrequent bonds between adjacent fibers resulted from spraying for 10 seconds. Spraying for more extended periods increased the PLLA coating over the PGA fibers, and the extent of bonding.

Figure 7A:
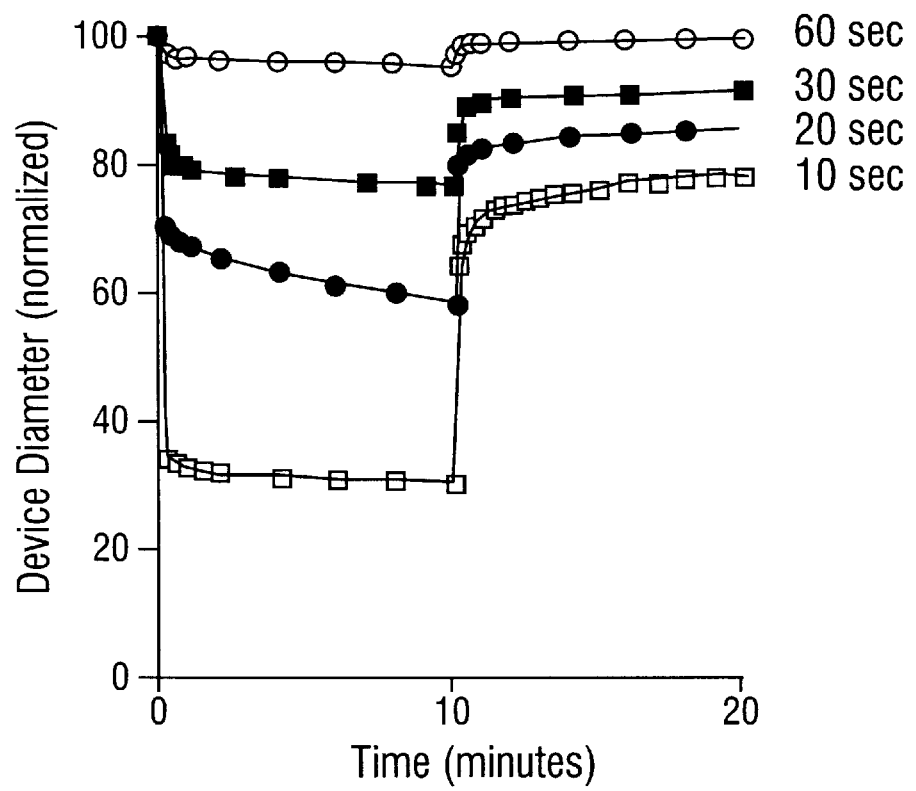
FIG. 7A. Representative strain diagrams of PGA tubes sprayed for various times (10 sec., □; 20 sec., ●; 30 sec., ■; 60 sec, o) with a 5% PLLA solution and subjected to a compressive force of 200 mN starting at 0 minutes. The force was removed at 10 minutes. The force application and the change in the diameter of the tube (normalized to the initial diameter) were monitored, as described in FIG. 6, both during and after the time of force application.
Figure 7B:
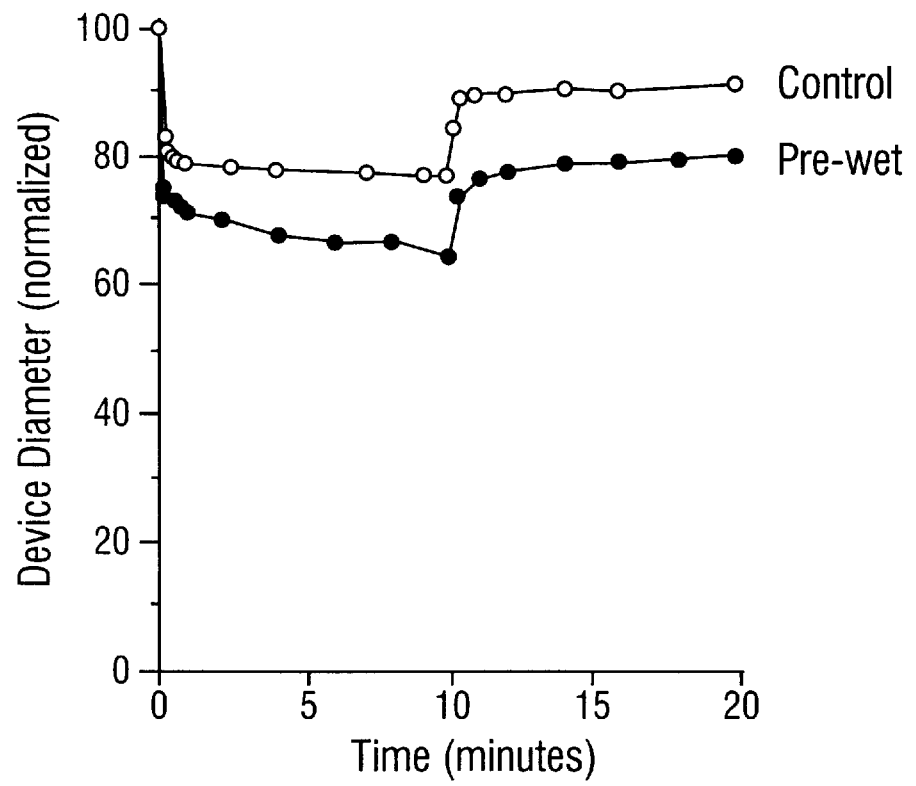
FIG. 7B. Devices sprayed with a 5% PLLA solution for 30 seconds and tested dry (Control; o) or after pre-wetting for 24 hr in a saline solution (Pre-wet; ●). The compressional force was again 200 mN.

The ability of these tubes to resist compressional forces and maintain their shape was quantitated again using thermal mechanical analysis. The compression resistance strongly depended on the extent of bonding, as tubes that were more extensively bonded had a greater resistance to deformation (FIG. 7A). The compression that did occur under these conditions was again a combination of a reversible, elastic strain, and an irreversible deformation. Some tubes were also exposed to an aqueous environment before testing to determine whether this environment for 24 hr would destabilize the tubes. The aqueous environment had a slight, detrimental effect on the stability of bonded tubes, but they were still capable of resisting large compressive forces (FIG. 7A and FIG. 7B).

2. Bonding Tubes with PLGA

To determine whether this technique of stabilizing PGA devices could be utilized with a variety of polymers, the previous study was repeated using a 50/50 copolymer of lactic and glycolic acid. The mass of polymer bonded to the devices and the extent of physical bonding was again regulated by the time an atomized dispersion of the bonding polymer was sprayed over the PGA fibers. Once again, bonding increased the compression resistance of devices formed into a tubular structure. However, these devices were not able to resist the same compressional forces as PLLA bonded devices.

Tubes bonded with PLLA were capable of resisting forces up to 200 mN, while tubes bonded with PLGA were only capable of resisting forces slightly greater than 50 mN. The difference between devices stabilized with PLLA and PLGA was even more striking when the devices were tested after immersion in phosphate buffered saline for 24 hr. PLGA bonded tubes, in contrast to PLLA bonded tubes, were significantly weakened by this treatment.

3. Tube Degradation in vitro

Figure 8:
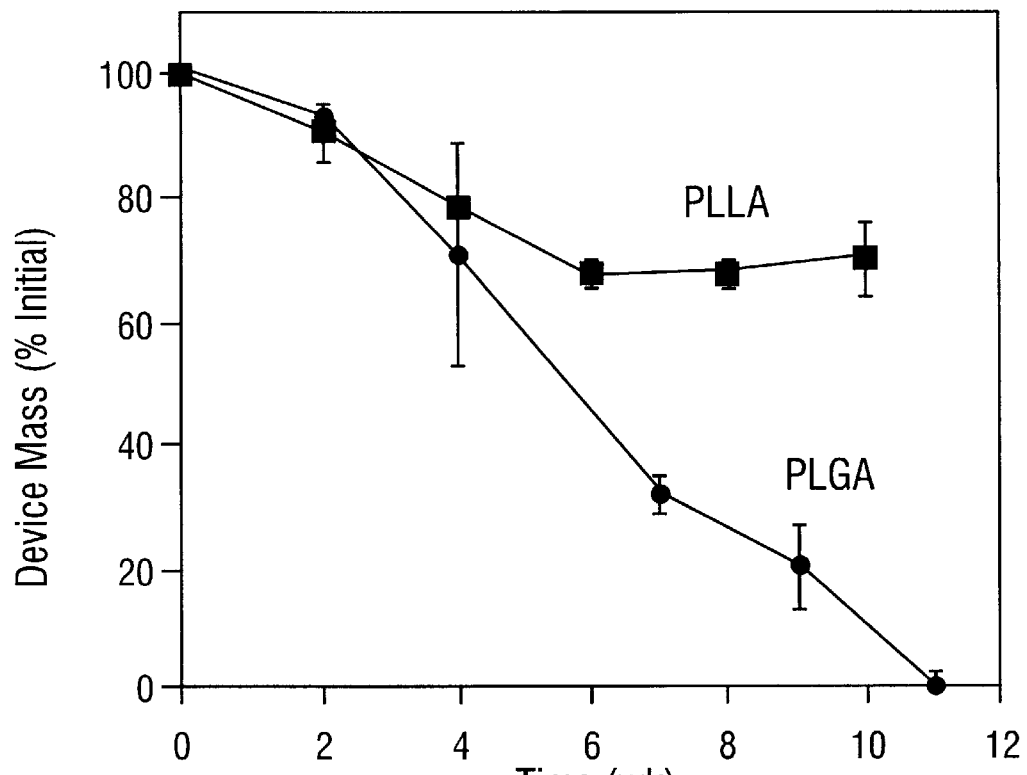
FIG. 8. The degradation of devices bonded by spraying with PLLA or PLGA (5% solution; spraying time=30 sec.), as measured by quantitating the change in device mass over time. Devices were incubated at 37° C. under static conditions in buffered saline, and removed at various times for analysis. Values in represent the mean and standard deviation calculated from 3 samples. PLLA, ■; PLGA, ●.

The time course for erosion of the tubes was determined by quantitating the mass loss and monomer release from tubes immersed in a pH balanced, isotonic saline solution. Devices bonded with PLGA were completely degraded by 11 weeks, while devices bonded with PLLA only lost 30% of their mass after 10 weeks (FIG. 8). The degradation of the PLLA bonded tubes was solely due to erosion of the PGA fibers, as glycolic acid was released from the tubes, but virtually no lactic acid was released over this time from the tubes. PLLA degrades slowly, and no significant loss of PLLA mass is expected until 1–2 years. Erosion of tubes bonded with PLGA was due to erosion of both the PGA fibers and the PLGA, as both glycolic acid and lactic acid were released from the tubes over this time frame.

4. Compression Resistance In vivo

To confirm that stabilized tubes were capable of resisting compressional forces in vivo as well as in vitro, devices bonded with PLLA (5% PLLA; 30 second spraying time) were implanted into the omentum of laboratory rats. The initial (3 day) host response was characterized by fibrin deposition and scattered inflammatory cells throughout the devices. A mature fibrovascular tissue was evident throughout the devices by 7 days, and the devices maintained their tubular structure with a central lumen for the 18 day duration of the study. The invading fibroblasts and the newly deposited matrix were aligned with the lumens of the tubes.

5. Cell Adhesion and Organization In vitro on Bonded Tubes

PLLA bonded tubes (5% PLLA; 30 second spraying time) were subsequently seeded with smooth muscle cells and endothelial cells to investigate the suitability of these devices to serve as cell delivery vehicles. Blood vessels are largely comprised of these two cell types. The smooth muscle cells adhered to the polymer fibers, and proliferated to fill the void space present between polymer fibers. Endothelial cells also adhered to the devices, and over time formed a lining on the interior section of the devices. Immunohistochemical staining for desmin confirmed that the cells filling the interstices between polymer fibers were smooth muscle cells, and staining for factor eight confirmed that the cells lining the luminal surface were endothelial in nature. This organization of the muscle and endothelial cells is similar to that observed in blood vessels.

This example therefore shows that three-dimensional tubes can be formed from PGA fiber scaffolds by physically bonding adjacent fibers. The compression resistance and degradation rate of these devices was controlled by the pattern and extent of physical bonding, and the type of polymer utilized to bond the PGA fibers. Fibrovascular tissue invaded the devices following implantation, leading to the formation of a tubular tissue with a central lumen. The potential of these devices to engineer tissues was exhibited by the finding that endothelial cells and muscle cells adhered to the devices and formed a new tissue in vitro with appropriate tissue organization. This is particularly relevant to the muscle cells of the tongue, in addition to the other oral tissues of this invention.

The compression resistance of devices was monitored by applying a constant force on the tubes. The resulting changes in the device diameters were partially elastic, as indicated by the partial decompression following removal of the applied force. The irreversible changes in the device diameters were likely caused by both crushing and bending of fibers, and by rearrangement of fibers.

Tubes which were bonded with PLLA were more resistant to compressional forces than tubes bonded with PLGA. This finding is because crystalline PLLA is typically much stiffer than amorphous PLGA (Gilding, 1981). Additionally, while the compression resistance of PLLA bonded devices was not greatly changed after exposure to an aqueous environment, PLGA bonded devices were markedly weakened after the same treatment. PLGA is more hydrophilic than PLLA (Gilding, 1981) due to the presence of the glycolic acid residues, and the absorbed water likely acts as a plasticizer, weakening the PLGA. The PLLA bonded devices were slightly weakened after this treatment, indicating that the PLLA was also somewhat plasticized.

The erosion of the devices was also dependent on the polymer utilized for bonding. PLLA is hydrolyzed very slowly, and virtually no lactic acid release was observed over the 10 weeks of the erosion study. The erosion of PLLA bonded devices was entirely due to hydrolysis of the glycolic acid bonds in the fibers. In contrast, both the PGA fibers and the PLGA used to bond the fibers eroded completely over 11 weeks. The release of glycolic acid from these devices occurred more rapidly than the release of lactic acid. This was likely caused by the more rapid erosion of the PGA fibers, followed by the slower release of both lactic acid and glycolic acid from the PLGA.

Biodegradable devices are attractive for cell transplantation and tissue engineering since they can be designed to erode once tissue development is complete, leaving a completely natural tissue. The approach described in this example to mechanically stabilize fiber-based scaffolds of PGA, PLGA, and PLLA can be used with a variety of other polymers, both erodible and non-erodible, for the medical, dental and non-clinical applications of this invention.

Various approaches have been previously taken to mechanically stabilize structures formed from PGA fibers. PGA fibers can be physically bonded with a second polymer in a similar manner as described here by simply dipping the PGA scaffold into a solution of poly-L-lactic acid (PLLA) dissolved in chloroform, and allowing the chloroform to evaporate (Vacanti et al., 1992). Alternatively, a thermal processing technique that results in temporary melting and subsequent bonding of PGA fibers has been reported (Mikos et al., 1993a).

The bonding approach described in this report is example permits a variety of bonding polymers to be utilized, and allows the fabrication of various three-dimensional scaffolds. It also results in bonding only of the outermost fibers of the device in contrast to other methods. This preserves the desirable features of the PGA mesh (high porosity, high surface area/polymer mass ratio) throughout the interior sections.

This approach also allows both the extent and pattern of bonding to be easily controlled. Extensive coating and bonding of fibers resulted when the polymer concentration in the atomized solution was low (1–5%). Increasing the concentration of polymer in the atomized solution to 10% resulted in the formation of a relatively smooth film over the external surface of PGA meshes, and utilizing a 15% solution resulted in the formation of a fibrous, nonhomogeneous film over the PGA meshes. Increasing the polymer concentration raises the viscosity of this solution, and this likely increases the droplet size which is formed during the atomization process. This will effect how these droplets penetrate the PGA mesh, how they aggregate on the PGA mesh, and the rate of solvent evaporation. All of these factors will effect the pattern of bonding.

In embodiments of this invention where the matrix-tissue is administered, the tissue delivery device should preferably maintain a pre-configured geometry in the face of external forces during the process of tissue development. The magnitude of the compressive forces that are exerted on implanted devices by the surrounding tissue are unclear and will vary depending on the implant site. The magnitude of forces utilized in the present example to quantitate the compression resistance of devices in vitro was 50–200 mN. This results in pressures ranging from approximately 50–200 mm Hg (assuming complete and continuous contact between the TMA compression tip and the tube). These pressures are in the same range observed in blood vessels.

Devices which were stable to high forces (PLLA bonded devices) were also stable after implantation into the omentum of laboratory rats. The omentum was chosen as the implant site because it is highly vascularized and easily accessed and manipulated surgically. It is used in the present context to exemplify stability under physiological conditions.

The formation of fibrovascular tissue in implanted tubes represents ingrowth into the porous, synthetic materials (Wesloki et al., 1961; White et al., 1981). The ingrowth and organization of the fibrovascular tissue will also exert compressional forces on the forming tissue, although the magnitude of these forces is unclear. It is expected that the ingrowing fibrovascular tissue would have eventually filled the central lumen of the implanted tubes since there was no epithelial cell lining of the lumen. An endothelial cell lining would likely prevent this outcome.

In addition to exemplifying proper biomechanics, the synthetic, biodegradable tubes described in this example also provide a means to provide appropriate mechanical properties to an engineered blood vessel while also promoting the formation of a complete and natural replacement from the appropriate cell types. It is also possible to combine the advantages of synthetic polymers (tailored mechanical and degradative properties, reproducible synthesis) with the biological specificity of extracellular matrix molecules, such as collagen, by producing templates from synthetic, biodegradable polymers which contain biologically active amino acid side chains (Barrera et al., 1993). As described herein, using the appropriate cell signaling molecules on these polymers allows one to promote endothelial cell adhesion in desirable spatial locations while preventing other cell types from adhering (Hubbell, 1995)

EXAMPLE VII

Biodegradable Sponge Matrices

The present example concerns sponges fabricated from poly-L-lactic acid (PLA) infiltrated with polyvinyl alcohol (PVA). Highly porous sponges (porosity=90–95%) were fabricated from PLA using a particulate leaching technique. To enable even and efficient cell seeding, the devices were infiltrated with the hydrophilic polymer polyvinyl alcohol (PVA). This reduced their contact angle with water from 79° to 23°, but did not inhibit the ability of hepatocytes to adhere to the polymer.

Porous sponges of PLA infiltrated with PVA readily absorbed aqueous solutions into 98% of their pore volume, and could be evenly seeded with high densities ($5 \times 10^7$ cells/ml) of cells. Hepatocyte-seeded devices were implanted into the mesentery of laboratory rats, and $6 \pm 2 \times 10^5$ of the hepatocytes engrafted per sponge. Fibrovascular tissue invaded through the device's pores, leading to a composite tissue consisting of hepatocytes, blood vessels and fibrous tissue, and the polymer sponge.

This example details yet another way of preparing biodegradable scaffolds fabricated from the poly-lactic-co-glycolic acid family (PLGA) (Mooney and Vacanti, 1993). The success of using the scaffold to localize transplanted cells, and guide the development of a new tissue consisting of these cells and elements of the host tissue is also shown. Following tissue development, these scaffolds will resorb, leaving a completely natural tissue. As mentioned, these polymers provide a flexible family to work with, as varying the ratio of lactic acid to glycolic acid controls the structure of the polymer, its mechanical properties, and degradation rate (Gilding, 1981).

The present example concerns the engineering of new liver tissue. An engineered liver tissue will require vascularization to both support the metabolic needs of these cells and to structurally integrate the new liver tissue with the host tissue. The success of the techniques described herein thus supports the clinical utility of the present invention in connection with oral tissues, as tissue integration is the underlying phenomenon being manipulated.

The inventors reasoned that highly porous sponges fabricated from the PLGA family would allow a large number of cells to be effectively delivered (Mikos et al., 1993b). However, the relative hydrophobicity of the PLGA polymers makes efficient and even cell seeding difficult (Wald et al., 1993). Prior to the present study, it had not been determined whether PLGA sponges could be utilized to transplant cells and provide a suitable environment for tissue engraftment.

Cell delivery devices could be fabricated from polymers such as polyvinyl alcohol (PVA) as an alternative to using polymers of the PLGA family. PVA with a high degree of hydrolysis is exceedingly hydrophilic. However, the desirable hydrophilicity of these polymers makes them unsuitable for fabricating stable three-dimensional structures unless the polymer is cross-linked with formaldehyde or other chemicals (Haupt and Myers, 1960; Fritsche 1967). The cross-linking eliminates the biodegradation of the polymers (Gilding, 1981), which is a desired feature in cell transplantation devices.

In this example the inventors have combined the advantages of PLGA and PVA to fabricate hydrophilic porous sponges by infiltrating poly-L-lactic acid (PLA) and PLGA sponges with the more hydrophilic (PVA). The inventors further show that these devices can be reproducibly seeded with high densities of hepatocytes, and used to transplant the cells to specific locations. The PVA dissolves once the devices are placed in a aqueous environment. Cells seeded into these devices and transplanted into laboratory rats have been found to engraft and form a new tissue with ingrown fibrovascular tissue of the host animal.

A. Sponge Fabrication and Characterization

Porous sponges were formed from PLA and an 85/15 copolymer of D,L lactic acid and glycolic acid (85/15 PLGA) (Medisorb; Cincinnati, Ohio) using a variation of a previously described particulate leaching technique (Mikos et al., 1994). The PLA and 85/15 PLGA had molecular weights ($M_w$) of 74,000 ($M_w/M_n$=1.6), and 69,000 ($M_w/M_n$=1.9), respectively. Molecular weight determination was performed using gel permeation chromatography with polystyrene molecular weight standards.

The polymers were dissolved in chloroform (Mallinkrodt; Paris, Ky.) to yield a solution ranging from 10–20% (w:v), and 0.12 ml of this solution was loaded into Teflon cylinders (diameter=21.5 cm, height=25 mm; Cole Parmer) packed with 0.4 g of sodium chloride particles sieved to a size between 250 and 500 $\mu$m. Following solvent evaporation, polymer films with entrapped salt particles (1 mm thick) were carefully removed from the molds. The salt was removed by immersing films in distilled water for 48 hr. The water bath was changed 3 times daily. The volume of polymer solution and salt mass loading were linearly increased to fabricate thicker sponges.

To infiltrate sponges with PVA (Aldrich Chem. Co.; Milwaukee, Wis.; MW 3000, 75% hydrolyzed) or the Pluronic F 108 surfactant (BASF; Parsippany, N.J.), sponges were immersed for 16 hr in an aqueous solution containing 1–100 mg/mL of PVA or Pluronic in phosphate buffered saline (PBS). The sponges were subsequently removed from the solution, dried, and lyophilized. The mass of devices before and after coating was quantitated to determine the mass of incorporated PVA or surfactant. To determine whether the incorporated PVA was permanently associated with the sponges, some sponges were subsequently soaked in a solution of PBS overnight, air dried at room temperature, lyophilized, and reweighed. All sponges were sterilized before use by exposure to ethylene oxide.

For scanning electron microscopic examination, samples were gold coated using a Sputter Coater (Desk II, Denton Vacuum; Cherry Hill, N.J.). An environmental scanning electron microscope (ElectroScan; Wilmington, Mass.) was operated at 30 kV with a water vapor environment of 5 torr to image samples. Polaroid 55 film was used for photomicrographs. Samples loaded with cells were glutaraldehyde fixed and dehydrated with methanol before gold coating.

The porosity and pore size of the devices was determined using mercury porosimetry (Poresizer 9320, Micromeritics; Norcross, Ga.) using a solid penetrometer with a 5 ml bulb volume (920-61707-00, Micromeritics) as previously described (Mikos et al., 1994).

The ability of aqueous solutions to wet the sponges was determined by placing a volume of distilled water equivalent to the void volume of the sponge (as determined using mercury porosimetry) onto one surface of the sponge, and allowing 10 minutes for the solution to soak into the sponge. The sponges were held at a 90° angle, and lightly shaken to remove water not absorbed into the sponge. Sponges were weighed to determine the volume of water which did absorb.

Solid discs were formed from various polymers in the PLGA family using compression molding. These discs were used to measure the contact angle of the polymers with water, and to test the ability of hepatocytes to adhere to the polymer films. Solid polymer discs were utilized in these studies instead of porous three-dimensional sponges as it simplified the analysis (e.g., it is simpler to measure the advancing water contact angle on a two-dimensional film than in a three dimensional sponge).

Discs (0.5 mm thick) were formed from 0.75 g of PLA, polyglycolic acid, poly-D,L-lactic acid, or a 85/15 or 50/50 copolymer of lactic and glycolic acid (all purchased from Medisorb) using a Carver Laboratory Press (Fred S. Carver, Inc.; Menominee Falls, Wis.). The polymer was heated to 185° C., and compressed at 1500 psi. Discs were coated with PVA or Pluronic F108 as described above. Contact angle measurements were made from an advancing water droplet using a goniometer (Rame-Hart, Inc.; Mountain Lakes, N.J.). Reported values represent the mean and standard error of the mean (SEM) calculated from the mean advancing contact angle of a minimum of three films at each condition. The mean advancing contact angle for each film was calculated from a minimum of three measurements.

B. Cell Studies

Hepatocytes were isolated from Lewis rats (Charles River, Wilmington, Mass.) using a two step collagenase perfusion, and purified by centrifugation through a percoll density gradient as previously reported (Mooney et al, 1992). To determine whether the PVA treatment inhibited the ability of hepatocytes to adhere to PLA, hepatocytes were plated onto treated and untreated solid PLA discs (10,000 cells/cm$^2$). The number of adherent hepatocytes was determined at 24 hr by washing plates with PBS to remove non-adherent cells, subsequently removing adherent cells by exposure to a solution of 0.05% trypsin, 0.53 mM EDTA (Gibco; Grand Island, N.Y.), and counting the detached cells using a Coulter counter.

To quantitate cell growth in the presence of soluble PVA, 3T3 fibroblasts (passage 4-17) were plated (10,000 cells/cm$^2$) into 24 well tissue culture dishes (Costar; Cambridge, Mass.) in Dulbecco's Modified Eagle Medium (Gibco) containing 10% calf serum (Hyclone Lab. Inc.; Logan, Utah) and 2% dissolved PVA. The number of adherent cells was determined 4, 24, 48, and 96 hr after plating by washing dishes with PBS, removing adherent cells with a solution of 0.05% trypsin/0.53 mM EDTA (Gibco), and counting the cells with a Coulter counter.

To seed sponges, a hepatocyte suspension (0.4 ml/device of 5×10$^7$ cells/ml) was placed on 1 mm thick sponges, and allowed to adhere for approximately 1 hr before implantation. To determine the number of cells which were actually delivered, the number of cells which remained in the petri dish after the sponge was removed and implanted were quantitated.

Devices (with or without cells) were implanted into the mesentery (3 sponges/animal) of Lewis rats with portal-caval shunts, harvested, and prepared for histological examination as previously described (Uyama et al., 1993). Seeding and implantation of PLA and 85/15 PLGA sponges were done on different days with hepatocytes from different isolations. The number of hepatocytes present in histological sections was determined using a computerized image analysis system (Image Technology Corp.). The area of each section comprised of hepatocytes was determined, and converted to cell numbers using a measured average area per hepatocyte. Hepatocytes were identified by their large size, large and spherical nuclei, and distinct cytoplasmic staining.

C. Results

Highly porous sponges were formed from PLA and 85/15 PLGA using a previously described technique (Mikos et al., 1993b). The size and shape of devices formed in this manner can be controlled by the geometry of the Teflon mold and the mass of salt particles and polymer loaded into the mold. The porosity and pore size of devices formed with this type of particulate leaching technique can be controlled by varying the ratio of polymer/salt particles and the size of the salt particles (Mikos et al., 1993b). In this study, the ratio of polymer/salt was varied from 0.06 to 0.03 to increase the device porosity from 90±1 to 95±1.5%, and cylindrical devices 1–5 mm thick (d=2 cm) were fabricated by increasing the mass of polymer and salt from 0.412 to 2.06 grams.

Polymers of the lactic/glycolic acid family are all relatively hydrophobic, as indicated by high contact angles with water. The contact angle of films fabricated from poly-L, lactic acid, polyglycolic acid, poly-D,L lactic acid, and 85/15 and 50/50 copolymers of lactic and glycolic acid were $79°±2°$, $73°±2°$, $72°±1°$, $73°±2°$, and $69°±3°$, respectively. To determine whether the hydrophobicity of these polymers could be decreased, solid films of PLA were coated with the hydrophilic polymer PVA or a surfactant, Pluronic F 108.

The advancing water contact angle decreased from $79°±2°$ to $23°±2°$ when devices were exposed to PBS containing 10 mg/mL solution of PVA. When PVA solutions ranging from 1 to 100 mg/mL were used for coating, a similar decrease in the contact angle of polymer films was noted. The contact angle of PLA films also decreased from $79°±2°$ to $22°±3°$ when a 1 mg/mL solution of the Pluronic surfactant was utilized in place of the PVA.

Contact angle decreases in the same range were found when devices fabricated from PGA, or copolymers of lactic and glycolic acid were similarly treated with PVA (e.g., the contact angle of films of a 50/50 copolymer decreased to $21°±7°$). The decrease in the hydrophobicity of the polymer films was not permanent, however, as immersion of coated polymer discs into a PBS solution led to a rebound in the contact angle over a 24 hr period. For example, the contact angle of Pluronic-coated devices returned to $76°±2°$ after 24 hr in PBS. These results suggest that the coating molecule re-dissolved over time in an aqueous environment.

To determine if this treatment detrimentally effected cell adhesion, hepatocytes were plated on PLA discs treated with PVA or left untreated. The efficiency of hepatocyte adhesion was 60±17% versus 58±10% for untreated and treated discs, respectively. This result indicated that the treatment did not detrimentally affect the ability of hepatocytes to adhere to this polymer. This was likely, as the PVA redissolves when placed in an aqueous environment (see above).

Fibroblast proliferation studies were next performed to determine whether soluble PVA would adversely effect cell proliferation. Fibroblasts are one of the major cell types that interact with implanted materials. These cells proliferated in the presence of soluble PVA, although the growth rate was slower than that of cells cultured without PVA exposure.

Porous sponges fabricated from PLA were subsequently treated with aqueous solutions of PVA to determine whether PVA infiltration would improve the ability of aqueous solutions to adsorb into three-dimensional sponges. The sponge weight increased from 8 to 98% as the PVA concentration was raised from 1 to 100 mg/mL. Infiltrating sponges with solutions of 1–10 mg/mL had a minimal effect on the device pore size and porosity, but infiltrating with a 100 mg/mL solution significantly decreased both. Devices infiltrated with a solution containing 10 mg/mL of PVA rapidly and reproducibly absorbed aqueous solutions equivalent to 98±1% of their pore volume, while untreated devices only absorbed a volume of water equivalent to 6±2% of their pore volume. Importantly, the porosity and pore size of devices returned to their original values following exposure to an aqueous environment for 24 hr. Re-dissolution of the PVA infiltrating the sponge occurred during this time, as the device weight returned to within 5±3% of the original value under these conditions (similar results were obtained when sponges fabricated from 85/15 PLGA were tested).

Freshly isolated, primary rat hepatocytes were next seeded onto 1 mm thick, 95% porous PLA and 85/15 PLGA sponges for transplantation. Examination of devices revealed that, as expected, a much higher density of hepatocytes was present in the PVA treated devices than in untreated devices. Quantitation of the seeding efficiency indicated that 90±1% of the cells seeded onto PVA treated devices were delivered in vivo.

PVA-treated sponges seeded with hepatocytes were next implanted into the mesentery of laboratory rats. Examination of histological sections of a device removed immediately after implantation confirmed that cells were evenly distributed throughout the pore volume of device. One week after implantation, the remaining devices were removed from the animals and processed for histological analysis. Fibrovascular tissue from the host grew through the devices during this time. Engrafted hepatocytes were found in 15 out of 15 implanted PLA devices, and 6 out of 6 implanted 85/15 PLGA sponges. In all cases, hepatocyte transplantation led to the formation of a tissue comprised of the polymer device, transplanted cells, and fibrovascular tissue from the host. Computerized image analysis revealed that $6±2×10^5$ hepatocytes engrafted per PLA sponge, and $2.4±1.5×10^5$ hepatocytes engrafted per 85/15 PLGA sponge.

In this example inventors describe the fabrication of modified PLA and 85/15 PLGA sponges that can be utilized to transplant large numbers of cells into experimental animals. To efficiently seed and deliver cells on three-dimensional sponges the inventors infiltrated the sponges with the more hydrophilic PVA. The PVA treatment allowed aqueous solutions to readily penetrate virtually the entire pore volume of the sponges, but had little effect on the ability of hepatocytes to adhere to PLA films. After exposure to the aqueous environment the PVA redissolved.

This approach combines the advantages of using the versatile PLGA polymer family for fabricating delivery devices with the advantages of hydrophilic polymers such as PVA. These two polymers could possibly be blended or copolymerized to achieve a similar effect, but the approach outlined here is simpler. The results also suggest that a temporary alteration of the PLGA sponge properties is sufficient for achieving uniform and efficient cell seeding, and this approach does not chemically alter the favorable properties of the PLGA utilized to fabricate the sponges.

Linear PVA has been reported to cause hypertension, nephrosis, and to accumulate in the liver following injection (Hall and Hall, 1962; Sanders and Matthews, 1990). However, low molecular weight PVA, such as that used in the present study (MW=3000), is filtered and secreted by the kidneys, and does not appear to accumulate in the body (Hall and Hall, 1962; Sanders and Matthews, 1990). Additionally, the low mass of PVA used to coat sponges in the present study (11 mg/sponge) is much lower than the doses noted to cause hypertension or other problems in experimental animals.

This method for fabricating devices has wide applicability. A variety of other types of water soluble molecules, such as the Pluronic surfactants, can also be utilized as the coating molecule. This type of treatment will be useful for improving cell seeding into a variety of hydrophobic polymer devices, both biodegradable and non-biodegradable.

This example also shows that significant numbers of hepatocytes survive and form a new tissue, with the ingrowing fibrovascular tissue and the polymer device, following transplantation. Fibrovascular tissue invasion leads to the formation of a vascular network that supplies the metabolic needs of the developing tissue. The implantation of porous, synthetic materials in vivo leads to this general type of response, and the rate of the tissue ingrowth is a function of the device porosity and pore size (Mikos et al., 1993b; Sanders and Matthews, 1990; Wesloski et al., 1961). No physical alterations in the polymer sponges were noted in these implantation studies.

Quantitation of the number of engrafted hepatocytes after two weeks in vivo revealed that $6 \times 10^5$ (PLA sponges) of these cells survived. Fewer hepatocytes engrafted when transplanted in 85/15 PLGA sponges, but the difference was not statistically significant. This difference may result from variations in the hepatocyte isolations in the two studies, or may reflect the small sample number of 85/15 PLGA sponges implanted. The number of engrafted hepatocytes in both cases is significant, indicating these sponges are useful for engineering liver tissue. Devices with a decreased thickness could also be utilized to transplant cells, or a lower cell density could be transplanted.

EXAMPLE VIII

Matrix-tissue Drug Delivery

Regenerated tissue or matrix-tissue materials can be utilized to deliver protein growth factors in vivo in order to alter the engraftment, proliferation and vascularization of the engineered tissues.

The present example shows epidermal growth factor (EGF) incorporation (0.11%) into microspheres (19+12 mm) fabricated from a copolymer of lactic and glycolic acid using a double emulsion technique. The incorporated EGF was steadily released over one month in vitro, and it remained biologically active, as determined by its ability to stimulate DNA synthesis, cell division, and long-term survival of cultured cells. EGF-containing microspheres were mixed with a suspension of cells, in this example, hepatocytes, seeded onto porous sponges, and implanted into the mesentery of two groups of Lewis rats. The engraftment of transplanted hepatocytes in animals was increased 2-fold by adding EGF microspheres, as compared to adding control microspheres.

These results first indicate that it is possible to design systems which can alter the microenvironment of transplanted cells, in this case exemplified by hepatocytes, to improve their engraftment.

Hepatocytes are used as a model system to exemplify that the cell-matrix-growth factor delivery methods of the present invention will have clinical utility. A variety of factors have been identified that induce hepatocyte growth. These include epidermal growth factor (EGF), α fibroblastic growth factor, hepatocyte growth factor, and transforming growth factor α (Fausto, 1991).

As with the oral tissue aspects of the present invention, the delivery vehicles in this example are fabricated from biodegradable polymers, which are especially attractive as the drug delivery can be controlled by diffusion through the polymer backbone and/or by erosion of the polymer. Systems to deliver factors relevant to hepatocytes, such as insulin (Brown et al., 1986) and EGF (Murray et al., 1983) have been previously developed. Small quantities of biologically active factors could be released over extended periods with these systems, but the form of the devices (solid polymer slabs) was not suitable for co-transplantation with cells.

In this example a technique is described to deliver biologically active factors, such as EGF, over extended periods to hepatocytes transplanted into heterotopic sites. This approach modulates the microenvironment of transplanted hepatocytes to improve engraftment. This example provides appropriate support for the oral drug delivery methods of the present invention as both hepatic and oral tissues are known to have the capacity to regenerate, which capacity is influenced by growth factors (see herein above).

A. Microsphere Preparation and Characterization

Microspheres containing EGF were prepared by a modification of a previously described double-emulsion technique (Cohen et al., 1991). In brief, a 75/25 copolymer of poly-(D,L-lactic-co-glycolic) acid (Resomer RG 75R, intrinsic viscosity 0.2; Henley Chem. Inc., Montvale, N.J.) was dissolved in ethyl acetate (Fisher Scientific) to yield a 5% solution (w:v). Mouse EGF (Collaborative Research; Bedford, Mass.) was dissolved in water to yield a solution of 2 mg/ml, and 50 ml of the EGF solution was added to 1 ml of the polymer solution. The polymer/EGF solution was sonicated continuously at 10 watts (Vibracell; Sonics and Materials, Danbury, Conn.) for 15 sec to yield a single emulsion.

An equal volume of an aqueous solution containing 1% polyvinyl alcohol (MW 25,000, 88% hydrolyzed; Polysciences Inc., Warrington, Pa.) and 7% ethyl acetate was added to the single emulsion, and the resulting solution was vortexed (Vortex Mixer; VWR) for 15 sec at the high setting to yield the double emulsion. This double emulsion was transferred to a rapidly stirring 250 ml beaker containing 150 ml of an aqueous solution of 0.3% polyvinyl alcohol/7% ethyl acetate. The ethyl acetate was allowed to evaporate over the ensuing 3 hr to yield polymer microspheres with entrapped EGF. The microspheres were then filtered, washed with water, and microspheres with a size between 32 and 0.4 mm were collected. The microspheres were lyophilized (Labconco Freeze Dryer, Kansas City, Mo.), and stored at −20° C. until use. Control beads were prepared with the same procedure, but the aqueous solution used to form the first, single emulsion (water in organic) contained no EGF.

To determine the efficiency of EGF incorporation, and the kinetics of EGF release from the microspheres, $^{125}$I-labeled mouse EGF (260 mCi/mg; Biomedical Tech. Inc., Stoughton, Mass.) was utilized as a tracer. Approximately 1 μCi of labeled EGF was added to the aqueous EGF solution before formation of the single emulsion, and the beads were prepared as described above. After bead fabrication, a known mass of beads was counted in a LKB CliniGamma 1272 (Wallac, Gaithersburg, Md.), and the incorporated cpm was compared to that of the initial aqueous EGF solution to calculate the percentage of the total EGF that was incorporated into the beads.

To determine the release of EGF from microspheres, a known mass of beads (approximately 10 mg) prepared with the labeled EGF were placed in a known volume (2 ml) of phosphate buffered saline (PBS) solution containing 0.1% Tween 20 (Sigma Chem. Co.) and placed in an incubator maintained at 37° C. At set times, the solution was centrifuged to concentrate the beads at the bottom of the vial, and samples (0.1 ml) of the PBS/Tween 20 solution were removed. The sample volume was replaced with fresh PBS/Tween 20 solution. The amount of $^{125}$I-EGF released from the microspheres was determined (n=4) at each time point by counting the removed sample in a gamma counter, and compared to the $^{125}$I-EGF loaded into the microspheres. The maximum theoretical EGF concentration in the release medium (approximately 5 mg/ml) was well below the maximum solubility of EGF, thus establishing sink conditions for the release study.

For scanning electron microscopic examination, samples were first gold coated using a Sputter Coater (Desk II, Denton Vacuum, Cherry Hill, N.J.), and imaged using an environmental scanning electron microscope (ElectroScan; Wilmington, Mass.). Photomicrographs were taken with Polaroid 55 film. The particle size distribution of microspheres was determined using a Coulter Multisizer II (Coulter Electronics, Luton, UK).

B. In vitro Analysis of the Biological Activity of Released EGF

Cultured hepatocytes were utilized to determine whether the EGF incorporated into and released from microspheres had retained its biological function. Hepatocytes were isolated from Lewis rats using a two-step collagenase perfusion, and purified using a Percoll gradient as previously described (Mooney et al., 1992). Hepatocytes were plated at a density of 10,000 cells/cm$^2$ on 24 well tissue culture dishes coated with 1 $\mu$g/cm$^2$ of type I collagen (Collagen Corp., Palo Alto, Calif.) using a carbonate buffer coating technique (Mooney et al., 1992). Serum-free William's E medium (Gibco, Grand Island, N.Y.) containing insulin (20 mU/ml; Sigma), dexamethasone (5 nM; Sigma), sodium pyruvate (20 mM; Gibco), a mixture of penicillin and streptomycin (100 U/ml; Irvine Scientific, Santa Ana, Calif.), and ascorbic acid (50 $\mu$g/ml, fresh daily; Gibco) was used for all studies. Varying amounts of soluble EGF (Collaborative Research, Bedford, Mass.) were added to the medium in certain studies.

For conditions in which EGF released from microspheres was utilized, medium with no EGF was incubated with EGF containing microspheres for 24–96 hr to allow release of known amounts of EGF (calculated using the known release kinetics), the solution was centrifuged, and the medium containing the released EGF was removed and used in subsequent studies.

To analyze cell entry into S phase of the cell cycle, tritiated thymidine autoradiography was utilized. Cultured hepatocytes were refed 48 hr after plating with medium containing 1 $\mu$Ci/ml $^3$H-thymidine (NEN; Boston, Mass.). At 72 hr cells were twice washed with PBS to wash out any non-incorporated $^3$H-thymidine, fixed with glutaraldehyde, and dehydrated with 100% methanol. Culture wells were overlaid with NTB-2 emulsion (Kodak; Rochester N.Y.), and the dishes were allowed to expose for 7 days in complete darkness. Dishes were developed with D-19 developer (Kodak), and photomicrographs of the cells were taken with TMAX-100 film (Kodak) on a Nikon Diaphot microscope.

In separate studies to determine the survival and division of cultured hepatocytes over time, the number of hepatocytes present in wells after 1, 4, 6, 8, and 11 days of culture was quantitated by removing the cells with a solution of 0.05% Trypsin/0.53 mM EDTA (Gibco) and counted in a Coulter counter.

C. In vivo Analysis of EGF Microsphere Co-Transplantation with Hepatocytes

Isolated and purified hepatocytes were mixed with EGF-containing or control microspheres, and seeded onto 95% porous cylindrical sponges (diameter=2.15 cm, thickness=1 mm) in a petri dish. The sponges were fabricated from poly-(L, lactic) acid (Medisorb; Cincinnati, Ohio), and coated with polyvinyl alcohol, as previously described (Mooney et al., 1992). Each sponge received 0.4 ml×50×10$^6$ hepatocytes/ml+10 mg of microspheres. Quantitation of the number of hepatocytes remaining in each petri dish after implantation of the polymer-cell devices revealed that 90+1% of the seeded hepatocytes were implanted.

Cell-polymer devices were implanted into the mesentery of laboratory rats as previously described (Uyama et al., 1993). Seven days before implantation of cell-polymer devices, ½ of the animals received an end to side portal caval shunt (PCS). A total of 6 polymer-cell devices were implanted per condition (2 animals per condition each received 3 implants).

Implants were removed after 14 days, fixed in formalin, and processed for sectioning. Sections of implants were stained with hematoxylin and eosin, and engrafted hepatocytes were identified by their large size, large and spherical nuclei, and distinct cytoplasmic staining. Immunohistochemical staining of sections with antibodies directed against albumin confirmed that cells identified by hematoxylin and eosin staining were indeed hepatocytes.

Computerized image analysis (Image Technologies Corp.) was utilized to quantitate the area of each section which was comprised of hepatocytes. The number of hepatocytes per histological section was calculated by dividing the area of each section comprised of hepatocytes by the average area of a single hepatocyte (experimentally determined by measuring the area of 30 individual hepatocytes and averaging). The number of hepatocytes per sponge was calculated by taking the number of hepatocytes per section and multiplying by the ratio of the volume of the total sponge to the volume of a histological section (this is equivalent to multiplying by the total number of sections with an equal volume which can be cut from the sponge).

D. Results

The size of the microspheres fabricated with the double-emulsion technique was dependent on the concentration of the initial polymer solution. A polymer solution of 5% (w:v) yielded microspheres in which the majority were in the desired size range of 10 to 30 mm (the approximate size of suspended hepatocytes). Analysis of these microspheres revealed that the average diameter was 19+12 mm. The yield of microspheres with this process was 92+5%.

Figure 9:
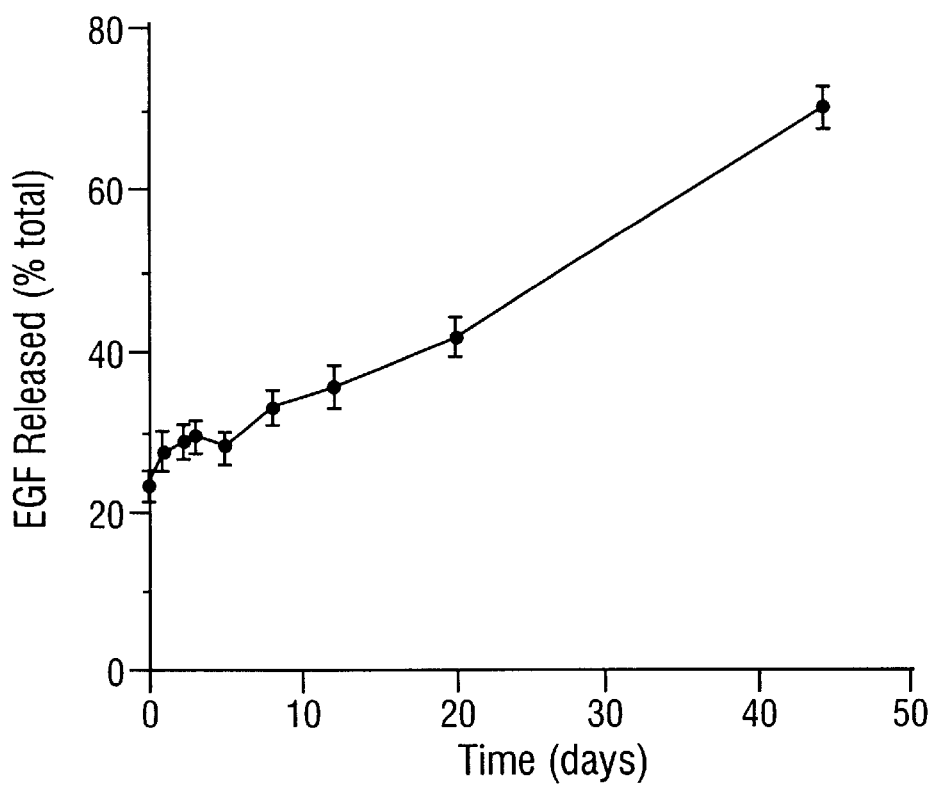
FIG. 9. Release of $^{125}$I-labeled EGF from polymer microspheres. Results were normalized to the $^{125}$I-labeled EGF incorporated into microspheres. Values represent the mean and standard deviation calculated from quadruplicate measurements.

To determine the efficiency of EGF incorporation into microspheres, and the release profile from the microspheres, $^{125}$I-labeled EGF was utilized as a tracer. Approximately ½ of the initial EGF (53+11%) was incorporated into microspheres. When EGF-containing microspheres were placed in an aqueous medium, an initial burst of EGF release was noted (FIG. 9). After this time EGF was released in a steady manner over the remainder of the 30 day time course (FIG. 9).

Studies with cultured hepatocytes were subsequently performed to determine whether the released EGF retained its biological activity. EGF released from microspheres stimulated hepatocyte entry into the synthetic (S) phase of the cell cycle, indicating that it retained its biological activity.

Figure 10A:
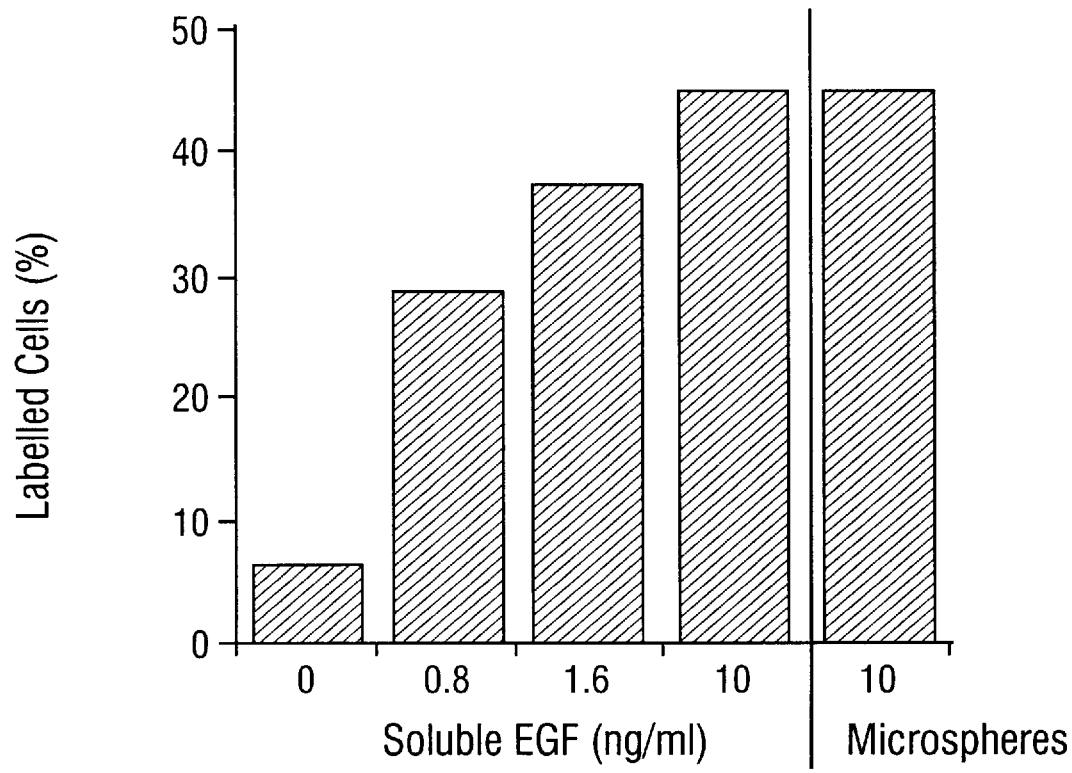
FIG. 10A and FIG. 10B.
Figure 10B:
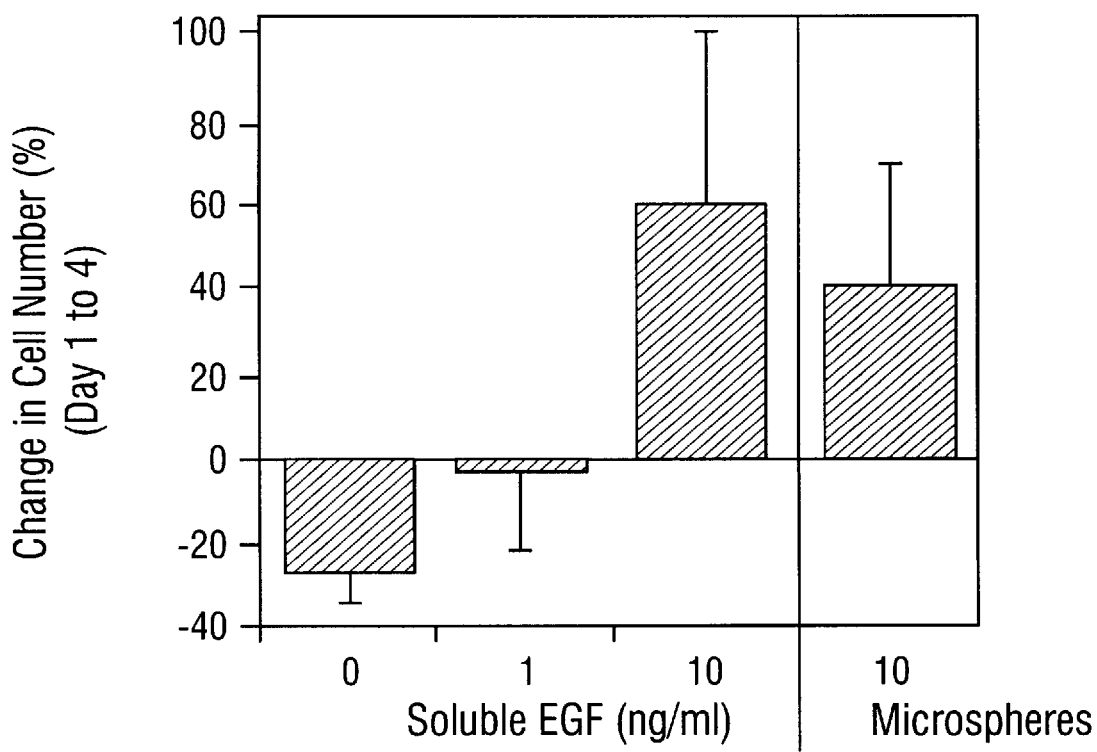

EGF stimulates hepatocyte growth in a dose-dependent manner, and quantitation of the number of hepatocytes entering S phase revealed that the same dose of EGF either released from microspheres or EGF never incorporated into microspheres (control) showed a similar stimulation (FIG. 10A). Incorporated and released EGF stimulated cells to proceed through mitosis. The number of cultured hepatocytes increased in a similar manner from day 1 to day 4 when the same concentration of either released EGF or control EGF was utilized (FIG. 10B). Not only is proliferation inhibited in medium containing no EGF or a low concentration of soluble EGF (1 ng/ml), but cell death occurred under these conditions (FIG. 10B).

The importance of EGF for maintenance of hepatocyte survival was even more pronounced over more extended periods in culture. The majority of hepatocytes died over eleven days in culture when no EGF was present, but EGF released from the microspheres was largely able to prevent this cell loss in vitro.

EGF-containing microspheres were next suspended in PBS and seeded onto polymer sponges (40 mg in 0.4 ml per sponge) to confirm that microspheres would evenly distribute throughout devices used to transplant hepatocytes. The devices were implanted in the mesentery of Lewis rats, removed after one week, and sectioned and stained for histological examination. The high seeding efficiency and even distribution of hepatocytes seeded onto these devices has been previously described (Mooney et al., 1995a). Cross-sections of the implanted devices revealed a relatively even distribution of microspheres throughout the fibrovascular tissue which invaded the devices during the implantation time.

To determine whether EGF released from microspheres could positively influence the engraftment of hepatocytes transplanted to a heterotopic site, hepatocytes ($2 \times 10^7$ cells/sponge) and microspheres (10 mg/sponge) were mixed together and seeded onto porous, biodegradable sponges fabricated from poly-(L-lactic) acid. Cell/microsphere-seeded devices were implanted into the mesentery of laboratory rats, ½ of which had previously received PCS. Retrieval of implants after two weeks, followed by histological preparation and observation, revealed that animals which had a PCS and received EGF containing microspheres had the greatest number of engrafted hepatocytes. Animals which had a PCS and received control microspheres had fewer engrafted hepatocytes, and animals which did not receive a PCS had even less.

Quantitation of these results using computerized image analysis confirmed that animals with a PCS and EGF microspheres contained two-fold more cells than animals with a PCS and control beads ($p<0.05$). Animals without a PCS, either with EGF or control microspheres, had approximately one third the number of engrafted hepatocytes as animals with PCS and EGF microspheres. No statistically significant difference between the control and EGF microsphere conditions was found in animals which did not receive a PCS.

The present system thus releases growth factors at the site of cell transplantation using polymer microspheres. The EGF incorporated and released from polymeric microspheres retained its biological activity in vitro, and was able to positively effect the engraftment of cells transplanted in animals.

Delivery of growth factors via sustained release from microspheres is thus shown to be a flexible technique to control the local environment of transplanted cells. A known dose of a factor can be delivered with this approach, and the dose required for a biological effect can be quite small (approximately 10 mg/sponge in this study) because of the localized delivery at the desired site of action.

The time over which a drug is released from a polymer matrix can typically be regulated by the drug loading, the type of polymer utilized, and the exact processing conditions (Mooney et al., 1992). The release of protein from copolymers of lactic and glycolic acid, such as utilized in this study, is generally controlled by the erosion of the polymer when the protein/polymer ratio is low (Cohen et al., 1991). The released protein must retain its biological activity for this approach to be useful. The biological activity of the EGF incorporated into and released from microspheres in this study was not adversely affected. This approach to deliver EGF could also be readily expanded to deliver other molecules, either alone or in combination.

The lack of blood vessels in the present implants immediately following implantation likely leads to low oxygen tensions in the interior sections of implanted devices. The majority of implanted hepatocytes in interior section of devices die after implantation (Mooney et al., 1995a), and surviving hepatocytes are typically observed at the exterior portions of the implants. However, establishing vascular connections is transplanted oral tissues is not believed to present any problem and the blood flow and oxygen transport to transplanted oral tissues suggests that oral tissue engraftment would be even more successful.

EXAMPLE IX

Growth of Pulp-derived Fibroblasts on Matrices

Tissue engineering of dental pulp tissue involves isolation of healthy cells from damaged or healthy tissue and multiplying them in culture on a three dimensional synthetic matrix to form a new tissue. The matrix material may be fabricated from naturally-derived (e.g., collagen) or synthetic materials (e.g., polymers). Synthetic, biodegradable polymers such as polyglycolic acid (PGA) meshes, as described herein above, may be used as scaffold materials due to their reproducible properties and structures. Because the polymer degrades over time, eventually only natural tissue remains, with no permanent foreign body.

As described herein above, PGA is an effective synthetic matrix for in vitro generation of dental pulp tissue. This Example describes the optimization of cell seeding in the process of tissue formation on PGA matrices. Also described is the use of other matrices (type I collagen, and alginate) to promote dental pulp tissue formation in vitro.

A. Materials

Cells were explanted and propagated from adult human dental pulp as previously described (Rutherford et al., 1992a). Cells were cultured in DMEM (Gibco; Grand Island, N.Y.) supplemented with penicillin/streptomycin (Gibco), and 10% fetal calf serum (Gibco). Cells between passages 7 to 10 were used.

Cells were seeded onto non-woven matrices (thickness=3 mm; bulk density=50 mg/cc) fabricated from PGA fibers (12 μm in diameter) utilizing a dynamic cell seeding protocol previously described (Kim et al., 1997). In brief, cells cultured on tissue culture flasks were trypsinized, pooled, and concentrated to $1\times10^7$ cells/ml in tissue culture medium. Each PGA scaffold (5×5 mm square) was placed in a 50 ml tube with 0.2 ml of the cell suspension and agitated for 20 hours. Matrices were removed from the tubes and subsequently cultured in standard tissue culture flasks for time periods ranging from 1 to 90 days.

Cells were seeded in collagen gel matrices by first preparing a solution of collagen (9 parts type I collagen (2.9 mg/ml; Collagen Corp.), 1 part 10× PBS, 1 part cell suspension ($2.9\times10^6$ cells/ml)). In each 1.5 cm diameter well, 0.35 ml of the collagen solution was deposited, and then gelled by warming to 37° C. Time points for these cell-seeded matrices were taken between 1 and 45 days. As controls, cells were also cultured on standard tissue culture plastic surfaces alone and coated with an adsorbed layer of type I collagen, both at a concentration of $2\times10^5$ cells/ml.

Gross measurements were made of the cell-polymer constructs at each time point. Samples were prepared for visualization with a scanning electron microscope by fixing with a 1% solution of glutaraldehyde for 30 min, dehydrating in ethanol, and sputter coating (Desk II; Denton Vacuum, Cherry Hill, N.J.) with gold. Photomicrographs were taken on Polaroid 55 film. Samples were prepared for sectioning and staining by fixing with a solution of 3.7% formalin in phosphate buffered saline. Thin sections (5 mm) were cut and stained with hematoxylin and eosin using standard techniques, or with a trichrome stain to visualize collagen. Photomicrographs were taken with Kodak Elite slide film.

The cell content of cell-polymer constructs was determined using a variation of a DNA dye binding assay previously described (Kim et al., 1997), which involves use of a fluorimeter (DyNA Quant 2000; Hoefer Sci. Inst.; San Francisco, Calif.) to assay the binding of the dye Hoechst 33258 to DNA. A calibration curve was constructed for this assay using known numbers of cultured cells. Cell densities were determined by dividing the number of cells in each construct (determined with DNA assay) by the volume of the tissue (determined with gross measurement).

Cells cultured in the collagen gel were removed for quantification by incubating the cells with 0.5 ml of a 3 mg/ml solution of type I collagenase (Sigma) in PBS for 45 minutes. A cell count was then obtained using a Coulter counter. Cells cultured on the control surfaces (tissue culture plastic and adsorbed collagen coating) were removed with trypsin and counted with the Coulter counter.

To assess cell metabolic activity, staining with (3-[4,5-Dimethylthiazol-zyl]-2,5-diphenyl tetrazolium bromide) or MTT (Sigma) was performed on cells seeded on PGA, alginate, and in a collagen gel at time points of 3 and 14 days. A stock solution of 5 mg/ml MTT in PBS was prepared, and 0.1 ml of this stock solution was added to each milliliter of cell culture media and incubated at 37° C. After 2 hours, photomicrographs were taken with Kodak Elite slide film.

B. Characterization of Pulp-Derived Fibroblast Growth

Pulp-derived fibroblasts were seeded onto PGA matrices utilizing a dynamic seeding method which greatly enhances cell-matrix contact and cellular adhesion to the matrix (Kim et al., 1997). Scanning electron microscopic observation of matrices following seeding revealed numerous cells adherent to individual polymer fibers. The cells were generally aggregated into large cell masses, although individual cells could be observed on fibers. The adherent cells subsequently proliferated on the fibers and began to span the space between adjacent fibers by day 7. Cellular proliferation and matrix contraction led to a confluent layer of cells on the exterior of the polymer matrices by 21 days, although polymer fibers were still visible at this time. However, by 35 days, no polymer fibers were visible on the exterior of the forming tissue, and a multilayered cell mass was observed at this time.

Figure 11A:
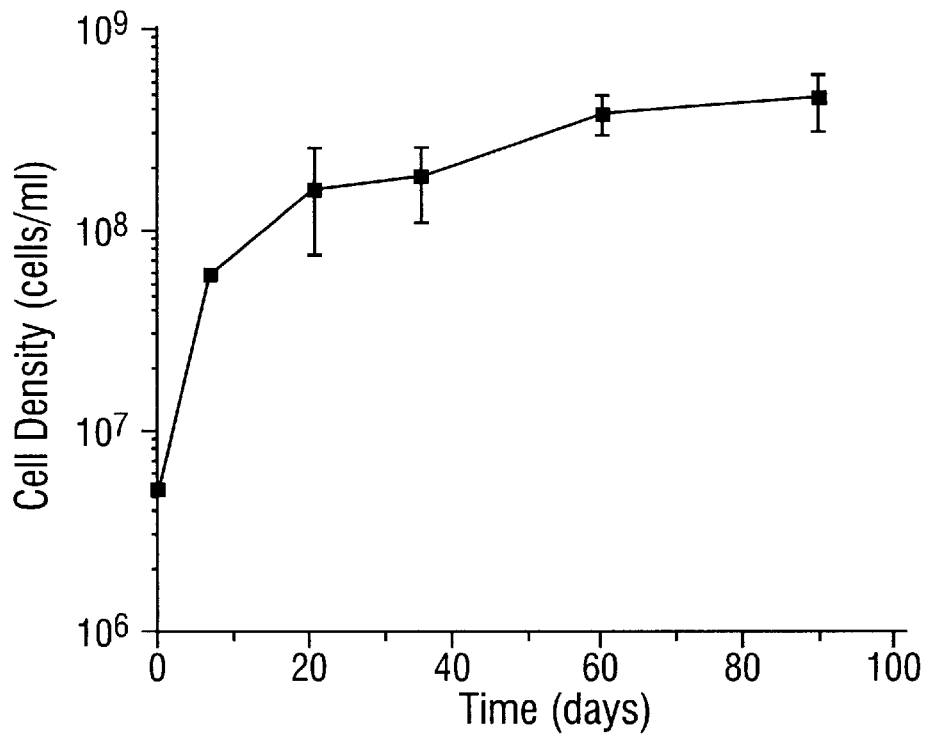
FIG. 11A and FIG. 11B. Growth of fibroblasts over time on matrices.

Quantitation of the number of cells on the PGA matrices indicated that approximately $5\times10^6$ cells/ml were adherent immediately following seeding. The initial cell density was approximately one order of magnitude higher than that obtained previously with a static seeding method (Mooney et al., 1996b). The cell density rapidly increased after this time, and by 21 days reached a value ($1.4\times10^8$ cells/ml) that was approximately 20× the initial cell density (FIG. 11A). The cell density remained approximately constant after this time for the remaining 70 days of the experiment.

Figure 11B:
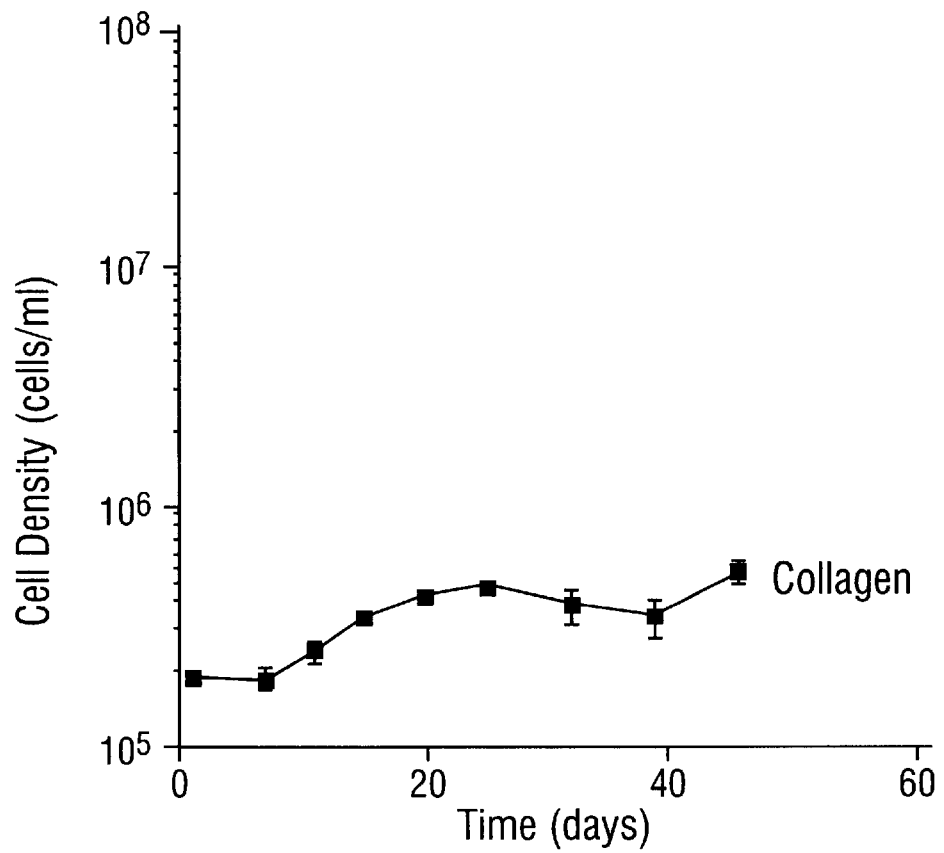
Figure 12:
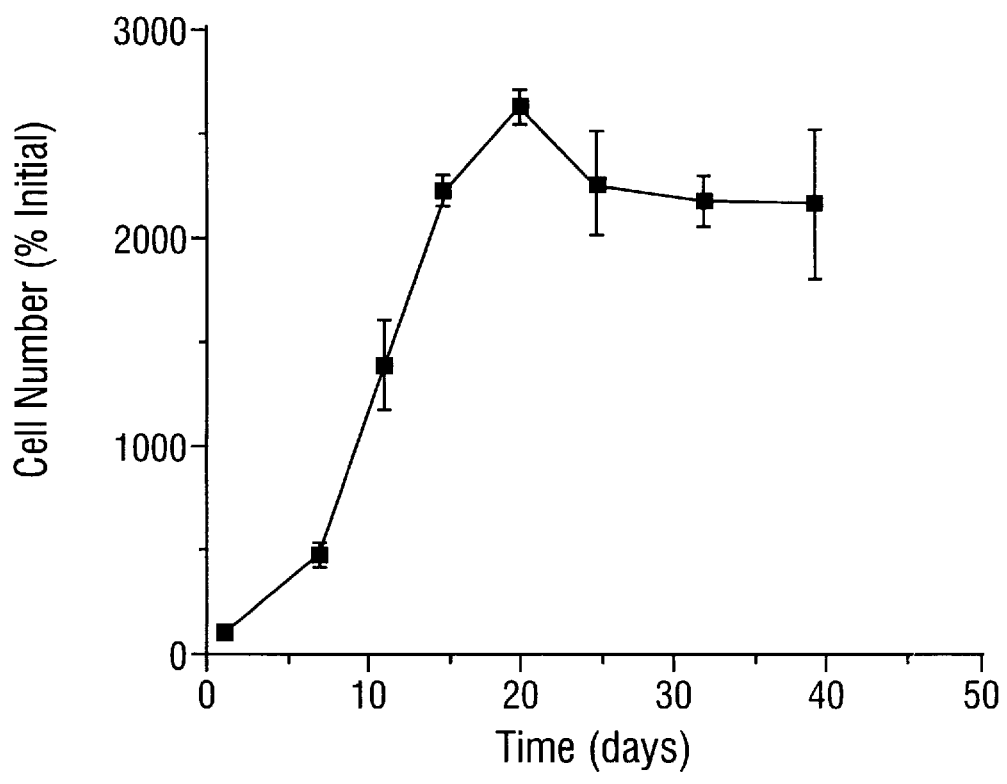
FIG. 12. Proliferation of fibroblasts over time on coating of adsorbed collagen.

In contrast to tissue development of PGA matrices, cells seeded within alginate or collagen hydrogels did not form new tissues with a high cell density. The cell density in alginate-seeded matrices remained constant for the 18 days of the experiment, while only a modest increase in cell density (to approximately $5\times10^5$ cells/ml) was observed over 45 days when a collagen gel matrix was utilized (FIG. 11B). Cell growth within the collagen gel was accompanied by contraction of the gel, as it pulled away from the well walls and assumed a size after 45 days that was approximately half its original diameter. Cells on alginate matrices rapidly lost metabolic activity (as indicated by MTT incorporation), while cells in collagen or PGA matrices remained highly active. The failure of cells to multiply in collagen matrices was not caused by a general inability of these cells to interact with collagen, as cells cultured on petri dishes coated with type I collagen proliferated rapidly (FIG. 12).

Histological examination of cell-PGA constructs cultured for extended time periods revealed tissues comprised of cells distributed evenly throughout a new matrix with little polymer remaining. Collagen was present in the matrix surrounding the cells, as indicated by Trichrome staining. In contrast to these findings, examination of cell-collagen constructs revealed a tissue with a low cellularity. Cells formed a monolayer on the exterior of the collagen matrix, and very few cells were visible in the interior of the matrix.

New dental pulp-derived tissues can be engineered in vitro by culturing pulp-derived human fibroblasts on synthetic ECM. Enhancing the cell seeding and culture techniques previously used resulted in a more efficient method of developing engineered pulp tissue on PGA matrices. The specific synthetic ECM utilized to engineer the tissues plays a critical role in the development of the new three-dimensional tissue in vitro. The use of collagen gels or alginate did not lead to the development of new tissues which resembled native pulp, while matrices fabricated from fibers of PGA did lead to the development of a high cell density new tissue with a high collagen content.

Optimization of the method for seeding cells on PGA led to an increase in initial cell density from approximately $9\times10^5$ cells/ml (Mooney et al., 1996b) when using static seeding to $5\times10^7$ cells/ml for stirred seeding. One advantage of obtaining a higher cell density is a quicker return of the engineered tissue to the patient. In addition, matrix stability is enhanced, as the degradation of the synthetic ECM can be coordinated with the development of the new tissue.

The use of alginate as a synthetic matrix for dental pulp tissue was the least preferred for this particular system. Cells did not adhere to the alginate, thus leading to no cell growth. However, in other embodiments, the use of alginate matrices is not excluded.

While cells did adhere and grow to the collagen I gel, the cell density in the matrix after 45 days was still quite low ($5\times10^5$ cells/ml). In contrast, cells on an adsorbed layer of collagen I exhibited rapid growth, proliferating at a rate comparable to that of the control cells on tissue culture polystyrene. This observation leads to the conclusion that collagen I is a suitable material for cell proliferation, but the manner in which the matrix is presented is critical. In the form of a gel, the collagen does not provide enough mechanical stability for the tissue to develop.

EXAMPLE X

Formation and Characterization of Pulp and Gingival Fibroblast/PGA Constructs Studies were performed to determine the optimum cell concentrations and stirring times to attach pulp and gingival fibroblasts to nonwoven polyglycolic acid (PGA) scaffolds. Cells were obtained as described herein above. It was shown that for each cell, stirring 1×1×0.3 cm scaffold pieces with $1\times10^6$ cells/ml media (alpha MEM supplemented with 10% fetal calf serum, penicillin and streptomycin), 5 ml/scaffold piece, for 24 hours was superior to shorter stirring intervals or $1\times10^5$ cells/ml media stirred for 2, 8 or 24 hours.

Immunocytochemical analysis of pulp fibroblast/PGA constructs incubated in vitro for 28 and 60 days revealed that type I collagen was secreted onto the scaffold, that the cells continued to divide, and that cell division was spread throughout the scaffold and not limited to the surface.

Human gingival and pulp fibroblast/PGA constructs were established as described above, incubated in fresh media (3 mls/scaffold piece) for an additional 24–48 hours and either analyzed for gene expression or surgically implanted subcutaneously into NIH-III (SCID-nude) mice, allowed to develop for 3 weeks in vivo, harvested and the tissues processed for light microscopy or RNA analysis.

The cell/scaffold constructs comprised of human pulp and gingival derived fibroblasts expressed the following genes associated with the development of bone and dentin; bone morphogenetic proteins −2, −4 and −7, bone morphogenetic protein receptors −IA, −IB and −II, activin receptor −1, type I collagen, and the transcription factor MSX-2, both before and after implantation in vivo. Light microscopic examination of cell/scaffold constructs comprised of human pulp and gingival derived fibroblasts incubated in vivo for 3 weeks revealed masses of tissue comprised of residual scaffold with attached cells, interspersed with unattached cells, connective tissue matrix and patent blood vessels which penetrate the mass. Analysis of RNA extracted from pulp and gingival fibroblast/PGA constructs by the reverse transcriptase polymerase chain reaction revealed the presence of human specific RNA for Alu sequences indicating that human cells had survived in vivo, whereas control implants without cells or containing mouse cells failed to express these human specific genes. Immunocytochemical analyses revealed that, whereas most of the fibrous connective tissue contained within the residual PGA fibers was of mouse origin, small amounts of human fibronectin was present.

The data from the in vivo experiments strongly suggests that the human cells delivered on PGA scaffolds survive implantation and are vascularized. These data also suggest that a portion of the extracellular matrix observed forming between the cells and residual scaffold was produced by the human cells.

All of the compositions, methods and/or apparatus disclosed and claimed herein can be made and executed without undue experimentation in light of the present disclosure. While the compositions, methods and apparatus of this invention have been described in terms of preferred embodiments, it will be apparent to those of skill in the art that variations may be applied to the compositions, methods and/or apparatus and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,137,921
U.S. Pat. No. 4,166,800
U.S. Pat. No. 4,181,983
U.S. Pat. No. 4,243,775
U.S. Pat. No. 4,279,249
U.S. Pat. No. 4,300,565
U.S. Pat. No. 4,347,234
U.S. Pat. No. 4,384,975
U.S. Pat. No. 4,390,519
U.S. Pat. No. 4,394,370
U.S. Pat. No. 4,409,332
U.S. Pat. No. 4,430,434
U.S. Pat. No. 4,530,449
U.S. Pat. No. 4,538,603
U.S. Pat. No. 4,539,981
U.S. Pat. No. 4,559,302
U.S. Pat. No. 4,563,489
U.S. Pat. No. 4,568,559
U.S. Pat. No. 4,578,384
U.S. Pat. No. 4,585,797
U.S. Pat. No. 4,596,574
U.S. Pat. No. 4,623,588
U.S. Pat. No. 4,682,195
U.S. Pat. No. 4,683,202
U.S. Pat. No. 4,703,108
U.S. Pat. No. 4,727,028
U.S. Pat. No. 4,741,337
U.S. Pat. No. 4,744,365
U.S. Pat. No. 4,795,804
U.S. Pat. No. 4,797,368
U.S. Pat. No. 4,818,542
U.S. Pat. No. 4,837,285
U.S. Pat. No. 4,839,130
U.S. Pat. No. 4,844,854
U.S. Pat. No. 4,877,864
U.S. Pat. No. 4,889,119
U.S. Pat. No. 4,898,186
U.S. Pat. No. 4,898,734
U.S. Pat. No. 4,916,193
U.S. Pat. No. 4,938,763
U.S. Pat. No. 4,960,704
U.S. Pat. No. 4,961,707
U.S. Pat. No. 4,968,590
U.S. Pat. No. 4,975,527

U.S. Pat. No. 5,004,602
U.S. Pat. No. 5,007,939
U.S. Pat. No. 5,011,691
U.S. Pat. No. 5,011,692
U.S. Pat. No. 5,013,649
U.S. Pat. No. 5,051,272
U.S. Pat. No. 5,077,049
U.S. Pat. No. 5,080,665
U.S. Pat. No. 5,081,106
U.S. Pat. No. 5,084,051
U.S. Pat. No. 5,106,748
U.S. Pat. No. 5,108,753
U.S. Pat. No. 5,108,755
U.S. Pat. No. 5,116,738
U.S. Pat. No. 5,128,136
U.S. Pat. No. 5,133,755
U.S. Pat. No. 5,139,941
U.S. Pat. No. 5,141,905
U.S. Pat. No. 5,143,730
U.S. Pat. No. 5,149,691
U.S. Pat. No. 5,162,430
U.S. Pat. No. 5,166,058
U.S. Pat. No. 5,168,053
U.S. Pat. No. 5,171,217
U.S. Pat. No. 5,185,152
U.S. Pat. No. 5,187,076
U.S. Pat. No. 5,192,741
U.S. Pat. No. 5,197,977
U.S. Pat. No. 5,206,028
U.S. Pat. No. 5,227,157
U.S. Pat. No. 5,231,169
U.S. Pat. No. 5,250,584
U.S. Pat. No. 5,268,178
U.S. Pat. No. 5,271,961
U.S. Pat. No. 5,278,201
U.S. Pat. No. 5,278,202
U.S. Pat. No. 5,281,419
U.S. Pat. No. 5,288,496
U.S. Pat. No. 5,308,623
U.S. Pat. No. 5,320,624
U.S. Pat. No. 5,324,307
U.S. Pat. No. 5,324,519
U.S. Pat. No. 5,324,520
U.S. Pat. No. 5,350,580
U.S. Pat. No. 5,354,855
U.S. Pat. No. 5,360,610
U.S. Pat. No. 5,366,508
U.S. Pat. No. 5,366,733
U.S. Pat. No. 5,366,734
U.S. Pat. No. 5,376,636
U.S. Pat. No. 5,614,396
U.S. Pat. No. 5,624,824
U.S. Pat. No. 5,624,830
U.S. Pat. No. 5,625,047

Alberts et al., *Molecular Biology of The Cell*, Garland Publishing, New York, 1983.

Allcock et al., "Hydrophilic polyphosphazenes as hydrogels: radiation cross-linking and hydrogel characteristics of poly [bis(methoxyethoxyethoxy) phosphazene]," *Biomaterials*, 9:509–513, 1988.

Allcock, "Phosphazene high polymers," In: *Comprehensive Polymer Science*, Vol 4. Allen G, ed., Pergamon Press, New York, 1989.

Alt, Kellems, Bertino and Schimke, *J. Biol. Chem.*, 253:1357, 1978.

Amiji and Park, "Surface modification of polymeric biomaterials with poly(ethylene oxide), albumin, and heparin for reduced thrombogenicity," *J. Biomater. Sci. Polym. Ed*, 4:217–234, 1993.

Anderson et al., "Morphology and Primary crystal structure of a silk-like protein polymer synthesized by genetically engineered *Escherichia coli* bacteria," *Biopolymers*, 34:1049–1058, 1994.

Angel, Bauman, Stein, Dellus, Rahmsdorf, and Herrlich, "12-0-tetradecanoyl-phorbol-13-acetate Induction of the Human Collagenase Gene is Mediated by an Inducible Enhancer Element Located in the 5' Flanking Region," *Mol. Cell. Biol.*, 7:2256, 1987a.

Angel, Imagawa, Chiu, Stein, Imbra, Rahmsdorf, Jonat, Herrlich, and Karin, "Phorbol Ester-Inducible Genes Contain a Common cis Element Recognized by a TPA-Modulated Trans-acting Factor," *Cell*, 49:729, 1987b.

Anselme, "Inhibition of calcification in vivo by acyl azide cross-linking of a collagen-glycosaminoglycan sponge," *Matrix*, 12:264–273, 1992.

Atala et al., "Endoscopic treatment of vesicoureteral reflux with a chondrocyte-alginate suspension," *J. Urology*, 152:641–643, 1994

Atala et al., "Injectable alginate seeded with chrondrocytes as a potential treatment for vesicoureteral reflux," *J. Urology*, 150:745–747, 1993.

Atchison and Perry, "Tandem Kappa Immunoglobulin Promoters are Equally Active in the Presence of the Kappa Enhancer: Implications for Model of Enhancer Function," *Cell*, 46:253, 1986.

Atchison and Perry, "The Role of the Kappa Enhancer and its Binding Factor NF-kappa B in the Developmental Regulation of Kappa Gene Transcription," *Cell*, 48:121, 1987.

Auerbach and Auerbach, "Angiogenesis inhibition: a review," *Pharmac. Ther.* 63:265, 1994.

Baichwal and Sugden, "Vectors for gene transfer derived from animal DNA viruses: Transient and stable expression of transferred genes," In: Kucherlapati R, ed. Gene transfer. New York: Plenum Press, pp. 117–148, 1986.

Banerji, Olson, and Schaffner, "A Lymphocyte-Specific Cellular Enhancer is Located Downstream of the Joining Region in Immunoglobulin Heavy-Chain Genes," *Cell*, 35:729, 1983.

Banerji, Rusconi, and Schaffner, "Expression of a Beta-Globin Gene is Enhanced by Remote SV40 DNA Sequences," *Cell*, 27:299, 1981.

Barakat et al., "Macromolecular engineering of polylactone and polylactide. XXI. Controlled synthesis of low molecular weight polylactide macromonomers," *J. Polym. Sci, Polym. Chem*, 34:497–502, 1996.

Barile, *Introduction to In vitro Cytotoxicity Mechanisms and Methods*, CRC Press Boca Raton, Fla., 1994.

Barrera et al., "Synthesis and RGD peptide modification of a new biodegradable copolymer: poly (lactic acid-co lysine)," *J. Am. Chem. Soc.*, 115:11010–11011, 1993.

Belcheva et al., "Crosslinking poly(ethylene oxide) for drug release systems," *Macromol. Symp.*, 103:193–211, 1996.

Bell et al., "Living tissue formed in vitro and accepted as skin-equivalent tissue of full thickness," *Science*, 211:1052–1054, 1981.

Benchokroun, Y., Couprie, J. and Larsen, A. K., "Aurintricarboxylic acid, a putative inhibitor of apoptosis, is a potent inhibitor of DNA topoisomerase II in vitro and in Chinese hamster fibrosarcoma cells," *Biochem. Pharmacol.* 49:305–313, 1995.

Berkhout, Silverman, and Jeang, "Tat Trans-activates the Human Immunodeficiency Virus Through a Nascent RNA Target," *Cell*, 59:273, 1989.

Berzal-Herranz et al., *Genes and Devel.*, 6:129–134, 1992.

Bessho, R. et al., "Pyrrolidine dithiocarbamate, a potent inhibitor of nuclear factor kappa B (NF-kappa B) activation, prevents apoptosis in human promyelocytic leukemia HL-60 cells and thymocytes," *Biochem. Pharmacol.* 48:1883–1889, 1994.

Black, *Biological Performance of Materials*, 2nd ed, Dekker, New York, 1992.

Blair et al., "Clinical trial of calcium alginate haemestatic swabs," *Br. J. Surg.*, 77:568–570, 1990.

Blanar, Baldwin, Flavell, and Sharp, "A Gamma-Interferon-Induced Factor That Binds the Interferon Response Sequence of the MHC Class I Gene, H-2Kb," *EMBO J.*, 8:1139, 1989.

Bodine and Ley, "An Enhancer Element Lies 3' to the Human A Gamma Globin Gene," *EMBO J.*, 6:2997, 1987.

Boileau, "Anionic Ring-Opening Polymerization: Epoxides and Episulfides," In: *Comprehensive Polymer Science*, Vol 3. Allen, ed., Pergamon Press, New York, 1989.

Borner, M. M., Myers, C. E., Sartor, O., Sei, Y., Toko, T., Trepel, J. B. and Schneider, E., "Drug-induced apoptosis is not necessarily dependent on macromolecular synthesis or proliferation in the p53-negative human prostate cancer cell line PC-3," *Cancer Res.* 55:2122–2128, 1995.

Boshart, Weber, Jahn, Dorsch-Hasler, Fleckenstein, and Schaffner, "A Very Strong Enhancer is Located Upstream of an Immediate Early Gene of Human Cytomegalovirus," *Cell*, 41:521, 1985.

Bosze, Thiesen, and Charnay, "A Transcriptional Enhancer with Specificity for Erythroid Cells is Located in the Long Terminal Repeat of the Friend Murine Leukemia Virus," *EMBO J.*, 5:1615, 1986.

Braddock, Chambers, Wilson, Esnouf, Adams, Kingsman, and Kingsman, "HIV-I Tat Activates Presynthesized RNA I nthe Nucleus," *Cell*, 58:269, 1989.

Brown et al., "Controlled release of insulin from polymer matrices," *Diabetes*, 35:684–691, 1986.

Bruno, S., Del Bino, G., Lassota, P., Giaretti, W. and Darzynkiewicz, Z., "Inhibitors of proteases prevent endonucleolysis accompanying apoptotic death of HL-60 leukemic cells and normal thymocytes," *Leukemia* 6:1113–1120, 1992.

Bulla and Siddiqui, "The Hepatitis B Virus Enhancer Modulates Transcription of the Hepatitis B Virus Surface-Antigen Gene From an Internal Location," *J. Virol.*, 62:1437, 1986.

Cain, K., Inayat-Hussain, S. H., Kokileva, L. and Cohen, G. M., "DNA cleavage in rat liver nuclei activated by $Mg^{2+}$ or $Ca^{2+}+Mg^{2+}$ is inhibited by a variety of structurally unrelated inhibitors," *Biochem. Cell. Biol.* 72:631–638, 1994.

Camerson and Lawson, "The failure of polyvinyl sponge as a bone substitute," *Res. Vet. Sci.*, 1:230–231, 1960.

Campbell and Villarreal, "Functional Analysis of the Individual Enhancer Core Sequences of Polyoma Virus: Cell-Specific Uncoupling of DNA Replication From Transcription," *Mol. Cell. Biol.*, 8:1993, 1988.

Campere and Tilghman, "Postnatal Repression of the α-fetoprotein Gene is Enhancer Independent," *Genes and Dev.*, 3:537, 1989.

Campo, Spandidos, Lang, and Wilkie, "Transcriptional Control Signals in the Genome of Bovine Papilloma Virus Type 1," *Nature*, 303:77, 1983.

Cao et al., "Generation of neotendon using synthetic polymers seeded with tenocytes," *Transplantation Proc.*, 26:3390–3392, 1994.

Cappello et al., "Genetic engineering of structural protein polymers," *Biotechnol. Prog.*, 6:198–202, 1990.

Carter et al., "Relationships between loading history and femoral cancellous bone architecture," *J. Biomech.*, 22:231–244, 1989.

Cavallaro et al., "Collagen fabrics as biomaterials," *Biotech. Bioeng.*, 43:781–791, 1994.

Cech et al., "In vitro splicing of the ribosomal RNA precursor of Tetrahymena: involvement of a guanosine nucleotide in the excision of the intervening sequence," *Cell*, 27:487–496, 1981.

Celander and Haseltine, "Glucocorticoid Regulation of Murine Leukemia Virus Transcription Elements is Specified by Determinants Within the Viral Enhancer Region," *J. Virology*, 61:269, 1987.

Celander, Hsu, and Haseltine, "Regulatory Elements Within the Murine Leukemia Virus Enhancer Regions Mediate Glucocorticoid Responsiveness," *J. Virology*, 62:1314, 1988.

Chalfie et al., *Science*, 263:802–805, 1994.

Chandler, Maler, and Yamamoto, "DNA Sequences Bound Specifically by Glucocorticoid Receptor in vitro Render a Heterlogous Promoter Hormone Responsive in vivo," *Cell*, 33:489, 1983.

Chang et al., "Foreign gene delivery and expression in hepatocytes using a hepatitis B virus vector," *Hepatology*, 14:134A, 1991.

Chang, Erwin, and Lee, "Glucose-regulated Protein (GRP94 and GRP78) Genes Share Common Regulatory Domains and are Coordinately Regulated by Common Trans-acting Factors," *Mol. Cell. Biol.*, 9:2153, 1989.

Chatterjee, Lee, Rentoumis, and Jameson, "Negative Regulation of the Thyroid-Stimulating Hormone Alpha Gene by Thyroid Hormone: Receptor Interaction Adjacent to the TATA Box," *Proc. Natl. Acad. Sci. U.S.A.*, 86:9114, 1989.

Chen and Okayama, "High-efficiency transformation of mammalian cells by plasmid DNA," *Mol. Cell. Biol.* 7:2745–2752, 1987

Chiego, In: *Oral Development and Histology;* Avery, ed, pp. 262–281, 1994.

Choi, Chen, Kriegler, and Roninson, "An Altered Pattern of Cross-Resistance in Multi-Drug-Resistant Human Cells Results From Spontaneous Mutations in the Mdr-1 (P-glycoprotein) Gene," *Cell*, 53:519, 1988.

Chowrira et al., "In vitro and in vivo comparison of hammerhead, hairpin, and hepatitis delta virus self-processing ribozyme cassetyes," *J. Biol. Chem.*, 269:25856–25864, 1994.

Chowrira et al., *Biochemistry*, 32:1088–1095, 1993.

Chujo et al., "Physical and chemical characteristics of polyglycolide," *Makromol. Chem.*, 100:267–270, 1967.

Chun, S. Y., Eisenhauer, K. M., Kubo, M. and Hsueh, A. J., "Interleukin-1 beta suppresses apoptosis in rat ovarian follicles by increasing nitric oxide production," *Endocrinology* 136:3120–3127, 1995.

Cima et al., "Hepatocyte response to PEO-tethered carbohydrates depend on tether conformation," *Transactions of the 21st Annual meeting of the Society for Biomaterials*, 18:147, 1995.

Clark, Voulgaropoulou, Fraley, and Johnson, "Cell lines for the production of recombinant adeno-associated virus," *Human Gene Therapy*, 6:1329–1341, 1995.

Clarkson, "Sponge implants for flat breasts," *Proc. Royal Soc. Med.*, 53:880–881, 1960.

Coffin, "Retroviridae and their replication," In: *Virology*, Fields et al. (eds.), New York: Raven Press, pp. 1437–1500, 1990.

Cohen et al., "Controlled delivery systems for proteins based on poly (lactic/glycolic acid) microspheres," *Pharm. Res.*, 8:713–720, 1991.

Cohen et al., "Ionically cross-linkable polyphosphazene: a novel polymer for microencapsulation," *J. Am. Chem. Soc.*, 112:7832–7833, 1990.

Cohen, Walter, and Levinson, "A Repetitive Sequence Element 3' of the Human c-Ha-ras1 Gene Has Enhancer Activity," *J. Cell. Physiol.*, 5:75, 1987.

Colberre-Garapin et al., *J. Mol. Biol.*, 150:1, 1981.

Compton et al., "Skin regenerated from cultured epithelial autografts on full-thickness wounds from 6 days to 5 years after grafting: a light, electron microscopic, and immunohistochemical study," *Lab. Invest.*, 60:600–612, 1989.

Cossarizza, A., Franceschi, C., Monti, D., Salvioli, S., Bellesia, E., Rivabene, R., Biondo, L., Rainaldi, G., Tinari, A. and Malorni, W., "Protective effect of N-acetylcysteine in tumor necrosis factor-alpha-induced apoptosis in U937 cells: the role of mitochondria," *Exp. Cell Res.* 220:232–40, 1995.

Costa, Lai, Grayson, and Darnell, "The Cell-Specific Enhancer of the Mouse Transthyretin (Prealbumin) Gene Binds a Common Factor at One Site and a Liver-Specific Factor(s) at Two Other Sites," *Mol. Cell. Biol.*, 8:81, 1988.

Cotten, Wagner, Zatloukal, Phillips, and Curiel, "High efficiency receptor-mediated delivery of small and large (48 kilobase) gene constructs using the endosome disruption activity of defective or inactivated adenovirus particles," P.N.A.S. USA, 89:6094–6098, 1992.

Couch et al., "Immunization with types 4 and 7 adenovirus by selective infection of the intestinal tract," *Am. Rev. Resp. Dis.*, 88:394–403, 1963.

Coupar et al., "A general method for the construction of recombinant vaccinia virus expressing multiple foreign genes," *Gene*, 68:1–10, 1988.

Craig, *Restorative Dental Materials*, 8th ed., Mosby Co., St. Louis, Mo., 1989.

Cripe, Haugen, Turk, Tabatabai, Schmid, Durst, Gissmann, Roman, and Turek, "Transcriptional Regulation of the Human Papilloma Virus-16 E6–E7 Promoter by a Keratinocyte-Dependent Enhancer, and by Viral E2 Trans-Activator and Repressor Gene Products: Implications for Cervical Carcinogenesis," *EMBO J.*, 6:3745, 1987.

Culotta and Hamer, "Fine Mapping of a Mouse Metallothionein Gene Metal-Response Element," *Mol. Cell. Biol.*, 9:1376, 1989.

Curiel, "Gene transfer mediated by adenovirus-polylysine DNA complexes," In: *Viruses in Human Gene Therapy*, J.-M. H. Vos (Ed.), Carolina Academic Press, Durham, N.C., pp. 179–212, 1994.

Dan and Tirrell, "Effect of bimodal molecular weight distribution on the polymer brush," *Macromol.*, 26:6467–6473, 1993.

Dandolo, Blangy, and Kamen, "Regulation of Polyma Virus Transcription in Murine Embryonal Carcinoma Cells," *J. Virology*, 47:55, 1983.

Darnell et al., *Molecular Cell Biology*, 2nd ed, Freeman, New York, 1990.

De Villiers, Schaffner, Tyndall, Lupton, and Kamen, "Polyoma Virus DNA Replication Requires an Enhancer," *Nature*, 312:242, 1984.

DeLustro et al., "Immune Responces to Allogeneic and Xenogeneic Implants of Collagen and Collagen Derivatives," *Clin. Orth. Rel. Res.*, 260:265–279, 1990.

Deschamps, Meijlink, and Verma, "Identification of a Transcriptional Enhancer Element Upstream From the Proto-Oncogene Fos," *Science*, 230:1174, 1985.

Dixit, "Development of a bioartificial liver using isolated hepatocytes," *Artificial Organs*, 18:371–384, 1994.

Doner and Douds, "Purification of commercial gellan to monovalent cation salts results in acute modification of solution and gel-forming properties," *Carbohydr. Res.*, 273:225–233, 1995.

Ducheyne, *Bioceramics: materials characteristics and in vivo behavior*, Ducheyne and Lemons, eds., New York Academy of Science, New York, Vol. 523, 1988.

Ecobichon, *The Basis of Toxicity Testing*, CRC Press, Boca Raton, Fla., 1992.

Edbrooke, Burt, Cheshire, and Woo, "Identification of cis-Acting Sequences Responsible for Phorbol Ester Induction of Human Serum Amyloid A Gene Expression Via a Nuclear-Factor-κB-like Transcription Factor," *Mol. Cell. Biol.*, 9:1908, 1989.

Edlund, Walker, Barr, and Rutter, "Cell-Specific Expression of the Rat Insulin Gene: Evidence for Role of Two Distinct 5' Flanking Elements," *Science*, 230:912, 1985.

Embleton and Tighe, "Polymers for biodegradable medical devices. X. Microencapsulation studies: Control of polyhydroxybutyrate-hydrovalerate microcapsules porosity via polycaprolactone blending," *J. Microencapsul.*, 10:341–352, 1993.

Emerich et al., "A novel approach to neural transplantation in Parkinson's disease: use of polymer-encapsulated cell therapy," *Neuroscience and Biobehavioral Reviews*, 16:437–447, 1992.

Engelberg and Kohn, "Physico-mechanical properties of degradable polymers used in medical applications: A comparative study," *Biomaterials*, 12: 292–304, 1991.

Escargueil-Blanc, I., Meilhac, O., Pieraggi, M. T., Arnal, J. F., Salvayre, R. and Negre-Salvayre, A., "Oxidized LDLs induce massive apoptosis of cultured human endothelial cells through a calcium-dependent pathway. Prevention by aurintricarboxylic acid," *Arterioscler. Thromb. Vasc. Biol.* 17:331–339, 1997.

Fausto, "Growth factors in liver development, regeneration, and carcinogenesis," *Prog. Growth Factor Res.*, 3:219–234, 1991.

Fechheimer, Boylan, Parker, Sisken, Patel and Zimmer, "Transfection of mammalian cells with plasmid DNA by scrape loading and sonication loading," *Proc. Nat'l. Acad. Sci. USA* 84:8463–8467, 1987

Feng and Holland, "HIV-I Tat Trans-Activation Requires the Loop Sequence Within Tar," *Nature*, 334:6178, 1988.

Ferrari G, Yan CY and Greene LA, "N-acetylcysteine (D- and L-stereoisomers) prevents apoptotic death of neuronal cells," *J. Neurosci.* 15:2857–2866, 1995.

Ficek and Peppas, "Novel preparation of poly(vinyl alcohol) microparticles without crosslinking agent for controlled drug delivery of proteins," *J. Controlled Release*, 27:259–264, 1993.

Fidler, I. J. and Ellis, L. M., "The implications of angiogenesis for the biology and therapy of cancer metastasis," *Cell* 79:185, 1994.

Finch, *Polyvinyl Alcohol: Properties and Applications*, Wiley, London, 1973.

Firak and Subramanian, "Minimal Transcription Enhancer of Simian Virus 40 is a 74-Base-Pair Sequence that Has Interacting Domains," *Mol. Cell. Biol.*, 6:3667, 1986.

Flaws, J. A., DeSanti, A., Tilly, K. I., Javid, R. O., Kugu, K., Johnson, A. L., Hirshfield, A. N. and Tilly, J. L., "Vasoactive intestinal peptide-mediated suppression of apoptosis in the ovary: potential mechanisms of action and evidence of a conserved antiatretogenic role through evolution," *Endocrinology* 136:4351–4359, 1995.

Flotte, Afione, Conrad, McGrath, Solow, Oka, Zeitlin, Guggino, and Carter, "Stable in vivo expression of the cystic fibrosis transmembrane conductance regulator with an adeno-associated virus vector," *Proc. Natl. Acad Sci. USA*, 90:10613–10617, 1993.

Flotte, Barraza-Ortiz, Solow, Afione, Carter, and Guggino, "An improved system for packaging recombinant adeno-associated virus vectors capable of in vivo transduction," *Gene Therapy*, 2:29–37, 1995.

Flotte, Solow, Owens, Afione, Zeitlin, and Carter, "Gene expression from adeno associated virus vector in airway epithelial cells," *Am. J Respir. Cell Mol. Biol.*, 7:349–356, 1992.

Foecking and Hofstetter, "Powerful and Versatile Enhancer-Promoter Unit for Mammalian Expression Vectors," *Gene*, 45:101, 1986.

Folkman and Klagsbrun, "Angiogenic factors," *Science*, 235:442–447, 1987.

Folkman, J., "Angiogenesis in cancer, vascular, rheumatoid and other disease," *Nature Med.* 1:27, 1995.

Folkman, J., "Hopw is blood vessel growth regulated in normal and neoplastic tissue," *Cancer Res.* 46:467, 1986.

Forster and Symons, "Self-cleavage of plus and minus RNAs of a virusoid and a structural model for the active sites," *Cell*, 49:211–220, 1987.

Fraley, Fornari and Kaplan, "Entrapment of a bacterial plasmid in phospholipid vesicles:potential for gene transfer," *Proc. Nat'l. Acad. Sci. USA* 76:3348–3352, 1979

Frangos, "Physical forces and the mammalian cell," Frangos, ed.; Academic Press, San Diego, Calif., 1993.

Frazza and Schmitt, "A new absorbable suture," *J. Biomed. Mater. Res.*, 1:43, 1971.

Freshney, *Culture of animal cells: a manual of basic technique*, Wiley-Liss, New York, 1994.

Friedmann, "Progress toward human gene therapy," *Science*, 244:1275–1281, 1989.

Fritsche, "Applicability of polymers as surgical suture materials," *Pharamzie*, 22:41, 1967.

Fujita, Shibuya, Hotta, Yamanishi, and Taniguchi, "Interferon-Beta Gene Regulation: Tandemly Repeated Sequences of a Synthetic 6-bp Oligomer Function as a Virus-Inducible Enhancer," *Cell*, 49:357, 1987.

Galli, C., Meucci, O., Scorziello, A., Werge, T. M., Calissano, P. and Schettini, G., "Apoptosis in cerebellar granule cells is blocked by high KCl, forskolin, and IGF-1 through distinct mechanisms of action: the involvement of intracellular calcium and RNA synthesis," *J. Neurosci.* 15:1172–1179, 1995.

Gerlach et al., "Construction of a plant disease resistance gene from the satellite RNA of tobacco rinspot virus," *Nature (London)*, 328:802–805, 1987.

Ghosh-Choudhury et al., "Protein IX, a minor component of the human adenovirus capsid, is essential for the packaging of full-length genomes," *EMBO J.*, 6:1733–1739, 1987.

Ghosh and Bachhawat, "Targeting of liposomes to hepatocytes," In: Wu G. and C. Wu ed. Liver diseases, targeted diagnosis and therapy using specific receptors and ligands. New York: Marcel Dekker, pp. 87–104, 1991.

Gilding, "Biodegradable polymers," *In: Biocompatibility of Clinical Implant Materials*, Williams, ed., CRC Press, Boca Raton, Fla., 1981.

Gilles, Morris, Oi, and Tonegawa, "A Tissue-Specific Transcription Enhancer Element is Lcoated in the Major Intron of a Rearranged Immunoglobulin Heavy-Chain Gene," *Cell*, 33:717, 1983.

Gius, Grossman, Bedell, and Laimins, "Inducible and Constitutive Enhancer Domains in the Noncoding Region of Human Papilloma Virus Type 18," *J. Virology*, 62:665, 1988.

Gjertsen, B. T., Cressey, L. I., Ruchaud, S., Houge, G., Lanotte, M. and Doskeland, S. O., "Multiple apoptotic death types triggered through activation of separate pathways by cAMP and inhibitors of protein phosphatases in one (IPC leukemia) cell line," *J. Cell Sci.* 107:3363–3377, 1994.

Gliding and Reed, "Biodegradable polymers for use in surgery—polyglycolic/poly(lactic acid) homo- and copolymers: 1," *Polymer*, 20:1459–1464, 1979.

Gloss, Bernard, Seedorf, and Klock, "The Upstream Regulatory Region of the Human Papilloma Virus-16 Contains an E2 Protein-Independent Enhancer Which is Specific for Cervical Carcinoma Cells and Regulated by Glucocorticoid Hormones," *EMBO J.*, 6:3735, 1987.

Godbout, Ingram, and Tilghman, "Fine-Structure Mapping of the Three Mouse Alpha-Fetoprotein Gene Enhancers," *Mol. Cell. Biol.*, 8:1169, 1988.

Goldberg et al., "Cloning and expression of a collagen-analog-encoding synthetic gene in *Escherichia coli*," *Gene*, 80:305–314, 1989.

Gombotz and Pettit, "Biodegradable polymers for protein and peptide drug delivery," *Bioconjugate Chem.*, 6:332–351, 1995.

Gomez-Foix et al., "Adenovirus-mediated transfer of the muscle glycogen phosphorylase gene into hepatocytes confers altered regulation of glycogen," *J. Biol. Chem.*, 267:25129–25134, 1992.

Goodbourn and Maniatis, "Overlapping Positive and Negative Regulatory Domains of the Human β-Interferon Gene," *Proc. Natl. Acad. Sci. USA*, 85:1447, 1988.

Goodbourn, Burstein, and Maniatis, "The Human Beta-Interferon Gene Enhancer is Under Negative Control," *Cell*, 45:601, 1986.

Gopal, "Gene transfer method for transient gene expression, stable transformation, and cotransformation of suspension cell cultures," *Mol. Cell. Biol.* 5:1188–1190, 1985

Goshima et al., "The origin of bone formed in composite grafts of porous calcium phosphate ceramic loaded with marrow cells," *Clin. Orthopod. Rel. Res.*, 269:274–283, 1991.

Graham and Prevec, "Adenovirus-based expression vectors and recombinant vaccines," *Biotechnology*, 20:363–390, 1992.

Graham and Prevec, "Manipulation of adenovirus vectors," *In: Gene Transfer and Expression Protocols*, Murray, E. J., ed., Humana, N.J., vol. 7, 109–128, 1991.

Graham and Van Der Eb, "A new technique for the assay of infectivity of human adenovirus 5 DNA," *Virology* 52:456–467, 1973

Graham et al., "Characteristics of a human cell line transformed by DNA from human adenovirus type 5", *J. Gen. Virol.*, 36:59–72, 1977.

Green et al., "Growth of cultured human epidermal cells into multiple epithelia suitable for grafting," *Proc. Natl. Acad. Sci. USA*, 76:5665–5668, 1979.

Greene, Bohnlein, and Ballard, "HIV-1, and Normal T-Cell Growth: Transcriptional Strategies and Surprises," *Immunology Today*, 10:272, 1989.

Gross, "Bacterials polyesters: Structural variability in a microbial synthesis," *In: Biomedical Polymers: Desiganed-to-Degrade Systems*. Shalaby, ed., Carl Hanser Verlag, Munich, 1994.

Grosschedl and Baltimore, "Cell-Type Specificity of Immunoglobulin Gene Expression is Regulated by at Least Three DNA Sequence Elements," *Cell*, 41:885, 1985.

Grunhaus and Horwitz, "Adenovirus as cloning vector," *Seminar in Virology,* 3:237–252, 1992.

Guenard et al., "Syngeneic Schwann cells derived from adult nerves seeded in semipermeable guidance channels enhance peripheral nerve regeneration," *J. Neuro.,* 12:3310–3320, 1992.

Guinchedi, P., Conti, B., Maggi, L. and Conte, U., "Cellulose acetate butyrate and polycaprolactone for ketoprofen spray dried microsphere preparation," *J. Microencapsul.* 11:381–393, 1994.

Guisti, P., Lazzeri, L. and Lelli, L., "Bioartificial polymeric materials: a new method to design biomaterials by testing both biological and synthetic polymers," *Tr. Polym. Sci.* 9:261–266, 1993.

Guisti, P., Soldani, G., Palla, M., Paci, M. and Levita, G., "New biolized polymers for cardiovascular applications," *Life Support Syst.* 3 (Suppl. 1):476–480, 1985.

Gupta and Desmuth, "Radiation effect on poly(lactic acid)," *Polymer,* 24:827–830, 1983.

Hall and Hall, "Polyvinyl alcohol nephrosis: relationship of degree of polymerization to pathophysiologic effects," *Proc. Soc. Exp. Biol. Med.,* 112:86–91, 1962.

Hansbrough et al., "Evaluation of a biodegradable matrix containing cultured human fibroblasts as a dermal replacement beneath meshed skin grafts on athymic mice," *Surgery,* 4:438–446, 1992.

Harland and Weintraub, "Translation of mRNA injected into Xenopus oocytes is specifically inhibited by antisense RNA," *J. Cell Biol.* 101:1094–1099, 1985

Haseloff and Gerlach, "Simple RNA enzymes with new and highly specific endoribonuclease activities," *Nature,* 334:585–591, 1988.

Haslinger and Karin, "Upstream Promoter Element of the Human Metallothionein-II Gene Can Act Like an Enhancer Element," *Proc. Natl. Acad. Sci. U.S.A.,* 82:8572, 1985.

Hauber and Cullen, "Mutational Analysis of the Trans-Activation-Responsive Region of the Human Immunodeficiency Virus Type I Long Terminal Repeat," *J. Virology,* 62:673, 1988.

Haupt and Myer, "Ivalon sponge in repair of diaphragmatic defects," *Arch. Surg.,* 80:613, 1960.

Hay et al., "Locking mechanism strength of absorbable ligating devices," *J. Biomed. Mater. Res.,* 22:179–190, 1988.

Heimbach et al., "Artificial dermis for major burns," *Ann. Surg.,* 208:313–320, 1988.

Heller and Daniels, "Poly(ortho esters)," *In: Biomedical Polymers: Designed-to-Degrade Systems.* Shalaby, ed., Carl Hanser Verlag, Munich, 1994.

Heller, "Controlled drug release from poly(orthoester)-a surface eroding polymer," *J. Controlled Release,* 2:167–177, 1985.

Hen, Borrelli, Fromental, Sassone-Corsi, and Chambon, "A Mutated Polyoma Virus Enhancer Which is Active in Undifferentiated Embryonal Carcinoma Cells is not Repressed by Adenovirus-2 E1A Products," *Nature,* 321:249, 1986.

Hensel, Meichle, Pfizenmaier, and Kronke, "PMA-Responsive 5' Flanking Sequences of the Human TNF Gene," *Lymphokine Res.,* 8:347, 1989.

Hermonat and Muzyczka, "Use of adeno-associated virus as a mammalian DNA cloning vector; transduction of neomycin resistance into mammalian tissue culture cells," *Proc. Nat'l. Acad. Sci. USA,* 81:6466–6470, 1984.

Herr and Clarke, "The SV40 Enhancer is Composed of Multiple Functional Elements That Can Compensate for One Another," *Cell,* 45:461, 1986.

Hersdorffer et al., "Efficient gene transfer in live mice using a unique retroviral packaging line," *DNA Cell Biol.,* 9:713–723, 1990.

Herz and Gerard, "Adenovirus-mediated transfer of low density lipoprotein receptor gene acutely accelerates cholesterol clearance in normal mice," *Proc. Nat'l. Acad. Sci. USA* 90:2812–2816, 1993.

Hill-West et al., "Inhibition of thrombosis and intimal thickening by in situ photo-polymerization of thin hydrogel barrier," *Proc. Natl. Acad. Sci., USA* 91:5967–5971, 1994.

Hirochika, Browker, and Chow, "Enhancers and Trans-Acting E2 Transcriptional Factors of Papilloma Viruses," *J. Virol.,* 61:2599, 1987.

Hirsch, Gaugler, Deagostini-Bauzin, Bally-Cuif, and Gordis, "Identification of Positive and Negative Regulatory Elements Governing Cell-Type-Specific Expression of the Neural-Cell-Adhesion-Molecule Gene," *Mol. Cell. Biol.,* 10:1959, 1990.

Holbrook, Gulino, and Ruscetti, "cis-Acting Transcriptional Regulatory Sequences in the Gibbon Ape Leukemia Virus (GALV) Long Terminal Repeat," *Virology,* 157:211, 1987.

Holland and Robinson, "Pulp Re-Innervation In Re-Implanted Canine Teeth of the Cat. Archs," *Oral Biol.,* 32:593–597, 1987.

Holmes, "Biologically produced (R)-3-hydroxyalkane polymers and copolymers," *In: Developments in Crystalline Polymers.* Bassett, ed., Elsevier, New York, 1988.

Horlick and Benfield, "The Upstream Muscle-Specific Enhancer of the Rat Muscle Creatine Kinase Gene is Composed of Multiple Elements," *Mol. Cell. Biol.,* 9:2396, 1989.

Horwich et al. "Synthesis of hepadenovirus particles that contain replication-defective duck hepatitis B virus genomes in cultured HuH7 cells," *J. Virol.,* 64:642–650, 1990.

Huang, "Biodegradable Polymers," *In: Polymers—Biomaterials and Medical Applications.* Kroschwitz, ed., Wiley & Sons, New York, 1989.

Huang, Ostrowski, Berard, and Hagar, "Glucocorticoid Regulation of the Ha-MuSV p21 Gene Conferred by Sequences From Mouse Mammary Tumor Virus," *Cell,* 27:245, 1981.

Hubbell, "Biomaterials in tissue engineering," *Bio/Technology,* 13:565–576, 1995.

Hubbell, "Chemical modification of polymer surfaces to improve biocompatibility," *Tr. Polym. Sci.* 2:20–25, 1993.

Hug, Costas, Staeheli, Aebi, and Weissmann, "Organization of the Murine Mx Gene and Characterization of its Interferon- and Virus-Inducible Promoter," *Mol. Cell. Biol.,* 8:3065, 1988.

Hwang, Lim, and Chae, "Characterization of the S-Phase-Specific Transcription Regulatory Elements in a DNA-Replication-Independent Testis-Specific H2B (TH2B) Histone Gene," *Mol. Cell. Biol.,* 10:585, 1990.

Hynes, "Integrins: a family of cell surface receptors," *Cell,* 48:549–554, 1987.

Hynes, *In: Fibronectins,* Springer-Verlag: New York, 1990.

Imagawa, Chiu, and Karin, "Transcription Factor AP-2 Mediates Induction by Two Different Signal-Transduction Pathways: Protein Kinase C and cAMP," *Cell,* 51:251, 1987.

Imbra and Karin, "Phorbol Ester Induces the Transcriptional Stimulatory Activity of the SV40 Enhancer," *Nature,* 323:555, 1986.

Imler, Lemaire, Wasvlyk, and Waslyk, "Negative Regulation Contributes to Tissue Specificity of the Immunoglobulin Heavy-Chain Enhancer," *Mol. Cell. Biol.,* 7:2558, 1987.

Imperiale and Nevins, "Adenovirus 5 E2 Transcription Unit: an E1A-Inducible Promoter with an Essential Element that Functions Independently of Position or Orientation," *Mol. Cell. Biol.,* 4:875, 1984.

Jakobovits, Smith, Jakobovits, and Capon, "A Discrete Element 3' of Human Immunodeficiency Virus 1 (HIV-1) and HIV-2 mRNA Initiation Sites Mediates Transcriptional Activation by an HIV Trans-Activator," *Mol. Cell. Biol.,* 8:2555, 1988.

Jameel and Siddiqui, "The Human Hepatitis B Virus Enhancer Requires Transacting Cellular Factor(s) for Activity," *Mol. Cell. Biol.,* 6:710, 1986.

Janda et al., "Animal Cell Culture Systems," Chapter 19, *In: Manual of Clinical Microbiology,* 5th Ed., Balows et al., eds., ASM Press, Washington, D.C., 1991.

Jarcho, "Calcium phosphate ceramics as hard tissue prosthetics," *Clin. Orthopod.,* 157:259–278, 1981.

Jaynes, Johnson, Buskin, Gartside, and Hauschka, "The Muscle Creatine Kinase Gene is Regulated by Multiple Upstream Elements, Including a Muscle-Specific Enhancer," *Mol. Cell. Biol.,* 8:62, 1988.

Jerome and Teyssie, "Anionic ring-opening polymerization," *Comp. Polym. Sci.,* Vol 3. New York: Pergamon Press, 1989.

Jiang, S., Chow, S. C., Nicotera, P. and Orrenius, S., "Intracellular Ca2+ signals activate apoptosis in thymocytes: studies using the Ca(2+)-ATPase inhibitor thapsigargin," *Exp. Cell Res.* 212:84–92, 1994.

Johnson et al., "The mesentery as a laminated vascular bed for hepatocyte transplantation," *Cell Transpl.,* 3:273, 1994.

Johnson, Wold, and Hauschka, "Muscle Creatine Kinase Sequence Elements Regulating Skeletal and Cardiac Muscle Expression in Transgenic Mice," *Mol. Cell. Biol.,* 9:3393, 1989a.

Jones and Shenk, "Isolation of deletion and substitution mutants of adenovirus type 5," *Cell,* 13:181–188, 1978.

Joyce, "RNA evolution and the origins of life," *Nature,* 338:217–244, 1989.

Jushasz et al., "Diffusion of rat atrial natriuretic factor n thermoreversible poluoxamer gels," *Biomaterials,* 10:265–268, 1989.

Kadesch and Berg, "Effects of the Position of the Simian Virus 40 Enhancer on Expression of Multiple Transcription Units in a Single Plasmid," *Mol. Cell. Biol.,* 6:2593, 1986.

Kallen et al., "Effect of encephalitogenic protein on migration in agarose of leukocytes from patients with multiple sclerosis. Variable effect of the antigen in a large dose range, with a literature review," *Acta. Neurol. Scand.,* 55:33–46, 1977.

Kaneda et al., "Increased expression of DNA cointroduced with nuclear protein in adult rat liver," *Science,* 243:375–378, 1989.

Kaplan et al., "Biosynthetic polysaccharides," *In: Biomedical Polymers: Designed-to-Degrade Systems,* Carl Hanser Verlag, Munich, 1994.

Kaplitt, Leone, Samulski, Siao, Pfaff, O'Malley, and During, "Long-term gene expression and phenotypic correction suing adeno-associated virus vectors in the mammalian brain," *Nature Genetics,* 8:148–154, 1994.

Karin, Haslinger, Heguy, Dietlin, and Cooke, "Metal-Responsive Elements Act as Positive Modulators of Human Metallothionein-IIA Enhancer Activity," *Mol. Cell. Biol.,* 7:606, 1987.

Karlsson et al., *EMBO J.,* 5:2377–2385, 1986.

Kasai et al., "Is the biological artificial liver clinically applicable?," *Artificial Organs,* 18:348–354, 1994.

Katinka, Vasseur, Montreau, Yaniv, and Blangy, "Polyoma DNA Sequences Involved in the Control of Viral Gene Expression in Murine Embryonal Carcinoma Cells," *Nature,* 290:720, 1981.

Katinka, Yaniv, Vasseur, and Blangy, "Expression of Polyoma Early Functions in Mouse Embryonal Carcinoma Cells Depends on Sequence Rearrangements in the Beginning of the Late Region," *Cell,* 20:393, 1980.

Kato et al., "Expression of hepatitis β virus surface antigen in adult rat liver," *J. Biol. Chem.,* 266:3361–3364, 1991.

Katz, A. R. and Turner, R., "Evaluation of tensile and adsorption properties of polyglycolic acid sutures," *Surg. Gynecol. Obstet.* 131:701–716, 1970.

Kaufman, "Selection and Coamplification of Heterologous Genes in Mammalian Cells," *Methods in Enzymology,* 185:537–566, 1990.

Kawamoto, Makino, Niw, Sugiyama, Kimura, Anemura, Nakata, and Kakunaga, "Identification of the Human Beta-Actin Enhancer and its Binding Factor," *Mol. Cell. Biol.,* 8:267, 1988.

Kelleher and Vos, "Long-term episomal gene delivery in human lymphoid cells using human and avian adenoviral-assisted transfection," *Biotechniques,* 17(6):1110–1117, 1994.

Kiledjian, Su, and Kadesch, "Identification and Characterization of Two Functional Domains Within the Murine Heavy-Chain Enhancer," *Mol. Cell. Biol.,* 8:145, 1988.

Kim and Cech, "Three dimensional model of the active site of the self-splicing rRNA precursor of Tetrahymena," *Proc. Natl. Acad. Sci. USA,* 84:8788–8792, 1987.

Kim et al., "Fluorometric Assay of DNA in Cartilage Explants Using Hoechst 33258," *Anal. Biochem.,* 174:168–176, 1988.

Kim, B. S., Putnam, A., Kulik, P. and Mooney, D. J., "Optimizing cell seeding and culture methods to engineer smooth muscle tissue in biodegradable polymer matrices," *Biotech. Bioeng.* in press, 1997.

Klamut, Gangopadyhay, Worton, and Ray, "Molecular and Functional Analysis of the Muscle-Specific Promoter Region of the Duchenne Muscular Dystrophy Gene," *Mol. Cell. Biol,* 10:193, 1990.

Klein et al., "High-velocity microprojectiles for delivering nucleic acids into living cells," *Nature,* 327:70–73, 1987.

Koch, Benoist, and Mathis, "Anatomy of a New B-Cell-Specific Enhancer," *Mol. Cell. Biol.,* 9:303, 1989.

Koide et al., "A new type of biomaterials for artificial skin: dehyrothermally cross-linked composites of fibrillar and denatured collagens," *J. Biomed. Mat. Res.,* 27:79–87, 1993.

Koller and Smithies, "Altering genes in animals by gene targeting", *Ann. Rev. Immun.,* 10:705–730, 1992.

Kotin, Siniscalco, Samulski, Zhu, Hunter, McLaughlin, Muzyczka, and Berns, "Site-specific integration by adeno-associated virus," *Proc. Natl. Acad. Sci. USA,* 87:2211–2215, 1990.

Kricheldorf and Kreiser-Saunders, "Polylactides—synthesis, characterization and medical applications," *Macromol. Symp.,* 103:85–102, 1996.

Kricheldorf and Lee, "Polylactones. 35. Macrocyclic and stereoselective polymerization of b-DL-butyrolactone with cyclic dibutyltin initiators," *Macromol.,* 28:6718–6725, 1995.

Kriegler and Botchan, "A Retrovirus LTR Contains a New Type of Eukaryotic Regulatory Element," *In: Eukaryotic Viral Vectors,* ed. Y. Gluzman. Cold Spring Harbor: Cold Spring Harbor Laboratory, NY, 1982.

Kriegler and Botchan, "Enhanced transformation by a simian virus 40 recombinant virus containing a Harvey murine sarcoma virus long terminal repeat," *Mol. Cell. Biol.* 3:325, 1983.

Kriegler, Perez, and Botchan, "Promoter Substitution and Enhancer Augmentation Increases the Penetrance of the SV40 A Gene to Levels Comparable to That of the Harvey Murine Sarcoma Virus Ras Gene in Morphologic Transformation," *In: Gene Expression,* eds. D. Hamer and M. Rosenberg. New York: Alan R. Liss, 1983.

Kriegler, Perez, Defay, Albert and Liu, "A Novel Form of TNF/Cachectin Is a Cell-Surface Cytotoxix Transmembrane Protein: Ramifications for the Complex Physiology of TNF," *Cell,* 53:45, 1988.

Kriegler, Perez, Hardy and Botchan, "Transformation Mediated by the SV40 T Antigens: Separation of the Overlapping SV40 Early Genes with a Retroviral Vector," *Cell,* 38:483, 1984a.

Kriegler, Perez, Hardy, and Botchan, "Viral Integration and Early Gene Expression Both Affect the Efficiency of SV40 Transformation of Murine Cells: Biochemical and Biological Characterization of an SV40 Retrovirus," *In: Cancer Cells 2/Oncogenes and Viral Genes,* G. F. Van de Woude, A. J. Levine, W. C. Topp, and J. D. Watson, Cold Spring Harbor: Cold Spring Harbor Laboratory, 1984b.

Ksaperczyk, "Microstructural analysis of poly[(L,L-lactide)-co-(glycolide)] by 1H and 13C N.M.R. spectroscopy," *Polymer,* 37:201–203, 1996.

Kuhl, De La Fuenta, Chaturvedi, Parinool, Ryals, Meyer, and Weissman, "Reversible Silencing of Enhancers by Sequences Derived From the Human IFN-alpha Promoter," *Cell,* 50:1057, 1987.

Kumar et al., *Basic Pathology,* 5th ed., Saunders, Philadelphia, Pa., 1992.

Kung et al., "Surface modifications of alginate/poly(L-lysine) microcapsular membrane with poly(ethylene glycol) and poly(vinyl alcohol)," *Biomaterials,* 16:649–655, 1995.

Kunz, Zimmerman, Heisig, and Heinrich, "Identification of the Promoter Sequences Involved in the Interleukin-6-Dependent Expression of the Rat Alpha-2-Macroglobulin Gene," *Nucl. Acids Res.,* 17:1121, 1989.

Lacy et al., "Maintenance of diabetic mice by subcutaneous xenografts of encapsulated islets," *Science,* 253:1782–1784, 1991.

LaFace, Hermonat, Wakeland, and Peck, "Gene transfer into hematopoietic progenitor cells mediated by an adeno-associated virus vector," *Viology,* 162:483–486, 1988.

Langer and Vacanti, "Tissue engineering," *Science,* 260:920–926, 1993.

Larsen, Harney, and Moore, "Repression Medaites Cell-Type-Specific Expression of the Rat Growth Hormone Gene," *Proc. Natl. Acad. Sci. U.S.A.,* 83:8283, 1986.

Laspia, Rice, and Mathews, "HIV-1 Tat Protein Increases Transcriptional Initiation and Stabilizes Elongation," *Cell,* 59:283, 1989.

Latimer, Berger, and Baumann, "Highly Conserved Upstream Regions of the $\alpha_1$-Antitrypsin Gene in Two Mouse Species Govern Liver-Specific Expression by Different Mechanisms," *Mol. Cell. Biol.,* 10:760, 1990.

Laughlin, Cardellichio, and Coon, "Latent Infection of KB Cells with Adeno-Associated Virus Type 2," *J. Virol.,* 60:515–524, 1986.

Laurencin et al., "Use of polyphosphazenes for skeletal tissue regeneration," *J. Biomed. Mater. Res.,* 27:963–973, 1993.

Laurencin, C. T. et al., "Use of polyphosphazenes for skeletal tissue regeneration," *J. Biomed. Mater. Res.* 27:963–973, 1987.

Le Gal La Salle et al., "An adenovirus vector for gene transfer into neurons and glia in the brain," *Science,* 259:988–990, 1993.

Lebkowski, McNally, Okarma, and Lerch, "Adeno-associated virus: a vector system for efficient introduction and integration of DNA into a variety of mammalian cell types," *Mol. Cell. Biol.,* 8:3988–3996, 1988.

Lee, Mulligan, Berg, and Ringold, "Glucocorticoids Regulate Expression of Dihydrofolate Reductase cDNA in Mouse Mammary Tumor Virus Chimaeric Plasmids," *Nature,* 294:228, 1981.

Leenslag et al., "Resorbable materials of poly(L-lactide). VII. In vivo and in vitro degradation," *Biomaterials,* 8:311–314, 1987.

Lemons, "Hydroxyapatite coatings," *Clin. Orth. Rel. Res.,* 235:220, 1988.

Lentz, "Polymer-induced membrane fusion: Potential mechanism and relation to cell fusion events," *Chem. Phys. Lipids,* 73:91–106, 1994.

Lesot et al., "Experimental Induction of Odontoblast Differentiation and Stimulation During Reparative Processes," *Cells and Materials,* 3:201–217, 1993.

Levesque et al., "Maintenance of long-term secretory function by microencapsulated islets of Langerhans," *Endocrinology,* 130:644–650, 1992.

Levinson, Khoury, VanDeWoude, and Gruss, "Activation of SV40 Genome by 72-Base-Pair Tandem Repeats of Moloney Sarcoma Virus," *Nature,* 295:79, 1982.

Levrero et al., "Defective and nondefective adenovirus vectors for expressing foreign genes in vitro and in vivo," *Gene,* 101:195–202, 1991.

Lieber and Strauss, "Selection of efficient cleavage sites in target RNAs by using a ribozyme expression library." *Mol. Cell. Biol.,* 15: 540–551, 1995.

Lim and Sun, "Microencapsulated islets as bioartificial endocrine pancreas," *Science,* 210:908–910, 1980.

Lin, Cross, Halden, Dragos, Toledano, and Leonard, "Delineation of an Enhancerlike Positive Regulatory Element in the Interleukin-2 Receptor α-Chain Gene," *Mol. Cell. Biol.,* 10:850, 1990.

Liu, J., Li, H., de Tribolet, N., Jaufeerally, R., Hamou, M. F. and Van Meir, E. G., "IL-6 stimulates growth and inhibits constitutive, protein synthesis-independent apoptosis of murine B-cell hybridoma 7TD1," *Cell. Immunol.* 155:428–435, 1994.

Lora et al., "Biocompatible polyphosphazene by radiation-induced graft copolymerization and heparinization," *Biomaterials,,* 12:275–280, 1991.

Luo, Zhou, Cooper, Munshi, Boswell, Broxmeyer, and Srivastava, "Adeno-associated virus 2 mediated transfer and functional expression of a gene encoding the human granulocyte-macrophage colony-stimulating factor," *Blood,*82 (Supp.): 1,303A, 1994.

Luria, Gross, Horowitz, and Givol, "Promoter Ehancer Elements in the Rearranged Alpha-Chain Gene of the Human T-Cell Receptor," *EMBO J.,* 6:3307, 1987.

Lusky and Botchan, "Transient Replication of Bovine Papilloma Virus Type 1 Plasmids: cis and trans Requirements," *Proc. Natl. Acad. Sci. U.S.A.,* 83:3609, 1986.

Lusky, Berg, Weiher, and Botchan, "Bovine Papilloma Virus Contains an Activator of Gene Expression at the Distal End of the Early Transcription Unit," *Mol. Cell. Biol.* 3:1108, 1983.

Majors and Varmus, "A Small Region of the Mouse Mammary Tumor Virus Long Terminal Repeat Confers Glucocorticoid Hormone Regulation on a Linked Heterologous Gene," *Proc. Natl. Acad. Sci. U.S.A.,* 80:5866, 1983.

Malorni, W., Rivabene, R., Straface, E., Rainaldi, G., Monti, D., Salvioli, S., Cossarizza, A. and Franceschi, C., "3-Aminobenzamide protects cells from UV-B-induced apoptosis by acting on cytoskeleton and substrate adhesion," *Biochem. Biophys. Res. Commun.* 207:715–724, 1995.

Mann et al., "Construction of a retrovirus packaging mutant and its use to produce helper-free defective retrovirus," *Cell*, 33:153–159, 1983.

Markowitz et al., "A safe packaging line for gene transfer: Separating viral genes on two different plasmids," *J. Virol.*, 62:1120–1124, 1988.

Maroto, R., De la Fuente, M. T., Artalejo, A. R., Abad, F., Lopez, M. G., Garcia-Sancho, J. and Garcia, A. G., "Effects of Ca2+ channel antagonists on chromaffin cell death and cytosolic Ca2+ oscillations induced by veratridine," *Eur. J. Pharmacol.* 270:331–339, 1994.

Massia and Hubbell, "An RGD spacing of 440 nm is sufficient for integrin alpha V beta 3-mediated fibroblast spreading and 140 nm for focal contact and stress fiber formation," *J. Cell. Biol.*, 114:1089–1100, 1991.

McCarty, Christensen, and Muzyczka, "Sequences Required for Coordinate Induction of Adeno-Associated Virus p19 and p40 Promoters by Rep Protein," *J. Virol.*, 65:2936–2945, 1991.

McGrath et al., "Genetically directed synthesis of new polymeric materials. Expression of artificial genes encoding proteins with repeating -(AlaGly)$_3$ProGluGly- elements," *J. Am. Chem. Soc.I*, 114:727–733, 1992.

McLaughlin, Collis, Hermonat, and Muzyczka, "Adeno-Associated Virus General Transduction Vectors: Analysis of Proviral Structures," *J. Virol.*, 62:1963–1973, 1988.

McNeall, Sanchez, Gray, Chesterman, and Sleigh, "Hyperinducible Gene Expression From a Metallotionein Promoter Containing Additional Metal-Responsive Elements," *Gene*, 76:81, 1989.

Merrill, "Poly(ethylene oxide) star molecules: synthesis, characterization, and applications in medicine and biology," *J. Biomater. Sci.*, Polym Ed 5:1–11, 1993.

Michel and Westhof, "Modeling of the three-dimensional architecture of group I catalytic introns based on comparative sequence analysis," *J. Mol. Biol.*, 216:585–610, 1990.

Migita, K., Eguchi, K., Kawabe, Y., Mizokami, A., Tsukada, T. and Nagataki, S., "Prevention of anti-CD3 monoclonal antibody-induced thymic apoptosis by protein tyrosine kinase inhibitors," *J. Immunol.* 153:3457–3465, 1994.

Mikos et al., "Preparation and characterization of poly (L-lactic acid) foams," *Polymer*, 35:1068, 1994.

Mikos et al., "Preparation of poly (glycolic acid) bonded fiber structures for cell attachment and transplantation," *J. Biomed. Mat. Res.*, 27:183, 1993a.

Mikos et al., "Prevascularization of porous biodegradable polymers," *Biotech. Bioeng.*, 42:716–723, 1993b.

Miksicek, Heber, Schmid, Danesch, Posseckert, Beato, and Schutz, "Glucocorticoid Responsiveness of the Transcriptional Enhancer of Moloney Murine Sarcoma Virus," *Cell*, 46:203, 1986.

Mooney and Vacanti, "Tissue engineering using cells and synthetic polymers," *Trans. Rev.*, 7:153–162, 1993.

Mooney et al., "Biodegradable Sponges for Hepatocyte Transplantation," *J. Biomed. Mat. Res.*, 29:959–965, 1995a.

Mooney et al., "Design and fabrication of cell delivery devices to engineer tubular tissues," *Cell Transplantation*, 3:203, 1994a.

Mooney et al., "Fabricating Tubular Devices From Polymers of Lactic and Glycolic Acid for Tissue Engineering," *Tiss. Eng.*, 1:107–118, 1995b.

Mooney et al., "Stabilized Polyglycolic Acid Fibre-Based Tubes for Tissue Engineering," *Biomaterials*, 17:115–124, 1996a.

Mooney et al., "Switching from differentiation to growth in hepatocytes control by extracellular matrix," *J. Cell. Phys.*, 151:497–505, 1992.

Mooney et al., "Transplantation of hepatocytes using porous, biodegradable sponges," *Transplan. Proc.*, 26(6):4025–4026, 1994b.

Mooney, D. J., Powell, C., Piana, J. and Rutherford, R. B., "Engineering dental pulp tissue," *Biotechnol. Prog.* 12:865–869, 1996b.

Mordacq and Linzer, "Co-localization of Elements Required for Phorbol Ester Stimulation and Glucocorticoid Repression of Proliferin Gene Expression," *Genes and Dev.*, 3:760, 1989.

Moreau, Hen, Wasylyk, Everett, Gaub, and Chambon, "The SV40 Base-Repair Repeat Has a Striking Effect on Gene Expression Both in SV40 and Other Chimeric Recombinants," *Nucl. Acids Res.*, 9:6047, 1981.

Morikawa et al., "Enhancement of therapeutic effects of recombinant interleukin-2 on a transplantable rat fibrosarcoma by the use of a sustained release vehicle, pluronic gel," *Cancer*, 47:37–41, 1987.

Murphy et al., "Partial dermal regeneration is induced by biodegradable collagen-glycosaminoglycan grafts," *Lab. Invest.*, 63:305–313, 1990.

Murray et al., "A micro sustained release system for epidermal growth factor," In vitro, 10:743–748, 1983.

Musesing, Smith, and Capon, "Regulation of mRNA Accumulation by a Human Immnunodeficiency Virus Trans-Activator Protein," *Cell*, 48:691, 1987.

Muzyczka, "Use of Adeno-Associated Virus as a General Transduction Vector for Mammalian Cells," *Curr. Top. Microbiol. Immunol.*, 158:97–129, 1992.

Myers and Fountain, "Dental Pulp Regeneration Aided by Blood and Blood Substitutes After Experimentally Induced Periapical Infection," *Oral Surg.*, 37, 441–450, 1974.

Nagy et al., "Pathogenesis of ascites tumor growth: vascular permeability factor, vascular hyperpermeability, and ascites fluid accumulation," *Cancer Res.* 55:360, 1995.

Nakajima, M., Kashiwagi, K., Ohta, J., Furukawa, S., Hayashi, K., Kawashima, T. and Hayashi, Y., "Nerve growth factor and epidermal growth factor rescue PC12 cells from programmed cell death induced by etoposide: distinct modes of protection against cell death by growth factors and a protein-synthesis inhibitor," *Neurosci. Lett.* 176:161–4, 1994.

Nakamura et al., "Bioabsorption of polylactides with different molecular properties," *J. Biomed. Mater. Res.*, 23:1115–1130, 1989.

Nakashima, "Induction of Dentin Formation on Canine Amputated Pulp by Recombinant Human Bone Morphogenetic Proteins (BMP)-2 and -4," *J. Dent. Res.*, 73:1515–1522, 1994.

Nathan and Kohn, "Amino acid derived polymers," *In: Biomedical Polymers: Designed-to-Degrade Systems*, Shalaby, ed. Carl Hanser Verlag, Munich, 1994.

Ng, Gunning, Liu, Leavitt, and Kedes, "Regulation of the Human Beta-Actin Promoter by Upstream and Intron Domains," *Nuc. Acids Res.*, 17:601, 1989.

Nicolas and Rubinstein, "Retroviral vectors," *In: Vectors: A survey of molecular cloning vectors and their uses*, Rodriguez and Denhardt (eds.), Stoneham: Butterworth, pp. 494–513, 1988.

Nicolau and Sene, "Liposome-mediated DNA transfer in eukaryotic cells: dependence of the transfer efficiency upon the type of liposomes used and the host cell cycle stage," *Biochim. Biophys. Acta* 721:185–190, 1982

Nicolau et al., "Liposomes as carriers for in vivo gene transfer and expression," *Methods Enzymol.,* 149:157–176, 1987.

O'Brien, "New structural polymers from Nature," *Trends in Polym. Sci.,* 8:228–232, 1993.

O'Shea et al., "Prolonged survival of transplanted islets of Langerhans encapsulated in a biocompatible membrane," *Biochim. Biophys. Acta,* 804:133–136, 1984.

Ohi, Dixit, Tillery, and Plonk, "Construction and replication of an adeno-associated virus expression vector that contains human λ-globin cDNA," Gene, 89L:279–282, 1990.

Ondek, Sheppard, and Herr, "Discrete Elements Within the SV40 Enhancer Region Display Different Cell-Specific Enhancer Activities," *EMBo J.,* 6:1017, 1987.

Ornitz, Hammer, Davison, Brinster, and Palmiter, "Promoter and Enhancer Elements From the Rat Elastase I Gene Function Independently of Each Other and of Heterologous Enhancers," *Mol. Cell. Biol.,* 7:3466, 1987.

Ott and Day, "Bacterials alginates: An alternative industrial polymer," *Trends in Polym. Sci.,* 3: 402–406, 1995.

Palmiter, Chen, and Brinster, "Differential Regulation of Metallothionein-Thymidine Kinase Fusion Genes in Transgenic Mice and Their Offspring," *Cell,* 29:701, 1982.

Palukaitis et al., "Characterization of a viroid associated with avacado sunblotch disease," *Virology,* 99:145–151, 1979.

Paskind et al., "Dependence of moloney murine leukemia virus production on cell growth," *Virology,* 67:242–248, 1975.

Pautian et al., "Intravenous Pluronic F-127 in early burn wound treatment in rats," *Burns,* 19:187–191, 1993.

Pech, Rao, Robbins, and Aaronson, "Functional Identification of Regulatory Elements Within the Promoter Region of Platelet-Derived Growth Factor 2," *Mol. Cell. Biol.,* 9:396, 1989.

Penczek and Kubisa, "Cationic Ring-Opening Polymerization: Ethers," In: *Comprehensive Polymer Science,* Vol 3, Allen, ed., Pergamon Press, New York, 1989.

Penczek and Slomkowski, "Cationic ring-opening polymerization: Cyclic ester,". In:
Comprehensive Polymer Science,Vol 3, Allen, ed., Pergamon Press, New York, 1989.

Peppas and Langer, "New challenges in biomaterials," *Science,* 263:1715–1720, 1994.

Peppas and Scott, "Controlled release from poly(vinyl alcohol) gels prepared by freezing-thrawing processes," *J. Controlled Release,* 18:95–100, 1992.

Perales et al., Proc. Natl. Acad. Sci. USA, 91:4086–4090, 1994.

Perez-Stable and Constantini, "Roles of Fetal γ-globin Promoter Elements and the Adult β-globin 3' Enhancer in the Stage-Specific Expression of Globin Genes," *Mol. Cell. Biol.,* 10:1116, 1990.

Perriman et al., "Extended target-site specificity for a hammerhead ribozyme," *Gene,* 113:157–163, 1992.

Peters and Smith, "Ivalon Breast Prostheses: Evaluation 19 years after implantation," *Plast. Rescontr. Surg.,* 67:514–518, 1981.

Picard and Schaffner, "A Lymphocyte-Specific Enhancer in the Mouse Immunoglobulin Kappa Gene," *Nature,* 307:83, 1984.

Pinkert, Omitz, Brinster, and Palmiter, "An Albumin Enhancer Located 10 kb Upstream Functions Along With its Promoter to Direct Efficient, Liver-Specific Expression in Transgenic Mice," *Genes and Dev.,* 1:268, 1987.

Polk et al., "Controlled release of albumin from chitosan-alginate microcapsules," *J. Pharm Sci.,* 83:178–185, 1994.

Ponta, Kennedy, Skroch, Hynes, and Groner, "Hormonal Response Region in the Mouse Mammary Tumor Virus Long Terminal Repeat Can Be Dissociated From the Proviral Pomoter and Has Enhancer Properties," *Proc. Natl. Acad. Sci. U.S.A.,* 82:1020, 1985.

Porton, Zaller, Lieberson, and Eckhardt, "Immunoglobulin Heavy-Chain Enhancer is Required to Maintain Transfected γ2A Gene Expression in a pre-B-cell Line," *Mol. Cell. Biol.,* 10:1076, 1990.

Potter et al., "Enhancer-dependent expression of human k immunoglobulin genes introduced into mouse pre-B lymphocytes by electroporation," *Proc. Nat'l Acad. Sci USA,* 81:7161–7165, 1984.

Prasad et al., "Utilization of 1-hydroxybenzotriazole in mixed anhydride coupling reactions. Int," *J. Pept. Protein Res.,* 25:408–13, 1985.

Prime and Whitesides, "Self-assembled organic monolayers: model systems for studying adsorption of proteins at surfaces," *Science,* 252:1164–1167, 1991.

Prody et al., "Autolytic processing of dimeric plant virus satellite RNA." *Science,* 231, 1577–1580, 1986.

Queen and Baltimore, "Immunoglobulin Gene Transcription is Activated by Downstream Sequence Elements," *Cell,* 35:741, 1983.

Quinn, Farina, Gardner, Krutzsch, and Levens, "Multiple Components are Required for Sequence Recognition of the AP1 Site in the Gibbon Ape Leukemia Virus Enhancer," *Mol. Cell. Biol.,* 9:4713, 1989.

Racher et al., Biotechnology Techniques, 9:169–174, 1995.

Ragot et al., "Efficient adenovirus-mediated transfer of a human minidystrophin gene to skeletal muscle of mdx mice," *Nature,* 361:647–650, 1993.

Razavi et al., "Clinical applications of a polyphosphazene-based resilent denture liner," *J. Prosthodontics,* 2:224–227, 1993.

Redondo, Hata, Brocklehurst, and Krangel, "A T-Cell-Specific Transcriptional Enhancer Within the Human T-Cell Receptor δ Locus," *Science,* 247:1225, 1990.

Reed and Gilding, "Biodegradable polymers for use in surgery—poly(glycolic)/poly(lactic acid) homo and copolymers: 2. In vitro degradation," *Polymer,* 22:494–498, 1981.

Reese and Betts, In: *Handbook of Antibiotics,* 2nd ed., Little, Brown and Company, Boston, 1993.

Reid, "Stem cell biology, hormone/matrix synergies and liver differentiation," *Current Opin. Cell Biol.,* 2:121–130, 1990.

Reinhold-Hurek and Shub, "Self-splicing introns in tRNA genes of widely divergent bacteria," *Nature,* 357:173–176, 1992.

Reisman and Rotter, "Induced Expression From the Moloney Murine Leukemia Virus Long Terminal Repeat During Differentiation of Human Myeloid Cells is Mediated Through its Transcriptional Enhancer," *Mol. Cell. Biol.,* 9:3571, 1989.

Renan, "Cancer genes: current status, future prospects, and applicants in radiotherapy/oncology," *Radiother. Oncol.,* 19:197–218, 1990.

Resendez Jr., Wooden, and Lee, "Identification of Highly Conserved Regulatory Domains and Protein-Binding Sites in the Promoters of the Rat and Human Genes Encoding the Stress-Inducible 78-kilodalton Glucose-Regulated Protein," *Mol. Cell. Biol.,* 8:4579, 1988.

Rich et al., "Development and analysis of recombinant adenoviruses for gene therapy of cystic fibrosis," *Hum. Gene Ther.,* 4:461–476, 1993.

Ricordi et al., "Reversal of diabetes in nude mice after transplantation of fresh and 7-day cultured human pancreatic islets," *Transplantation*, 45:994–996, 1988.

Ridgeway, "Mammalian expression vectors," In: Rodriguez RL, Denhardt DT, ed. Vectors: A survey of molecular cloning vectors and their uses. Stoneham: Butterworth, pp. 467–492, 1988.

Ripe, Lorenzen, Brenner, and Breindl, "Regulatory Elements in the 5° Flanking Region and the First Intron Contribute to Transcriptional Control of the Mouse alpha-1-type Collagen Gene," *Mol. Cell. Biol.*, 9:2224, 1989.

Rippe, Brenner and Leffert, "DNA-mediated gene transfer into adult rat hepatocytes in primary culture," *Mol. Cell Biol.*, 10:689–695, 1990.

Rittling, Coutinho, Amarm, and Kolbe, "AP-1/jun-binding Sites Mediate Serum Inducibility of the Human Vimentin Promoter," *Nuc. Acids Res.*, 17:1619, 1989.

Rosen, Sodroski, and Haseltine, "The Location of cis-acting Regulatory Sequences in the Human T-Cell Lymphotropic Virus Type III (HTLV-111/LAV) Long Terminal Repeat," *Cell*, 41:813, 1988.

Rosenfeld, Siegfried, Yoshimura, Yoneyama, Fukayama, Stier, Paakko, Gilardi, Stratford-Perricaudet, Perricaudet, Jallat, Pavirani, Lecocq, Crystal, "Adenovirus-mediated transfer of a recombinant α 1-antitrypsin gene to the lung epithelium in vivo," *Science*, 252:431–434, 1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, "In vivo transfer of the human cystic fibrosis transmembrane conductance regulator gene to the airway epithelium," *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Rutherford et al., "Induction of Reparative Dentin Formation in Monkeys by Recombinant Human Osteogenic Protein-1," *Archs Oral Biol.*, 38:571–576, 1993b.

Rutherford et al., "Platelet derived and insulin-like growth factors stimulate regeneration of periodontal attachment in monkeys," *J. Perio Res.*, 27:285–290, 1992b.

Rutherford et al., "Synergistic Effects of Dexamethasone on Platelet-Derived Growth Factor Mitogenesis In vitro,". *Archs Oral Biol.*, 37:139–145, 1992a.

Rutherford et al., "Time Course of the Induction of Reparative Dentin Formation in Monkeys by Recombinant Human Osteogenic Protein-1," *Arch Oral Biol.*, 39:833–838, 1994.

Rutherford et al., "Transdentinal Stimulation of Reparative Dentin Formation by Osteogenic Protein-1," *Archs. Oral Biol.*, 40:681–683, 1995.

Rutherford et al., "Platelet-derived growth factor and dexamethasone combined with a collagen matrix induced regeneration of the periodontium in monkeys," *J. Clin. Perio.*, 20:537–544, 1993a.

Sagan et al., "Transplants of immunologically isolated xenogeneic chromaffin cells provide a long-term source of pain-reducing neuroactive substances," *J. Neuroscience*, 13:2415–2423, 1993.

Sakai, Helms, Carlstedt-Duke, Gustafsson, Rottman, and Yamamoto, "Hormone-Mediated Repression: A Negative Glucocorticoid-Response Element From the Bovine Prolactin Gene," *Genes and Dev.*, 2:1144, 1988.

Samulski, Chang, and Shenk, "Helper-free stocks of recombinant adeno-associated viruses: Normal integration does not require viral gene expression," *J. Virol.*, 63:3822–3828, 1989.

Samulski, Zhu, Xiao, Brook, Housman, Epstein, and Hunter, "Targeted integration of adeno-associated virus (AAV) into human chromosome 19," *EMBO J.*, 10:3941–3950, 1991.

Sanders and Matthews, "Vaginal absorption of polyvinyl alcohol in Fischer 344 rats," *Hum. and Exper. Toxicol.*, 9:71–77, 1990.

Santerre, et al., *Gene*, 30:147, 1984.

Sarin, A., Adams, D. H. and Henkart, P. A., "Protease inhibitors selectively block T cell receptor-triggered programmed cell death in a murine T cell hybridoma and activated peripheral T cells," *J. Exp. Med* 178:1693–1700, 1993.

Sarin, A., Clerici, M., Blatt, S. P., Hendrix, C. W., Shearer, G. M. and Henkart, P. A., "Inhibition of activation-induced programmed cell death and restoration of defective immune responses of HIV+ donors by cysteine protease inhibitors," *J. Immunol.* 153:862–872, 1994.

Sarver et al., "Ribozymes as potential anti-HIV-1 therapeutic agents," *Science*, 247:1222–1225, 1990.

Satake, Furukawa, and Ito, "Biological Activities of Oligonucleotides Spanning the F9 Point Mutation Within the Enhancer Region of Polyoma Virus DNA," *J. Virology*, 62:970, 1988.

Sato, N., Iwata, S., Nakamura, K., Hori, T., Mori, K. and Yodoi, J., "Thiol-mediated redox regulation of apoptosis. Possible roles of cellular thiols other than glutathione in T cell apoptosis," *J. Immunol.* 154:3194–3203, 1995.

Sawhney et al., "Bioerodible hydrogels based on photopolymerized poly(ethylene glycol)-co-poly(a-hydroxy acid) diacrylate macromonomers," *Macromol*, 26:581–587, 1993.

Sawhney et al., "Optimization of photopolymerized bioerodible hydrogel properties for adhesion prevention," *J. Biomed. Mater. Res.*, 28:831–838, 1994.

Scanlon et al., "Ribozyme-mediated cleavages of c-fos mRNA reduce gene expression of DNA synthesis enzymes and metallothionein," *Proc Natl Acad Sci USA*, 88:10591–10595, 1991.

Schaffner, Schirm, Muller-Baden, Wever, and Schaffner, "Redundancy of Information in Enhancers as a Principle of Mammalian Transcription Control," *J. Mol. Biol.*, 201:81, 1988.

Schmaltz, "Use of Cell Cultures for Toxicity Testing of Dental Materials—Advantages and Limitations," *J. Dent.* 2(Suppl.):S6–S11, 1974.

Schmolka, "Artificial skin. I Preparation and properties of pluronic F-127 gels for treatments of burns," *J. Biomed. Mater. Res.*, 6:571–582, 1972.

Schwartz and Ingber, "Integrating with integrins," *Mol. Biol. Cell*, 5:389–393, 1994.

Schwartz, A. W. and Erich, J. B., "Experimental study of polyvinyl alcohol-formal (Ivalon) sponge as a substitute for tissue," *Plast. Reconstr. Surg.* 25:1, 1960.

Scopelianos, "Polyphophazenes as new biomaterials," *In: Biomedical Polymers: Designed-to-Degrade Systems*, Shalaby, ed., Carl Hanser Verlag, New York, 1994.

Scouten, W. H., "Matrices and immobilization methods for cell adhesion/immobilization studies," *Bioprocess. Technol.* 20:233–265, 1995.

Searle, Stuart, and Palmiter, "Building a Metal-Responsive Promoter With Synthetic Regulatory Elements," *Mol. Cell. Biol.*, 5:1480, 1985.

Sell, C., Baserga, R. and Rubin, R., "Insulin-like growth factor I (IGF-I) and the IGF-I receptor prevent etoposide-induced apoptosis," *Cancer Res.* 55:303–306, 1995.

Serwer, "Agarose gel electrophoresis of bacteriophages and related particles," *J. Chromatogr.*, 418:345–357, 1987.

Shalaby and Johnson, "Synthetic absorbable polyesters," *In: Biomedical Polymers: Designed-to-Degrade Systems*, Shalaby, ed., Carl Hanser Verlag, New York, 1994.

Sharp and Marciniak, "HIV Tar: an RNA Enhancer?," *Cell*, 59:229, 1989.

Shaul and Ben-Levy, "Multiple Nuclear Proteins in Liver Cells are Bound to Hepatitis B Virus Enhancer Element and its Upstream Sequences," *EMBO J.*, 6:1913, 1987.

Sherman, Basta, Moore, Brown, and Ting, "Class II Box Consensus Sequences in the HLA-DRα Gene: Transcriptional Function and Interaction with Nuclear Proteins," *Mol. Cell. Biol.*, 9:50, 1989.

Singhvi et al., "Engineering cell shape and function," *Science*, 264:696–698, 1994.

Sioud et al., "Preformed ribozyme destroys tumour necrosis factor mRNA in human cells," *J Mol. Biol.*, 223:831–835, 1992.

Skjak-Braek et al., "Tailoring of alginates by enzymatic modification in vitro," *Int. J. Biol. Macromol.*, 8:330–336, 1986.

Sleigh and Lockett, "SV40 Enhancer Activation During Retinoic-Acid-Induced Differentiation of F9 Embryonal Carcinoma Cells," *J. EMBO*, 4:3831, 1985.

Smidsrod, O. and Skjak-Braek, G., "Alginate as immobilization matrix for cells," *TRIBTECH* 8:71–78, 1990.

Sogah et al., "De Novo design and synthesis of protein-based hybrid polymers," *Macromol. Reports*, A31:1003–1008, 1994.

Soldani et al., "Small diameter polyurethane-polydimethylsiloxane vascular prostheses made by a spraying, phase-inversion process," *J. Mater. Sci. Mater. Med.*, 3:106–113, 1992.

Soon-Shiong et al., "First human clinical trial of immuno-protected islet allografts in alginate capsules," *Soc. Biomater. Ann. Mtg.*, abstract 356, Boston, Mass., 1994.

Spalholz, Yang, and Howley, "Transactivation of a Bovine Papilloma Virus Transcriptional Regulatory Element by the E2 Gene Product," *Cell*, 42:183, 1985.

Spandau and Lee, "Trans-Activation of Viral Enhancers by the Hepatitis B Virus X Protein," *J. Virology*, 62:427, 1988.

Spandidos and Wilkie, "Host-Specificities of Papilloma Virus, Moloney Murine Sarcoma Virus and Simian Virus 40 Enhancer Sequences," *EMBO J.*, 2:1193, 1983.

Squier, M. K., Miller, A. C., Malkinson, A. M. and Cohen, J. J., "Calpain activation in apoptosis," *J. Cell. Physiol.* 159:229–237, 1994.

Stephens and Hentschel, "The Bovine Papilloma Virus Genome and its Uses as a Eukaryotic Vector," *Biochem. J.*, 248:1, 1987.

Stern et al., "Histologic study of artificial skin used in the treatment of full-thickness thermal injury," *J. Burn Care Rehabil.*, 11:7–13, 1990.

Stoker et al., "Designer microenvironments for the analysis of cell and tissue function," *Curr. Opin. Cell Biol. I*, 2:864–874, 1990.

Stratford-Perricaudet and Perricaudetp. 51–61, *In: Human Gene Transfer*, Eds, O. Cohen-Haguenauer and M. Boiron, Editions John Libbey Eurotext, France, 1991.

Stratford-Perricaudet et al., *Hum. Gene. Ther.* 1:241–256, 1991.

Stuart, Searle, and Palmiter, "Identification of Multiple Metal Regulatory Elements in Mouse Metallothionein-I Promoter by Assaying Synthetic Sequences," *Nature*, 317:828, 1985.

Stupp and Ciegler, "Organoapatites: materials for artificial bone. I. synthesis and microstructure," *J. Biomed. Matls. Res.*, 26:169–183, 1992.

Stupp et al., "Organoapatites: materials for artificial bone. II. hardening reactions and properties," *J. Biomed. Matls. Res.*, 27:289–299, 1993a.

Sullivan and Peterlin, "Transcriptional Enhancers in the HLA-DQ Subregion," *Mol. Cell. Biol.*, 7:3315, 1987.

Sullivan et al., "Biohydrid artificial pancreas: long-term implantation studies in diabetic, pancreatomized dogs," *Science*, 252:718–721, 1991.

Sun et al., "Injectable microencapsulated islet cells as a bioartificial pancreas," *Appl. Biochem. Biotech.*, 10:87, 1984.

Sutherland, "Alginates," *In: Biomaterials, Novel Materials from Biological Sources*, Byron, ed., Stockton Press, New York, 1991.

Swartzendruber and Lehman, "Neoplastic Differentiation: Interaction of Simian Virus 40 and Polyoma Virus with Murine Teratocarcinoma Cells," *J. Cell. Physiology*, 85:179, 1975.

Symons, R. H. "Small catalytic RNAs." *Annu. Rev. Biochem.*, 61:641–671, 1992.

Symons, R. H., "Avacado sunblotch viroid: primary sequence and proposed secondary structure." *Nucl. Acids Res.*, 9:6527–6537, 1981.

Takebe, Seiki, Fujisawa, Hoy, Yokota, Arai, Yoshida, and Arai, "SRα Promoter: An Efficient and Versatile Mammalian cDNA Expression System Composed of the Simian Virus 40 Early Promoter and the R-U5 Segment of Human T-Cell Leukemia Virus Type 1 Long Terminal Repeat," *Mol. Cell. Biol.*, 8:466, 1988.

Tan, "A colorometric assay for glycolic acid," *Clinica Chimica Acta*, 89:13, 1978.

Tavernier, Gheysen, Duerinck, Can Der Heyden, and Fiers, "Deletion Mapping of the Inducible Promoter of Human IFN-beta Gene," *Nature*, 301:634, 1983.

Taylor and Kingston, "Ela Trans-Activation of Human HSP70 Gene Promoter Substitution Mutants is Independent of the Composition of Upstream and TATA Elements," *Mol. Cell. Biol.*, 10:176, 1990b.

Taylor and Kingston, "Factor Substitution in a Human HSP70 Gene Promoter: TATA-Dependent and TATA-Independent Interactions," *Mol. Cell. Biol.*, 10:165, 1990a.

Taylor, Solomon, Weiner, Paucha, Bradley, and Kingston, "Stimulation of the Human Heat-Shock Protein 70 Promoter in vitro by Simian Virus 40 Large T Antigen," *J. Biol. Chem.*, 264:15160, 1989.

Temin, "Retrovirus vectors for gene transfer: Efficient integration into and expression of exogenous DNA in vertebrate cell genome," *In: Gene Transfer*, Kucherlapati (ed.), New York: Plenum Press, pp. 149–188, 1986.

Tepper, C. G., Jayadev, S., Liu, B., Bielawska, A., Wolff, R., Yonehara, S., Hannun, Y. A. and Seldin, M. F., "Role for ceramide as an endogenous mediator of Fas-induced cytotoxicity," *Proc. Natl. Acad. Sci. USA* 92:8443–8447, 1995.

Thiesen, Bosze, Henry, and Charnay, "A DNA Element Responsible for the Different Tissue Specificities of Friend and Moloney Retroviral Enhancers," *J. Virology*, 62:614.

Thompson, J. D. et al., "Ribozymes in gene therapy." *Nature Medicine*, 1:277–278, 1995.

Tilly, J. L. and Tilly, K. I., "Inhibitors of oxidative stress mimic the ability of follicle-stimulating hormone to suppress apoptosis in cultured rat ovarian follicles," *Endocrinology* 136:242–252, 1995.

Timmins and Lenz, "Enzymatic biodegradation of polymers: The polymer chemist's perspective," *Trends Polymer Sci.,* 2:15–19, 1994.

Tirrell et al., "Biomolecular Materials," *In: Chemical and Engineering News* (December 19), Jacobs, ed., Washington, DC: American Chemical Society, 1994.

Top et al., "Immunization with live types 7 and 4 adenovirus vaccines. II. Antibody response and protective effect against acute respiratory disease due to adenovirus type 7," *J. Infect. Dis.,* 124:155–160, 1971.

Traganos, F. Kapuscinski, J., Gong, J., Ardelt, B., Darzynkiewicz, R. J. and Darzynkiewicz, Z., "Caffeine prevents apoptosis and cell cycle effects induced by camptothecin or topotecan in HL-60 cells," *Cancer Res.* 53:4613–4618, 1993.

Tratschin, Miller, Smith, and Carter, "Adeno-associated virus vector for high-frequency integration, expression and rescue of genes in mammalian cells," *Mol. Cell. Biol.,* 5:32581–3260, 1985.

Tratschin, West, Sandbank, and Carter, "A human parvovirus, adeno-associated virus, as a eucaryotic vector: transient expression and encapsidation of the procaryotic gene for chloramphenicol acetyltransferase," *Mol. Cell. Biol.,* 4:2072–2081, 1984.

Treisman, "Transient Accumulation of c-fos RNA Following Serum Stimulation Requires a Conserved 5' Element and c-fos 3' Sequences," *Cell,* 42:889, 1985.

Tronche, Rollier, Bach, Weiss, and Yaniv, "The Rat Albumin Promoter: Cooperation with Upstream Elements is Required When Binding of APF/HNF 1 to the Proximal Element is Partially Impaired by Mutation or Bacterial Methylation," *Mol. Cell. Biol.,* 9:4759, 1989.

Tronche, Rollier, Herbomel, Bach, Cereghini, Weiss, and Yaniv, "Anatomy of the Rat Albumin Promoter," *Mol. Biol. Med.,* 7:173, 1990.

Trudel and Constantini, "A 3' Enhancer Contributes to the Stage-Specific Expression of the Human Beta-Globin Gene," *Genes and Dev.,* 6:954, 1987.

Tur-Kaspa, Teicher, Levine, Skoultchi and Shafritz, "Use of electroporation to introduce biologically active foreign genes into primary rat hepatocytes," *Mol. Cell Biol.,* 6:716–718, 1986.

Tyndall, La Mantia, Thacker, Favaloro, and Kamen, "A Region of the Polyoma Virus Genome Between the Replication Origin and Late Protein-Coding Sequences is Required in cis for Both Early Gene Expression and Viral DNA Replication," *Nuc. Acids. Res.,* 9:6231, 1981.

Urry et al., "The capacity to vary the bioactive elastic protein-based polymers," *PMSE Prepr.,* August 1995 399–402, 1995.

Urry, "Entropic elastic processes in protein mechanisms. I. Elastic structure due to an inverse temperature transition and elasticity due to internal chain dynamics," *J. Protein Chem.,* 7:1–34, 1988a.

Urry, "Entropic elastic processes in protein mechanisms. II. Simple (passive) and coupled (active) development of elastic forces," *J. Protein Chem.,* 7:81–114, 1988b.

Urry, "Molecular machines: How motion and other function of living organisms can result from reversible chemical changes," *Angew Chem. Int. Ed. Engl.,* 32:819–841, 1993.

Uyama et al., "Delivery of a whole liver equivalent hepatic mass using polymer devices and hepatotrophic stimulation," *Transplantation,* 55:932–935, 1993.

Vacanti et al., "Selective cell transplantation using bioabsorbable artificial polymers as matrices," *J. Ped. Surg.,* 23:3–9, 1988.

Vacanti et al., "Tissue engineered growth of new cartilage in the shape of a human ear using synthetic polymers seeded with chondrocytes." *In: Tissue inducing biomaterials,* Cima and Ron, eds., *Mat. Res. Soc. Symp. Proc.,* 252:367–374, 1992.

Vainionpaa et al., "Strength and strength retention in vitro, of absorbable, self-reinforced polyglycolide (PGA) rods for fracture fixation," *Biomaterials,* 8:46–48, 1987.

Vandenburgh et al., "Computer-aided mechanogenesis of skeletal muscle organs from single cells in vitro," *FASEB J.,* 5:2860–2867, 1991.

Vannice and Levinson, "Properties of the Human Hepatitis B Virus Enhancer: Position Effects and Cell-Type Nonspecificity," *J. Virology,* 62:1305, 1988.

Vasseur, Kress, Montreau, and Blangy, "Isolation and Characterization of Polyoma Virus Mutants Able to Develop in Multipotential Murine Embryonal Carcinoma Cells," *Proc. Natl. Acad. Sci. U.S.A.,* 77:1068, 1980.

Vert and Guerin, "Biodegradable aliphatic polyesters of the poly(hydroxy acid)-type for temporary therapeutic applications," *In: Biomaterials Degradation.* Barbosa, ed., Elsvier Science, New York, 1991.

Vert et al., "Bioresorbable plastic materials for bone surgery," *In: Macromolecular Biomaterials.* Hastings and Ducheyne, eds., CRC Press, Boca Raton, Fla., 1984.

von Recum, ed., *Handbook of Biomaterials Evaluation: Scientific, Technical and Clinical Testing of Implant Materials,* Macmillan, New York, 1986.

Wagner et al., *Science,* 260:1510–1513, 1990.

Wald et al., "Cell seeding in porous transplantation devices," *Biomaterials,* 14:270–279, 1993.

Walsh, Nienhuis, Samulski, Brown, Miller, Young, and Liu, "Phenotypic correction of Fanconi anemia in human hematopoietic cells with a recombinant adeno-associated virus vector," *J. Clin. Invest.,* 94:1440–1448, 1994.

Wang and Calame, "SV40 Enhancer-Binding Factors are Required at the Establishment but not the Maintenance Step of Enhancer-Dependent Transcriptional Activation," *Cell,* 47:241, 1986.

Wang, "Compressed poly(vinyl alcohol)-polycaprolactone admixture as a model to evaluate erodible implants for sustained drug delievery," *J. Biomed. Mater. Res.,* 23:91–104, 1989.

Weber, De Villiers, and Schaffner, "An SV40 'Enhancer Trap' Incorporates Exogenous Enhancers or Generates Enhancers From its Own Sequences," *Cell,* 36:983, 1984.

Wei, Wei, Samulski, and Barranger, "Expression of the human glucocerebrosidase and arylsulfatase A genes in murine and patient primary fibroblasts transduced by an adeno-associated virus vector," *Gene Therapy,* 1:261–268, 1994.

Weinberger, Jat, and Sharp, "Localization of a Repressive Sequence Contributing to B-cell Specificity in the Immunoglobulin Heavy-Chain Enhancer," *Mol. Cell. Biol.,* 8:988, 1984.

Wesloski et al., "Porosity: primary determinant of ultimate fate of synthetic vascular grafts," *Surgery,* 50:91–96, 1961.

White et al., "Histopathologic observations after short-term implantation of porous elastomers in dogs," *Biomaterials,* 2:171–176, 1981.

Wight et al., "Proteoglycans: Structure and Function," *In: Cell Biology of Extracellular Matrix,* Hay, ed., Plenum Press, New York, 1991.

Williams, McClanahan, and Morimoto, "Ela Transactivation of the Human HSP70 Promoter is Mediated Through the Basal Transcriptional Complex," *Mol. Cell. Biol.,* 9:2574, 1989.

Winoto and Baltimore, "αβ-lineage-specific Expression of the α T-Cell Receptor Gene by Nearby Silencers," *Cell,* 59:649, 1989.

Wong, W. H. and Mooney, D. J., "Synthesis and properties of biodegradable polymers used in tissue engineering," in *Synthetic Biodegradable Polymer Scaffolds,* (Atala and Mooney, eds.), Birkhauser Press, Boston, Mass., pp. 51–82, 1997.

Wong et al., "Appearance of β-lactamase activity in animal cells upon liposome mediated gene transfer," *Gene,* 10:87–94, 1980.

Wong, "Design, Synthesis and Properties of Protein Based Hybrid Polymers." Ph.D. Thesis, Cornell University, Ithaca, N.Y., 1996.

Wu and Wu, "Receptor-mediated in vitro gene transfections by a soluble DNA carrier system," *J. Biol. Chem.,* 262:4429–4432, 1987.

Wu and Wu, *Adv. Drug Delivery Rev.,* 12:159–167, 1993.

Yalpani, *Polysaccharides: Syntheses, Modifications and Structure/Properties Relations,* Elsevier, Amsterdam, 1988.

Yang et al., "Hollow fibers for hepatocyte encapsulation and transplantation: studies of survival and function in rats," *Cell Transplantation,* 3:001, 1994.

Yang, Burkholder, Roberts, Martinell and McCabe, "In vivo and in vitro gene transfer to mammalian somatic cells by particle bombardment," *Proc. Nat'l Acad. Sci. USA,* 87:9568–9572, 1990.

Yang, Chen, Trempe, "Characterization of cell lines that inducibly express the adeno-associated virus Rep proteins," *J. Virol.,* 68:4847–4856, 1994.

Yannas et al., "Wound tissue can utilize a polymeric template to synthesize a functional extension of skin," *Science,* 215:174–176, 1981.

Yannas et al., "Synthesis and characterization of a model of extracellular matrix that induces partial regeneration of adult mammalian skin," *Proc. Natl. Acad Sci. USA,* 86:933–937, 1989.

Yasin and Tighe, "Polymers for biodegradable medical devices. VIII. Hydroxybutyrate-hydroxyvalerate copolymers: physical and degradative properties of blends with polycaprolactone," *Biomaterials,* 13:9–16, 1992.

Yoder, Kang, Zhou, Luo, and Srivastava, "In vivo gene transfer in murine hematopoietic reconstituting stem cells mediated by the adeno-associated virus 2-based vectors," *Blood,* 82 (Supp.): 1:347A, 1994.

Yuan and Altman, "Selection of guide sequences that direct efficient cleavage of mRNA by human ribonuclease P," *Science,* 263:1269–1273, 1994.

Yuan et al., "Targeted cleavage of mRNA by human RNase P," *Proc. Natl. Acad. Sci. USA,* 89:8006–8010, 1992.

Yutzey, Kline, and Konieczny, "An Internal Regulatory Element Controls Troponin I Gene Expression," *Mol. Cell. Biol.,* 9:1397, 1989.

Zalipsky, "Functionalized poly(ethylene glycol) for preparation of biologically relevant conjugates," *Bioconjugate Chem.,* 6:150–165, 1995.

Zhou, Broxmyer, Cooper, Harrington, and Srivastava, "Adeno-associated virus 2 mediated gene transfer in murine hematopoietic cells, *Exp. Hematol.* (N.Y.), 21:928–933, 1993.

Zhou, Cooper, Kang, Ruggieri, Heimfeld, Srivastava, and Broxmeyer, "Adeno-associated virus 2-mediated high efficiency gene transfer into immature and mature subsets of hematopoietic progenitor cells in human umbilical cord blood," *J. Exp. Med.,* 179:1867–1875, 1994.

What is claimed is:

1. A method for culturing oral tissue cells, comprising growing viable oral tissue cells on a synthetic matrix in vitro under conditions effective and for a period of time sufficient to allow proliferation of viable oral tissue cells.

2. A method for generating a tissue sample comprising oral tissue cells, the method comprising culturing viable starting cells obtained from an oral tissue sample on a synthetic matrix in vitro under conditions effective and for a period of time sufficient to allow the formation of a tissue sample that comprises viable oral tissue cells.

3. The method of claim 2, wherein said viable starting cells are gingival cells obtained from a gingival tissue sample.

4. The method of claim 3, wherein said gingival cells are cultured to form a tissue sample that comprises viable gingival submucosal cells.

5. The method of claim 3, wherein said gingival cells are cultured to form a tissue sample that comprises viable dental pulp tissue cells.

6. The method of claim 3, wherein said gingival cells are cultured to form a tissue sample that comprises viable dentin tissue cells.

7. The method of claim 3, wherein said gingival cells are cultured to form a tissue sample that comprises viable cementum tissue cells.

8. The method of claim 3, wherein said gingival cells are cultured to form a tissue sample that comprises viable periodontal tissue cells.

9. The method of claim 3, wherein said gingival cells are cultured to form a tissue sample that comprises viable oral submucosa tissue cells.

10. The method of claim 3, wherein said gingival cells are cultured to form a tissue sample that comprises viable tongue tissue cells.

11. The method of claim 2, wherein a mixture of viable starting cells are used.

12. The method of claim 2, wherein the tissue sample formed comprises viable dental pulp tissue cells.

13. The method of claim 12, wherein the tissue sample is formed by culturing viable starting cells obtained from an oral tissue sample enriched in fibroblasts obtained from dental pulp.

14. The method of claim 13, wherein said oral tissue sample enriched in fibroblasts obtained from dental pulp is obtained from an extracted tooth.

15. The method of claim 13, wherein said oral tissue sample enriched in fibroblasts obtained from dental pulp is obtained from a tissue sample extracted from a tooth that remains in an animal.

16. The method of claim 12, wherein the tissue sample is formed by culturing viable starting cells obtained from an oral tissue sample enriched in gingival submucosal fibroblasts.

17. The method of claim 2, wherein the tissue sample formed comprises viable dentin tissue cells.

18. The method of claim 17, wherein the tissue sample is formed by culturing viable starting cells obtained from an oral tissue sample enriched in dental pulp cells.

19. The method of claim 17, wherein the tissue sample is formed by culturing viable starting cells obtained from an oral tissue sample enriched in gingival submucosal fibroblasts.

20. The method of claim 2, wherein the tissue sample formed comprises viable gingival submucosa tissue cells.

21. The method of claim 20, wherein the tissue sample is formed by culturing viable starting cells obtained from an oral tissue sample enriched in gingival submucosal fibroblasts.

22. The method of claim 2, wherein the tissue sample formed comprises viable cementum tissue cells.

23. The method of claim 22, wherein the tissue sample is formed by culturing viable starting cells obtained from an oral tissue sample enriched in gingival submucosal fibroblasts.

24. The method of claim 2, wherein the tissue sample formed comprises viable periodontal tissue cells.

25. The method of claim 24, wherein the tissue sample is formed by culturing viable starting cells obtained from an oral tissue sample enriched in periodontal ligament cells.

26. The method of claim 24, wherein the tissue sample is formed by culturing viable starting cells obtained from an oral tissue sample enriched in gingival submucosal fibroblasts.

27. The method of claim 2, wherein the tissue sample formed comprises viable oral submucosa tissue cells.

28. The method of claim 27, wherein the tissue sample is formed by culturing viable starting cells obtained from an oral tissue sample enriched in oral submucosal fibroblasts.

29. The method of claim 27, wherein the tissue sample is formed by culturing viable starting cells obtained from an oral tissue sample enriched in gingival submucosal fibroblasts.

30. The method of claim 2, wherein the tissue sample formed comprises viable tongue tissue cells.

31. The method of claim 30, wherein the tissue sample is formed by culturing viable starting cells obtained from an oral tissue sample enriched in gingival submucosal fibroblasts.

32. The method of claim 2, wherein the tissue sample formed comprises viable oral tissue cells of at least two different cell types.

33. The method of claim 2, wherein the tissue sample formed comprises a plurality of distinct viable oral tissue cells.

34. The method of claim 2, wherein the viable starting cells are cultured on the synthetic matrix in vitro in the presence of an effective amount of an exogenous factor that stimulates the growth or proliferation of the cells.

35. The method of claim 34, wherein said exogenous factor is produced by a cell present during the culture.

36. The method of claim 35, wherein said exogenous factor is produced by a recombinant cell present during the culture, the cell being engineered to produce said factor.

37. The method of claim 2, wherein said viable starting cells are cultured on the synthetic matrix in vitro in the presence of an amount of an antimicrobial agent effective to inhibit the growth of microbial cells in the culture.

38. The method of claim 2, wherein said viable starting cells are pre-cultured in vitro for a period of time effective to prepare an expanded population of viable cells for culture on said synthetic matrix in vitro.

39. The method of claim 2, wherein the synthetic matrix is a biocompatible synthetic matrix.

40. The method of claim 2, wherein the synthetic matrix is a non-biocompatible synthetic matrix.

41. The method of claim 2, wherein the synthetic matrix is a biodegradable synthetic matrix.

42. The method of claim 2, wherein the synthetic matrix is a non-biodegradable synthetic matrix.

43. The method of claim 2, wherein the synthetic matrix is a sponge-like synthetic matrix.

44. The method of claim 2, wherein the synthetic matrix is a tubular or fiber-based synthetic matrix.

45. The method of claim 2, wherein the synthetic matrix is a synthetic polymer matrix.

46. The method of claim 45, wherein the synthetic matrix is a polylactic acid (PLA) polymer matrix, a polyglycolic acid (PGA) polymer matrix or a polylactic acid-polyglycolic acid (PLGA) co-polymer synthetic matrix.

47. The method of claim 2, wherein the synthetic matrix is a synthetic polymer matrix operatively attached to a biologically active molecule.

48. The method of claim 2, wherein the individual components of the synthetic matrix are coated with a coating agent.

49. The method of claim 48, wherein the synthetic matrix is a synthetic fiber matrix, the individual fiber components of which matrix are coated with a collagen, polylysine or FBS coating agent.

50. The method of claim 2, wherein the viable oral tissue cells are provided with an exogenous gene that expresses an exogenous factor in said cells.

51. The method of claim 50, wherein the viable oral tissue cells are provided with said exogenous gene by providing said exogenous gene to the viable starting cells towards the beginning of the in vitro synthetic matrix culture process.

52. The method of claim 50, wherein the viable oral tissue cells are provided with said exogenous gene by providing said exogenous gene to the viable oral tissue cells of the tissue sample that forms towards the end of the in vitro synthetic matrix culture process.

53. The method of claim 50, wherein said exogenous gene expresses an exogenous factor that stimulates the growth or proliferation of the cells.

54. The method of claim 50, wherein said exogenous gene expresses an exogenous therapeutic factor that is released by said cells.

55. The method of claim 54, wherein said exogenous therapeutic factor is an antibiotic, a growth factor, a cytokine, a blood clotting factor or insulin.

56. A method for culturing oral tissue cells, comprising growing viable starting cells obtained from an oral tissue sample in functional association with a three dimensional synthetic matrix in vitro under conditions effective and for a period of time sufficient to allow proliferation and organization of viable oral tissue cells to form a three dimensional biological structure comprising cells that express at least one marker indicative of oral tissue cells.

57. A method for generating an oral tissue sample, comprising growing viable starting cells obtained from an oral tissue sample in functional association with a three dimensional synthetic matrix in vitro under conditions effective and for a period of time sufficient to allow proliferation and organization of viable oral tissue cells to form a three dimensional oral tissue structure comprising a population of cells that express at least one biological marker indicative of oral tissue cells.

58. The method of claim 57, wherein said viable starting cells are obtained from a gingival tissue sample.

59. The method of claim 57, wherein said three dimensional oral tissue structure resembles the corresponding native oral tissue.

60. A method for reconstructing an oral tissue, comprising obtaining a composition comprising viable cells from an oral tissue of an animal, culturing the viable cells of said composition on a synthetic matrix ex vivo under conditions effective and for a period of time sufficient to allow the formation of the corresponding native oral tissue.

61. The method of claim 60, wherein said viable starting cells are obtained from a gingival tissue sample.

62. The method of claim 60, wherein said viable starting cells are obtained from an oral tissue sample that is obtained from an oral tissue site compatible with, but distinct from, the oral tissue to be reconstructed or replaced.

63. The method of claim 60, wherein said viable starting cells are obtained from an oral tissue sample that is obtained from the damaged oral tissue site to be reconstructed or replaced.

64. The method of claim 60, wherein said viable starting cells are cultured on the synthetic matrix in vitro in the presence of an amount of an antimicrobial agent effective to inhibit the growth of microbial cells in the culture.

65. The method of claim 60, wherein said viable starting cells are pre-cultured in vitro for a period of time effective to prepare an expanded population of viable cells for culture on said synthetic matrix in vitro.

66. The method of claim 60, wherein said tissue sample is separated from said synthetic matrix prior to application to said animal.

67. The method of claim 60, wherein said tissue sample is applied to said animal in combination with said synthetic matrix.

68. The method of claim 60, wherein said tissue sample has a structure that resembles the corresponding native oral tissue structure.

69. The method of claim 60, wherein the tissue sample is applied to the oral tissue site to be reconstructed or replaced in the presence of an exogenous factor that stimulates the growth or proliferation of the tissue in the animal.

70. The method of claim 69, wherein said exogenous factor is produced by a cell that is also applied to the oral tissue site of said animal.

71. The method of claim 70, wherein the exogenous factor-producing cell is a recombinant cell engineered to produce said factor.

72. The method of claim 70, wherein the exogenous factor-producing cell is a cultured oral tissue cell of the applied tissue sample, said cell being provided with an exogenous gene that expresses said exogenous factor.

73. The method of claim 60, wherein the oral tissue cells of said tissue are provided with an exogenous gene that expresses an exogenous factor in said cells prior to application of said tissue sample to said animal.

74. The method of claim 73, wherein the oral tissue cells of said tissue sample are provided with said exogenous gene by providing said exogenous gene to the viable starting cells towards the beginning of the in vitro synthetic matrix culture process.

75. The method of claim 73, wherein the oral tissue cells of said tissue sample are provided with said exogenous gene by providing said exogenous gene to the oral tissue cells of said tissue sample towards the end of the in vitro synthetic matrix culture process.

76. The method of claim 73, wherein said exogenous gene expresses an exogenous factor that stimulates the growth or proliferation of the oral tissue cells of the tissue sample when applied to the animal.

77. The method of claim 76, wherein said exogenous gene expresses an angiogenic factor that stimulates the growth or proliferation of blood vessels in or around the oral tissue cells of the tissue sample following application to the animal.

78. The method of claim 73, wherein said exogenous gene expresses an exogenous therapeutic factor that is released by the cells of the tissue following application to the animal.

79. The method of claim 78, wherein said exogenous therapeutic factor is an antibiotic, a growth factor, a cytokine, a blood clotting factor or insulin.

80. A method for filling a root canal, comprising culturing viable starting cells on a synthetic matrix in vitro under conditions effective and for a period of time sufficient to allow the formation of regenerated dental pulp tissue within said synthetic matrix and implanting said regenerated dental pulp tissue into the root canal.

81. The method of claim 80, wherein said starting oral tissue sample is enriched in dental pulp-derived fibroblasts.

82. The method of claim 81, wherein said starting oral tissue sample is obtained from the dental pulp tissue of an extracted tooth.

83. The method of claim 81, wherein said starting oral tissue sample is obtained from a dental pulp tissue sample obtained from a tooth that remains in an animal.

84. The method of claim 83, wherein said dental pulp tissue sample is obtained from a healthy molar or wisdom tooth of said animal distinct from the target tooth.

85. The method of claim 83, wherein said dental pulp tissue sample is obtained from the target tooth to be treated.

86. The method of claim 80, wherein said starting oral tissue sample is enriched in gingival submucosal fibroblasts.

87. The method of claim 80, wherein said regenerated dental pulp tissue is separated from said synthetic matrix prior to application into the tissue space of the root canal.

88. The method of claim 80, wherein said regenerated dental pulp tissue is applied to the tissue space of the root canal in combination with said synthetic matrix.

89. The method of claim 80, comprising the steps of:
 (a) removing infected dental pulp tissue from the root of a diseased tooth of an animal to create a root chamber;
 (b) obtaining a composition comprising viable dental pulp cells or gingival submucosal fibroblasts from said animal and culturing the cells of said composition on a synthetic matrix ex vivo under conditions effective and for a period of time sufficient to allow the formation of a synthetic matrix-tissue preparation containing regenerated dental pulp tissue; and
 (c) implanting said regenerated dental pulp tissue into the root chamber created in step (a).

90. The method of claim 80, comprising the steps of:
 (a) removing infected dental pulp tissue from the root of a diseased tooth of an animal to create a cleansed root chamber;
 (b) placing a temporary implant in said root chamber;
 (c) obtaining viable dental pulp-regenerative tissue from a healthy molar or wisdom tooth or from a gingival sample of said animal;
 (d) culturing viable fibroblast cells from said dental pulp tissue in vitro in the presence of an effective inhibitory amount of at least one antimicrobial agent;
 (e) implanting said cultured cells on a biocompatible synthetic matrix to form a synthetic matrix-cell preparation;
 (f) maintaining said synthetic matrix-cell preparation under conditions effective and for a period of time sufficient to allow the formation of a synthetic matrix-tissue preparation containing regenerated dental pulp tissue;
 (g) admixing said synthetic matrix-tissue preparation with an exogenous factor that stimulates the growth or proliferation of oral tissue;
 (h) removing said temporary implant from said root chamber; and
 (i) implanting the synthetic matrix-tissue admixture into the root chamber re-created in step (h).

91. A method for delivering a selected factor to an animal, comprising culturing viable oral tissue cells on a synthetic matrix in vitro under conditions effective and for a period of time sufficient to allow formation of a tissue sample that comprises viable oral tissue cells and delivering said tissue sample to an oral tissue site of an animal in the presence of a selected factor.

92. The method of claim 91, wherein said selected factor is produced by a cell and said cell is delivered to said oral tissue site in the presence of said tissue sample.

93. The method of claim 91, wherein said selected factor is produced by a recombinant cell engineered to produce said factor and the recombinant cell is delivered to said oral tissue site in the presence of said tissue sample.

94. The method of claim 91, wherein said selected factor is produced by an oral tissue cell of the delivered tissue sample, the oral tissue cell being provided with an exogenous gene that expresses said selected factor.

95. The method of claim 91, wherein said selected factor stimulates the growth or proliferation of the oral tissue cells of the tissue sample delivered to said animal.

96. The method of claim 91, wherein said selected factor stimulates the growth or proliferation of blood vessels in or around the oral tissue cells of the tissue sample delivered to said animal.

97. The method of claim 91, wherein said selected factor provides an oral therapeutic benefit upon delivery to an oral tissue site of an animal.

98. The method of claim 91, wherein said selected factor provides a systemic therapeutic benefit upon delivery to an oral tissue site of an animal and subsequent uptake into the systemic circulation of the animal.

99. The method of claim 98, wherein said selected factor is an antibiotic, a growth factor, a cytokine, a blood clotting factor or insulin therapeutic factor.

100. The method of claim 91, wherein said selected factor is subsequently removed from said animal by removing the delivered tissue sample from the oral tissue site of the animal.

101. A population of cultured oral tissue cells prepared by a process comprising culturing viable starting cells obtained from an oral tissue sample on a synthetic matrix in vitro under conditions effective and for a period of time sufficient to allow proliferation of viable oral tissue cells.

102. A tissue sample that comprises viable oral tissue cells prepared by a process comprising culturing viable starting cells obtained from an oral tissue sample on a synthetic matrix in vitro under conditions effective and for a period of time sufficient to allow formation of a tissue sample that comprises viable oral tissue cells.

103. A three dimensional synthetic matrix housing a regenerated oral tissue sample prepared by a process comprising culturing viable starting cells obtained from an oral tissue sample on a synthetic matrix in vitro under conditions effective and for a period of time sufficient to allow proliferation and organization of said cells to form an oral tissue sample within said synthetic matrix.

104. The synthetic matrix of claim 103, wherein said synthetic matrix is a biocompatible synthetic matrix.

105. The synthetic matrix of claim 103, wherein said synthetic matrix is a slowly biodegradable synthetic matrix.

106. The synthetic matrix of claim 103, wherein said synthetic matrix is a polylactic acid (PLA) polymer, polyglycolic acid (PGA) polymer or polylactic-polyglycolic acid (PLGA) co-polymer synthetic matrix.

107. The synthetic matrix of claim 103, wherein said regenerated oral tissue sample is a regenerated dental pulp tissue sample.

108. A method for testing the suitability of a candidate substance for use in the oral cavity, comprising applying a candidate substance to a regenerated, three-dimensional oral tissue sample, and analyzing the effect of said candidate substance on the viability of said tissue sample, wherein a candidate substance that is not unacceptably toxic to said tissue sample is a substance suitable for use in the oral cavity.

109. An oral or dental kit comprising, in a container means, a three dimensional synthetic matrix housing a regenerated oral tissue sample.

\* \* \* \* \*

UNITED STATES PATENT AND TRADEMARK OFFICE
CERTIFICATE OF CORRECTION

PATENT NO.    :   5,885,829
DATED         :   March 23, 1999
INVENTOR(S)   :   Mooney et al.

It is certified that error appears in the above-identified patent and that said Letters Patent is hereby corrected as shown below:

On the title page, item [51], line 1 through 2, delete "C12N 5/00; C12N 5 02; C12N 5 08; C12N 15 09" and insert -- C12N 5/06, 5/08, 5/10, A61L 27/00, A61K 6/00 --.

Signed and Sealed this

Twenty-sixth Day of October, 1999

Attest:

Q. TODD DICKINSON

Attesting Officer    Acting Commissioner of Patents and Trademarks